US012173051B2

(12) United States Patent
Haynes et al.

(10) Patent No.: US 12,173,051 B2
(45) **Date of Patent: *Dec. 24, 2024**

(54) BISPECIFIC MOLECULES COMPRISING AN HIV-1 ENVELOPE TARGETING ARM

(71) Applicants: Duke University, Durham, NC (US); MacroGenics, Inc., Rockville, MD (US); The University of North Carolina at Chapel Hill, Chapel Hill, NC (US)

(72) Inventors: Barton F. Haynes, Durham, NC (US); Guido Ferrari, Durham, NC (US); Scott Koenig, Rockville, MD (US); Leslie S. Johnson, Rockville, MD (US); Chia-Ying Kao Lam, San Jose, CA (US); Julia A. Sung, Chapel Hill, NC (US); David M. Margolis, Chapel Hill, NC (US); Liqin Liu, Germantown, MD (US); Jeffrey Lee Nordstrom, Olney, MD (US)

(73) Assignees: Duke University, Durham, NC (US); MacroGenics, Inc., Rockville, MD (US); The University of North Carolina at Chapel Hill, Chapel Hill, NC (US)

( * ) Notice: Subject to any disclaimer, the term of this patent is extended or adjusted under 35 U.S.C. 154(b) by 738 days.

This patent is subject to a terminal disclaimer.

(21) Appl. No.: 16/890,380

(22) Filed: Jun. 2, 2020

(65) Prior Publication Data

US 2020/0354439 A1 Nov. 12, 2020

Related U.S. Application Data

(63) Continuation of application No. 15/514,420, filed as application No. PCT/US2015/053027 on Sep. 29, 2015, now Pat. No. 10,717,778.

(60) Provisional application No. 62/206,586, filed on Aug. 18, 2015, provisional application No. 62/056,834, filed on Sep. 29, 2014.

(51) Int. Cl.

| | |
|---|---|
| ***C07K 16/10*** | (2006.01) |
| ***A61K 39/395*** | (2006.01) |
| ***A61K 39/42*** | (2006.01) |
| ***A61K 45/06*** | (2006.01) |
| ***C07K 16/28*** | (2006.01) |
| ***C07K 16/44*** | (2006.01) |
| ***C07K 16/46*** | (2006.01) |
| *A61K 39/00* | (2006.01) |

(52) U.S. Cl.

CPC .... *C07K 16/1063* (2013.01); *A61K 39/39541* (2013.01); *A61K 39/42* (2013.01); *A61K 45/06* (2013.01); *C07K 16/2803* (2013.01); *C07K 16/2809* (2013.01); *C07K 16/2812* (2013.01); *C07K 16/283* (2013.01); *C07K 16/44* (2013.01); *C07K 16/468* (2013.01); *A61K 2039/505* (2013.01); *C07K 2317/31* (2013.01); *C07K 2317/52* (2013.01); *C07K 2317/626* (2013.01); *C07K 2317/72* (2013.01); *C07K 2317/73* (2013.01); *C07K 2317/732* (2013.01); *C07K 2317/76* (2013.01)

(58) Field of Classification Search

None

See application file for complete search history.

(56) References Cited

U.S. PATENT DOCUMENTS

| | | | |
|---|---|---|---|
| 3,842,067 | A | 10/1974 | Sarantakis |
| 3,862,925 | A | 1/1975 | Sarantakis et al. |
| 3,972,859 | A | 8/1976 | Fujino et al. |
| 4,105,603 | A | 8/1978 | Vale, Jr. et al. |
| 4,752,601 | A | 6/1988 | Hahn |
| 4,816,567 | A | 3/1989 | Cabilly et al. |
| 5,116,964 | A | 5/1992 | Capon et al. |
| 5,169,933 | A | 12/1992 | Anderson et al. |
| 5,348,876 | A | 9/1994 | Michaelsen et al. |
| 5,565,332 | A | 10/1996 | Hoogenboom et al. |
| 5,576,184 | A | 11/1996 | Better et al. |
| 5,580,717 | A | 12/1996 | Dower et al. |
| 5,585,089 | A | 12/1996 | Queen et al. |

(Continued)

FOREIGN PATENT DOCUMENTS

| | | | |
|---|---|---|---|
| CN | 103703024 | A | 4/2014 |
| EP | 0308936 | A2 | 3/1989 |

(Continued)

OTHER PUBLICATIONS

US 6,331,391 B1, 12/2001, Wittrup et al. (withdrawn)

(Continued)

*Primary Examiner* — Michael Szperka
*Assistant Examiner* — Lia E Taylor
(74) *Attorney, Agent, or Firm* — Baker Donelson

(57) ABSTRACT

The invention is directed to bispecific molecules comprising an HIV-1 envelope targeting arm and an arm targeting an effector cell, compositions comprising these bispecific molecule and methods of use. In certain aspects, the bispecific molecules of the present invention can bind to two different targets or epitopes on two different cells within the first epitope is expressed on a different cell type than the second epitope, such that the bispecific molecules can bring the two cells together. In certain aspects, the bispecific molecules of the present invention can bind to two different cells, wherein the bispecific molecules comprises an arm with the binding specificity of A32, 7B2, CH27, CH28 or CH44.

16 Claims, 92 Drawing Sheets

Specification includes a Sequence Listing.

(56) References Cited

U.S. PATENT DOCUMENTS 5,624,821 A 4/1997 Winter et al.
5,648,260 A 7/1997 Winter et al.
5,698,449 A 12/1997 Baumann et al.
5,723,584 A 3/1998 Schatz
5,731,168 A 3/1998 Carter et al.
5,733,743 A 3/1998 Johnson et al.
5,736,135 A 4/1998 Goeddel et al.
5,736,137 A 4/1998 Anderson et al.
5,807,706 A 9/1998 Carter et al.
5,807,715 A 9/1998 Morrison et al.
5,821,333 A 10/1998 Carter et al.
5,866,692 A 2/1999 Shitara et al.
5,874,239 A 2/1999 Schatz
5,932,433 A 8/1999 Schatz
5,985,599 A 11/1999 McKenzie et al.
6,025,485 A 2/2000 Kamb et al.
6,114,147 A 9/2000 Frenken et al.
6,165,745 A 12/2000 Ward et al.
6,180,370 B1* 1/2001 Queen .................... A61P 19/02 435/69.6
6,194,551 B1 2/2001 Idusogie et al.
6,218,149 B1 4/2001 Morrison et al.
6,242,195 B1 6/2001 Idusogie et al.
6,265,150 B1 7/2001 Terstappen et al.
6,277,375 B1 8/2001 Ward
6,300,065 B1 10/2001 Kieke et al.
6,331,415 B1 12/2001 Cabilly et al.
6,423,538 B1 7/2002 Wittrup et al.
6,455,263 B2 9/2002 Payan
6,472,511 B1 10/2002 Leung et al.
6,492,123 B1 12/2002 Holliger et al.
6,528,624 B1 3/2003 Idusogie et al.
6,538,124 B1 3/2003 Idusogie et al.
6,613,884 B1 9/2003 Johansson
6,623,940 B1 9/2003 Ledbetter et al.
6,727,349 B1 4/2004 LaRosa et al.
6,737,056 B1 5/2004 Presta
6,821,505 B2 11/2004 Ward
7,122,646 B2 10/2006 Holliger et al.
7,315,786 B2 1/2008 Dahiyat et al.
7,317,091 B2 1/2008 Lazar et al.
7,351,803 B2 4/2008 Johnson et al.
7,425,619 B2 9/2008 Koenig et al.
7,429,652 B2 9/2008 Wang et al.
7,507,797 B2 3/2009 Knackmuss et al.
7,521,542 B2 4/2009 Johnson et al.
7,632,497 B2 12/2009 Stavenhagen
7,642,228 B2 1/2010 Carter et al.
7,695,936 B2 4/2010 Carter et al.
7,700,100 B2 4/2010 Johnson et al.
7,960,512 B2 6/2011 Stavenhagen et al.
8,003,774 B2 8/2011 Stavenhagen et al.
8,044,180 B2 10/2011 Koenig et al.
8,133,982 B2 3/2012 Johnson et al.
8,187,593 B2 5/2012 Koenig et al.
8,192,737 B2 6/2012 Stavenhagen et al.
8,193,318 B2 6/2012 Koenig et al.
8,211,866 B2 7/2012 Zeichner et al.
8,216,574 B2 7/2012 Stavenhagen et al.
8,216,579 B2 7/2012 Johnson et al.
8,216,805 B2 7/2012 Carter et al.
8,217,147 B2 7/2012 Stavenhagen et al.
8,313,746 B2 11/2012 Dimitrov et al.
8,586,713 B2 11/2013 Davis et al.
8,642,743 B2 2/2014 Herne
8,784,821 B1 7/2014 Kufer et al.
8,999,398 B2 4/2015 Lum et al.
9,284,375 B2 3/2016 Johnson et al.
9,296,816 B2 3/2016 Johnson et al.
9,376,495 B2 6/2016 Bonvini et al.
9,889,197 B2* 2/2018 Johnson ................. A61P 37/02
9,908,938 B2 3/2018 Koenig et al.
10,647,768 B2 5/2020 Johnson et al.
10,717,778 B2 7/2020 Haynes et al.
10,730,947 B2 8/2020 Koenig et al.
11,421,031 B2 8/2022 Koenig et al.
2002/0028486 A1 3/2002 Morrison et al.
2003/0077282 A1 4/2003 Bigler et al.
2003/0115614 A1 6/2003 Kanda et al.
2003/0158389 A1 8/2003 Idusogie et al.
2003/0207346 A1 11/2003 Arathoon et al.
2004/0002587 A1 1/2004 Watkins et al.
2004/0038339 A1 2/2004 Kufer et al.
2004/0058400 A1 3/2004 Holliger et al.
2004/0110226 A1 6/2004 Lazar et al.
2004/0132101 A1 7/2004 Lazar et al.
2004/0185045 A1 9/2004 Koenig et al.
2004/0220388 A1 11/2004 Mertens et al.
2004/0259075 A1 12/2004 Dimitrov et al.
2005/0037000 A1 2/2005 Stavenhagen et al.
2005/0054832 A1 3/2005 Lazar et al.
2005/0064514 A1 3/2005 Stavenhagen et al.
2005/0100543 A1 5/2005 Hansen et al.
2005/0142539 A1 6/2005 Herman
2005/0257285 A1 11/2005 Gupta
2005/0260213 A1 11/2005 Koenig et al.
2006/0099216 A1 5/2006 Nicholas Cardy et al.
2006/0193849 A1 8/2006 Krauss et al.
2007/0004909 A1 1/2007 Johnson et al.
2007/0036799 A1 2/2007 Stavenhagen et al.
2007/0041977 A1 2/2007 Knackmuss et al.
2007/0135338 A1 6/2007 O'Neil et al.
2007/0140966 A1 6/2007 Chang et al.
2007/0274998 A1 11/2007 Utku
2008/0085277 A1 4/2008 Cho et al.
2008/0187517 A1 8/2008 Herne
2009/0060910 A1 3/2009 Johnson et al.
2009/0162353 A1 6/2009 Johnson et al.
2010/0040601 A1 2/2010 Cantin et al.
2010/0040635 A1 2/2010 Horowitz et al.
2010/0093979 A1 4/2010 Lazar
2010/0174053 A1 7/2010 Johnson et al.
2010/0196362 A1 8/2010 Stavenhagen et al.
2010/0196372 A1 8/2010 Johnson et al.
2010/0322924 A1 12/2010 Johnson et al.
2011/0033389 A1 2/2011 Chen et al.
2011/0076268 A1 3/2011 Williamson et al.
2011/0081347 A1 4/2011 Gorlatov
2011/0212076 A1 9/2011 Vyakarnam et al.
2011/0243941 A1 10/2011 Stavenhagen et al.
2011/0268656 A1 11/2011 Ho et al.
2011/0305714 A1 12/2011 Stavenhagen et al.
2011/0319871 A1 12/2011 Wood
2012/0009186 A1 1/2012 Koenig et al.
2012/0093834 A1 4/2012 Horowitz et al.
2012/0128669 A1 5/2012 Depla et al.
2012/0141476 A1 6/2012 Johnson et al.
2012/0219551 A1 8/2012 Johnson et al.
2012/0258108 A1 10/2012 Ghayur et al.
2012/0263711 A1 10/2012 Stavenhagen et al.
2012/0269811 A1 10/2012 Johnson et al.
2012/0276094 A1 11/2012 Stavenhagen et al.
2012/0283418 A1 11/2012 Wu et al.
2012/0283438 A1 11/2012 Lazarides et al.
2013/0295121 A1 11/2013 Johnson et al.
2014/0088295 A1 3/2014 Smith et al.
2014/0099318 A1 4/2014 Huang et al.
2014/0162956 A1 6/2014 Ekblad et al.
2014/0170149 A1 6/2014 Neijssen et al.
2014/0205612 A1 7/2014 Chan-Hui et al.
2014/0206846 A1 7/2014 Beckmann
2014/0328836 A1 11/2014 Johnson et al.
2015/0152183 A1 6/2015 Chamberlain et al.
2015/0175697 A1 6/2015 Bonvini et al.
2017/0247452 A1* 8/2017 Koenig et al. ....... C07K 16/468

FOREIGN PATENT DOCUMENTS

EP 0327378 A1 8/1989
EP 0359096 A1 3/1990
EP 1354600 A1 10/2003
EP 1670826 A1 6/2006
EP 2158221 A2 3/2010
EP 2376109 A1 10/2011

(56) References Cited

FOREIGN PATENT DOCUMENTS

| | | | | |
|---|---|---|---|---|
| EP | 2714079 | B1 | 9/2016 | |
| EP | 2601216 | B1 | 1/2018 | |
| JP | 2001-523971 | A | 11/2001 | |
| JP | 2007-531788 | A | 11/2007 | |
| JP | 2008-69150 | A | 3/2008 | |
| JP | 2009-535059 | A | 10/2009 | |
| SG | 191712 | A1 | 8/2013 | |
| WO | WO-1988/007089 | A1 | 9/1988 | |
| WO | WO-1989/007142 | A1 | 8/1989 | |
| WO | WO-1992/016562 | A1 | 10/1992 | |
| WO | WO-1993/008829 | A1 | 5/1993 | |
| WO | WO-1993/0022332 | A2 | 11/1993 | |
| WO | WO-1994/018330 | A1 | 8/1994 | |
| WO | WO-1994/029351 | A2 | 12/1994 | |
| WO | WO-1995/005468 | A1 | 2/1995 | |
| WO | WO-1996/027011 | A1 | 9/1996 | |
| WO | WO-1997/028267 | A1 | 8/1997 | |
| WO | WO-1997/034631 | A1 | 9/1997 | |
| WO | WO-1997/044362 | A1 | 11/1997 | |
| WO | WO-1998/005787 | A1 | 2/1998 | |
| WO | WO-1998/023289 | A1 | 6/1998 | |
| WO | WO-1998/052975 | A1 | 11/1998 | |
| WO | WO-1998050431 | A2 | 11/1998 | |
| WO | WO-1999/043713 | A1 | 9/1999 | |
| WO | WO-1999/051642 | A1 | 10/1999 | |
| WO | WO-1999/058572 | A1 | 11/1999 | |
| WO | WO-2000/009560 | A2 | 2/2000 | |
| WO | WO-2000/042072 | A2 | 7/2000 | |
| WO | WO-2001/011059 | A1 | 2/2001 | |
| WO | WO-2002/002781 | A1 | 1/2002 | |
| WO | WO-2002/060919 | A2 | 8/2002 | |
| WO | WO-2002/086070 | A2 | 10/2002 | |
| WO | WO-2003/035835 | A2 | 5/2003 | |
| WO | WO-2003/074679 | A2 | 9/2003 | |
| WO | WO-2003/101485 | A1 | 12/2003 | |
| WO | WO-2004/001064 | A2 | 12/2003 | |
| WO | WO-2004/016750 | A2 | 2/2004 | |
| WO | WO-2004/029207 | A2 | 4/2004 | |
| WO | WO-2004/063351 | A2 | 7/2004 | |
| WO | WO-2004/065423 | A2 | 8/2004 | |
| WO | WO-2004/074455 | A2 | 9/2004 | |
| WO | WO-2004/099249 | A2 | 11/2004 | |
| WO | WO-2005/035580 | A1 | 4/2005 | |
| WO | WO-2005/061547 | A2 | 7/2005 | |
| WO | WO-2005/070963 | A1 | 8/2005 | |
| WO | WO-2005/097202 | A2 | 10/2005 | |
| WO | WO-2006/020114 | A2 | 2/2006 | |
| WO | WO-2006/044410 | A2 | 4/2006 | |
| WO | WO-2006/113665 | A2 | 10/2006 | |
| WO | WO-07/042261 | A2 | 4/2007 | |
| WO | WO-2007130493 | A2 | 11/2007 | |
| WO | WO-2008/157379 | A2 | 12/2008 | |
| WO | WO-2009/058888 | A1 | 5/2009 | |
| WO | WO-2010/080538 | A1 | 7/2010 | |
| WO | WO-2011057124 | A1 | 5/2011 | |
| WO | WO-2011/085289 | A1 | 7/2011 | |
| WO | WO-2011/133886 | A2 | 10/2011 | |
| WO | WO-2012/004384 | A2 | 1/2012 | |
| WO | WO-2012018687 | A1 * | 2/2012 | ........... A61K 38/164 |
| WO | WO-2012/030904 | A2 | 3/2012 | |
| WO | WO-2012/106587 | A1 | 8/2012 | |
| WO | WO-2012/162068 | A2 | 11/2012 | |
| WO | WO-2012162067 | A2 * | 11/2012 | ................ A61P 1/00 |
| WO | WO-2013/163427 | A1 | 10/2013 | |
| WO | WO-2013/192589 | A1 | 12/2013 | |
| WO | WO-2014/052620 | A1 | 4/2014 | |
| WO | WO-14/164959 | A2 | 10/2014 | |
| WO | WO-2014/159940 | A1 | 10/2014 | |
| WO | WO-2015/026892 | A1 | 2/2015 | |
| WO | WO-2015/026894 | A2 | 2/2015 | |
| WO | WO-2015021089 | A1 * | 2/2015 | ............. A61P 29/00 |
| WO | WO-2015/048462 | A1 | 4/2015 | |
| WO | WO-2015/184203 | A1 | 12/2015 | |
| WO | WO-2016/048938 | A1 | 3/2016 | |
| WO | WO-2016/054101 | A1 | 4/2016 | |

OTHER PUBLICATIONS

Kontermann, Roland E. mAbs vol. 4,2 (2012): 182-97. doi:10.4161/mabs.4.2.19000 (Year: 2012).*

Ferrari, Guido et al. Journal of virology vol. 85, 14 (2011): 7029-36. doi: 10.1128/JVI.00171-11 (Year: 2011).*

Craig, Ryan B et al. PloS one vol. 7,10 (2012): e46778. doi:10.1371/journal.pone.0046778 (Year: 2012).*

Kipriyanov, Sergey M., and Fabrice Le Gall. "Generation and production of engineered antibodies." Molecular biotechnology 26.1 (2004): 39-60. (Year: 2004).*

Janeway, Charles A. "Immunobiology: The Immune System in Health and Disease." 2001 (Year: 2001).*

Acharya, P., et al., "Structural Definition of an Antibody-Dependent Cellular Cytotoxicity Response Implicated in Reduced Risk for HIV-1 Infection," J. Virol., vol. 88, No. 21, pp. 12895-12906 (Nov. 2014).

Adachi, A., et al., "Production of acquired immunodeficiency syndrome-associated retrovirus in human and nonhuman cells transfected with an infectious molecular clone," J. Virol., vol. 59, No. 2, pp. 284-291 (Aug. 1986).

Alt, M., et al., "Novel Tetravalent and Bispecific IgG-Like Antibody Molecules Combining Single-Chain Diabodies with the Immunoglobulin Gamma1 Fc or CH3 Region," FEBS Letters, vol. 454, pp. 90-94 (1999).

Altman, J.D., et al., "Phenotypic Analysis of Antigen-Specific T Lymphocytes", Science, vol. 274, pp. 94-96 (Oct. 4, 1996).

Angal, S., et al., "A single amino acid substitution abolishes the heterogeneity of chimeric mouse/human (IgG4) antibody," Mol. Immunol., vol. 30, No. 1, pp. 105-108, 5 total pages (Jan. 1993).

Anonymous, "Boehringer Ingelheim and MacroGenics Announce Global Alliance to Discover, Develop and Commercialize DART™-Based Antibody Therapeutics," Press Release of MacroGenics, Inc., 3 total pages (Oct. 26, 2010).

Anonymous, "MacroGenics Enters Global Research Collaboration and License Agreement with Pfizer;" Press Release of MacroGenics, Inc., 2 total pages (Oct. 26, 2010).

Apostolovic, B., et al., "pH-Sensitivity of the E3/K3 Heterodimeric Coiled Coil," Biomacromolecules, vol. 9, pp. 3173-3180 (Oct. 21, 2008).

Arbiza, J., et al., "Characterization of Two Antigenic Sites Recognized by Neutralizing Monoclonal Antibodies Directed Against the Fusion Glycoprotein of Human Respiratory Syncytial Virus," J. Gen. Virol., vol. 73, pp. 2225-2234 (1992).

Archin, N.M., et al., "Administration of vorinostat disrupts HIV-1 latency in patients on antiretroviral therapy," Nature, vol. 487, No. 7408, pp. 482-485, Author Manuscript—12 pages (Jul. 8, 2013).

Archin, N.M., et al., "Valproic acid without intensified antiviral therapy has limited impact on persistent HIV infection of resting CD4+ T cells," AIDS, vol. 22, No. 10, pp. 1131-1135, Author Manuscript—9 pages (Jun. 19, 2008).

Armour, K.L., et al., "Differential binding to human FcgammaRIIa and FcgammaRIIb receptors by human IgG wildtype and mutant antibodies," Mol. Immunol., vol. 40, pp. 585-593 (2003).

Armour, K.L., et al., "Recombinant Human IgG Molecules Lacking Fcgamma Receptor | Binding And Monocyte Triggering Activities," Eur. J. Immunol., vol. 29, No. 8, pp. 2613-2624, 13 total pages (1999).

Armour, K.L., et al., "The contrasting IgG-binding interactions of human and herpes simplex virus Fc receptors," Biochemical Society Transactions, vol. 30, Part 4, pp. 495-500 (2002).

Armstrong, S., et al. "Heterogeneity of IgG1 monoclonal anti-Rh(D): an investigation using ADCC and macrophage binding assays," Brit. J. Haematol., vol. 66, pp. 257-262 (1987).

Arndt, K.M., et al., "Helix-stabilized Fv (hsFv) Antibody Fragments: Substituting the Constant Domains of a Fab Fragment for a Heterodimeric Coiled-coil Domain," J. Molec. Biol., vol. 312, pp. 221-228 (2001).

Arndt, K.M., et al., "Comparison of in Vivo Selection and Rational Design of Heterodimeric Coiled Coils," Structure, vol. 10, pp. 1235-1248 (Sep. 2002).

(56) References Cited

OTHER PUBLICATIONS

Aruffo, A., et al., "Molecular Cloning of a CD28 cDNA by a High-Efficiency COS Cell Expression System," Proc. Natl. Acad. Sci. (U.S.A.), vol. 84, pp. 8573-8577 (Dec. 1987).
Asano, R., et al., "A Diabody For Cancer Immunotherapy and its Functional Enhancement by Fusion Of Human Fc Region," Antibody Engineering & Cell Engineering—Exhibition Hall, Abstract 3P-683, vol. 76, No. 8, p. 992 (Oct. 15, 2004).
Atwell, S., et al., "Stable Heterodimers from Remodeling the Domain Interface of a Homodimer Using a Phage Display Library," J. Mol. Biol., vol. 270, pp. 26-35 (1997).
Babcock, G.J., et al., "Epstein-Barr Virus-Infected Resting Memory B Cells, Not Proliferating Lymphoblasts, Accumulate in The Peripheral Blood of Immunosuppressed Patients," J. Exp. Med., vol. 190, No. 4, pp. 567-576 (Aug. 16, 1999).
Baeuerle, P. A., et al., "BiTE: A New Class of Antibodies That Recruit T Cells," Drugs of the Future, vol. 33, No. 2, pp. 137-147 (2008).
Baggiolini, M. and Dewald, B., "Cellular models for the detection and evaluation of drugs that modulate human phagocyte activity," Experientia, vol. 44, pp. 841-848, (1988).
Bargou, R., et al., "Tumor Regression in Cancer Patients by Very Low Doses of a T Cell-Engaging Antibody," Science, vol. 321, pp. 974-977, 5 total pages (Aug. 15, 2008).
Barouch, D.H., et al., "Therapeutic efficacy of potent neutralizing HIV-1-specific monoclonal antibodies in SHIV-infected rhesus monkeys," Nature, vol. 503, No. 7475, pp. 224-228, Author Manuscript—24 pages (Nov. 14, 2013).
Beasley, D.W.C. , "Vaccines and Immunotherapeutics for The Prevention and Treatment of Infections with West Nile Virus," Immunotherapy, vol. 3, No. 2, pp. 269-285 (2011).
Bedzyk, W.D., et al., "Comparison of Variable Region Primary Structures Within an Anti-Fluorescein Idiotype Family," J. Biol. Chem, vol. 264, Issue No. 3, pp. 1565-1569 (1989).
Beeler, J.A., et al., "Neutralization Epitopes of the F Glycoprotein of Respiratory Syncytial Virus: Effect of Mutation Upon Fusion Function," J. Virol. Vol. 63, No. 7, pp. 2941-2950 (Jul. 1989).
Beigel, J. and Bray, M., "Current and Future Antiviral Therapy of Severe Seasonal and Avian Influenza," Antiviral Res., vol. 78, No. 1, pp. 91-102, Author Manuscript—22 pages (Apr. 2008).
Bera T.K., et al., "Specific killing of HIV-infected lymphocytes by a recombinant immunotoxin directed against the HIV-1 envelope glycoprotein," Molecular Medicine, vol. 4, No. 6, pp. 384-391 (Jun. 1998).
Berg, J., et al., "Bispecific Antibodies That Mediate Killing of Cells Infected with Human Immunodeficiency Virus of Any Strain," Proc. Natl. Acad. Sci. U.S.A., vol. 88, pp. 4723-4727 (Jun. 1991).
Bernard, A et al., "T and B Cell Cooperation: A Dance of Life and Death," Transplantation, vol. 79, No. 3, pp. S8-S11—Supplement (Feb. 15, 2005).
Berry, J.D., et al., "Antibodies in Infectious Diseases: Polyclonals, Monoclonals and Niche Biotechnology," Nature Biotechnol., vol. 28, No. 5, pp. 489-501 (Sep. 2011).
Betts, M.R., et al., "Sensitive and viable identification of antigen-specific CD8+ T cells by a flow cytometric assay for degranulation," J. Immunol. Methods, vol. 281, pp. 65-78 (Jul. 2003).
Bird, R.E., et al., "Single-Chain Antigen-Binding Proteins," Science, vol. 242, pp. 423-426 (Oct. 21, 1988).
Blackburn, S.D., et al., "Coregulation of CD8+ T cell exhaustion during chronic viral infection by multiple inhibitory receptors," Nat Immunol., vol. 10, No. 1, pp. 29-37, Author Manuscript—23 pages (Jan. 2009).
Boder, E.T. and Wittrup, K.D., "Optimal screening of surface-displayed polypeptide libraries," Biotechnol. Prog., vol. 14, No. 1, pp. 55-62, 9 total pages (Jan./Feb. 1998).
Boder, E.T. and Wittrup, K.D., "Yeast surface display for directed evolution of protein expression, affinity, and stability," Methods in Enzymology, vol. 328, pp. 430-444 (2000).
Boder, E.T. and Wittrup, K.D., "Yeast surface display for screening combinatorial polypeptide libraries", Nature Biotechnology, vol. 15, pp. 553-557 (Jun. 1997).
Boder, E.T., et al., "Directed evolution of antibody fragments with monovalent femtomolar antigen- binding affinity," Proc. Natl. Acad. Sci. USA, vol. 97, No. 20, pp. 10701-10705 (Sep. 26, 2000).
Bosque, A., et al., "Homeostatic Proliferation Fails to Efficiently Reactivate HIV-1 Latently Infected Central Memory CD4+ T Cells," PLoS Pathog., vol. 7, Issue 10, e1002288, pp. 1-8 (Oct. 2011).
Boucher, C., et al., "Protein Detection by Western Blot Via Coiled-Coil Interactions," Analytical Biochemistry, vol. 399, pp. 138-140 (2010).
Bredius, R.G.M., et al., "Role of neutrophil FcgammaRIIa (CD32) and FcgammaRIIIb (CD16) polymorphic forms in phagocytosis of human IgG1- and IgG3-opsonized bacteria and erythrocytes," Immunology, vol. 83, Issue 4, pp. 624-630, 8 total pages (Dec. 1994).
Brekke, O.H., et al., "Human IgG isotype-specific amino acid residues affecting complement-mediated cell lysis and phagocytosis. ," Eur. J. Immunol., vol. 24, No. 10, pp. 2542-2547, 7 total pages (1994).
** Brown, E.J., "In Vitro Assays of Phagocytic Function of Human Peripheral Blood Leukocytes: Receptor Modulation and Signal Transduction," Methods in Cell Biology, vol. 45, Chapter 8, pp. 147-164, 19 total pages (1994).
Buchacher, A., et al., "Generation of Human Monoclonal Antibodies Against HIV-1 Proteins; Electrofusion and Epstein-Barr Virus Transformation for Peripheral Blood Lymphocyte Immortalization," AIDS Res. Hum. Retroviruses, vol. 10, No. 4, pp. 359-369 (1994).
Bullen, C.K., et al., "Novel ex vivo approaches distinguish effective and ineffective single agents for reversing HIV-1 latency in vivo," Nat. Med., vol. 20, No. 4, pp. 425-429, Author Manuscript—14 pages (Apr. 2014).
Burmeister, W.P., et al., "Crystal Structure of the Complex of Rat Neonatal Fc Receptor with Fc," Nature, vol. 372, pp. 379-383 (Nov. 24, 1994).
Burton, "Immunoglobulin G: functional sites," Mol. Immunol., vol. 22, No. 3, pp. 161-206, 25 total pages (Mar. 1985).
Burton, D.R., et al., "Molecular recognition of antibody (IgG) by cellular Fc receptor (FcRI)," Mol. Immunol., vol. 25, No. 11, pp. 1175-1181 (1988).
Burton,D.R. and Woof, J.M., "Human antibody effector function," Advances in Immunology, vol. 51, pp. 1-84, 46 total pages (1992).
Byrne et al. "A tale of two specificities: bispecific antibodies for therapeutic and diagnostic applications" Trends in Biotechnology, vol. 31, Issue 11, Nov. 2013, pp. 621-632.
Cachia, P.J. et al., "Synthetic Peptide Vaccine Development: Measurement of Polyclonal Antibody Affinity and Cross-Reactivity Using a New Peptide Capture and Release System for Surface Plasmon Resonance Spectroscopy," J. Mol. Recognit., vol. 17, pp. 540-557 (May 14, 2004).
Canfield, S.M. and Morrison, S.L., "The binding affinity of human IgG for its high affinity Fc receptor is determined by multiple amino acids in the $C_H2$ domain and is modulated by the hinge region," J. Exp. Med., vol. 173, pp. 1483-1491 (Jun. 1991).
Cao, J. and Lam, L., "Bispecific Antibody Conjugates In Therapeutics," Adv. Drug. Deliv. Rev., vol. 55, pp. 171-197 (2003).
Cao, J., et al., "Molecular determinants of acute single-cell lysis by human immunodeficiency virus type 1," J. Virol., vol. 70, No. 3, pp. 1340-1354 (Mar. 1996).
Carcelain, et al., "Transient Mobilization of Human Immunodeficiency Virus (HIV)Specific CD4 T-Helper Cells Fails To Control Virus Rebounds during Intermittent Antiretroviral Therapy in Chronic HIV Type 1 Infection," J. Virol., vol. 75, No. 1, pp. 234-241 (Jan. 2001).
Caron, P.C., et al., "Engineered humanized dimeric forms of IgG are more effective antibodies," J. Exp. Med., vol. 176, pp. 1191-1195 (Oct. 1992).
Carter, P., et al., "Humanization of an anti-p185HER2 antibody for human cancer therapy," Proc. Natl. Acad. Sci. USA—Immunology, vol. 89, pp. 4285-4289 (May 1992).

(56) References Cited

OTHER PUBLICATIONS

Cartron, G., et al., "Therapeutic activity of humanized anti-CD20 monoclonal antibody and polymorphism in IgG Fc receptor FcgammaRIIIa gene," Blood, vol. 99, No. 3, pp. 754-758 (Feb. 2002).
Casazza, J.P., et al., "Acquisition of direct antiviral effector functions by CMV-specific CD4+ T lymphocytes with cellular maturation," JEM, vol. 203, No. 13, pp. 2865-2877 (Dec. 25, 2006).
Castillo, J., et al., "Newer monoclonal antibodies for hematological malignancies," Exp. Hematol., vol. 36, pp. 755-768 (2008).
Chan, C.E.Z., et al., "The Use of Antibodies in The Treatment of Infectious Diseases," Singapore Med. J., vol. 50, No. 7, pp. 663-673 (2009).
Chappel, M.S., et al., "Identification of a secondary FcgammaRI binding site within a genetically engineered human IgG antibody," J Biol. Chem., vol. 268, No. 33, pp. 25124-25131 (Nov. 25, 1993).
Chappel, M.S., et al., "Identification of the Fcgamma receptor class I binding site in human IgG through the use of recombinant IgG1-IgG2 hybrid and point-mutated antibodies," Proc. Natl. Acad. Sci USA, vol. 88, pp. 9036-9040 (Oct. 1991).
Chen, Y.-P., et al., "Rapid Detection of Hepatitis B Virus Surface Antigen by an Agglutination Assay Mediated by a Bispecific Diabody against Both Human Erythrocytes and Hepatitis B Virus Surface Antigen," Clinical and Vaccine Immunology, vol. 14, No. 6, pp. 720-725 (Jun. 2007).
Cheson, B.D., et al., "Monoclonal Antibody Therapy For B-Cell Non-Hodgkin's Lymphoma," N. Engl. J. Med., vol. 359, No. 6, pp. 613-626 (Aug. 7, 2008).
Chichili, G.R., et al., "A CD3xCD123 bispecific DART for redirecting host T cells to myelogenous leukemia: Preclinical activity and safety in nonhuman primates," Sci. Transl. Med., vol. 7, Issue 289-289ra82, pp. 1-13, 14 total pages (May 27, 2015).
Chomont, N., et al., "HIV reservoir size and persistence are driven by T cell survival and homeostatic proliferation," Nat. Med., vol. 15, No. 8, pp. 893-900, Author Manuscript—18 pages (Aug. 2009).
Chu, p. G., et al., "CD79: A Review," Appl. Immunohistochem. Molec. Morphol., vol. 9, No. 2, pp. 97-106 (Jun. 2001).
Chuang, G.-Y., et al., "Eliminating antibody polyreactivity through addition of N-linked glycosylation," Protein Science, vol. 24, pp. 1019-1030 (2015).
Chun, T.-W et al., "Quantification of latent tissue reservoirs and total body viral load in HIV-1 infection," Nature., vol. 387, pp. 183-188 (May 8, 1997).
Chun, T.-W., et al., "In vivo fate of HIV-I-infected T cells: Quantitative analysis of the transition to stable latency," Nat Med., vol. 1, No. 12, pp. 1284-1290 (Dec. 1995).
Ciccimarra, F., et al., "Localization of the IgG effector site for monocyte receptors," Proc. Natl. Acad. Sci. U.S.A., vol. 72, No. 6, pp. 2081-2083 (Jun. 1975).
Cillo, A.R., et al., "Quantification of HIV-1 latency reversal in resting CD4+ T cells from patients on suppressive antiretroviral therapy," Proc. Natl. Acad. Sci. USA, vol. 111, No. 19, pp. 7078-7083 (May 13, 2014).
Clynes, R. and Ravetch, J.V., "Cytotoxic antibodies trigger inflammation through Fc receptors," Immunity, vol. 3, pp. 21-26 (Jul. 1995).
Clynes, R., et al., "Fc receptors are required in passive and active immunity to melanoma," Proc. Natl. Acad. Sci USA, vol. 95, pp. 652-656 (Jan. 1998).
Clynes, R., et al., "Uncoupling of immune complex formation and kidney damage in autoimmune glomerulonephritis," Science, vol. 279, pp. 1052-1054 (Feb. 13, 1998).
Clynes, R.A., et al., "Inhibitory Fc receptors modulate in vivo cytoxicity against tumor targets," Nature Medicine, vol. 6, No. 4, pp. 443-446 (Apr. 2000).
Clynes,R. et al., "Modulation of immune complex-induced inflammation in vivo by the coordinate expression of activation and inhibitory Fc receptors," J. Exp. Med., vol. 189, No. 1, pp. 179-185 (Jan. 4, 1999).
Co, M. S., et al., "Humanized Antibodies for Antiviral Therapy," Proc. Natl. Acad. Sci. (U.S.A.), vol. 88, pp. 2869-2873 (Apr. 1991).
Co, M.S., et al., "Chimeric and Humanized Antibodies with Specificity for The CD33 Antigen," J. Immunol., vol. 148, No. 4, pp. 1149-1154 (Feb. 15, 1992).
Conner, R. I., et al., "Fc receptors for IgG (FcgammaRs) on human monocytes and macrophages are not infectivity receptors for human immunodeficiency virus type 1 (HIV-1): Studies using bispecific antibodies to target HIV-1 to various myeloid cell surface molecules, including the FcgammaR," PNAS USA—Immunology, vol. 88, pp. 9593-9597 (Nov. 1991).
Craig, R.B., et al., "Anti-HIV Double Variable Domain Immunoglobulins Binding Both gp41 and gp120 for Targeted Delivery of Immunoconjugates," PLoS ONE, vol. 7, Issue 10, e46778, pp. 1-12 (Oct. 2012).
Cuesta, A.M., et al., "Multivalent Antibodies: When Design Surpasses Evolution," Trends in Biotechnol., vol. 28, No. 7, pp. 355-362 (2010).
Davey, R.T., et al., "HIV-1 and T cell dynamics after interruption of highly active antiretroviral therapy (HAART) in patients with a history of sustained viral suppression," Proc. Natl. Acad. Sci. USA, vol. 96, No. 26, pp. 15109-15114 (Dec. 21, 1999).
Davey, R.T., et al., "Use Of Recombinant Soluble CD4 Pseudomonas Exotoxin, A Novel Immunotoxin, For Treatment Of Persons Infected With Human Immunodeficiency," Virus. J. Infect. Dis., vol. 170, pp. 1180-1188 (Nov. 1994).
De Crescenzo, G.D., et al., "Real-Time Monitoring of the Interactions of Two-Stranded de novo Designed Coiled-Coils: Effect of Chain Length on the Kinetic and Thermodynamic Constants of Binding," Biochemistry, vol. 42, pp. 1754-1763 (Jan. 25, 2003).
De Haas, Masja, "IgG-Fc receptors and the clinical relevance of their polymorphisms," Wien Klin Wochenschr, vol. 113, Nos. 20-21, pp. 825-831 (2001).
De Kruif, J., et al., "Leucine Zipper Dimerized Bivalent and Bispecific scFv Antibodies from a Semi-Synthetic Antibody Phage Display Library," J. Biol. Chem., vol. 271, No. 13, pp. 7630-7634 (Mar. 29, 1996).
Deisenhofer, Johann, "Crystallographic refinement and atomic models of a human Fc fragment and its complex with fragment B of protein A Form *Staphylococcus aureus* at 2.9- and 2.8-A resolution," Biochem., vol. 20, No. 9, pp. 2361-2370, 11 total pages (Apr. 28, 1981).
Deng, K., et al., "Broad CTL response is required to clear latent HIV-1 due to dominance of escape mutations," Nature, vol. 517, No. 7534, pp. 381-385, Author Manuscript—26 pages (Jan. 15, 2015).
Denton, P.W., et al., "Generation of HIV latency in humanized BLT mice," J. Virol., vol. 86, No. 1, pp. 630-634 (Jan. 2012).
Denton, P.W., et al., "Targeted cytotoxic therapy kills persisting HIV infected cells during ART," PLoS Pathog., vol. 10, No. 1, e1003872, pp. 1-9 (Jan. 9, 2014).
Deo, Y.M., et al., "Clinical significance of IgG Fc receptors and FcgammaR-directed immunotherapies," Immunology Today, vol. 18, No. 3, pp. 127-135, 10 total pages (Mar. 1997).
Dinoso, J.B., et al., "Treatment intensification does not reduce residual HIV-1 viremia in patients on highly active antiretroviral therapy," Proc. Natl. Acad. Sci. USA, vol. 106, No. 23, pp. 9403-9408 (Jun. 9, 2009).
Dong, C., et al., "Immune Regulation by Novel Costimulatory Molecules," Immunolog. Res., vol. 28, No. 1, pp. 39-48 (2003).
Duncan, A.R. and Winter, G., "The binding site for CIq on IgG," Nature, vol. 332, pp. 738-740 (Apr. 1988).
Duncan, A.R., et al., "Localization of the binding site for the human high-affinity Fc receptor on IgG," Nature, vol. 332, pp. 563-564 (Apr. 1988).
Durand, C.M., et al., "Developing strategies for HIV-1 eradication," Trends Immunol., vol. 33, No. 11, pp. 554-562, Author Manuscript—18 pages (Nov. 2012).
Duval, M., et al., "A Bispecific Antibody Composed of a Non-neutralizing Antibody to the gp41 Immunodominant Region and an Anti-CD89 Antibody Directs Broad Human Immunodeficiency Virus Destruction by Neutrophils," J. Virol., vol. 82, No. 9, pp. 4671-4674 (May 2008).

(56) References Cited

OTHER PUBLICATIONS

Edberg, J.C. and Kimberly, R.P., "Modulation of Fcgamma and Complement Receptor Function by the Glycosyl-Phosphatidylinositol-Anchored Form of FcgammaRIII," Journal of Immunology, vol. 152, pp. 5826-5835 (1994).
Edmonds, T.G., et al., "Replication competent molecular clones of HIV-1 expressing Renilla luciferase facilitate the analysis of antibody inhibition in PBMC," Virology, vol. 408, No. 1, pp. 1-13, Author Manuscript—31 pages (Dec. 5, 2010).
Elkabetz, Y., et al., "Cysteines in CH1 Underlie Retention of Unassembled Ig Heavy Chains," J. Biol. Chem., vol. 280, No. 15, pp. 14402-14412, 12 total pages (Apr. 15, 2005).
Extended European Search Report issued in European Patent Application No. 08771050.5 mailed Nov. 2, 2010 (13 total pages).
Fang, C.-Y., et al., "Construction and Characterization of Monoclonal Antibodies Specific to Epstein-Barr Virus Latent Membrane Protein 1," J. Immunol. Methods, vol. 287, pp. 21-30 (Jan. 2004).
Fernandez-Rodriguez, J., et al., "Induced Heterodimerization and Purification of Two Target Proteins by A Synthetic Coiled-Coil Tag," Protein Sci., vol. 21, pp. 511-519 (Jan. 2012).
Ferrari, G., et al., "An HIV-1 gp120 Envelope Human Monoclonal Antibody That Recognizes a C1 Conformational Epitope Mediates Potent Antibody-Dependent Cellular Cytotoxicity (ADCC) Activity and Defines a Common ADCC Epitope in Human HIV-1 Serum," J. Virol., vol. 85, No. 14, pp. 7029-7036 (Jul. 2011).
Finnegan, C.M., et al., "Antigenic properties of the human immunodeficiency virus envelope during cell-cell fusion," J Virol., vol. 75, No. 22, pp. 11096-11105 (Nov. 2001).
Finzi, D., et al., "Identification of a reservoir for HIV-1 in patients on highly active antiretroviral therapy," Science, vol. 278, pp. 1295-1300, 7 total pages (Nov. 14, 1997).
Fitzgerald, K., et al., "Improved tumour targeting by disulphide stabilized diabodies expressed in Pichia pastoris," Protein Engineering, vol. 10, No. 10, pp. 1221-1225 (1997).
Flesch, B.K. and Neppert, J., "Functions of the Fc receptors for immunoglobulin G," J. Clin. Lab. Anal., vol. 14, pp. 141-156 (Feb. 2000).
Froude, J.W. et al., "Antibodies for Biodefense," mAbs, vol. 3. No. 6, pp. 517-527 (Nov./Dec. 2011).
Fruehling, S. et al., "Identification of Latent Membrane Protein 2A (LMP2A) Domains Essential for the LMP2A Dominant-Negative Effect On B-Lymphocyte Surface Immunoglobulin Signal Transduction," J. Virol., vol. 70, No. 9, pp. 6216-6226 (Sep. 1996).
Fruehling, S., et al., "Tyrosine 112 Of Latent Membrane Protein 2A Is Essential for Protein Tyrosine Kinase Loading and Regulation of Epstein-Barr Virus Latency," J. Virol., vol. 72, No. 10., pp. 7796-7806 (Oct. 1998).
Galun, E., et al., "Clinical Evaluation (Phase I) of a Combination of Two Human Monoclonal Antibodies to HBV: Safety and Antiviral Properties," Hepatology, vol. 35, pp. 673-679 (2002).
Gandhi, R.T., et al., "No Evidence for Decay of the Latent Reservoir in HIV-1-Infected Patients Receiving Intensive Enfuvirtide-Containing Antiretroviral Therapy," J. Infect. Dis., vol. 201, No. 2, pp. 293-296, Author Manuscript—8 pages (Jan. 15, 2010).
Ganesan, A., "Solid-Phase Synthesis in The Twenty-First Century," Mini Rev. Med. Chem. vol. 6, No. 1, pp. 3-10 (2006).
Gao, Y., et al., "Efficient Inhibition of Multidrug-Resistant Human Tumors with a Recombinant Bispecific Anti-P-Glycoprotein X Anti-CD3 Diabody," Leukemia, vol. 18, pp. 513-520 (2004).
Garber, K., "Bispecific anitbodies rise again," Nature Reviews—Drug Discovery, vol. 13, pp. 799-801 (Nov. 2014).
Geevarghese, B. and Simoes, E.A.F., "Antibodies for Prevention and Treatment of Respiratory Syncytial Virus Infections in Children," Antivir. Ther., vol. 17(1 Pt B), pp. 201-211 (2012).
Genbank accession No. AFQ31502.1, "anti-HIV gp41 antibody 7B2 immunoglobulin heavy heavy chain variable region, partial [*Homo sapiens*]," 2 total pages (Sep. 11, 2012).
Genbank accession No. AFQ31503.1, "anti-HIV gp41 antibody 7B2 immunoglobulin kappa light chain variable region, partial [*Homo sapiens*]," 3 total pages (Sep. 11, 2012).
Gergeley, J et al., "Fc receptors on lymphocytes and K cells," Biochemical Society Transactions, vol. 12, pp. 739-743, 6 total pages (1984).
Gergely, J. and Sarmay, G., "The two binding-site models of human IgG Binding Fcgamma receptors," Faseb J., vol. 4, pp. 3275-3283 (Dec. 1990).
Ghosh, T.S., "End-To-End and End-To-Middle Interhelical Interactions: New Classes of Interacting Helix Pairs in Protein Structures," Acta Cryst., vol. D65, pp. 1032-1041 (Jul. 2009).
Giorgi, J.V., et al., "Elevated levels of CD38+ CD8+ T cells in HIV infection add to the prognostic value of low CD4+ T cell levels: results of 6 years of follow-up," Journal of Acquired Immune Deficiency Syndromes, vol. 6, No. 8, pp. 904-912 (1993).
Gorman, S. D et al., "Reshaping A Therapeutic CD4 Antibody," Proc. Natl. Acad. Sci. (U.S.A.), vol. 88, pp. 4181-4185 (May 1991).
Greenwood, J. and Clark, M., "Effector functions of matched sets of recombinant human IgG subclass antibodies," Cambridge University Department of Pathology—Immunology Division, pp. 1-23, 24 totatl pages (Feb. 11, 1993).
Greenwood, J. et al., "Structural motifs involved in human IgG antibody effector functions," Eur. J. Immunol., vol. 23, pp. 1098-1104 (1993).
Greenwood, J., et al., "Engineering multiple-domain forms of the therapeutic antibody CAMPATH-1H: effects on complement lysis," Therapeutic Immunology, vol. 1, pp. 247-255 (1994).
Grigoryan, G., et al., "Structural Specificity in Coiled-Coil Interactions," Curr. Opin. Struc. Biol., vol. 18, pp. 477-483 (Jun. 2008).
Groux, H., et al., Activation-induced death by apoptosis in CD4+ T cells from human immunodeficiency virus-infected asymptomatic individuals. J. Exp. Med., vol. 175, pp. 331-340 (Feb. 1992).
Gruber, M., et al., "Efficient Tumor Cell Lysis Mediated by A Bispecific Single Chain Antibody Expressed in *Escherichia coli*," J. Immunol., vol. 152, pp. 5368-5374 (Mar. 1994).
Guan, Y., et al., "Diverse specificity and effector function among human antibodies to HIV-1 envelope glycoprotein epitopes exposed by CD4 binding," PNAS, vol. 110, pp. E69-E78 (Dec. 13, 2012).
Guo, J., et al., "[New Type Recombinant Antibody Fragment scFv Multimer and Cancer Targeting]," Sheng Wu Yi Xue Gong Cheng Xue Za Zhi, vol. 20, No. 2, pp. 361-365, Article in Chinese: English Abstract Only—1 page total (2003).
Guo, N., et al., "The Development of New Formats of Engineered Bispecific Antibodies," Trends in Immunology Research, Chp. 3, pp. 33-54 (2005).
Gustchina, E., et al., "Affinity Maturation By Targeted Diversification Of The CDR-H2 Loop Of A Monoclonal Fab Derived From A Synthetic Naive Human Antibody Library And Directed Against The Internal Trimeric Coiled-Coil Of Gp41 Yields A Set Of Fabs With Improved HIV-1 Neutralization Potency And Breadth," Virology, vol. 393, pp. 112-119 (2009).
Hadley, A.G., et al., "The functional activity of FcgammaRII and FcgammaRIII on subsets of human lymphocytes," Immunology, vol. 76, No. 3, pp. 446-451, 7 total pages (Jul. 1992).
Hansel, T.T., et al., "The Safety and Side Effects of Monoclonal Antibodies," Nat. Rev. Drug Discov., vol. 9, pp. 325-338 (Apr. 2010).
Harris, A., et al., "Trimeric HIV-1 Glycoprotein gp140 Immunogens and Native HIV-1 Envelope Glycoproteins Display the Same Closed and Open Quaternary Molecular Architectures," Proc. Natl. Acad. Sci. (U.S.A.), vol. 108, No. 28, pp. 11440-11445 (Jul. 12, 2011).
Hatta, Y. et al., "Association of Fcgamma receptor IIIB, but not of Fcgamma receptor IIA and IIIA, polymorphisms with systemic lupus erythematosus in Japanese," Genes and Immunity, vol. 1, No. 1, pp. 53-60, 9 total pages (Sep. 1999).
Hayes, R., "Fc Engineering to Enhance Monoclonal Antibody Effector Functions," Presentation: Xencor: Monrovia, California, pp. 1-6 (Jul. 8, 2003).
Heijtink, R.A., et al., "Administration of A Human Monoclonal Antibody (TUVIRUMAB) To Chronic Hepatitis B Patients Pre-Treated with Lamivudine: Monitoring of Serum TUVIRUMAB in Immune Complexes," J. Med. Virol., vol. 64, pp. 427-434 (2001).
Herzenberg, L.A., et al., "The history and future of the fluorescence activated cell sorter and flow cytometry: a view from Stanford," Clinical Chem., vol. 48, No. 10, pp. 1819-1827 (Jul. 2002).

(56) References Cited

OTHER PUBLICATIONS

Heyman, B., "Regulation of antibody responses via antibodies, complement, and Fc receptors," Annu Rev Immunol, vol. 18, pp. 709-737, 16 total pages (2000).
Ho, Y.-C., et al., "Replication-Competent Noninduced Proviruses in the Latent Reservoir Increase Barrier to HIV-1 Cure," Cell, vol. 155, pp. 540-551 (Oct. 24, 2013).
Hogarth, P.M., et al., "Characterization of FcR Ig-binding sites and epitope mapping," Immunomethods, vol. 4, No. 1, pp. 17-24, 9 total pages (Mar. 21, 1994).
Holler, P.D., et al., "In vitro evolution of a T cell receptor with high affinity for peptide-MHC," Proc. Natl. Acad. Sci. U.S.A., vol. 97, No. 10, pp. 5387-5392 (May 9, 2000).
Holliger, P. and Hudson, P.J., "Engineered antibody fragments and the rise of single domains," Nature Biotechnology, vol. 23, No. 9, pp. 1126-1135 (Sep. 2005).
Holliger, P., et al., "Diabodies': Small Bivalent and Bispecific Antibody Fragments," Proc. Natl. Acad. Sci. (U.S.A.), vol. 90, pp. 6444-6448 (Jul. 1993).
Holliger, P., et al., "Carcinoembryonic Antigen (CEA)-Specific T-Cell Activation in Colon Carcinoma Induced By Anti-CD3 x Anti-CEA Bispecific Diabodies and B7 x Anti-CEA Bispecific Fusion Proteins," Cancer Res., vol. 59, pp. 2909-2916, 9 total pages (Jun. 15, 1999).
Holliger, P., et al., "Specific Killing of Lymphoma Cells By Cytotoxic T-Cells Mediated By A Bispecific Diabody," Protein Eng., vol. 9, No. 3, pp. 299-305 (1996).
Houghten, R.A., "General Method for the Rapid Solid-Phase Synthesis of Large Numbers of Peptides: Specificity of Antigen-Antibody Interaction at the Level of Individual Amino Acids," Proc. Natl. Acad. Sci. (U.S.A.), vol. 82, pp. 5131-5135 (Aug. 1985).
Howell, A.L., et al., "Targeting HIV-1 to FcgammaR on human phagocytes via bispecific antibodies reduces infectivity of HIV-1 to T cells," J. Leukoc. Biol., vol. 55, pp. 385-391 (Mar. 1994).
Huang, J.X., et al., "Development of Anti-Infectives Using Phage Display: Biological Agents Against Bacteria, Viruses, And Parasites," Antimicrob. Agents Chemother., vol. 56, No. 9, pp. 4569-4582 (Sep. 2012).
Huber, M., et al., "Antibodies for HIV Treatment and Prevention: Window of Opportunity?," Curr. Top. Microbiol. Immunol., vol. 317, p. 39-66 (2008).
Hudson, p. J., et al., "High avidity scFv multimers; diabodies and triabodies," J. Immunol. Methods, vol. 231, pp. 177-189 (1999).
Hulett, M.D., et al., "Chimeric Fc receptors identify functional domains of the murine high affinity receptor for IgG," J. Immunol., vol. 147, No. 6, pp. 1863-1868, 7 total pages (Sep. 15, 1991).
Hulett, M.D., et al., "Identification of the IgG binding site of the human low affinity receptor for IgG FcgammaRII—Enhancement and ablation of binding by site-directed mutagenesis," J. Biol. Chem., vol. 269, No. 21, pp. 15287-15293 (1994).
Hulett, M.D., et al., "Multiple regions of human FcgammaRII (CD32) contribute to the binding of IgG," J. Biol. Chem., vol. 270, No. 36, pp. 21188-21194 (1995).
Ian, G. A.O., "Role of Passive Immunotherapies in Managing Infectious Outbreaks," Biologicals, vol. 40, No. 3, pp. 196-199 (Jan. 12, 2012).
Idusogie, E.E., et al., "Engineered antibodies with increased activity to recruit complement," J. Immunol., vol. 166, pp. 2571-2575 (2001).
Idusogie, E.E., et al., "Mapping of the C1q binding site on rituxan, a chimeric antibody with a human IgG1 Fc," J. Immunol., vol. 164, pp. 4178-4184 (Feb. 10, 2000).
International Search Report and Written Opinion issued Jul. 30, 2014 by United States Patent and Trademark Office in PCT/US2014/025491 (20 pages).
Isaacs, J.D., et al., "A therapeutic human IgG4 monoclonal antibody that depletes target cells in humans," Clin. Exp. Immunol. vol. 106, pp. 427-433 (Aug. 22, 1996).
Isaacs, J.D., et al., "Therapy with monoclonal antibodies—An in vivo model for the assessment of therapeutic potential," J. Immunol., vol. 148, pp. 3062-3071 (May 15, 1992).
Isaacs, J.D., et al., "Therapy with monoclonal antibodies. II. The contribution of Fcgamma receptor binding and the influence of $C_H1$ and $C_H3$ domains on in vivo effector function," J. Immunol., vol. 161, pp. 3862-3869 (1998).
Jassal, R., et al., "Remodelling glycans on IgG by genetic re-engineering," Biochem. Soc. Trans., vol. 26, pp. S113, 2 total pages (1998)—abstract from 663rd Meeting Galway held Sep. 3-5, 1997 at University of Galway.
Jefferis, R. and Lund, J., "Interaction sites on human IgG-Fc for FcgammaR: current models," Immunology Letters, vol. 82, pp. 57-65 (2002).
Jefferis, R., et al., "IgG-Fc-mediated effector functions: molecular definition of interaction sites for effector ligands and the role of glycosylation," Immunol. Rev., vol. 163, pp. 59-76, 19 total pages (Jun. 1998).
Jefferis, R., et al., "Molecular definition of interaction sites on human IgG for Fc receptors (huFcgammaR)," Mol. Immunol., vol. 27, No., 12, pp. 1237-1240, 5 total pages (Dec. 1990).
Jefferis, R., et al., "Recognition sites on human IgG for Fcgamma receptors: the role of glycosylation," Immunol. Lett., vol. 44, pp. 111-117 (1995).
Jendeberg, L. et al., "Engineering of Fc(1) and Fc(3) from human immunoglobulin G to analyse subclass specificity for staphylococcal protein A," J. Immunological Methods, vol. 201, pp. 25-34 (1997).
Johnson, S., et al. "Development of a Humanized Monoclonal Antibody (MEDI-493) with Potent In Vitro and In Vivo Activity against Respiratory Syncytial Virus." J. Infect. Dis., vol. 176, pp. 1215-1224 (Nov. 1997).
Johnson, S., et al., "Cooperativity of HIV-Specific Cytolytic CD4 T Cells and CD8 T Cells in Control of HIV Viremia," J. Virol., vol. 89, No. 15, pp. 7494-7505 (Aug. 2015).
Johnson, S., et al., "Effector Cell Recruitment with Novel Fv-based Dual-affinity Re-targeting Protein Leads to Potent Tumor Cytolysis and in Vivo B-cell Depletion," J. Mol. Biol., vol. 399, pp. 436-449 (Apr. 9, 2010).
Kadar, J., et al., "Modulatory effect of synthetic human IgG Fc peptides on the in vitro immune response of murine spleen cells," Int. J. Immunpharmacol. vol. 13, No. 8, pp. 1147-1155, 10 total pages (Dec. 20, 1991).
Kadar, J., et al., "Synthetic peptides comprising defined sequences of CH-2 and CH-3 domains of human IgG(1) induce prostaglandin E(2) production from human peripheral blood mononuclear cells," Immunol. Lett., vol. 32, No. 1, pp. 59-63, 6 total pages (Mar. 1992).
Kato, K., et al., "Structural basis of the interaction between IgG and Fcγ receptors," J. Mol. Biol., vol. 295, No. 2, pp. 213-224, 13 total pages (Jan. 14, 2000).
Keler, T., et al., "Differential effect of cytokine treatment on Fcalpha receptor I- and Fcgamma receptor I-mediated tumor cytotoxicity by monocyte-derived macrophages," J. of Immunol., vol. 164, pp. 5746-5752 (Mar. 16, 2000).
Kettleborough, C. A., et al., "Humanization of a Mouse Monoclonal Antibody by CDR-Grafting: The Importance of Framework Residues on Loop Conformation," Protein Engineering, vol. 4, No. 7, pp. 773-783 (1991).
Khawli, L.A., et al., "Cytokine, Chemokine, and Co-Stimulatory Fusion Proteins for the Immunotherapy of Solid Tumors," Exper. Pharmacol., vol. 181, pp. 291-328 (2008).
Kieke, M.C., et al., "Selection of functional T cell receptor mutants from a yeast surface-display library," Proc. Natl. Acad. Sci. U.S.A., vol. 96, pp. 5651-5656 (May 1999).
Kiick, K.L., et al., "Identification of an Expanded Set of Translationally Active Methionine Analogues in *Escherichia coli*," FEBS Lett., vol. 502, pp. 25-30 (Jul. 9, 2001).
Kim, T.D., et al., "Analysis of FcyRIII and IgG Fc polymorphism reveals functional and evolutionary implications of protein-protein interaction," J. Mol. Evol., vol. 53, No. 1, pp. 1-9 (Jul. 2001).
Klein, M. et al., "Expression of biological effector functions by immunoglobulin G molecules lacking the hinge region," Proc. Natl. Acad. Sci. U.S.A., vol. 78, No. 1, pp. 524-528 (Jan. 1981).

(56) References Cited

OTHER PUBLICATIONS

Ko, S.-Y., et al., "Enhanced neonatal Fc receptor function improves protection against primate SHIV infection," Nature, vol. 514, No. 7524, pp. 642-645, Author Manuscript—22 pages (Oct. 30, 2014).
Koene, H.R., et al., "FcgammaRIIIa-158V-F polymorphism influences the binding of IgG by natural killer cell FcgammaRIIIa, independently of the FcgammaRIIIa-48L/R/H phenotype," Blood, vol. 90, No. 3, pp. 1109-1114 (Aug. 1, 1997).
Koenig, S., "Harnessing Effector and Regulatory Pathways for Immunotherapy," presented at the Strategies for an HIV Cure Meeting, Rockville MD, 21 total pages (Oct. 1, 2014).
Kohler, G. and Milstein, C., "Continuous Cultures of Fused Cells Secreting Antibody of Predefined Specificity," Nature, vol. 256, pp. 495-497 (August 7, 9175).
Kontermann, R.E., "Recombinant Bispecific Antibodies for Cancer Therapy," Acta. Pharmacol. Sin., vol. 26, No. 1, pp. 1-9 (Jan. 2005).
Kontermann, R.E., et al., "Complement recruitment using bispecific diabodies," Nature Biotechnology, vol. 15, pp. 629-631 (Jul. 1997).
Kontermann, Roland E., "Dual targeting strategies with bispecific antibodies," Landes Bioscience—mAbs, vol. 4, No. 2, pp. 182-197 (Mar./Apr. 2012).
Korman, A.J., et al., "Checkpoint Blockade in Cancer Immunotherapy," Adv. Immunol., vol. 90, pp. 297-339, Author Manuscript—32 pages (2006).
Kortt, A.A., et al., "Dimeric and Trimeric Antibodies: High Avidity scFvs for Cancer Targeting," Biomol. Eng., vol. 18, pp. 95-108 (2001).
Kostelny, S.A., et al., "Formation of a bispecific antibody by the use of leucine zippers," J. Immunol., vol. 148, No. 5, pp. 1547-1553, 8 pages in total (Mar. 1, 1992).
Kranz, D.M. and Voss, E.W., Jr., "Partial elucidation of an anti-hapten repertoire in BALB/c mice: comparative characterization of several monoclonal anti-fluorescyl antibodies," Mol. Immunol., vol. 18, No. 10, pp. 889-898 (Mar. 1981).
Kranz, D.M., et al., "Mechanisms of ligand binding by monoclonal anti-fluorescyl antibodies," J. Biol. Chem., vol. 257, No. 12, pp. 6987-6995 (Jun. 25, 1982).
Kumpel, B.M., et al., "Human monoclonal anti-D antibodies," British J. Haematol., vol. 71, pp. 415-420 (1989).
Kuo, T. T. and Aveson, V. G., "Neonatal Fc receptor and IgG-based therapeutics," mAbs, vol. 3, Issue 5, pp. 422-430 (Sep./Oct. 2011).
Lagrange, M., et al., "Binding of Human Papillomavirus 16 E6 to P53 and E6AP Is Impaired by Monoclonal Antibodies Directed Against the Second Zinc-Binding Domain of E6," J. Gen. Virol., vol. 86, pp. 1001-1007 (2005).
Le Gall, F., et al., "Effect of Linker Sequences Between the Antibody Variable Domains On the Formation, Stability and Biological Activity of a Bispecific Tandem Diabody," Protein Eng des Sel., vol. 17, No. 4, pp. 357-366 (2004).
Le, P.U., et al., "*Escherichia coli* Expression and Refolding of E/K-Coil-Tagged EGF Generates Fully bioactive EGF for Diverse Applications," Protein Expression and Purification, vol. 64, pp. 108-117 (2009).
Lehmann, A.K., et al., "Phagocytosis: measurement by flow cytometry," J Immunol Methods., vol. 243, pp. 229-242, 15 total pages (2000).
Lehrnbecher, et al., "Variant genotypes of the low-affinity Fcgamma receptors in two control populations and a review of low-affinity Fcgamma receptor polymorphisms in control and disease populations," Blood, vol. 94, No. 12, pp. 4220-4232 (Dec. 15, 1999).
Li, L., et al., "Immunotherapy for Prion Diseases: Opportunities and Obstacles," Immunotherapy, vol. 2, No. 2, pp. 269-282 (2010).
Li, M., et al., "Reconstitution of human FcgammaRIII cell type specificity in transgenic mice," J. Exp. Med. Vol. 183, pp. 1259-1263 (Mar. 1996).
Liao, H.-X., et al., "A group M consensus envelope glycoprotein induces antibodies that neutralize subsets of subtype B and C HIV-1 primary viruses," Virology, vol. 353, pp. 268-282 (2006).
Linsley, P.S. and Nadler, S.G., "The Clinical Utility of Inhibiting CD28-Mediated Costimulation," Immunol. Rev., vol. 229, pp. 307-321 (2009).
Litowski, J.R. and Hodges, R.S., "Designing Heterodimeric Two-Stranded α-Helical Coiled-Coils: Effects of Hydrophobicity and α-Helical Propensity On Protein Folding, Stability, And Specificity," J. Biol. Chem., vol. 277, pp. 37272-37279 (2002).
Liu, A.Y., et al., "Production of a mouse-human chimeric monoclonal antibody to CD20 with potent Fc-dependent biologic activity," J. Immunol., vol. 139, pp. 3521-3526 (Nov. 15, 1987).
LoBuglio, A.F., et al. "Mouse/Human Chimeric Monoclonal Antibody in Man: Kinetics and Immune Response," Proc. Natl. Acad. Sci. (U.S.A.), vol. 86, pp. 4220-4224 (Jun. 1989).
Lonberg, N., et al., "Human Antibodies from Transgenic Mice," Int. Rev. Immunol, vol. 13, pp. 65-93 (1995).
Lu, D., et al., "A Fully Human Recombinant IgG-like Bispecific Antibody to Both the Epidermal Growth Factor Receptor and the Insulin-like Growth Factor Receptor for Enhanced Antitumor Activity," The Journal of Biological Chemistry, vol. 280, No. 20, pp. 19665-19672 (2006).
Lu, D., et al., "Di-Diabody: A Novel Tetravalent Bispecific Antibody Molecule by Design," J. Immunol. Meth., vol. 279, pp. 219-232 (2003).
Lu, D., et al., "The Effect of Variable Domain Orientation and Arrangement On the Antigen-Binding Activity of a Recombinant Human Bispecific Diabody," Biochem. And Biophys. Res. Comm., vol. 318, pp. 507-513 (2004).
Lum, L.G., et al., "Targeting Cytomegalovirus-Infected Cells Using T Cells Armed with Anti-CD3 Anti-CMV Bispecific Antibody," American Society for Blood and Marrow Transplantation—Biology, vol. 18, pp. 1012-1022 (2012).
Lund, J., et al., "Expression and characterization of truncated forms of humanized L243 IgG1—Architectural features can influence synthesis of its oligosaccharide chains and affect superoxide production triggered through human Fcgamma receptor I," Eur. J. Biochem., vol. 267, pp. 7246-7257 (2000).
Lund, J., et al., "Human FcgammaRI and FcgammaRII interact with distinct but overlapping sites on human IgG," J. Immunol., vol. 147, No. 8, pp. 2657-2662 (Oct. 15, 1991).
Lund, J., et al., "Multiple binding sites on the $C_H2$ domain of IgG for mouse FcgammaR11," Molecular Immunology, vol. 29, No. 1, pp. 53-59 (1992).
Lund, J., et al., "Multiple interactions of IgG with its core oligosaccharide can modulate recognition by complement and human Fcgamma receptor I and influence the synthesis of its oligosaccharide chains," J. Immunol., vol. 157, pp. 4963-4969, (1996).
Lund, J., et al., "Oligosaccharide-protein interactions in IgG can modulate recognition by Fcgamma receptors," FASEB J., vol. 9, pp. 115-119 (1995).
Luo, D., et al., "VL-Linker-VH Orientation-Dependent Expression of Single Chain Fv Containing an Engineered Disulfide-Stabilized Bond in The Framework Regions," J. Biochem., vol. 118, pp. 825-831 (1995).
Maeda, H., et al., "Construction of Reshaped Human Antibodies with HIV-Neutralizing Activity," Human Antibodies Hybridoma, vol. 2, pp. 124-134 (Jul. 1991).
Maenaka, K., et al., "The human low affinity Fcgamma receptors IIa, IIb, and III bind IgG with fast kinetics and distinct thermodynamic properties," J. Biol. Chem., vol. 276, No. 48, pp. 44898-904 (Sep. 2001).
Mahato, R.I., et al., "Cationic Lipid-Based Gene Delivery Systems: Pharmaceutical Perspectives," Pharm. Res., vol. 14, pp. 853-859 (Apr. 1997).
Mangham, D.C., et al., "A Novel Immunohistochemical Detection System Using Mirror Image Complementary Antibodies (MICA)," Histopathology, vol. 35, pp. 129-133 (Jan. 1999).
Mariuzza, R.A., et al., "The Structural Basis of Antigen-Antibody Recognition," Annual Review of Biophysics and Biophysical Chemistry, vol. 16, pp. 139-159 (1987).
Marvin, U.S. and Zhu, Z., "Recombinant approaches to IgG-like bispecific antibodies," Acta Pharmacologica Sinica, vol. 26, No. 6, 649-658 (Jun. 2005).
Masiero, S., "T-cell engineering by a chimeric T-cell receptor with antibody-type specificity for the HIV-1 gp120," Gene Therapy, vol. 12, pp. 299-310 (2005).

(56) References Cited

OTHER PUBLICATIONS

Merrifield, B., "Solid Phase Synthesis," Science, vol. 232, No. 4748, pp. 341-347, 8 total pages (Apr. 18, 1986).
Mertens, N., et al., "New Recombinant Bi- And Trispecific Antibody Derivatives," Novel Frontiers In The Production Of Compounds For Biomedical Use, vol. 1, van Broekhoven, A., et al. (Eds.); Kluwer Academic Publishers, Dordrecht, The Netherlands, pp. 195-208 (2001).
Michaelsen, T.E., et al., "One disulfide bond in front of the second heavy chain constant region is necessary and sufficient for effector functions of human IgG3 without a genetic hinge," Proc. Natl. Acad. Sci. USA, vol. 91, pp. 9243-9247 (Sep. 1994).
Moldt, B., et al., "A nonfucosylated variant of the anti-HIV-1 monoclonal antibody b12 has enhanced FcγRIIIa-mediated antiviral activity in vitro but does not improve protection against mucosal SHIV challenge in macaques," Journal of Virology, vol. 86, No. 11, pp. 66189-6196 (Jun. 2012).
Montgomery, D. L., et al., "Affinity Maturation and Characterization of a Human Monoclonal Antibody Against HIV-1 gp41," mAbs, vol. 1, No. 5, pp. 462-474 (Oct. 2009).
Moore, J. P., et al., "Exploration of Antigenic Variation in gp120 from Clades A through F of Human Immunodeficiency Virus Type 1 by Using Monoclonal Antibodies," Journal of Virology, vol. 68, No. 12, pp. 8350-8364 (Dec. 1994).
Moore, J.P., et al., "Immunochemical Analysis of the gp120 Surface Glycoprotein of Human Immunodeficiency Virus Type 1: Probing the Structure of the C4 and V 4 Domains and the Interaction of the C4 Domain with the V3 Loop," Journal of Virology, vol. 67, No. 8, pp. 4785-4796 (Aug. 1993).
Moore, P. L., et al., "Nature of Nonfunctional Envelope Proteins on the Surface of Human Immunodeficiency Virus Type 1," Journal of Virology, vol. 80, No. 5, pp. 2515-2528 (Mar. 2006).
Moore, P.A., et al., "Application of Dual Affinity Retargeting Molecules to Achieve Optimal Redirected T-Cell Killing of B-Cell Lymphoma," Blood, vol. 117, pp. 4542-4551, 11 total pages (Apr. 28, 2011).
Morgan,A., et al., "The N-terminal end of the $C_H2$ domain of chimeric human IgG1 anti-HLA-DR is necessary for C1q, FcgammaRI and FcgammaRIII binding," Immunology, vol. 86, pp. 319-324 (1995).
Morrison, S.L., et al., "Structural determinants of IgG structure," Immunologist, vol. 2, No. 4, pp. 119-124 (Jul./Aug. 1994).
Mouquet, H., "Complex-type N-glycan recognition by potent broadly neutralizing HIV antibodies," PNAS, vol. 109:, pp. E3268-E3277 (Oct. 30, 2012).
Munn, D.H. and Cheung, N.-K., "Phagocytosis of tumor cells by human monocytes cultured in recombinant macrophage colony-stimulating factor," J. Exp. Med., vol. 172, 231-237 (Jul. 1990).
Munro, S., et al., "Use of Peptide Tagging to Detect Proteins Expressed from Cloned Genes: Deletion Mapping Functional Domains of Drosophila hsp 70," EMBO J., vol. 3, No. 13, pp. 3087-3093 (1984).
Nagarajan, S., et al., "Ligand Binding and Phagocytosis by CD16 (Fc gamma Receptor III) Isoforms—Phagocytic signaling by associated zeta and gamma subunits in Chinese hamster ovary cells," J. Biol. Chem., vol. 270, No. 43, pp. 25762-25770 (Oct. 27, 1995).
Nagorsen, D. and Baeuerle, P.A., "Immunomodulatory therapy of cancer with T cell-engaging BiTE antibody blinatumomab," Experimental Cell Research, vol. 317, pp. 1255-1260 (Mar. 2011).
Nakamura, T., et al., "Heterogeneity of Immunoglobulin-Associated Molecules On Human B Cells Identified by Monoclonal Antibodies," Proc. Natl. Acad. Sci. (USA), vol. 89, pp. 8522-8526 (Sep. 1992).
Neuberger, M.S., et al., "Recombinant antibodies possessing novel effector functions," Nature, vol. 312, pp. 604-608 (Dec. 1984).
Norderhaug, L., et al., "Chimeric mouse human IgG3 antibodies with an IgG4-like hinge region induce complement-mediated lysis more efficiently than IgG3 with normal hinge," Eur. J. Immunol., vol. 21, pp. 2379-2384 (1991).
Nose, M. and Leanderson, T., "Substitution of asparagine324 with aspartic acid in the Fc portion of mouse antibodies reduces their capacity for C1q binding," Eur. J. Immunol. vol. 19, pp. 2179-2181 (1989).
Nossal, G.J.V., "Vaccines of The Future," Vaccine, vol. 29S, pp. D111-115 (Dec. 18, 2011).
Oganesyan, V., et al. "Structural characterization of a human Fc fragment engineered for extended serum half-life," Molecular Immunology, vol. 46, pp. 1175-1755 (Feb. 2009).
Okazaki, A., et al., "Fucose depletion from human IgG1 oligosaccharide enhances binding enthalpy and association rate between IgG1 and FcgammaRIIIa," J. Mol. Biol., vol. 336, pp. 1239-1249 (2004).
Olafsen, T., et al., "Covalent disulfide-linked anti-CEA Diabody allows site-specific conjugation and radiolabeling for tumor targeting applications," Protein Engineering, Design & Selection, vol. 17, No. 1, pp. 21-27 (2004).
Oleksiewicz, M.B., et al., "Anti-Bacterial Monoclonal Antibodies: Back to The Future?," Arch. Biochem. Biophys., vol. 526, pp. 124-131 (Jun. 13, 2012).
Orfao, A. and Ruiz-Arguelles, A., "General concepts about cell sorting techniques," Clinical Biochem., vol. 29, pp. 5-9, 6 total pages (Feb. 1996).
Pack, P. and Pluckthun, A., "Miniantibodies: Use of Amphipathic Helices to Produce Functional, Flexibly Linked Dimeric Fv Fragments with High Avidity in *Escherichia coli*," vol. 31, No. 6, pp. 1579-1584 (Feb. 18, 1992).
Palmer, S., et al., "Low-level viremia persists for at least 7 years in patients on suppressive antiretroviral therapy," Proceedings of the National Academy of Sciences USA, vol. 105, No. 10, pp. 3879-3884 (Mar. 11, 2008).
Palmer, S., et al., "New Real-Time Reverse Transcriptase-Initiated PCR Assay with SingleCopy Sensitivity for Human Immunodeficiency Virus Type 1 RNA in Plasma," Journal of Clinical Microbiology vol. 41, No. 10, pp. 4531-4536 (Oct. 2003).
Partridge, L.J., et al., "The use of anti-IgG monoclonal antibodies in mapping the monocyte receptor site on IgG," Mol. Immunol., vol. 23, No. 12, pp. 1365-1372 (Dec. 1986).
Peeters, K., et al., "Production of Antibodies and Antibody Fragments in Plants," Vaccine, vol. 19, 2756-2761 (2001).
Perfetto, S. P., et al., "CD38 Expression on Cryopreserved CD8+ T Cells Predicts HIV Disease Progression" Cytometry, vol. 33, No. 2, pp. 133-137 (Oct. 1, 1998).
Perussia, B. and Loza, M.J., "Human Natural Killer Cell Protocols—Cellular and Molecular Methods" in Methods Molecular Biology, vol. 121, Chapter 16, pp. 179-192, (Campbell, K.S. and Colonna, M.,eds.), Humana Press Inc., Totowa, NJ (2000).
Phaeton, R., et al., "Radioimmunotherapy with an Antibody to The HPV16 E6 Oncoprotein Is Effective in an Experimental Cervical Tumor Expressing Low Levels of E6," Cancer Biol. Ther., vol. 10, No. 10, pp. 1041-1047, 8 total pages (Nov. 15, 2010).
Pierson, T. C., et al., "Molecular Characterization of Preintegration Latency in Human Immunodeficiency Virus Type 1 Infection," Journal of Virology, vol. 76, No. 17, pp. 8518-8531 (Sep. 2002).
Pincus, S. H., "Mini Review: Therapeutic potential of anti-HIV immunotoxins," Antiviral Research, vol. 33, pp. 1-9 (Jul. 1996).
Pincus, S.H., et al., "In Vivo Efficacy of Anti-Glycoprotein 41, But Not Anti-Glycoprotein 120, Immunotoxins in a Mouse Model of HIV Infection," J. Immunol., vol. 170, pp. 2236-2241 (2003).
Pollara, J., et al., "Epitope Specificity of Human Immunodeficiency Virus-1 Antibody Dependent Cellular Cytotoxicity [ADCC] Responses," Current HIV Research, vol. 11, No. 5, pp. 378-387 (Jul. 2013).
Pollara, J., et al., "High-Throughput Quantitative Analysis of HIV-1 and SIV-Specific ADCC-Mediating Antibody Responses," Cytometry Part A, vol. 79A, Issue 8, pp. 603-612 (Aug. 2011).
Pollara, J., et al., "HIV-1 Vaccine-Induced C1 and V2 Env-Specific Antibodies Synergize for Increased Antiviral Activities," Journal of Virology, vol. 88, Issue 14, pp. 7715-7726 (Jul. 2014).
Pollock, D.P., et al., "Transgenic Milk as A Method for The Production of Recombinant Antibodies," J. Immunol. Methods, vol. 231, pp. 147-157 (1999).

(56) References Cited

OTHER PUBLICATIONS

Pomerantz, R. J., "Reservoirs of Human Immunodeficiency Virus Type 1: The Main Obstacles to Viral Eradication," Clinical Infectious Diseases, vol. 34, Issue 1, Jan. 1, 2002).
Radaev, S. and Sun, P., "Recognition of immunoglobulins by Fcgamma receptors," Molecular Immunology, vol. 38, No. 14, pp. 1073-1083, 12 total pages (May 2002).
Rader, C., "DARTs take aim at BiTEs," Blood, vol. 117, No. 17, pp. 4403-4404 (Apr. 28, 2011).
Rankin, C.T., et al., "CD32B, The Human Inhibitory Fc-y Receptor IIB, As A Target for Monoclonal Antibody Therapy of B-Cell Lymphoma," Blood, vol. 108, No. 7, pp. 2384-2391 (Oct. 1, 2006).
Ravetch, J.V. and Bolland, S., "IgG Fc receptors," Annu. Rev. Immunol., vol. 19, pp. 275-290, 19 total pages (2001).
Ravetch, J.V. and Clynes, R.A., "Divergent roles for Fc receptors and complement in vivo," Annu. Rev. Immunol., vol. 16, pp. 421-432, 14 total pages (1998).
Ravetch, J.V. and Kinet, J.-P., "Fc receptors," Annu. Rev. Immunol., vol. 9, pp. 457-492 (1991).
Ravetch, J.V., "Fc Receptors: Rubor Redux," Cell, vol. 78, pp. 553-560 (Aug. 26, 1994).
Ravetech, J.V. and Lanier, L.L., "Immune inhibitory receptors," Science, vol. 290, No. 5489, pp. 84-89, 7 total pages (Oct. 6, 2000).
Redpath, S., et al., "The influence of the hinge region length in binding of human IgG to human Fcgamma receptors," Hum. Immunol., vol. 59, pp. 720-727 (1998).
Reff, M.E., et al., "Depletion of B cells in vivo by a chimeric mouse human monoclonal antibody to CD20," Blood, vol. 83, No. 2, pp. 435-445 (Jan. 15, 1994).
Ridgway, J.B., et al., "Knobs-Into-Holes' Engineering of Antibody $C_H3$ Domains for Heavy Chain Heterodimerization," Protein Engr., vol. 9, No. 7, pp. 617-621 (1996).
Riechmann, L., et al., "Reshaping human antibodies for therapy," Nature, vol. 332, pp. 323-327 (Mar. 1988).
Robb, M. L., et al., "Shot in the HAART: vaccine therapy for HIV," The Lancet Infectious Diseases, vol. 14, No. 4, pp. 259-260, (Apr. 2014).
Robbie, G., et al., "A Novel Investigational Fe-Modified Humanized Monoclonal Antibody, Motavizumab-YTE, Has an Extended Half-Life in Healthy Adults" Antimicrobial Agents and Chemotherapy, vol. 57, No. 12, pp. 6147-6153 (Dec. 2013).
Romain, G., et al., "Antibody Fc engineering improves frequency and promotes kinetic boosting of serial killing mediated by NK cells," Blood, vol. 124, No. 22, pp. 3241-3249, (Nov. 2014).
Rosenberg, H.F., et al., "Inflammatory Responses to Respiratory Syncytial Virus (RSV) Infection and The Development of Immunomodulatory Pharmacotherapeutics," Curr. Med. Chem., vol. 19, No. 10, pp. 1424-1431, Author Manuscript—17 total pages (2012).
Rothenberger, M. K., et al., "Large number of rebounding/founder HIV variants emerge from multifocal infection in lymphatic tissues after treatment interruption," Proceedings of the National Academy of Sciences USA, pp. E1126-E1134 (Feb. 23, 2015) www.pnas.org/cgi/doi/10.1073/pnas. 1414926112.
Rothlisberger, D., et al., "Domain Interactions in the Fab Fragment: A Comparative Evaluation of the Single-chain Fv and Fab Format Engineered with Variable Domains of Different Stability," J. Molec. Biol., vol. 347, pp. 773-789 (2005).
Rouet, R., et al., "Bispecific antibodies with native chain structure," Nature Biotechnology, vol. 32, No. 2, pp. 136-137 (2014).
Rudicell, R., et al., "Enhanced Potency of a Broadly Neutralizing HIV-I Antibody In Vitro Improves Protection against Lentiviral Infection In Vivo," Journal of Virology, vol. 88, pp. 12669-12682 (Nov. 2014).
Sanders, R. W., et al., "A Next-Generation Cleaved, Soluble HIV-1 Env Trimer, BGSOS SOSIP.664 gp140, Expresses Multiple Epitopes for Broadly Neutralizing but Not Non-Neutralizing Antibodies," PLOS Pathogens, vol. 9, Issue 9, pp. 1-20 (Sep. 2013).
Sarmay, G., et al., "Ligand inhibition studies on the role of Fc receptors in antibody-dependent cell-mediated cytotoxicity," Mol. Immunol., vol. 21, pp. 43-51, 10 totatl pages (1984).
Sarmay, G., et al., "Mapping and comparison of the interaction sites on the Fc region of IgG responsible for triggering antibody dependent cellular cytotoxicity (ADCC) through different types of human Fcgamma receptor," Mol. Immunol., vol. 29, No. 5, pp. 633-639 (1992).
Sarmay, G., et al., "The effect of synthetic peptides corresponding to Fc sequences in human IgG1 on various steps in the B cell activation pathway," Eur. J. Immunol., vol. 18, pp., No. 2, 289-294, 7 total pages (1988).
Sautes-Fridman, C., et al., "Fc gamma receptors: a magic link with the outside world," ASHI Quarterley, 4th Quarter, pp. 148-151 (2003).
Schaffner, et al., "Chimeric interleukin 2 receptor alpha chain antibody derivatives with fused mu and gamma chains permit improved recruitment of effector functions," Mol. Immunol., vol. 32, No. 1, pp. 9-20 (1995).
Schatz, P.J., "Use of peptide libraries to map the substrate specificity of a peptide-modifying enzyme: a 13 residue consensus peptide specifies biotinylation in *Escherichia coli*," Bio./Technology, vol. 11, pp. 1138-1143 (Oct. 11, 1993).
Sensel, M.G., et al., "Amino acid differences in the N-terminus of C(H)2 influence the relative abilities of IgG2 and IgG3 to activate complement," Molecular Immunology, vol. 34, No. 14, pp. 1019-1029 (1997).
Shadman, K.A. and Wald, E.R., "A Review of Palivizumab and Emerging Therapies for Respiratory Syncytial Virus," Expert Opin. Biol. Ther., vol. 11, No. 11, pp. 1455-1467, 14 total pages (Aug. 2011).
Shan, L., et al., "Stimulation of HIV-I-Specific Cytolytic T Lymphocytes Facilitates Elimination of Latent Viral Reservoir after Virus Reactivation," Immunity, vol. 36, pp. 491-501 (Mar. 23, 2012).
Shen, R., "GP41-Specific Antibody Blocks Cell-Free HIV Type 1 Transcytosis Through Human Rectal Mucosa and Model Colonic Epithelium," J. Immunol., vol. 184, No. 7, pp. 3648-3655, Author Manuscript—20 total pages (Apr. 1, 2010).
Shields, R.L., et al., "High resolution mapping of the binding site on human IgG1 for FcgammaRI, FcgammaRII, FcgammaRIII, and FcRn and design of IgG1 variants with improved binding to the FcGammaR," J. Biol. Chem., vol. 276, No. 9, pp. 6591-6604 (Mar. 2, 2001).
Shingai, M., et al., "Antibody-Mediated Immunotherapy of Macaques Chronically Infected with SHIV Suppresses Viraemia," Nature, 503(7475) pp. 277-280 (Nov. 14, 2013).
Shopes, B., "A genetically engineered human IgG mutant with enhanced cytolytic activity," J. Immunol., vol. 148, pp. 2918-2922 (May 1, 1992).
Shopes, B., "A genetically engineered human IgG with limited flexibility fully initiates cytolysis via complement," Molecular Immunology, vol. 30, No. 6, pp. 603-609 (1993).
Shopes, B., et al., "Recombinant human IgG1-murine IgE chimeric Ig—Construction, expression, and binding to human Fcgamma receptors," J. Immunol., vol. 145, pp. 3842-3848 (Dec. 1, 1990).
Shusta, E.V., et al., "Directed evolution of a stable scaffold for T-cell receptor engineering," Nature Biotechnology, vol. 18, pp. 754-759, 7 total pages (Jul. 2000).
Shusta, E.V., et al., "Increasing the secretory capacity of *Saccharomyces cerevisiae* for production of single-chain antibody fragments," Nature Biotechnology, vol. 16, pp. 773-777, 6 total pages (Aug. 1998).
Shusta, E.V., et al., "Yeast polypeptide fusion surface display levels predict thermal stability and soluble secretion efficiency," J. Mol. Biol., vol. 292, No., 5, pp. 949-956, 9 total pages (Oct. 8, 1999).
Singer, M. and Berg, P., "Genes and genomes," Moscow, Mir., vol. 1, pp. 63-64 with English translation—7 total pages (1998).
Sloan, D.D., et al., "Targeting HIV Reservoir in Infected CD4 T Cells by Dual-Affinity Re-targeting Molecules (DARTs) that Bind HIV Envelope and Recruit Cytotoxic T Cells" PLoS Pathog., vol. 11, No. 11, e1005233, pp. 1-29 (Nov. 5, 2015).

(56) References Cited

OTHER PUBLICATIONS

Smith, R.I.F. and Morrison, S.L., "Recombinant polymeric IgG: an approach to engineering more potent antibodies," Bio.-Technology, vol. 12, pp. 683-688 (Jul. 12, 1994).
Sondermann, P. and Oosthuizen, V., "The structure of Fc Receptor/Ig complexes: considerations on stoichiometry and potential inhibitors," Immunology Letters, vol. 82, Nos. 1-2, pp. 51-56, 7 total pages (Jun. 3, 2002).
Sondermann, P., et al., "Crystal structure of the soluble form of the human fcgamma-receptor IIb: a new member of the immunoglobulin superfamily at 1.7 A resolution," EMBO J., vol. 18, No. 5, pp. 1095-1103 (1999).
Sondermann, P., et al., "Molecular basis for immune complex recognition: a comparison of Fc-receptor structures," J. Mol. Biol., vol. 309, No. 3, pp. 737-749,14 totatal pages (Jun. 8, 2001).
Sondermann, P., et al., "The 3.2-A crystal structure of the human IgG1 Fc Fragment-Fc gammaRIII complex," Nature, vol. 406, pp. 267-273, (Jul. 20, 2000).
Songsivilai, S., et al., "Bispecific Antibody: A Tool for Diagnosis and Treatment of Disease," Clinical and Experimental Immunology, vol. 79, pp. 315-321 (1990).
Soriano-Sarabia, N., et al., "Quantitation of Replication-Competent HIV-I in Populations of Resting CD4+ T Cells," Journal of Virology, vol. 88, No. 24, pp. 14070-14077 (Dec. 2014).
Staerz, U. D., et al., "Hybrid Antibodies Can Target Sites For Attack By T Cells," Nature, vol. 314, pp. 628-631 (Apr. 18, 1985).
Staerz, U.D., et al., "Hybrid hybridoma producing a bispecific monoclonal antibody that can focus effector T-cell activity," PNAS, vol. 83, pp. 1453-1457 (Mar. 1986).
Stavenhagen, J.B., et al., "Fc Optimization of Therapeutic Antibodies Enhances Their Ability to Kill. Tumor Cells in Vitro and Controls Tumor Expansion in Vivo Via Low-Affinity Activating Fcgamma Receptors," Cancer Res., vol. 67, No. 18, pp. 8882-8890 (Sep. 15, 2007).
Steinkruger, J.D., et al., "The d'-- d--d' Vertical Triad is Less Discriminating Than the a'--a--a' Vertical Triad in the Antiparallel Coiled-coil Dimer Motif," J. Amer. Chem. Soc., vol. 134, No. 5, pp. 2626-2633, Author Manuscript—19 total pages (Feb. 8, 2012).
Stephan, J.P., et al., "Distribution and Function of the Adhesion Molecule BEN During Rat Development," Dev. Biol., vol. 212, pp. 264-277 (1999).
Stephan, J.P., et al., "Selective Cloning of Cell Surface Proteins Involved in Organ Development: Epithelial Glycoprotein Is Involved in Normal Epithelial Differentiation," Endocrinology, vol. 140, No., 12, pp. 5841-5854 (1990).
Steplewski, Z., et al., "Biological activity of human-mouse IgG1, IgG2, IgG3, and IgG4 chimeric monoclonal antibodies with antitumor specificity," Proc. Natl. Acad. Sci. U.S.A., vol. 85, pp. 4852-4856 (Jul. 1988).
Stork, R., et al., "A Novel Tri-Functional Antibody Fusion Protein with Improved Pharmacokinetic Properties Generated by Fusing a Bispecific Single-Chain Diabody with an Albumin-Binding Domain from Streptococcal Protein G," Protein Engineering, Design & Selection, vol. 20, No. 11, pp. 569-576 (Nov. 3, 2007).
Straussman, R., et al., "Kinking the Coiled Coil—Negatively Charged Residues at the Coiled-coil Interface," J. Molec. Biol., vol. 366, pp. 1232-1242 (2007).
Strohmeier, G.R., et al., "Role of the FcGammaR Subclasses FcgammaRII and FcgammaRIII in the activation of human neutrophils by low and high valency immune complexes," J. Leukocyte Biol., vol. 58, pp. 415-422 (Oct. 1995).
Sung, J. A., et al., "Expanded Cytotoxic T-Cell Lymphocytes Target the Latent HIV Reservoir," Journal of Infectious Diseases, vol. 212, pp. 258-263 (Jul. 2015).
Sung, J.,A., "Dual-Affinity Re-Targeting proteins direct T cell-mediated cytolysis of latently HIV-infected cells," J. Clin. Invest., vol. 125, No. 11, pp. 4077-4090 (Nov. 2015).
Supplementary European Search Report issued in European Patent Application No. 06750508.1 dated Oct. 13, 2010 (19 total pages).
Sylvestre, D.L. and Ravetch, J.V., "A dominant role for mast cell Fc receptors in the Arthus reaction," Immunity, vol. 5, No. 4, pp. 387-390, 5 total pages (Oct. 1996).
Sylvestre, D.L., and Ravetch, J.V., "Fc receptors initiate the Arthus reaction: redefining the inflammatory cascade," Science, vol. 265, No. 5175, , pp. 1095-1098, 5 total pages (Aug. 19, 1994).
Takai, T., "Roles of Fc receptors in autoimmunity," Nature Reviews, vol. 2, pp. 580-592 (Aug. 2002).
Takai, T., et al., "Augmented humoral and anaphylactic responses in FcgammaRII-deficient mice," Nature, vol. 379, No. 6563, pp. 346-349, 5 total pages (Jan. 25, 1996).
Takai, T., et al., "FcR gamma chain deletion results in pleiotrophic effector cell defects," Cell, vol. 76, No. 3, pp. 519-529, 12 total pages (Feb. 11, 1994).
Takemura, S., et al., "Construction of A Diabody (Small Recombinant Bispecific Antibody) Using A Refolding System," Protein Eng., vol. 13, No. 8, pp. 583-588 (2000).
Tamm, A. et al., "The IgG binding site of human FcγRIIIB receptor involves CC' and FG loops of the membrane-proximal domain," J. Biol. Chem., vol. 271, No. 7, pp. 3659-3666 (1996).
Tang, Y. and Tirrell, D.A., "Biosynthesis of A Highly Stable Coiled-Coil Protein Containing Hexafluoroleucine in an Engineered Bacterial Host," J. Am. Chem. Soc., vol. 123, No. 44, pp. 11089-11090 (2001).
Tao, et al., "The differential ability of human IgG1 and IgG4 to activate complement is determined by the COOH-terminal sequence of the $C_H2$ domain," J. Exp. Med. Vol. 173, pp. 1025-1028 (Apr. 1991).
Tao, M.-H, et al., "Structural features of human immunoglobulin G that determine isotype-specific differences in complement activation," J. Exp. Med., vol. 178, pp. 661-667 (Aug. 1993).
Tempest, P.R., et al., "Reshaping A Human Monoclonal Antibody to Inhibit Human Respiratory Syncytial Virus Infection in vivo," Bio/Technology, vol. 9, pp. 266-271 (Mar. 1991).
Ter Meulen, J., "Monoclonal Antibodies for Prophylaxis and Therapy of Infectious Diseases," Expert Opin. Emerg. Drugs., vol. 12, No. 4, pp. 525-540, 17 total pages (Nov. 2007).
Ter Meulen, J., "Monoclonal Antibodies in Infectious Diseases: Clinical Pipeline in 2011," Infect. Dis. Clin. North Am., vol. 25, pp. 789-802 (2011).
Todorovska, A., et al., "Design and Application of Diabodies, Triabodies and Tetrabodies for Cancer Targeting," J. Immunol. Methods, vol. 248, pp. 47-66 (2001).
Topp, M. S., et al., "Phase II Trial of the Anti-CD19 Bispecific T Cell-Engager Blinatumomab Shows Hematologic and Molecular Remissions in Patients With Relapsed or Refractory BPrecursor Acute Lymphoblastic Leukemia," Journal of Clinical Oncology, vol. 32, No. 36, pp. 4134-4140 (Dec. 20, 2014).
Topp, M. S., et al., "Safety and activity of blinatumomab for adult patients with relapsed or refractory B-precursor acute lymphoblastic leukaemia: a multicentre, single-arm, phase 2 study," Lancet Oncology, vol. 16, pp. 57-66 (Jan. 2015).
Trautmann, L., et al., "Upregulation of PD-1 expression on HIVspecific CD8+ T cells leads to reversible immune dysfunction," Nature Medicine, vol. 12, No. 10, pp. 1198-1202 (Oct. 2006).
Trindandapani, S., et al., "Regulated Expression and Inhibitory Function of FcgammaRIIB in Human Monocytic Cells," J. Biol. Chem., vol. 277, No. 7, pp. 5082-5089 (Feb. 15, 2002).
Tripet, B., et al., "Kinetic Analysis of the Interactions between Troponin C and the C-terminal Troponin I Regulatory Region and Validation of a New Peptide Delivery/Capture System used for Surface Plasmon Resonance," Journal of Molecular Biology, vol. 323, pp. 345-362 (2002).
Trkola, A., et al., "Delay of HIV-1 Rebound After Cessation of Antiretroviral Therapy Through Passive Transfer of Human Neutralizing Antibodies," Nat. Med., vol. 11, No. 6, pp. 615-622 (Jun. 2005).
Unkeless, J.C., et al., "Function of Human FcGammaRIIA and FcGammaRIIIB," Semin. Immunol., vol. 7, pp. 37-44 (1995).
Van Hest, J.C.M., et al., "Protein-Based Materials, Toward A New Level of Structural Control," Chem. Comm., vol. 19, pp. 1897-1904 (2001).

(56) References Cited

OTHER PUBLICATIONS

Van Praag, R.M.E., et al. "OKT3 and IL-2 Treatment for Purging of the Latent HIV-1 Reservoir in Vivo Results in Selective Long-Lasting CD4+ T Cell Depletion ." J Clin Immunol. vol. 21, No. 3 pp. 218-226, (2001).
Van Sorge, N.M., et al., "FcgammaR polymorphisms: Implications for function, disease susceptibility and immunotherapy," Tissue Antigens, vol. 61, pp. 189-202 (2003).
VanAntwerp, J.J. and Wittrup, K.D., "Fine affinity discrimination by yeast surface display and flow cytometry," Biotechnol. Prog., vol. 16, pp. 31-37 (2000).
Vasiliver-Shamis, G., et al., "Human Immunodeficiency Virus Type 1 Envelope gp120 Induces a Stop Signal and Virological Synapse Formation in Noninfected CD4+ T Cells," J. Virology, vol. 82, No. 19, pp. 9445-9457 (Oct. 2008).
Veillette M et al. "Interaction with Cellular CD4 Exposes HIV-I Envelope Epitopes Targeted by Antibody-Dependent Cell-Mediated Cytotoxicity." J Viral. Vol. 88, No. 5, pp. 2633-2644 (Mar. 2014).
Verhoeyen, M., et al., "Reshaping Human Antibodies: Grafting an Antilysozyme Activity," Science, vol. 239, No. 4847, pp. 1534-1536 (Mar. 25, 1988).
Veri, M.-C., et al., "Monoclonal antibodies capable of discriminating the human inhibitory Fcgamma-receptor IIb (CD32B) from the activating Fcgamma-receptor IIa (CD32A): biochemical, biological and functional characterization," Immunology, vol. 121, pp. 392-404 (Jan. 2007).
Veri, M.-C., et al., "Therapeutic Control of B Cell Activation via Recruitment of Fcgamma Receptor IIb (CD32B) Inhibitory Function with a Novel Bispecific Antibody Scaffold," Arthritis & Rheumatism, vol. 62 No. 7, pp. 1933-1943 (Jul. 2010).
Vidarte, L., et al., "Serine 132 is the C3 covalent attachment point on the CH1 domain of human IgG1," J. Biol. Chem., vol. 276, No. 41, pp. 38217-38233 (Oct. 12, 2001).
Viglietta, V. and Khoury, S.J., "Modulating Co-Stimulation," Neurotherapeutics: The Journal of the American Society for Experimental NeuroTherapeutics, vol. 4, pp. 666-675 (Oct. 2007).
Vinikoor MJ et al. "Antiretroviral Therapy Initiated During Acute HIV Infection Fails to Prevent Persistent T-Cell Activation." J. Acquire Immune Defic Syndr. vol. 62, No. 5, pp. 505-508 (Apr. 15, 2013).
Wang, D., et al., "Palivizumab for Immunoprophylaxis of Respiratory Syncytial Virus (RSV) Bronchiolitis in High-Risk Infants and Young Children: A Systematic Review and Additional Economic Modelling of Subgroup Analyses," Health Technol. Assess. vol. 15, No. 5, Table of Contents and pp. 1-124, 140 total pages (Jan. 2011).
Wang, L., et al., "Expanding The Genetic Code of *Escherichia coli*," Science, vol. 292, pp. 498-500 (Apr. 20, 2001).
Wang, L., et al., "Expanding The Genetic Code," Chem. Comm., vol. 1, pp. 1-11 (2002).
Ward, E.S. and Ghetie, V., "The effector functions of immunoglobulins: implications for therapy," Therapeutic Immunology, vol. 2, pp. 77-94 (1995).
Weng, W.-K. and Levym R., "Two immunoglobulin G Fragment C receptor polymorphisms independently predict response to rituximab in patients with follicular lymphoma," J. Clin. Oncol., vol. 21, No. 21, pp. 3940-3947 (Nov. 11, 2003).
Whaley, K.J., et al., "Emerging Antibody Products and Nicotiana Manufacturing," Hum. Vaccin., vol. 7, No. 3, pp. 349-356 (Mar. 2011).
Wiener, E., et al., "Differences between the activities of human monoclonal IgG1 and IgG3 anti-D antibodies of the Rh blood group system in their abilities to mediate effector functions of monocytes," Immunol., vol. 65, pp. 159-163 (1988).
Wing, M.G., et al., "Mechanism of first-dose cytokine-release syndrome by CAMPATH 1-H: Involvement of CD16 (FcγRIII) and CD11a-CD18 (LFA-1) on NK cells," J. Clin. Invest., vol. 98, No. 12, pp. 2819-2826 (Dec. 1996).
Wingren, C., et al., "Comparison of surface properties of human IgA, IgE, IgG and IgM antibodies with identical and different specificities," Scand. J. Immunol., vol. 44, pp. 430-436 (Jul. 1996).
Winter, G., et al., "Making Antibodies by Phage Display Technology," Annu. Rev. Immunol., vol. 12, pp. 433-455 (1994).
Wittrup, K.D., "Protein engineering by cell-surface display," Curr. Opin. Biotechnol., vol. 12, pp. 395-399 (2001).
Wittrup, K.D., "The single cell as a microplate well," Nat. Biotechnol., vol. 18, pp. 1039-1040 (Oct. 2000).
Wlazlo, A.P., et al., "Generation and Characterization of Monoclonal Antibodies Against the E6 and E7 Oncoproteins of HPV," Hybridoma, vol. 20, No. 4, pp. 257-263 (Jun. 2001).
Wong, J.K,, et al. "Recovery of Replication-Competent HIV Despite Prolonged Suppression of Plasma Viremia," Science, vol. 278, Issue. 5341, pp. 1291-1295, 6 total pages (Nov. 14, 1997).
Woof, J.M., et al., "Localisation of the monocyte-binding region on human immunoglobulin G," Mol. Immunol., vol. 23, No. 3, pp. 319-330, 13 total pages (1986).
Woolfson, D.N., "The Design of Coiled-Coil Structures and Assemblies," Adv. Prot. Chem., vol. 70, pp. 79-112 (2005).
Wu, A.M and Yazaki, P.J., "Designer Genes: Recombinant Antibody Fragments for Biological Imaging," Q. J. Nucl. Med., vol. 44, No. 3, pp. 268-283 (Sep. 2000).
Wu, A.M., et al., "Multimerization of a chimeric anti-CD20 single-chain Fv-Fc fusion protein is mediated through variable domain exchange," Protein Engineering, vol. 14, No. 12, pp. 1025-1033 (2001).
Wu, A.M., et al., "Multimerization Of A Chimeric Anti-CD20 Single-Chain Fv-Fc Fusion Protein Is Mediated Through Variable Domain Exchange," Protein Engineering, vol. 14, No. 2, pp. 1025-1033 (2001).
Wu, J., et al., "A novel polymorphism of FcγRIIIa (CD16) alters receptor function and predisposes to autoimmune disease," J. Clin. Invst., vol. 100, No. 5, pp. 1059-1070 (Sep. 1997).
Wyatt R et al. "Involvement of the V1/V2 variable loop structure in the exposure of human immunodeficiency virus type 1 gp120 epitopes induced by receptor binding." J Virol. Vol. 69, No. 9, pp. 5723-5733 (Sep. 1995).
Xie, Z., et al., "A New Format of Bispecific Antibody: Highly Efficient Heterodimerization, Expression And Tumor Cell Lysis," J. Immunol. Methods, vol. 296, pp. 95-101 (2005).
Xiong, D., et al., "Efficient Inhibition of Human B-Cell Lymphoma Xenografts with an Anti-CD20 × Anti-CD3 Bispecific Diabody," Cancer Lett., vol. 177, pp. 29-39 (2002).
Xu, Y. et al., "Residue at position 331 in the IgG1 and IgG4 CH2 domains contributes to their differential ability to bind and activate complement," J. Biol. Chem., vol. 269, No. 5, pp. 3469-3474 (Feb. 4, 1994).
Yamada, T., "Therapeutic Monoclonal Antibodies," Keio J. Med., vol. 60, No. 2, pp. 37-46 (Jun. 2011).
Yamamoto T et al. "Surface expression patterns of negative regulatory molecules identify |determinants of virus-specific CD8+ T-cell exhaustion in HIV infection." Blood. vol. 117, No. 18, pp. 4805-4815, (May 5, 2011).
Yeung, Y.A. and Wittrup, K.D., "Quantitative screening of yeast surface-displayed polypeptide libraries by magnetic bead capture," Biotechnol. Prog., vol. 18, pp. 212-220 (2002).
Yin, S., et al., "Elimination of Latently HIV-1-Infected Cells by Lymphoblasts Armed with Bifunctional Antibody", Microbiology and Immunology, vol. 45, No. 1, pp. 101-108 (2001).
Zeidler, R., et al., "The Fc-region of a new class of intact bispecific antibody mediates activation of accessory cells and NK cells and induces direct phagocytosis of tumour cells," British J. Cancer, vol. 83, pp. 261-266 (Mar. 2000).
Zeng, Y., et al., "A Ligand-Pseudoreceptor System Based On de novo Designed Peptides For The Generation Of Adenoviral Vectors With Altered Tropism," J. Gene Med., vol. 10, pp. 355-367 (Jan. 14, 2008).
Zhang M-Y et al. "Identification and characterization of a broadly cross-reactive HIV-I human monoclonal antibody that binds to both gp120 and gp41." PLoS ONE. vol. 7, No. 9, e44241, pp. 1-14 (Sep. 2012).
Zhu, J., et al., "Mining the antibodyome for HIV-1-neutralizing antibodies with next-generation sequencing and phylogenetic pairing of heavy/light chains," PNAS—Early Edition, vol. 110, pp. 1-6 (Feb. 2013).

(56) References Cited

OTHER PUBLICATIONS

Zhu, Z., et al., "Remodeling Domain Interfaces to Enhance Heterodimer Formation," Protein Sci., vol. 6, pp. 781-788 (Jan. 1997).
Zlevsky et al., "Enhnaced antibody half-life improves in vivo activity." Nature Biotechnology, vol. 28, No. 2, pp. 157-159, (Feb. 2010).
Zuckier, L.S., et al., "Chimeric human-mouse IgG antibodies with shuffled constant region exons demonstrate that multiple domains contribute to in vivo half-life," Cancer Res., vol. 58, No. 17, pp. 3905-3908, 5 total pages (Sep. 1, 1998).
Chamow, et al., "A Humanized, Bispecific Immunoadhesin-Antibody That Retargets CD3+ Effectors to Kill HIV-1-Infected Cells," The Journal of Immunology, vol. 153, pp. 4268-4280 (1994).
Liao, et al., "Immunogenicity of Constrained Monoclonal Antibody A32-Human Immunodeficiency Virus (HIV) Env gp120 Complexes Compared to That of Recombinant HIV Type 1 gp120 Envelope Glycoproteins," J. Virol., vol. 78, pp. 5270-5278 (May 2004).
Ashkenazi, A., et al., "Mapping the CD4 binding site for human immunodeficiency virus by alanine-scanninz mutazenesis," Proc. Natl. Acad. Sci. USA, vol. 87, pp. 7150-7154 (1990).
Archin, N.M., et al., "Emerging strategies to deplete the HIV reservoir," Curr. Opin. Infect. Dis., vol. 27, No. 1, pp. 29-35, Author Manuscript—13 total pages (Feb. 2014).
Tomaras, G.D., et al., "Vaccine-induced plasma IgA speci?c for the C1 region of the HIV-1 envelope blocks binding and effector function of IgG," PNAS, vol. 110, No. 22, pp. 9019-9024 (May 2013.
English translation of Notice of Reasons for Rejection issued Nov. 5, 2019 by Japanese Patent Office in Japanese Patent Application No. 2017-536234 (9 total pages).
Darwish, I. A., "Immunoassay Methods and their Applications in Pharmaceutical Analysis: Basic Methodology and Recent Advances," Int. J. Biomed. Sci. vol. 2, No. 3, pp. 217-235 (2003).
Leland, D.S. and Ginocchio, C.C., "Role of Cell Culture for Virus Detection in the Age of Technology," Clin. Microbiol. Rev. vol. 20, No. 1, pp. 49-78 (Jan. 2007).
Munshaw, S. and Kepler, T.B., "SoDA2: a Hidden Markov Model approach for identi?cation of immunoglobulin rearrangements," Bioinformatics, vol. 26, No. 7, pp. 867-872 (Feb. 2010).
Martin, A.C..R, "Chapter3: Protein Sequence and Structure Analysis of Antibody Variable Domains," Antibody Engineering, vol. 2 (2nd ed.), Springer-Verlag, Berlin Heidelberg, pp. 33-51 (2010).
International Search Report and Written Opinion issued by the U.S. Patent and Trademark Office as International Searching Authority for International Application No. PCT/US2015/053027 dated Jan. 29, 2016 (17 pages).
Shalaby, M.R., et al., "Development of Humanized Bispecific Antibodies Reactive with Cytotoxic Lymphocytes and Tumor Cells Overexpressing the HER2 Protooncogene," J. Exp. Med., vol. 175, pp. 217-225 (Jan. 1992).

* cited by examiner

Effector cells: CD8+ T cells;Effector/Target ratio: 33:1

Effector/Target ratio = 11:1

CDR1 is bold.CDR2 is bold green/underlined.CDR3 is bold red/italicized.

mAb CH27: original cDNA sequences

>H004021_CH27_HC SEQ ID NO: 57

GAGGTKCAGCTGGTGGAGTCTGGGGGTGGCTTGGTCCAGCCGGGGGGGTCCCTGAGACTCTCTTGTGC
AGCCTCTGGATTCAGCGTCAGCTACGACTATATGGCCTGGGTCCGCCAGGCTCCAGGGAAGGGACTGG
AGTGGGTCTCTATTATTTATGGTGGTGGTAGTCCATATTACGCAGACTCTGTGAAGGGCCGATTCGCC
ATCTCCAGAGACACCTCCAGGAATACACTGGATCTTCAAATGAGCAGCCTGAGACGTGACGACAGCGG
TGTTTACTTCTGTGCGAGGGGACTCGCCTCGCTCTTCGATCTCTGGGGCCGAGGCACCCTGGTCACTG
TCTCGTCAGCATCCCCGACCAGCCCCAAGGTCTTCCCGCTGAGCCTCGACAGCACCAGC

>K003061_CH27_KC SEQ ID NO: 58

GAAATTGTGTTGACRCAGTCTCCAGGCACCCTGTCTTTGTCTCCAGGAGAAACAGCCACCCTCTCCTG
CAGGGCCAGTCGGCGTGTTAACGTCAACTACCTAGCCTGGTATCAACACAGACCTGGCCAGAGTCCCA
GGCTCCTCATGTACGGTCCTTACAACAGGCCCACTGGCATCCCGGGCAGGTTCTGGGGCGAGTGGTCT
GGGCCACTCTTCACTCTCAACATCGACAGACTGGAGCCTGTTGATCGAGCAGTCTATTACTGTCTACA
CTTTGACTCTGATACTTCTTCGTGGGCGTTCGGCCGAGGGACCAAGGTGGAGGTCAAACGAACTGTGG
CTGCACCATCTTCTTCACTCTTCCAAAAACATCTGAAGCAGTTTTAATCTCAACTTCTCTCATCAAAC
CCGGGGGGGGAGATCAAGACCGATGGGCCAGCCACGGTTGGTTGGACCGGCACGGGGGCCGGCCCACA
GCGAAAAAAAGGGGGAGACCCAGAGTGTGAGGGCACTAGAGGGGTGGGGACAGACCCTTCTGGGGACT
TGAAGGGGGAGAGTCGCCCCCACATGCCCAACCGGGGGCCCACCACCGGGCGGTTTCACGGACGTTAT
TAACGGGCCGGAATTTTTCCCCCGTGTTTCATACAAGCCCCCCCCTGGAGGGGGGAAACAAACCCCGC
CAAAAAGGGGCCTTTATTCTCAAACCAACAACGCGCGCCCCCAAACCCTCCAAAATTTTTCCCCCCAA
ACCAAACACAAACCCCCCCCCCCCCCCCCCCCCCCCCCCCCCCCCCCCCCCCCCCCCCCC
CCCCCCCCCCCCCCCCCCCCCCCCCCCCCC

Figure 5 mAb CH27: cleaned DNA sequences

>H004021_CH27_HC_clean SEQ ID NO: 59

GAGGTKCAGCTGGTGGAGTCTGGGGGTGGCTTGGTCCAGCCGGGGGGGTCCCTGAGACTCTCTTGTGC
AGCCTCTGGATTCAGCGTCAGCTACGACTATATGGCCTGGGTCCGCCAGGCTCCAGGGAAGGGACTGG
AGTGGGTCTCTATTATTTATGGTGGTGGTAGTCCATATTACGCAGACTCTGTGAAGGGCCGATTCGCC
ATCTCCAGAGACACCTCCAGGAATACACTGGATCTTCAAATGAGCAGCCTGAGACGTGACGACAGCGG
TGTTTACTTCTGT*GCGAGGGGACTCGCCTCGCTCTTCGATCTC*TGGGGCCGAGGCACCCTGGTCACTG
TCTCGTCAGCA

>K003061_CH27_KC_clean SEQ ID NO: 60

GAAATTGTGTTGACRCAGTCTCCAGGCACCCTGTCTTTGTCTCCAGGAGAAACAGCCACCCTCTCCTG
CAGGGCCAGTCGGCGTGTTAACGTCAACTACCTAGCCTGGTATCAACACAGACCTGGCCAGAGTCCCA
GGCTCCTCATGTACGGTCCTTACAACAGGCCCACTGGCATCCCGGGCAGGTTCTGGGGCGAGTGGTCT
GGGCCACTCTTCACTCTCAACATCGACAGACTGGAGCCTGTTGATCGAGCAGTCTATTACTGT***CTACA
CTTTGACTCTGATACTTCTTCGTGGGCG***TTCGGCCGAGGGACCAAGGTGGAGGTCAAACGA mAb CH27: amino acid sequences

>H004021_CH27_HC_AA SEQ ID NO: 61

EVQLVESGGGLVQPGGSLRLSCAASGFSVSYDYMAWVRQAPGKGLEWVSIIYGGGSPYYADSVKGRFA
ISRDTSRNTLDLQMSSLRRDDSGVYFC*ARGLASLFDL*WGRGTLVTVSSA

>K003061_CH27_KC_AA SEQ ID NO: 62

EIVLTQSPGTLSLSPGETATLSCRASRRVNVNYLAWYQHRPGQSPRLLMYGPYNRPTGIPGRFWGEWS
GPLFTLNIDRLEPVDRAVYYC*LHFDSDTSSWA*FGRGTKVEVKR

Figure 5 cont.

mAb CH28: original cDNA sequences

>H004367_CH28_HC SEQ ID NO: 63

CAGGTGCAGCTGGTRCAGTCTGGGACTTAATCCTCTACACACACCCATATCTCCTACGCTCCATAACG
GACCTACTTTGCACTAATCCTTAGGACACGCCGACTCCTCCTCGGGGTAAACTCTATAAAGATGACAA
AAGATAGTAACCTAGGAATAGAACAATGCAATATACTAAAGAACTGATCCTTGACACTGCTACCGCCT
AGGTATTCGCAATATAACAAATATCATCATCCGACCCAAGTATATGCTGGATTTGTTAAAATAGTCAG
AGAACTATATCTATCTGCAATGGCTTACAGCTAAGCCAGAATCTACAATAAAAACAACAAGCGGGAAC
GCTTCCAAAGAAAAAAACCATATACTCAGGTCTGTTCACCATCTCAATCACCGACTTTCACACATTTT
TTCCCAGGCTTACAAAGATATTCAGGGTTTTTTTTCCTTTTCCATTCCAGAGGAACCACAGTGCAGC
GTGTCAGTAGGGGGGTAAGGAAAATAAGCCTGGTTCCTCAGTGTGTCTCTCTGGCAAGTCTTGGGGCG
CCTCCTTTAGAAATAATCTCACCCCAGCCCCCCGCCACCTCCAGGGAATGGACGAGTAGTCGAGACAA
ATCTTCCCCCTTATGTTAGAAGAAACAACCAACCCAGATAAAATGCCGCGGAAGCGTCACATTTCTCC
CAAACTCAACCTATATCGCATCTAACAGGGGATAAAGCAGCTCAAAAAAAGACACGGCGGCCTGTATG
TGGGAGAGATCGGTTTCTCTCCTTACAGAACGGAGACCCCCGCGAATTAAAAATGGGGCCAAGAGAAA
AGAGTTAATTTTTCTTCTGGGTATGTGATGGGGGGGGAGAATAATCTGCGCACCAGACCACAGGGTAG
CTGCGTACGTCTCGGGGGGTCCCTGAGACTCTCCTGTGCAGCCTCTGGATTCAGCGTCAGGAACGACC
AGATGGCCTGGGTCCGCCAGGCTCCAGGGAAGCGACTGGAGTGGGTCT

>K003331_CH28_KC SEQ ID NO: 64

GAAATTGTGTTGACRCAGTCTCCAGGCACCCTGTCCTTGTCTCCAGGGGAGAGAGCCACCCTCTCCTG
CAGGGCCAATCGGCGGATTGACATGAACGCCTTGGCCTGGTACCAGCACCGATCTGGCCAGGCTCCCA
GGCTCCTCACCCATGGTGTCTATAACAGGGCCACTGGCATCCCAGACAGGTTCAGTGGCTATTGGTCT
GGGCCAGAGTTCACCCTCGTCATCAGCAGACTGGAGCCTGAAGATTTTGCAGTCTATTACTGTGTACA
CTTTCTCTACGAAAATCCAGCGTGGGCGTTCGGCCGAGGGACCAAGATAGAGGTCAAGCGAACTGTGG
CTGCACCATCTGCTCACATCTTCCAACCATATGATGAGCACTTGAAATCTGAAACTGCCTCATCACCC
CTGGCGGGGAAAAACAAGAACGGTGGGGGCGCCACAGGTGCCAAAAACTTTATGTCGCTCCGGGCAAA
AGCCCCCGTGGAATTTCATGAAAAAGGGGTACCCATTAGTAGACCGCAAAATGCCGGGCCAAATCTCC
TAAATAACAGAGGTAGAATTAACCAAACAGATGTCCAAAGAACTTTGCTGGAACACCGTAAGCGGTAT
CAAAGAGGAGGGGGGAGAGAACCGGGGGGCCCCTGCCGGATATATATCTGTAAACAGCCGGGCCAATG
GATTTCCTCCCCCCTGTGGGCCCTAAAAAAAGGGGGTGTTCTTAAACCCACAAAAAAAGGGAAAACGG
TGTCCCGGGAAACACACCTTTCTCCCAATATTATTTCGCGCGGGGAAAAAAAGAAAAACAAAAAAAAA
AACCCC

Figure 5 cont.

mAb CH28: cleaned DNA sequences

>H004367_CH28_HC_clean SEQ ID NO: 65

GAGGTGCAGCTGGTGGAGTCTGGGGGTAGCTGCGTACGTCTCGGGGGGTCCCTGAGACTCTCCTGTGC
AGCCTCTGGATTCAGCGTCAGGAACGACCAGATGGCCTGGGTCCGCCAGGCTCCAGGGAAGCGACTGG
AGTGGGTCTCTATTATTAACGATGGTGCTAGTCCATACTACGCAGACTCTGTGAAGGGCCGCTTCGCC
ATGTCCAGAGACACCTCCAAGAATACAGTGTTTCTTCAGATGAACAGCCTGAGACGTGACGACACAGC
TGTTTATTTCTGT*GCGAGGGGGATCGCCTCATTCTTCGATGTC*TGGGGCCGTGGCACGCTGGTCGCTG
TCTCGTCAGCA

>K003331_CH28_KC_clean SEQ ID NO: 66

GAAATTGTGTTGACRCAGTCTCCAGGCACCCTGTCCTTGTCTCCAGGGGAGAGAGCCACCCTCTCCTG
CAGGGCCAATCGGCGGATTGACATGAACGCCTTGGCCTGGTACCAGCACCGATCTGGCCAGGCTCCCA
GGCTCCTCACCCATGGTGTCTATAACAGGGCCACTGGCATCCCAGACAGGTTCAGTGGCTATTGGTCT
GGGCCAGAGTTCACCCTCGTCATCAGCAGACTGGAGCCTGAAGATTTTGCAGTCTATTACTGT*GTACA*
*CTTTCTCTACGAAAATCCAGCGTGGGCG*TTCGGCCGAGGGACCAAGATAGAGGTCAAGCGA mAb CH28: amino acid sequences

>H004367_CH28_HC_AA SEQ ID NO: 67

EVQLVESGGSCVRLGGSLRLSCAASGFSVRNDQMAWVRQAPGKRLEWVSIINDGASPYYADSVKGRFA
MSRDTSKNTVFLQMNSLRRDDTAVYFC*ARGIASFFDV*WGRGTLVAVSSA

>K003331_CH28_KC_AA SEQ ID NO: 68

EIVLTQSPGTLSLSPGERATLSCRANRRIDMNALAWYQHRSGQAPRLLTHGVYNRATGIPDRFSGYWS
GPEFTLVISRLEPEDFAVYYC*VHFLYENPAWA*FGRGTKIEVKR

Figure 5 cont.

mAb CH44: original cDNA sequences

>H004016_CH44_HC SEQ ID NO: 69

GAGGTKCAGCTGGTGGAGTCTGGGGGTGGCGTGGTCCACCCTGGGGGGTCCCTGAGACTCTCCTGTGC
AGCCTCTGGATTCAGCGTCAGTCACGACTTCATGGCCTGGATCCGCCAGGCTCCAGGAAAGGGACTGG
AGTGGATCTCTATCATATATAACACTGGTTCTCGATACTACTACGCAGACTCTGTGAAGGGCCGCTTC
GCCCTCTCCAGAGATACGTCCAACAACACACTGATTCTTCACATGAGCGGCCTGAGACGTGACGACAC
GGCTATTTATTTCTGTGCCAGGGGAGTCGCCTCGTTCTTCGAATTGTGGGGCCGTGGCACCCTGGTCA
CTGTCTCGTCAGCCTCCACCAAGGGCCCATCGGTCTTCCCCCTGGCACCCTCCTCCAAGAGC

>K003056_CH44_KC SEQ ID NO: 70

GAAACGACACTCACGCAGTCTCCAGCCATCCTGTCTGTGTCTCCAGGGGAAACCGCCACCCTCTCCTG
CAGGGCCAGTCGCCGTGTTGACATGAACGGCCTCGCCTGGTACCAACACAGGCCTGGCCAGGCTCCCA
GGCTCCTCATGCATGGTGTTTATAATAGGGCCGCCGGCATCTCAGGCAGGTTCACTGGCAGTTGGTCT
GGGCCAGTCTTCACTCTCACCATCAGCAGACTGGAGCCTGAAGATTTTGGAGTCTATTACTGTCAACA
CTTTTACTATGAGACTTCAGCGTGGGCGTTCGGCCGAGGGACCAGGGTGGAGGGCAAACGAACTGTGG
CTGCACCATCTTCTCCTATCTTCCAAAAAAACAACCTCCCAATGACAGCTGTAAATGTAACATAACTG
TGGCACAATCCATCAGCATCCGCCGCGGAAGGGCGAGCAAAGGGCCCCCCGCCGCCCGCCCGGGGGGG
GGGGGGGGGGGGTGGGGGGGGCCCCCCTGGGCGGGGGGCCCCACCCCCCCCGGCCCCCCCCCGGGCCC
GGCCCCCCCCCCCCCCCGGCCCCCCCCCCCGGGCGGGGCCCCCACAGGGCCCCGGGGGGGCCCCCTCC
CCCCCCCCCCCAAACCCCCCCCCCCCCCCCCCCCCCCCCCCGCCGCCCCCCCCCCCCCCCCCCCCCCC
CCCCCCCCCCAAACCCCCCCCCCCCCCCCCCCCCCCCCCCCCCCCCCCCCCCCCCCCCCCCCCCCCCC
CCCCCCCCCCCCCCCCCCCCCCCCCCCCCCCCCCCCCCCCCCCCCCCCCCCCCCCCCCCCCCCCCCCC
CCCCCCCCCCCCCCCCCCCC

Figure 5 cont.

mAb CH44: cleaned DNA sequences

>H004016_CH44_HC_clean SEQ ID NO: 71

GAGGTKCAGCTGGTGGAGTCTGGGGGTGGCGTGGTCCACCCTGGGGGGTCCCTGAGACTCTCCTGTGC
AGCCTCTGGATTCAGCGTCAGTCACGACTTCATGGCCTGGATCCGCCAGGCTCCAGGAAAGGGACTGG
AGTGGATCTCTATCATATATAACACTGGTTCTCGATACTACTACGCAGACTCTGTGAAGGGCCGCTTC
GCCCTCTCCAGAGATACGTCCAACAACACACTGATTCTTCACATGAGCGGCCTGAGACGTGACGACAC
GGCTATTTATTTCTGT*GCCAGGGGAGTCGCCTCGTTCTTCGAATTG*TGGGGCCGTGGCACCCTGGTCA
CTGTCTCGTCAGCC

>K003056_CH44_KC_clean SEQ ID NO: 72

GAAACGACACTCACGCAGTCTCCAGCCATCCTGTCTGTGTCTCCAGGGGAAACCGCCACCCTCTCCTG
CAGGGCCAGTCGCCGTGTTGACATGAACGGCCTCGCCTGGTACCAACACAGGCCTGGCCAGGCTCCCA
GGCTCCTCATGCATGGTGTTTATAATAGGGCCGCCGGCATCTCAGGCAGGTTCACTGGCAGTTGGTCT
GGGCCAGTCTTCACTCTCACCATCAGCAGACTGGAGCCTGAAGATTTTGGAGTCTATTACTGT*CAACA
CTTTTACTATGAGACTTCAGCGTGGGCG*TTCGGCCGAGGGACCAGGGTGGAGGGCAAACGA mAb CH44: amino acid sequences

>H004016_CH44_HC_AA SEQ ID NO: 73

EVQLVESGGGVVHPGGSLRLSCAASGFSVSSHDFMAWIRQAPGKGLEWISIIYNTGSRYYYADSVKGRF
ALSRDTSNNTLILHMSGLRRDDTAIYFC*ARGVASFFEL*WGRGTLVTVSSA

>K003056_CH44_KC_AA SEQ ID NO: 74

ETTLTQSPAILSVSPGETATLSCRASRRVDMNGLAWYQHRPGQAPRLLMHGVYNRAAGISGRFTGSWS
GPVFTLTISRLEPEDFGVYYC*QHFYYETSAWA*FGRGTRVEGKR

Figure 5 cont.

>A32VH
CAGGTGCAGCTGTGCGGAGTCGGGCCAGGACTGGTGAAGCCTTCACAGACCTTGTCCCTCAGTTGCACTGTC
TCTGGTGGCTCCAGCAGTAGTGGTGCTCACTACTGGAGTTGGATCCGCCAGTACCCAGGGAAGGGCCTGGAG
TGGATTGGTTACATCCATTACAGTGGGAACACTTACTACAACCCGTCCCTCAAGAGTCGAATTACCATATCA
CAACACACGTCTGAGAACCAGTTCTCCCTGAAGCTCAACTCTGTGACTGTTGCAGACACGGCCGTCTATTAC
TGTGCGAGAGGGACCCGTCTCCGGACACTACGGAATGCTTTTGATATTTGGGGCCAGGGGACAAGGGTCACC
GTCTCTTCA (SEQ ID NO:75)

>A32VL
CAGTCTGCCCTGACTCAGCCTCCCTCCGCGTCCGGGTCTCCTGGACAGTCAGTCACCATCTCCTGCACTGGA
ACCAGCAGTGACGTTGGTGGTTATAACTATGTTTCCTGGTACCAACACCACCCAGGCAAAGCCCCCAAACTC
ATAATTTCTGAGGTCAATAACCGGCCCTCAGGGGTCCCTGATCGTTTCTCTGGCTCCAAGTCTGGCAACACG
GCCTCCCTGACCGTCTCTGGGCTCCAGGCTGAGGATGAGGCTGAATATTACTGCAGCTCATACACAGACATC
CACAATTTCGTCTTCGGCGGAGGGACCAAGCTGACCGTCCTA (SEQ ID NO:76)

>A32VH
QVQLCGVGPGLVKPSQTLSLSCTVSGGSSSSGAHYWSWIRQYPGKGLEWIGYIHYSGNTYYNPSLKSRITIS
QHTSENQFSLKLNSVTVADTAVYYCARGTRLRTLRNAFDIWGQGTRVTVSS (SEQ ID NO:77)

>A32VL
QSALTQPPSASGSPGQSVTISCTGTSSDVGGYNYVSWYQHHPGKAPKLIISEVNNRPSGVPDRFSGSKSGNT
ASLTVSGLQAEDEAEYYCSSYTDIHNFVFGGGTKLTVL (SEQ ID NO:78)

Figure 6

>7B2VH
CAGGTGCAGCTGGTGCAGTCTGGGGGAGGCGTTTTCAAGCCTGGAGGGTCCCTGAGACTCTCCTG
TGAAGCCTCTGGATTCACATTTACTGAATATTACATGACTTGGGTCCGCCAGGCTCCTGGGAAGG
GGCTGGAGTGGCTTGCGTATATTAGTAAGAATGGTGAATATTCAAAATATTCACCGTCCTCAAAC
GGCCGGTTCACCATCTCCAGAGACAACGCCAAGAACTCAGTGTTTCTGCAATTGGACAGACTGAG
CGCCGACGACACGGCCGTCTATTACTGTGCGAGAGCGGACGGATTAACATACTTCTCTGAATTAC
TCCAATACATTTTTGACCTCTGGGGCCAGGGAGCCCGGGTCACCGTCTCCTCG(SEQ ID NO:79)

>7B2VH
METDTLLLWVLLLWVPGSTGDQVQLVQSGGGVFKPGGSLRLSCEASGFTFTEYYMTWVRQAPGKG
LEWLAYISKNGEYSKYSPSSNGRFTISRDNAKNSVFLQLDRLSADDTAVYYCARADGLTYFSELL
QYIFDLWGQGARVTVSS(SEQ ID NO:80)

>7B2VK
METDTLLLWVLLLWVPGSTGDETTLTQSPDSLAVSPGERATIHCKSSQTLLYSSNNRHSIAWYQQ
RPGQPPKLLLYWASMRLSGVPDRFSGSGSGTDFTLTINNLQAEDVAIYYCHQYSSHPPTFGHGTR
VELR (SEQ ID NO:81)
>7B2VK
GAAACGACACTCACGCAGTCTCCAGACTCCCTGGCTGTGTCTCCGGGCGAGAGGGCCACCATCCA
CTGCAAGTCCAGCCAGACTCTTTTGTACAGCTCCAACAATAGACACTCCATTGCTTGGTACCAAC
AGAGACCAGGACAGCCTCCTAAATTACTCCTTTATTGGGCATCTATGCGGCTTTCCGGGGTCCCT
GACCGATTCAGTGGCAGCGGGTCTGGGACAGATTTCACTCTCACCATCAACAACCTGCAGGCTGA
GGATGTGGCCATCTATTACTGTCACCAATATTCCAGTCATCCCCCGACGTTCGGCCACGGGACCA
GGGTGGAGCTCAGA (SEQ ID NO:82)

Figure 7

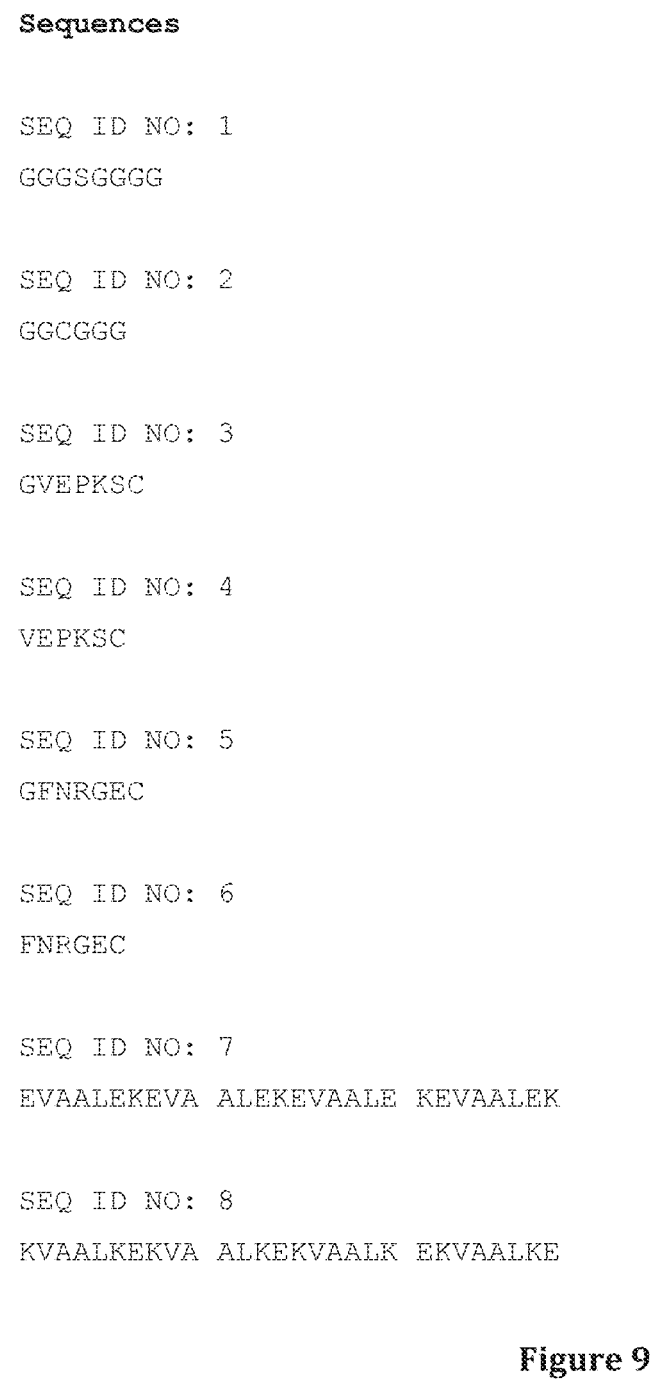

Sequences

SEQ ID NO: 1
GGGSGGGG

SEQ ID NO: 2
GGCGGG

SEQ ID NO: 3
GVEPKSC

SEQ ID NO: 4
VEPKSC

SEQ ID NO: 5
GFNRGEC

SEQ ID NO: 6
FNRGEC

SEQ ID NO: 7
EVAALEKEVA ALEKEVAALE KEVAALEK

SEQ ID NO: 8
KVAALKEKVA ALKEKVAALK EKVAALKE

Figure 9

SEQ ID NO: 9

QSALTQPPSA SGSPGQSVTI SCTGTSSDVG GYNYVSWYQH HPGKAPKLII
SEVNNRPSGV PDRFSGSKSG NTASLTVSGL QAEDEAEYYC SSYTDIHNFV
FGGGTKLTVL GGGSGGGGEV QLVESGGGLV QPGGSLRLSC AASGFTFSTY
AMNWVRQAPG KGLEWVGRIR SKYNNYATYY ADSVKGRFTI SRDDSKNSLY
LQMNSLKTED TAVYYCVRHG NFGNSYVSWF AYWGQGTLVT VSSGGCGGGE
VAALEKEVAA LEKEVAALEK EVAALEK

SEQ ID NO: 10 cagagcgcac tgactcagcc cccttccgcc tccgggtctc ctggacagag cgtgacaatc
tcatgcactg ggacttcaag cgatgtgggc gggtacaact atgtgagttg gtaccagcac
catcccggga aggcacctaa actgatcatt agcgaagtga acaatcgacc aagcggcgtc
cccgaccggt tcagcggcag caagtctggc aataccgcca gtctgacagt ctcaggcctg
caggccgagg atgaagctga gtactattgc tcatcataca ctgacatcca taacttcgtc
ttcggcggcg gaactaaact gaccgtgctg ggtggcggat ccggcggcgg aggcgaggtg
cagctggtgg agtctggggg aggcttggtc cagcctggag ggtccctgag actctcctgt
gcagcctctg gattcacctt cagcacatac gctatgaatt gggtccgcca ggctccaggg
aaggggctgg agtgggttgg aaggatcagg tccaagtaca acaattatgc aacctactat
gccgactctg tgaagggtag attcaccatc tcaagagatg attcaaagaa ctcactgtat
ctgcaaatga acagcctgaa aaccgaggac acggccgtgt attactgtgt gagacacggt
aacttcggca attcttacgt gtcttggttt gcttattggg gacaggggac actggtgact
gtgtcttccg gaggatgtgg cggtggagaa gtggccgcac tggagaaaga ggttgctgct
ttggagaagg aggtcgctgc acttgaaaag gaggtcgcag ccctggagaa a

SEQ ID NO: 11

QAVVTQEPSL TVSPGGTVTL TCRSSTGAVT TSNYANWVQQ KPGQAPRGLI GGTNKRAPWT
PARFSGSLLG GKAALTITGA QAEDEADYYC ALWYSNLWVF GGGTKLTVLG GGGSGGGGQV
QLQESGPGLV KPSQTLSLSC TVSGGSSSSG AHYWSWIRQY PGKGLEWIGY IHYSGNTYYN
PSLKSRITIS QHTSENQFSL KLNSVTVADT AVYYCARGTR LRTLRNAFDI WGQGTLVTVS
SGGCGGGKVA ALKEKVAALK EKVAALKEKV AALKE

Figure 9 cont.

SEQ ID NO: 12 caggctgtgg tgactcagga gccttcactg accgtgtccc caggcggaac tgtgaccctg
acatgcagat ccagcacagg cgcagtgacc acatctaact acgccaattg ggtgcagcag
aagccaggac aggcaccaag gggcctgatc ggggtacaa acaaaagggc tccctggacc
cctgcacggt ttctggaag tctgctgggc ggaaaggccg ctctgactat taccggggca
caggccgagg acgaagccga ttactattgt gctctgtggt atagcaatct gtgggtgttc
gggggtggca caaaactgac tgtgctggga gggggtggat ccggcggcgg aggccaggtg
cagctgcagg agtccggccc cggactggtc aaaccctctc agactctgtc tctgtcatgt
accgtgtcag gcggctcttc cagctccggg gcacactact ggagctggat caggcagtat
cccggcaagg ggctggagtg gatcggatac attcattata gcggcaacac atactataat
ccttctctga agagtcggat cactatttca cagcacacca gcgaaaacca gttcagcctg
aagctgaaca gcgtgaccgt cgccgacaca gccgtgtact attgcgcccg gggcaccaga
ctgagaactc tgagaaacgc atttgacatc tggggacagg ggacactggt gacagtgagc
tccggaggat gtggcggtgg aaaagtggcc gcactgaagg agaaagttgc tgctttgaaa
gagaaggtcg ccgcacttaa ggaaaaggtc gcagccctga aagag

SEQ ID NO: 13

DIVMTQSPDS LAVSPGERAT IHCKSSQTLL YSSNNRHSIA WYQQRPGQPP KLLLYWASMR
LSGVPDRFSG SGSGTDFTLT INNLQAEDVA IYYCHQYSSH PPTFGHGTRV EIKGGGSGGG
GEVQLVESGG GLVQPGGSLR LSCAASGFTF STYAMNWVRQ APGKGLEWVG RIRSKYNNYA
TYYADSVKGR FTISRDDSKN SLYLQMNSLK TEDTAVYYCV RHGNFGNSYV SWFAYWGQGT
LVTVSSGGCG GGEVAALEKE VAALEKEVAA LEKEVAALEK

SEQ ID NO: 14 gacatcgtga tgacccagtc tccagactcc ctggctgtgt ctccgggcga gagggccacc
atccactgca agtccagcca gactcttttg tacagctcca acaatagaca ctccattgct
tggtaccaac agagaccagg acagcctcct aaattactcc tttattgggc atctatgcgg
ctttccgggg tccctgaccg attcagtggc agcgggtctg ggacagattt cactctcacc
atcaacaacc tgcaggctga ggatgtggcc atctattact gtcaccaata ttccagtcat
cccccgacgt tcggccacgg gaccagggtg gagatcaaag gtggaggatc cggcggcgga
ggcgaggtgc agctggtgga gtctggggga ggcttggtcc agcctggagg gtccctgaga
ctctcctgtg cagcctctgg attcaccttc agcacatacg ctatgaattg ggtccgccag

Figure 9 cont.

gctccaggga aggggctgga gtgggttgga aggatcaggt ccaagtacaa caattatgca
acctactatg ccgactctgt gaagggtaga ttcaccatct caagagatga ttcaaagaac
tcactgtatc tgcaaatgaa cagcctgaaa accgaggaca cggccgtgta ttactgtgtg
agacacggta acttcggcaa ttcttacgtg tcttggtttg cttattgggg acaggggaca
ctggtgactg tgtcttccgg aggatgtggc ggtggagaag tggccgcact ggagaaagag
gttgctgctt tggagaagga ggtcgctgca cttgaaaagg aggtcgcagc cctggagaaa SEQ ID NO: 15
QAVVTQEPSL TVSPGGTVTL TCRSSTGAVT TSNYANWVQQ KPGQAPRGLI GGTNKRAPWT
PARFSGSLLG GKAALTITGA QAEDEADYYC ALWYSNLWVF GGGTKLTVLG GGGSGGGGQV
QLVQSGGGVF KPGGSLRLSC EASGFTFTEY YMTWVRQAPG KGLEWLAYIS KNGEYSKYSP
SSNGRFTISR DNAKNSVFLQ LDRLSADDTA VYYCARADGL TYFSELLQYI FDLWGQGARV
TVSSGGCGGG KVAALKEKVA ALKEKVAALK EKVAALKE SEQ ID NO: 16
caggctgtgg tgactcagga gccttcactg accgtgtccc caggcggaac tgtgaccctg
acatgcagat ccagcacagg cgcagtgacc acatctaact acgccaattg ggtgcagcag
aagccaggac aggcaccaag ggcctgatc gggggtacaa acaaaagggc tccctggacc
cctgcacggt ttctggaag tctgctgggc ggaaaggccg ctctgactat taccggggca
caggccgagg acgaagccga ttactattgt gctctgtggt atagcaatct gtgggtgttc
gggggtggca caaaactgac tgtgctggga gggggtggat ccggcggagg tggacaggtg
cagctggtgc agtctggggg aggcgttttc aagcctggag ggtccctgag actctcctgt
gaagcctctg gattcacatt tactgaatat tacatgactt gggtccgcca ggctcctggg
aaggggctgg agtggcttgc gtatattagt aagaatggtg aatattcaaa atattcaccg
tcctcaaacg gccggttcac catctccaga gacaacgcca agaactcagt gtttctgcaa
ttggacagac tgagcgccga cgacacggcc gtctattact gtgcgagagc ggacggatta
acatacttct ctgaattact ccaatacatt tttgacctct ggggccaggg agcccgggtc
accgtctcct ccggaggatg tggcggtgga aaagtggccg cactgaagga gaaagttgct
gctttgaaag agaaggtcgc cgcacttaag gaaaaggtcg cagccctgaa agag

Figure 9 cont.

SEQ ID NO: 17

EIVLTQSPGT LSLSPGERAT LSCRANRRID MNALAWYQHR SGQAPRLLTH GVYNRATGIP
DRFSGYWSGP EFTLVISRLE PEDFAVYYCV HFLYENPAWA FGQGTKLEIK GGGSGGGGEV
QLVESGGGLV QPGGSLRLSC AASGFTFSTY AMNWVRQAPG KGLEWVGRIR SKYNNYATYY
ADSVKGRFTI SRDDSKNSLY LQMNSLKTED TAVYYCVRHG NFGNSYVSWF AYWGQGTLVT
VSSASTKGEV AACEKEVAAL EKEVAALEKE VAALEK

SEQ ID NO: 18 gaaattgtgt tgacgcagtc tccaggcacc ctgtccttgt ctccagggga gagagccacc
ctctcctgca gggccaatcg gcggattgac atgaacgcct tggcctggta ccagcaccga
tctggccagg ctcccaggct cctcacccat ggtgtctata acagggccac tggcatccca
gacaggttca gtggctattg gtctgggcca gagttcaccc tcgtcatcag cagactggag
cctgaagatt ttgcagtcta ttactgtgta cactttctct acgaaaatcc agcgtgggcg
ttcggccagg ggaccaagct ggagatcaag ggtggaggat ccggcggcgg aggcgaggtg
cagctggtgg agtctggggg aggcttggtc cagcctggag ggtccctgag actctcctgt
gcagcctctg gattcacctt cagcacatac gctatgaatt gggtccgcca ggctccaggg
aaggggctgg agtgggttgg aaggatcagg tccaagtaca acaattatgc aacctactat
gccgactctg tgaagggtag attcaccatc tcaagagatg attcaaagaa ctcactgtat
ctgcaaatga acagcctgaa aaccgaggac acggccgtgt attactgtgt gagacacggt
aacttcggca attcttacgt gtcttggttt gcttattggg gacaggggac actggtgact
gtgtcttccg cctccaccaa gggcgaagtg gccgcatgtg agaaagaggt tgctgctttg
gagaaggagg tcgctgcact tgaaaaggag gtcgcagccc tggagaaa

SEQ ID NO: 19

QAVVTQEPSL TVSPGGTVTL TCRSSTGAVT TSNYANWVQQ KPGQAPRGLI GGTNKRAPWT
PARFSGSLLG GKAALTITGA QAEDEADYYC ALWYSNLWVF GGGTKLTVLG GGGSGGGGEV
QLVESGGGVV HPGGSLRLSC AASGFSVRND QMAWVRQAPG KRLEWVSIIN DGASPYYADS
VKGRFAMSRD TSKNTVFLQM NSLRRDDTAV YFCARGIASF FDVWGRGTLV TVSSASTKGK
VAACKEKVAA LKEKVAALKE KVAALKE

Figure 9 cont.

SEQ ID NO: 20 caggctgtgg tgactcagga gccttcactg accgtgtccc caggcggaac tgtgaccctg
acatgcagat ccagcacagg cgcagtgacc acatctaact acgccaattg ggtgcagcag
aagccaggac aggcaccaag gggcctgatc gggggtacaa acaaaagggc tccctggacc
cctgcacggt ttctggaag tctgctgggc ggaaaggccg ctctgactat taccggggca
caggccgagg acgaagccga ttactattgt gctctgtggt atagcaatct gtgggtgttc
gggggtggca caaaactgac tgtgctggga gggggtggat ccggcggagg tggagaggtg
cagctggtgg agtctggagg tggcgtggtc caccctggag gaagcctgag actctcctgt
gcagcctctg gattcagcgt caggaacgac cagatggcct gggtccgcca ggctccaggg
aagcgactgg agtgggtctc tattattaac gatggtgcta gtccatacta cgcagactct
gtgaagggcc gcttcgccat gtccagagac acctccaaga atacagtgtt tcttcagatg
aacagcctga gacgtgacga cacagctgtt tatttctgtg cgagggggat cgcctcattc
ttcgatgtct ggggccgtgg cacgctggtc actgtctcgt cagcctccac caagggcaaa
gtggccgcat gtaaggagaa agttgctgct ttgaaagaga aggtcgccgc acttaaggaa
aaggtcgcag ccctgaaaga
g

SEQ ID NO: 21

EIVLTQSPAI LSVSPGETAT LSCRASRRVD MNGLAWYQHR PGQAPRLLMH GVYNRAAGIS
GRFTGSWSGP VFTLTISRLE PEDFGVYYCQ HFYYETSAWA FGQGTRLEIK GGGSGGGGEV
QLVESGGGLV QPGGSLRLSC AASGFTFSTY AMNWVRQAPG KGLEWVGRIR SKYNNYATYY
ADSVKGRFTI SRDDSKNSLY LQMNSLKTED TAVYYCVRHG NFGNSYVSWF AYWGQGTLVT
VSSASTKGEV AACEKEVAAL EKEVAALEKE VAALEK

SEQ ID NO: 22 gaaattgtgt tgacgcagtc tccagccatc ctgtctgtgt ctccagggga aaccgccacc
ctctcctgca gggccagtcg ccgtgttgac atgaacggcc tcgcctggta ccaacacagg
cctggccagg ctcccaggct cctcatgcat ggtgtttata atagggccgc cggcatctca
ggcaggttca ctggcagttg gtctgggcca gtcttcactc tcaccatcag cagactggag
cctgaagatt ttggagtcta ttactgtcaa cacttttact atgagacttc agcgtgggcg
ttcggccagg ggaccaggct ggagatcaaa ggtggaggat ccggcggcgg aggcgaggtg
cagctggtgg agtctggggg aggcttggtc cagcctggag ggtccctgag actctcctgt

Figure 9 cont.

gcagcctctg gattcacctt cagcacatac gctatgaatt gggtccgcca ggctccaggg
aaggggctgg agtgggttgg aaggatcagg tccaagtaca acaattatgc aacctactat
gccgactctg tgaagggtag attcaccatc tcaagagatg attcaaagaa ctcactgtat
ctgcaaatga acagcctgaa aaccgaggac acggccgtgt attactgtgt gagacacggt
aacttcggca attcttacgt gtcttggttt gcttattggg gacaggggac actggtgact
gtgtcttccg cctccaccaa gggcgaagtg gccgcatgtg agaaagaggt tgctgctttg
gagaaggagg tcgctgcact tgaaaaggag gtcgcagccc tggagaaa SEQ ID NO: 23
QAVVTQEPSL TVSPGGTVTL TCRSSTGAVT TSNYANWVQQ KPGQAPRGLI GGTNKRAPWT
PARFSGSLLG GKAALTITGA QAEDEADYYC ALWYSNLWVF GGGTKLTVLG GGGSGGGGEV
QLVESGGGVV HPGGSLRLSC AASGFSVSHD FMAWIRQAPG KGLEWISIIY NTGSRYYYAD
SVKGRFALSR DTSNNTLILH MSGLRRDDTA IYFCARGVAS FFELWGRGTL VTVSSASTKG
KVAACKEKVA ALKEKVAALK EKVAALKE SEQ ID NO: 24
caggctgtgg tgactcagga gccttcactg accgtgtccc caggcggaac tgtgaccctg
acatgcagat ccagcacagg cgcagtgacc acatctaact acgccaattg ggtgcagcag
aagccaggac aggcaccaag ggcctgatc gggggtacaa acaaaagggc tccctggacc
cctgcacggt ttctggaag tctgctgggc ggaaaggccg ctctgactat taccggggca
caggccgagg acgaagccga ttactattgt gctctgtggt atagcaatct gtgggtgttc
gggggtggca caaaactgac tgtgctggga gggggtggat ccggcggagg tggagaggtg
cagctggtgg agtctggagg tggcgtggtc caccctggag gaagcctgag actctcctgt
gcagcctctg gattcagcgt cagtcacgac ttcatggcct ggatcaggca ggctccagga
aagggactgg agtggatctc tatcatatat aacactggtt ctcgatacta ctacgcagac
tctgtgaagg gccgcttcgc cctctccaga gatacgtcca acaacacact gattcttcac
atgagcggcc tgagacgtga cgacacggct atttatttct gtgccagggg agtcgcctcg
ttctttgaat tgtggggccg tggcaccctg gtcactgtct cgtcagcctc caccaagggc
aaagtggccg catgtaagga gaaagttgct gctttgaaag agaaggtcgc cgcacttaag
gaaaaggtcg cagccctgaa
agag

Figure 9 cont.

SEQ ID NO: 25

DIVMTQSPDS LAVSPGERAT IHCKSSQTLL YSSNNRHSIA WYQQRPGQPP KLLLYWASMR
LSGVPDRFSG SGSGTDFTLT INNLQAEDVA IYYCHQYSSH PPTFGHGTRV EIKGGGSGGG
GQVTLRESGP ALVKPTQTLT LTCTFSGFSL STSGMGVGWI RQPPGKALEW LAHIWWDDDK
RYNPALKSRL TISKDTSKNQ VVLTMTNMDP VDTATYYCAQ INPAWFAYWG QGTLVTVSSG
GCGGGEVAAL EKEVAALEKE VAALEKEVAA LEK

SEQ ID NO: 26 gacatcgtga tgacccagtc tccagactcc ctggctgtgt ctccgggcga gagggccacc
atccactgca agtccagcca gactcttttg tacagctcca acaatagaca ctccattgct
tggtaccaac agagaccagg acagcctcct aaattactcc tttattgggc atctatgcgg
ctttccgggg tccctgaccg attcagtggc agcgggtctg ggacagattt cactctcacc
atcaacaacc tgcaggctga ggatgtggcc atctattact gtcaccaata ttccagtcat
cccccgacgt tcggccacgg gaccagggtg gagatcaaag gtggaggatc cggcggcgga
ggccaggtta ccctgagaga gtctggccct gcgctggtga agcccacaca gaccctcaca
ctgacttgta ccttctctgg gttttcactg agcacttctg gtatgggtgt aggctggatt
cgtcagcctc ccgggaaggc tctagagtgg ctggcacaca tttggtggga tgatgacaag
cgctataatc cagccctgaa gagccgactg acaatctcca aggatacctc caaaaaccag
gtagtcctca caatgaccaa catggacccc gtggatactg ccacatacta ctgtgctcaa
ataaaccccg cctggtttgc ttactggggc caagggactc tggtcactgt gagctccgga
ggatgtggcg gtggagaagt ggccgcactg gagaaagagg ttgctgcttt ggagaaggag
gtcgctgcac ttgaaaagga ggtcgcagcc ctggagaaa

SEQ ID NO: 27

DIVMTQSPDS LAVSLGERAT INCKASQSVD FDGDSFMNWY QQKPGQPPKL LIYTTSNLES
GVPDRFSGSG SGTDFTLTIS SLQAEDVAVY YCQQSNEDPY TFGQGTKLEI KGGGSGGGGQ
VQLVQSGGGV FKPGGSLRLS CEASGFTFTE YYMTWVRQAP GKGLEWLAYI SKNGEYSKYS
PSSNGRFTIS RDNAKNSVFL QLDRLSADDT AVYYCARADG LTYFSELLQY IFDLWGQGAR
VTVSSGGCGG GKVAALKEKV AALKEKVAAL KEKVAALKE

Figure 9 cont.

SEQ ID NO: 28 gacatcgtga tgacccaatc tccagactct ttggctgtgt ctctagggga gagggccacc
atcaactgca aggccagcca aagtgttgat tttgatggtg atagttttat gaactggtac
caacagaaac caggacagcc acccaaactc ctcatctata ctacatccaa tctagaatct
ggggtcccag acaggtttag tggcagtggg tctgggacag acttcaccct caccatcagc
agcctgcagg ctgaggatgt ggcagtttat tactgtcagc aaagtaatga agatccgtac
acgttcggac aggggaccaa gcttgagatc aaaggaggcg gatccggcgg aggtggacag
gtgcagctgg tgcagtctgg gggaggcgtt ttcaagcctg gagggtccct gagactctcc
tgtgaagcct ctggattcac atttactgaa tattacatga cttgggtccg ccaggctcct
gggaaggggc tggagtggct tgcgtatatt agtaagaatg gtgaatattc aaaatattca
ccgtcctcaa acggccggtt caccatctcc agagacaacg ccaagaactc agtgtttctg
caattggaca gactgagcgc cgacgacacg gccgtctatt actgtgcgag agcggacgga
ttaacatact tctctgaatt actccaatac atttttgacc tctggggcca gggagcccgg
gtcaccgtct cctccggagg atgtggcggt ggaaaagtgg ccgcactgaa ggagaaagtt
gctgctttga aagagaaggt cgccgcactt aaggaaaagg tcgcagccct gaaagag

SEQ ID NO: 29

QAVVTQEPSL TVSPGGTVTL TCRSSTGAVT TSNYANWVQQ KPGQAPRGLI GGTNKRAPWT
PARFSGSLLG GKAALTITGA QAEDEADYYC ALWYSNLWVF GGGTKLTVLG GGGSGGGGEV
KLDETGGGLV QPGRPMKLSC VASGFTFSDY WMNWVRQSPE KGLEWVAQIR NKPYNYETYY
SDSVKGRFTI SRDDSKSSVY LQMNNLRVED MGIYYCTGSY YGMDYWGQGT SVTVSSGGCG
GGEVAALEKE VAALEKEVAA LEKEVAALEK

SEQ ID NO: 30

DVVMTQTPFS LPVSLGDQAS ISCRSSQSLV HSNGNTYLRW YLQKPGQSPK VLIYKVSNRF
SGVPDRFSGS GSGTDFTLKI SRVEAEDLGV YFCSQSTHVP WTFGGGTKLE IKGGGSGGGG
QVQLQESGPG LVKPSQTLSL SCTVSGGSSS SGAHYWSWIR QYPGKGLEWI GYIHYSGNTY
YNPSLKSRIT ISQHTSENQF SLKLNSVTVA DTAVYYCARG TRLRTLRNAF DIWGQGTLVT
VSSGGCGGGK VAALKEKVAA LKEKVAALKE KVAALKE

Figure 9 cont.

SEQ ID NO: 31
DVVMTQTPFS LPVSLGDQAS ISCRSSQSLV HSNGNTYLRW YLQKPGQSPK VLIYKVSNRF
SGVPDRFSGS GSGTDFTLKI SRVEAEDLGV YFCSQSTHVP WTFGGGTKLE IKGGGSGGGG
QVTLRESGPA LVKPTQTLTL TCTFSGFSLS TSGMGVGWIR QPPGKALEWL AHIWWDDDKR
YNPALKSRLT ISKDTSKNQV VLTMTNMDPV DTATYYCAQI NPAWFAYWGQ GTLVTVSSGG
CGGGEVAALE KEVAALEKEV AALEKEVAAL EK

SEQ ID NO: 32
DIVMTQSPDS LAVSLGERAT INCKASQSVD FDGDSFMNWY QQKPGQPPKL LIYTTSNLES
GVPDRFSGSG SGTDFTLTIS SLQAEDVAVY YCQQSNEDPY TFGQGTKLEI KGGGSGGGGE
VKLDETGGGL VQPGRPMKLS CVASGFTFSD YWMNWVRQSP EKGLEWVAQI RNKPYNYETY
YSDSVKGRFT ISRDDSKSSV YLQMNNLRVE DMGIYYCTGS YYGMDYWGQG TSVTVSSGGC
GGGKVAALKE KVAALKEKVA ALKEKVAALK E

SEQ ID NO: 33
DIVMTQSPDS LAVSPGERAT IHCKSSQTLL YSSNNRHSIA WYQQRPGQPP KLLLYWASMR
LSGVPDRFSG SGSGTDFTLT INNLQAEDVA IYYCHQYSSH PPTFGHGTRV EIKGGGSGGG
GEVKLDETGG GLVQPGRPMK LSCVASGFTF SDYWMNWVRQ SPEKGLEWVA QIRNKPYNYE
TYYSDSVKGR FTISRDDSKS SVYLQMNNLR VEDMGIYYCT GSYYGMDYWG QGTSVTVSSG
GCGGGEVAAL EKEVAALEKE VAALEKEVAA LEK

SEQ ID NO: 34
DVVMTQTPFS LPVSLGDQAS ISCRSSQSLV HSNGNTYLRW YLQKPGQSPK VLIYKVSNRF
SGVPDRFSGS GSGTDFTLKI SRVEAEDLGV YFCSQSTHVP WTFGGGTKLE IKGGGSGGGG
QVQLVQSGGG VFKPGGSLRL SCEASGFTFT EYYMTWVRQA PGKGLEWLAY ISKNGEYSKY
SPSSNGRFTI SRDNAKNSVF LQLDRLSADD TAVYYCARAD GLTYFSELLQ YIFDLWGQGA
RVTVSSGGCG GGKVAALKEK VAALKEKVAA LKEKVAALKE

SEQ ID NO: 35
QSALTQPPSA SGSPGQSVTI SCTGTSSDVG GYNYVSWYQH HPGKAPKLII SEVNNRPSGV
PDRFSGSKSG NTASLTVSGL QAEDEAEYYC SSYTDIHNFV FGGGTKLTVL GGGSGGGGEV
KLDETGGGLV QPGRPMKLSC VASGFTFSDY WMNWVRQSPE KGLEWVAQIR NKPYNYETYY
SDSVKGRFTI SRDDSKSSVY LQMNNLRVED MGIYYCTGSY YGMDYWGQGT SVTVSSGGCG
GGEVAALEKE VAALEKEVAA LEKEVAALEK

SEQ ID NO: 36
DVVMTQTPFS LPVSLGDQAS ISCRSSQSLV HSNGNTYLRW YLQKPGQSPK VLIYKVSNRF
SGVPDRFSGS GSGTDFTLKI SRVEAEDLGV YFCSQSTHVP WTFGGGTKLE IKGGGSGGGG
QVQLQESGPG LVKPSQTLSL SCTVSGGSSS SGAHYWSWIR QYPGKGLEWI GYIHYSGNTY
YNPSLKSRIT ISQHTSENQF SLKLNSVTVA DTAVYYCARG TRLRTLRNAF DIWGQGTLVT
VSSGGCGGGK VAALKEKVAA LKEKVAALKE KVAALKE

Figure 9 cont.

SEQ ID NO: 37

QAVVTQEPSL TVSPGGTVTL TCRSSTGAVT TSNYANWVQQ KPGQAPRGLI GGTNKRAPWT
PARFSGSLLG GKAALTITGA QAEDEADYYC ALWYSNLWVF GGGTKLTVLG GGGSGGGGQV
TLRESGPALV KPTQTLTLTC TFSGFSLSTS GMSVGWIRQP PGKALEWLAD IWWDDKKDYN
PSLKSRLTIS KDTSKNQVVL KVTNMDPADT ATYYCARSMI TNWYFDVWGA GTTVTVSSGG
CGGGEVAALE KEVAALEKEV AALEKEVAAL EK

SEQ ID NO 38

DIQMTQSPST LSASVGDRVT ITCRASQSVG YMHWYQQKPG KAPKLLIYDT SKLASGVPSR
FSGSGSGTEF TLTISSLQPD DFATYYCFQG SGYPFTFGGG TKLEIKGGGS GGGGEVQLVE
SGGGLVQPGG SLRLSCAASG FTFSTYAMNW VRQAPGKGLE WVGRIRSKYN NYATYYADSV
KGRFTISRDD SKNSLYLQMN SLKTEDTAVY YCVRHGNFGN SYVSWFAYWG QGTLVTVSSG
GCGGGKVAAL KEKVAALKEK VAALKEKVAA LKE

SEQ ID NO: 39

APSSS

SEQ ID NO: 40

APSSSPME

SEQ ID NO: 41

APELLGGPSV FLFPPKPKDT LMISRTPEVT CVVVDVSHED PEVKFNWYVD GVEVHNAKTK
PREEQYNSTY RVVSVLTVLH QDWLNGKEYK CKVSNKALPA PIEKTISKAK GQPREPQVYT
LPPSREEMTK NQVSLTCLVK GFYPSDIAVE WESNGQPENN YKTTPPVLDS DGSFFLYSKL
TVDKSRWQQG NVFSCSVMHE ALHNHYTQKS LSLSPGK

SEQ ID NO:42

APEAAGGPSV FLFPPKPKDT LMISRTPEVT CVVVDVSHED PEVKFNWYVD GVEVHNAKTK
PREEQYNSTY RVVSVLTVLH QDWLNGKEYK CKVSNKALPA PIEKTISKAK GQPREPQVYT
LPPSREEMTK NQVSLWCLVK GFYPSDIAVE WESNGQPENN YKTTPPVLDS DGSFFLYSKL
TVDKSRWQQG NVFSCSVMHE ALHNHYTQKS LSLSPGK

SEQ ID NO: 43

APEAAGGPSV FLFPPKPKDT LMISRTPEVT CVVVDVSHED PEVKFNWYVD GVEVHNAKTK
PREEQYNSTY RVVSVLTVLH QDWLNGKEYK CKVSNKALPA PIEKTISKAK GQPREPQVYT
LPPSREEMTK NQVSLSCAVK GFYPSDIAVE WESNGQPENN YKTTPPVLDS DGSFFLVSKL
TVDKSRWQQG NVFSCSVMHE ALHNRYTQKS LSLSPGK

Figure 9 cont.

SEQ ID NO: 44
SQSALTQPPS ASGSPGQSVT ISCTGTSSDV GGYNYVSWYQ HHPGKAPKLI ISEVNNRPSG
VPDRFSGSKS GNTASLTVSG LQAEDEAEYY CSSYTDIHNF VFGGGTKLTV LGGGSGGGGQ
VTLRESGPAL VKPTQTLTLT CTFSGFSLST SGMGVGWIRQ PPGKALEWLA HIWWDDDKRY
NPALKSRLTI SKDTSKNQVV LTMTNMDPVD TATYYCAQIN PAWFAYWGQG TLVTVSSGGC
GGGEVAALEK EVAALEKEVA ALEKEVAALE K

SEQ ID NO: 45
DIVMTQSPDS LAVSLGERAT INCKASQSVD FDGDSFMNWY QQKPGQPPKL LIYTTSNLES
GVPDRFSGSG SGTDFTLTIS SLQAEDVAVY YCQQSNEDPY TFGQGTKLEI KGGGSGGGGQ
VQLQESGPGL VKPSQTLSLS CTVSGGSSSS GAHYWSWIRQ YPGKGLEWIG YIHYSGNTYY
NPSLKSRITI SQHTSENQFS LKLNSVTVAD TAVYYCARGT RLRTLRNAFD IWGQGTLVTV
SSGGCGGGKV AALKEKVAAL KEKVAALKEK VAALKE

SEQ ID NO: 46
DIVMTQSPDS LAVSPGERAT IHCKSSQTLL YSSNNRHSIA WYQQRPGQPP KLLLYWASMR
LSGVPDRFSG SGSGTDFTLT INNLQAEDVA IYYCHQYSSH PPTFGHGTRV EIKGGGSGGG
GEVQLVESGG GLVQPGGSLR LSCAASGFTF STYAMNWVRQ APGKGLEWVG RIRSKYNNYA
TYYADSVKGR FTISRDDSKN SLYLQMNSLK TEDTAVYYCV RHGNFGNSYV SWFAYWGQGT
LVTVSSGGCG GGEVAALEKE VAALEKEVAA LEKEVAALEK GGGDKTHTCP PCPAPEAAGG
PSVFLFPPKP KDTLMISRTP EVTCVVVDVS HEDPEVKFNW YVDGVEVHNA KTKPREEQYN
STYRVVSVLT VLHQDWLNGK EYKCKVSNKA LPAPIEKTIS KAKGQPREPQ VYTLPPSREE
MTKNQVSLWC LVKGFYPSDI AVEWESNGQP ENNYKTTPPV LDSDGSFFLY SKLTVDKSRW
QQGNVFSCSV MHEALHNHYT QKSLSLSPGK

SEQ ID NO: 47

QAVVTQEPSL TVSPGGTVTL TCRSSTGAVT TSNYANWVQQ KPGQAPRGLI GGTNKRAPWT
PARFSGSLLG GKAALTITGA QAEDEADYYC ALWYSNLWVF GGGTKLTVLG GGGSGGGGQV
QLVQSGGGVF KPGGSLRLSC EASGFTFTEY YMTWVRQAPG KGLEWLAYIS KNGEYSKYSP
SSNGRFTISR DNAKNSVFLQ LDRLSADDTA VYYCARADGL TYFSELLQYI FDLWGQGARV
TVSSGGCGGG KVAALKEKVA ALKEKVAALK EKVAALKE

SEQ ID NO: 48
APEAAGGPSV FLFPPKPKDT LMISRTPEVT CVVVDVSHED PEVKFNWYVD GVEVHNAKTK
PREEQYNSTY RVVSVLTVLH QDWLNGKEYK CKVSNKALPA PIEKTISKAK GQPREPQVYT
LPPSREEMTK NQVSLSCAVK GFYPSDIAVE WESNGQPENN YKTTPPVLDS DGSFFLVSKL
TVDKSRWQQG NVFSCSVMHE ALHNRYTQKS LSLSPGK

Figure 9 cont.

SEQ ID NO: 49 (Linker 3)
DKTHTCPPCP

SEQ ID NO: 50 (Spacer Linker 3)
GGGDKTHTCPPCP

SEQ ID NO: 51 (VH CD3)
EVQLVESGGG LVQPGGSLRL SCAASGFTFS TYAMNWVRQA PGKGLEWVGR IRSKYNNYAT YYADSVKGRF TISRDDSKNS LYLQMNSLKT EDTAVYYCVR HGNFGNSYVS WFAYWGQGTL VTVSS

SEQ ID NO: 52 (VL CD3)
QAVVTQEPSL TVSPGGTVTL TCRSSTGAVT TSNYANWVQQ KPGQAPRGLI GGTNKRAPWT PARFSGSLLG GKAALTITGA QAEDEADYYC ALWYSNLWVF GGGTKLTVLG

SEQ ID NO: 53 (VH CD16)
QVTLRESGP ALVKPTQTLT LTCTFSGFSL STSGMGVGWI RQPPGKALEW LAHIWWDDDK RYNPALKSRL TISKDTSKNQ VVLTMTNMDP VDTATYYCAQ INPAWFAYWG QGTLVTVSS

SEQ ID NO: 54 (VL CD16)
DIVMTQSPDS LAVSLGERAT INCKASQSVD FDGDSFMNWY QQKPGQPPKL LIYTTSNLES GVPDRFSGSG SGTDFTLTIS SLQAEDVAVY YCQQSNEDPY TFGQGTKLEI K

SEQ ID NO: 55 (VL 7B2 GenBank: AFQ31503.1DIVMTQSPDS LAVSPGERAT IHCKSSQTLL YSSNNRHSIA WYQQRPGQPP KLLLYWASMR LSGVPDRFSG SGSGTDFTLT INNLQAEDVA IYYCHQYSSH PPTFGHGTRV SEQ ID NO: 56 (VH 7B2 GenBank: AFQ31502.1)
QVQLVQSGGG VFKPGGSLRL SCEASGFTFT EYYMTWVRQA PGKGLEWLAY ISKNGEYSKY SPSSNGRFTI SRDNAKNSVF LQLDRLSADD TAVYYCARAD GLTYFSELLQ YIFDLWGQGA RVTVSS

Figure 9 cont.

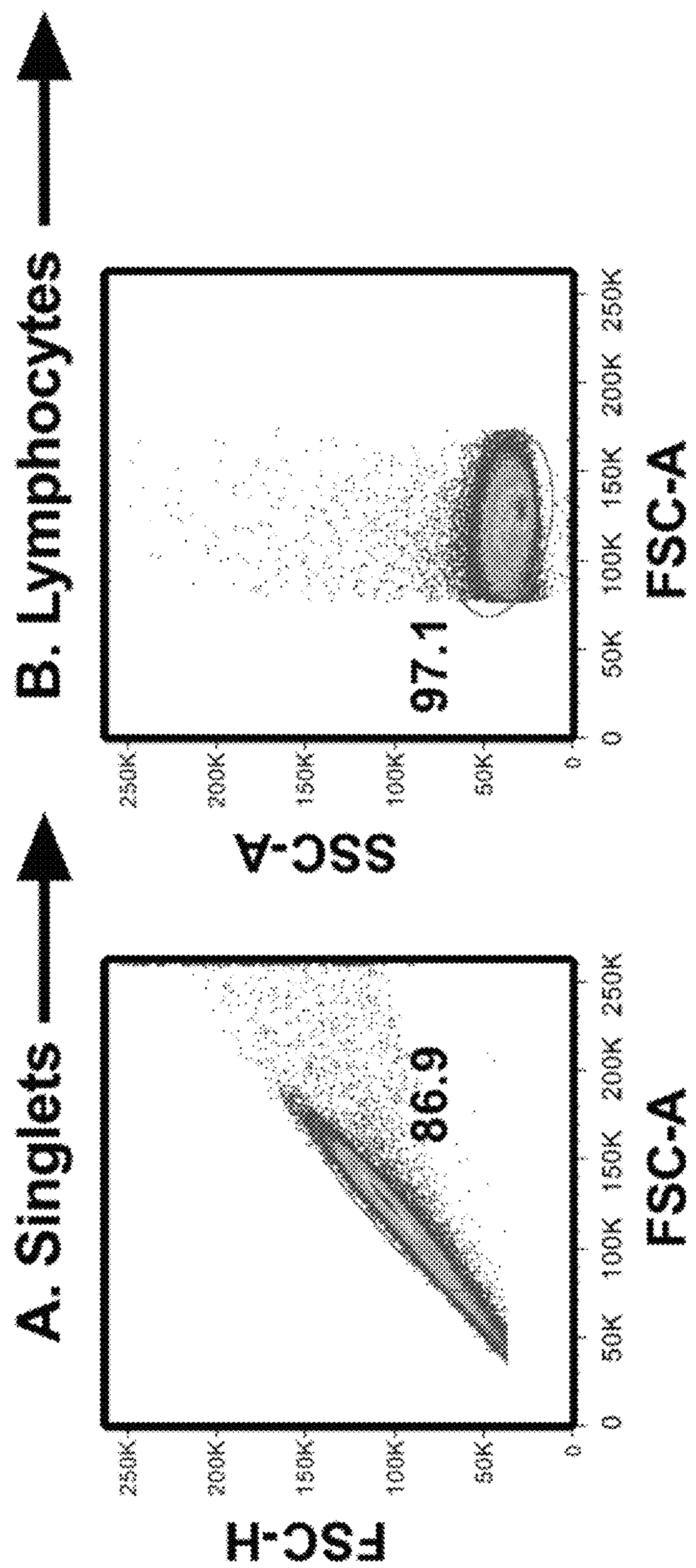
Figures 14A-B

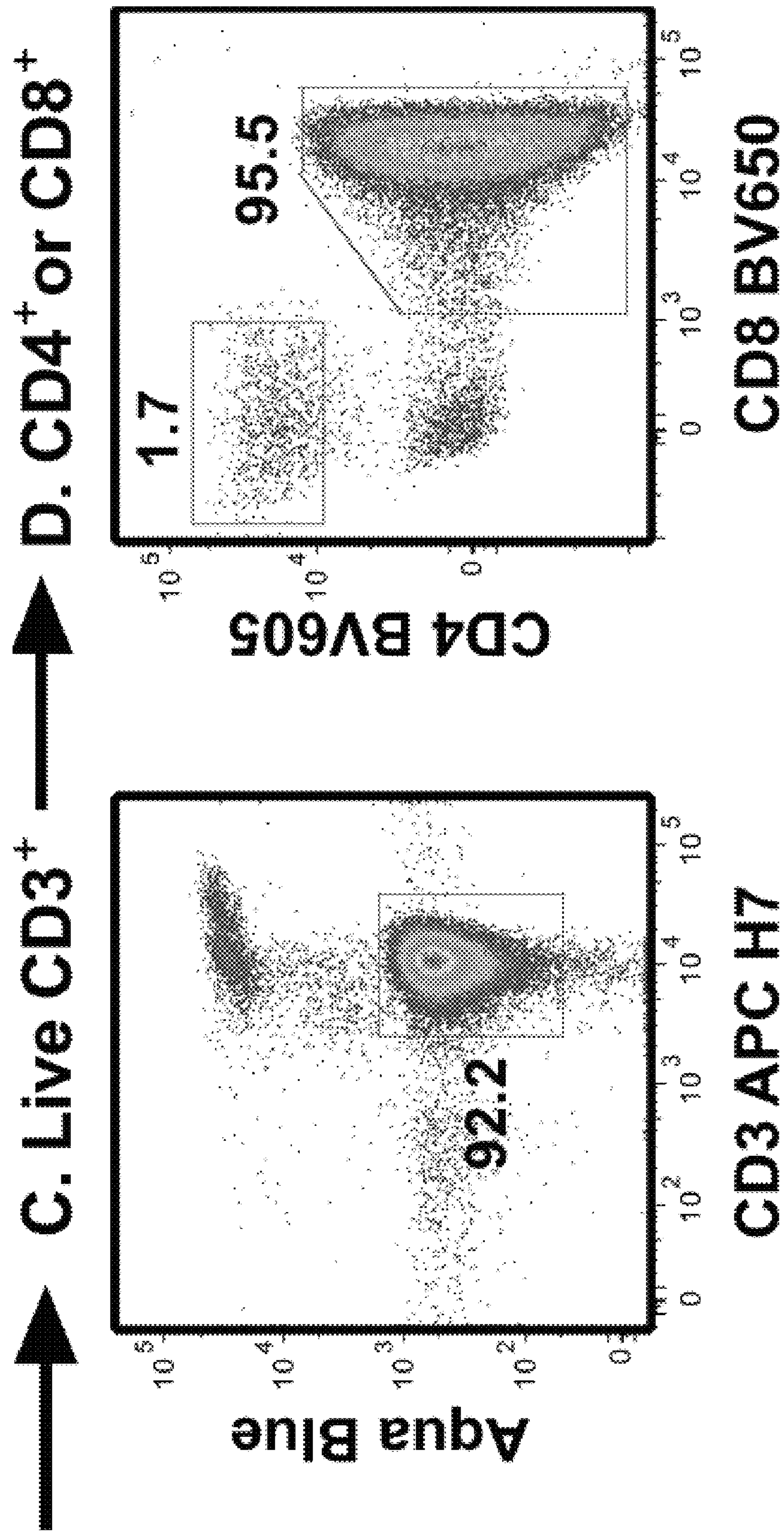
Figures 14C-D

G. Gating strategy to identify $CD4^+$ $CD107^+$ Effector Cells.

G. Gating strategy to identify $CD4^+$ $CD107^+$ Effector Cells.

G. Gating strategy to identify CD4+ CD107+ Effector Cells.

G. Gating strategy to identify CD4+ CD107+ Effector Cells.

| | Subtype A | Subtype AE | Subtype B | Subtype C |
|---|---|---|---|---|
| Tier 1 | Q32.17 | 92TH023 | BaL<br>SF162 | MW96.5 |
| Tier 2 | | CM235<br>CM244<br>C1080.C03<br>427299<br>816763 | CH040<br>CH058<br>SUMA<br>WITO<br>YU2 | CAP45<br>CH505<br>DU151<br>DU422<br>TV1<br>1086.C<br>246-F3.C10 |

Figure 18

| Antigen | DART | $k_a$ (±SD), $M^{-1}s^{-1}$ | $k_d$ (±SD), $s^{-1}$ | $K_D$ (±SD), nM |
|---|---|---|---|---|
| Human CD3ε/δ | A32xCD3 | 6.8 (± 0.1) $x10^5$ | 2.4 (± 0.0) $x10^{-3}$ | 3.6 (± 0.1) |
| | 7B2xCD3 | 4.1 (± 0.0) $x10^4$ | 2.5 (± 0.0) $x10^{-4}$ | 6.1 (± 0.0) |
| M.ConS gp140 | A32xCD3 | 1.7 (± 0.0) $x10^4$ | 8.1 (± 1.8) $x10^{-4}$ | 47.7 (± 10.8) |
| JR-FL gp140 | 7B2xCD3 | 2.0 (± 0.1) $x10^4$ | 3.1 (± 0.9) $x10^{-4}$ | 15.1 (± 3.5) |

Figure 19

| Patient | Virus used for infection in VCA* | Pre-ART Viral Load (copies/ml) | Nadir CD4 | Current CD4 count | Duration of suppression (years) |
|---|---|---|---|---|---|
| **493** | JR-CSF | 78,115 | 257 | 637 | 2.5 |
| **532** | JR-CSF | unknown | 130 | 623 | 14 |
| **673** | JR-CSF | Unknown | unknown | 707 | 7 |
| **527** | JR-CSF, AR | 184,781 | 600 | 718 | 4.5 |
| **728** | JR-CSF, AR | 45,000 | 354 | 456 | 4 |
| **749** | JR-CSF, AR | unknown | 404 | 402 | 1.5 |
| **725** | JR-CSF, AR | 234.048 | 475 | 789 | 3 |
| **720** | JR-CSF, AR | 586,930 | 166 | 446 | 3 |
| **425** | Autologous | 750,001 | 604 | 783 | 8 |
| **407** | Autologous | 1,042,734 (AHI) | 499 | 706 | 2 |
| **408** | Autologous | 6095 (AHI) | 830 | 1168 | 2 |
| **795** | Autologous | 175,718 | 526 | 850 | 2.5 |
| **674** | Autologous | 185,042 | 338 | 1045 | 4.5 |

* Virus Clearance Assay
AR = autologous reservoir virus
Autologous indicates patient cells used in latency clearance assay, no superinfection used.
AHI = Acute HIV Infection

Figure 20

| Patient | E:T Ratio | HIV-1 gag p24 concentration (ng/ml) (SEM) | | | | | |
|---|---|---|---|---|---|---|---|
| | | No DART | CD3x4420 | 7B2x4420 | 7B2xCD3 | A32xCD3 | Combo |
| 493 | No CD8s | 10.6(2) | 12.6(4) | NT | 1.44(1.0) | 10.8 (2.2) | NT |
| | 1:10 | 4.7(1.0) | 7.35 (2.1) | NT | 1.05 (0.6) | 3.5 (1.3) | NT |
| | 1:1 | .92 (0.2) | 1.29 (.03) | NT | .04 (.02) | .343 (.01) | NT |
| 532 | No CD8s | 12.9 (2.7) | 12.6 (3.9) | NT | 1.44(1.0) | 10.8(4.1) | NT |
| | 1:10 | 8.9(1.7) | 7.35(2.1) | NT | 1.05(.629) | 3.5(1.3) | NT |
| | 1:1 | 0.92(0.2) | 1.5(0.16) | NT | 0.04(0.02) | 0.16 (0.03) | NT |
| 673 | No CD8s | 345(6.4) | 194(25) | 253(17) | 213(28) | 139(4.6) | NT |
| | 1:10 | 329(1.2) | 137(5.2) | 184(12) | 73(4.6) | 57(5.2) | NT |
| | 1:1 | 94(6.9) | 8.8(0.2) | 13.5(0.5) | 4.4(0.5) | 11.4(1.0) | NT |
| 527 | No CD8s | 154(5.2) | 185(22) | 106(9.4) | 27.3(12.3) | 54.2(29.3) | 62.9(3.4) |
| | 1:10 | 164(16) | 210(11) | 78(6.6) | 12.1(2.1) | 21(2.8) | 68(5.9) |
| | 1:1 | 116(53) | 139(10.8) | 80(21) | 13(6) | 8.4(0.9) | 34.9(5.6) |
| 728 | No CD8s | 103(25) | 111(10) | 92(24) | 19(10) | 122(51) | 30(11) |
| | 1:10 | 114(18) | 117(13) | 90(2.2) | 3.7(2.6) | 54(11) | 15.9(5.4) |
| | 1:1 | 178(14) | 121(32) | 60(23) | 1.9(1.1) | 44(9.5) | 0.9(0.4) |
| 749 | No CD8s | 27.9(11) | 7.3(6.8) | 13.8(2.9) | 0.9(0.5) | 19.3(7.7) | 16.5(12.2) |
| | 1:1 | 11.4(0.5) | 6.8(3.3) | 5.5(3) | **ND** | **ND** | **ND** |
| 725 | No CD8s | 191(3.7) | 177(37) | 189(24) | 29(21) | 134(16) | 45(13) |
| | 1:10 | 234(53) | 187(14) | 163(22) | 6.5(5.5) | 122(17) | **ND** |
| | 1:1 | 60(22) | 71(5) | 53(17) | **ND** | 4.5(3.3) | **ND** |
| 720 | No CD8s | 15(4.8) | 26.3(4.8) | 22(2.3) | 0.7(0.2) | 5.9(2.6) | 0.6(0.2) |
| | 1:10 | 5.7(2.5) | 17(2.3) | 16(4.6) | 0.4(0.1) | 2.5(0.5) | 1.0(0.6) |
| | 1:1 | 1.1(0.1) | 0.4(0.3) | 1.1(0.3) | **ND** | 1.3(0.4) | 0.2(0.02) |

SEM=standard error of the mean of 3 replicates

ND = not detected

NT = not tested due to cell availability

Figure 21

| LRA | Patient | #wells plated | #positive wells after addition of DART MOLECULE | | | | | |
|---|---|---|---|---|---|---|---|---|
| | | | No Effectors | No DART | 4420 xCD3 | 7B2 xCD3 | A32 xCD3 | Combo |
| PHA | 425 | 12 | 8 | 8 | 9 | 6 | 7 | 7 |
| | 728 | 12 | 7 | 9 | 6 | NT | NT | 0 |
| | 725 | 12 | 11 | 7 | 7 | 6 | 3 | 5 |
| | 749 | 12 | 7 | 5 | 3 | 3 | 1 | 2 |
| | 674 | 12 | 6 | 4 | 4 | NT | NT | 2 |
| | 795* | 12 | 10 | 4 | 6 | NT | NT | 0 |
| VOR | 674 | 12 | 6 | 6 | 7 | NT | NT | 3 |
| | 408 | 12 | 2 | 1 | 1 | 0 | 0 | NT |
| | 407 | 24 | 6 | 5 | 6 | NT | NT | 2 |
| | 795 | 36 | 28 | 17 | 21 | NT | NT | 22 |
| | 795* | 12 | 3 | 1 | 2 | NT | NT | 0 |

LRA=latency reversing agent

NT=not tested due to cell availability combo= Addition of 50ng/ml of 7B2xCD3 DART and 50ng/ml of A32xCD3 DART

* evaluated using 96 hours co-culture

VOR=vorinostat

Figure 22

| | | | | |
|---|---|---|---|---|
| IMC Recognized | 21 | 20 | 22 | 1 |
| Percentage | 95 | 91 | 100 | 5 |
| Mean Max %SL | 43.69 | 39.58 | 48.25 | 9.73 |
| Range %SL | 12-86 | 15-74 | 24-84 | 2-22 |

| HIV-1 *Env* (# isolates) | Residues Influencing 7B2 Binding | Residues Influencing A32 Binding |
| --- | --- | --- |
| All subtypes (4556) | All<br>Probability<br>Ref seq pos | All<br>Probability<br>Ref seq pos |
| Subtype B (1529) | Subtype: B<br>Probability<br>Ref seq pos | Subtype: B<br>Probability<br>Ref seq pos |

Figure 24

SEQUENCE LISTING

```
<160> NUMBER OF SEQ ID NOS: 82

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Gly Gly Ser Gly Gly Gly Gly
1               5


<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gly Cys Gly Gly Gly
1               5


<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Val Glu Pro Lys Ser Cys
1               5


<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4
```

Val Glu Pro Lys Ser Cys
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 5

Gly Phe Asn Arg Gly Glu Cys
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

Phe Asn Arg Gly Glu Cys
1               5

<210> SEQ ID NO 7
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 7

Glu Val Ala Ala Leu Glu Lys Glu Val Ala Ala Leu Glu Lys Glu Val
1               5                   10                  15

Ala Ala Leu Glu Lys Glu Val Ala Ala Leu Glu Lys
            20                  25

<210> SEQ ID NO 8
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 8

Lys Val Ala Ala Leu Lys Glu Lys Val Ala Ala Leu Lys Glu Lys Val
1               5                   10                  15

Ala Ala Leu Lys Glu Lys Val Ala Ala Leu Lys Glu
            20                  25

<210> SEQ ID NO 9
<211> LENGTH: 277
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

Gln Ser Ala Leu Thr Gln Pro Pro Ser Ala Ser Gly Ser Pro Gly Gln
1               5                   10                  15

```
Ser Val Thr Ile Ser Cys Thr Gly Thr Ser Ser Asp Val Gly Gly Tyr
            20                  25                  30

Asn Tyr Val Ser Trp Tyr Gln His His Pro Gly Lys Ala Pro Lys Leu
        35                  40                  45

Ile Ile Ser Glu Val Asn Asn Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Glu Tyr Tyr Cys Ser Ser Tyr Thr Asp Ile
                85                  90                  95

His Asn Phe Val Phe Gly Gly Gly Thr Lys Leu Thr Val Leu Gly Gly
            100                 105                 110

Gly Ser Gly Gly Gly Gly Glu Val Gln Leu Val Glu Ser Gly Gly Gly
        115                 120                 125

Leu Val Gln Pro Gly Gly Ser Leu Arg Leu Ser Cys Ala Ala Ser Gly
    130                 135                 140

Phe Thr Phe Ser Thr Tyr Ala Met Asn Trp Val Arg Gln Ala Pro Gly
145                 150                 155                 160

Lys Gly Leu Glu Trp Val Gly Arg Ile Arg Ser Lys Tyr Asn Asn Tyr
                165                 170                 175

Ala Thr Tyr Tyr Ala Asp Ser Val Lys Gly Arg Phe Thr Ile Ser Arg
            180                 185                 190

Asp Asp Ser Lys Asn Ser Leu Tyr Leu Gln Met Asn Ser Leu Lys Thr
        195                 200                 205

Glu Asp Thr Ala Val Tyr Tyr Cys Val Arg His Gly Asn Phe Gly Asn
    210                 215                 220

Ser Tyr Val Ser Trp Phe Ala Tyr Trp Gly Gln Gly Thr Leu Val Thr
225                 230                 235                 240

Val Ser Ser Gly Gly Cys Gly Gly Gly Glu Val Ala Ala Leu Glu Lys
                245                 250                 255

Glu Val Ala Ala Leu Glu Lys Glu Val Ala Ala Leu Glu Lys Glu Val
            260                 265                 270

Ala Ala Leu Glu Lys
        275
```

<210> SEQ ID NO 10
<211> LENGTH: 831
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

```
cagagcgcac tgactcagcc cccttccgcc tccgggtctc ctggacagag cgtgacaatc      60

tcatgcactg ggacttcaag cgatgtgggc gggtacaact atgtgagttg gtaccagcac     120

catcccggga aggcacctaa actgatcatt agcgaagtga acaatcgacc aagcggcgtc     180

cccgaccggt tcagcggcag caagtctggc aataccgcca gtctgacagt ctcaggcctg     240

caggccgagg atgaagctga gtactattgc tcatcataca ctgacatcca taacttcgtc     300

ttcggcggcg gaactaaact gaccgtgctg ggtggcggat ccggcggcgg aggcgaggtg     360

cagctggtgg agtctggggg aggcttggtc cagcctggag ggtccctgag actctcctgt     420

gcagcctctg gattcacctt cagcacatac gctatgaatt gggtccgcca ggctccaggg     480
```

```
aaggggctgg agtgggttgg aaggatcagg tccaagtaca acaattatgc aacctactat    540

gccgactctg tgaagggtag attcaccatc tcaagagatg attcaaagaa ctcactgtat    600

ctgcaaatga acagcctgaa aaccgaggac acggccgtgt attactgtgt gagacacggt    660

aacttcggca attcttacgt gtcttggttt gcttattggg gacaggggac actggtgact    720

gtgtcttccg gaggatgtgg cggtggagaa gtggccgcac tggagaaaga ggttgctgct    780

ttggagaagg aggtcgctgc acttgaaaag gaggtcgcag ccctggagaa a             831


<210> SEQ ID NO 11
<211> LENGTH: 275
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Gln Val Gln Leu Gln Glu Ser Gly Pro Gly
        115                 120                 125

Leu Val Lys Pro Ser Gln Thr Leu Ser Leu Ser Cys Thr Val Ser Gly
    130                 135                 140

Gly Ser Ser Ser Ser Gly Ala His Tyr Trp Ser Trp Ile Arg Gln Tyr
145                 150                 155                 160

Pro Gly Lys Gly Leu Glu Trp Ile Gly Tyr Ile His Tyr Ser Gly Asn
                165                 170                 175

Thr Tyr Tyr Asn Pro Ser Leu Lys Ser Arg Ile Thr Ile Ser Gln His
            180                 185                 190

Thr Ser Glu Asn Gln Phe Ser Leu Lys Leu Asn Ser Val Thr Val Ala
        195                 200                 205

Asp Thr Ala Val Tyr Tyr Cys Ala Arg Gly Thr Arg Leu Arg Thr Leu
    210                 215                 220

Arg Asn Ala Phe Asp Ile Trp Gly Gln Gly Thr Leu Val Thr Val Ser
225                 230                 235                 240

Ser Gly Gly Cys Gly Gly Gly Lys Val Ala Ala Leu Lys Glu Lys Val
                245                 250                 255

Ala Ala Leu Lys Glu Lys Val Ala Ala Leu Lys Glu Lys Val Ala Ala
            260                 265                 270

Leu Lys Glu
        275


<210> SEQ ID NO 12
```

<211> LENGTH: 825
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

```
caggctgtgg tgactcagga gccttcactg accgtgtccc caggcggaac tgtgaccctg     60

acatgcagat ccagcacagg cgcagtgacc acatctaact acgccaattg ggtgcagcag    120

aagccaggac aggcaccaag ggcctgatc gggggtacaa acaaaagggc tccctggacc    180

cctgcacggt tttctggaag tctgctgggc ggaaaggccg ctctgactat taccggggca    240

caggccgagg acgaagccga ttactattgt gctctgtggt atagcaatct gtgggtgttc    300

gggggtggca caaaactgac tgtgctggga gggggtggat ccggcggcgg aggccaggtg    360

cagctgcagg agtccggccc cggactggtc aaaccctctc agactctgtc tctgtcatgt    420

accgtgtcag gcggctcttc cagctccggg gcacactact ggagctggat caggcagtat    480

cccggcaagg ggctggagtg gatcggatac attcattata gcggcaacac atactataat    540

ccttctctga agagtcggat cactatttca cagcacacca gcgaaaacca gttcagcctg    600

aagctgaaca gcgtgaccgt cgccgacaca gccgtgtact attgcgcccg gggcaccaga    660

ctgagaactc tgagaaacgc atttgacatc tggggacagg ggacactggt gacagtgagc    720

tccggaggat gtggcggtgg aaaagtggcc gcactgaagg agaaagttgc tgctttgaaa    780

gagaaggtcg ccgcacttaa ggaaaaggtc gcagccctga aagag                    825
```

<210> SEQ ID NO 13
<211> LENGTH: 280
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

```
Asp Ile Val Met Thr Gln Ser Pro Asp Ser Leu Ala Val Ser Pro Gly
1               5                   10                  15

Glu Arg Ala Thr Ile His Cys Lys Ser Ser Gln Thr Leu Leu Tyr Ser
            20                  25                  30

Ser Asn Asn Arg His Ser Ile Ala Trp Tyr Gln Gln Arg Pro Gly Gln
        35                  40                  45

Pro Pro Lys Leu Leu Leu Tyr Trp Ala Ser Met Arg Leu Ser Gly Val
    50                  55                  60

Pro Asp Arg Phe Ser Gly Ser Gly Ser Gly Thr Asp Phe Thr Leu Thr
65                  70                  75                  80

Ile Asn Asn Leu Gln Ala Glu Asp Val Ala Ile Tyr Tyr Cys His Gln
                85                  90                  95

Tyr Ser Ser His Pro Pro Thr Phe Gly His Gly Thr Arg Val Glu Ile
            100                 105                 110

Lys Gly Gly Gly Ser Gly Gly Gly Gly Glu Val Gln Leu Val Glu Ser
        115                 120                 125

Gly Gly Gly Leu Val Gln Pro Gly Gly Ser Leu Arg Leu Ser Cys Ala
    130                 135                 140

Ala Ser Gly Phe Thr Phe Ser Thr Tyr Ala Met Asn Trp Val Arg Gln
145                 150                 155                 160

Ala Pro Gly Lys Gly Leu Glu Trp Val Gly Arg Ile Arg Ser Lys Tyr
```

```
                165                 170                 175

Asn Asn Tyr Ala Thr Tyr Tyr Ala Asp Ser Val Lys Gly Arg Phe Thr
            180                 185                 190

Ile Ser Arg Asp Asp Ser Lys Asn Ser Leu Tyr Leu Gln Met Asn Ser
        195                 200                 205

Leu Lys Thr Glu Asp Thr Ala Val Tyr Tyr Cys Val Arg His Gly Asn
    210                 215                 220

Phe Gly Asn Ser Tyr Val Ser Trp Phe Ala Tyr Trp Gly Gln Gly Thr
225                 230                 235                 240

Leu Val Thr Val Ser Ser Gly Gly Cys Gly Gly Gly Glu Val Ala Ala
                245                 250                 255

Leu Glu Lys Glu Val Ala Ala Leu Glu Lys Glu Val Ala Ala Leu Glu
            260                 265                 270

Lys Glu Val Ala Ala Leu Glu Lys
        275                 280


<210> SEQ ID NO 14
<211> LENGTH: 840
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

gacatcgtga tgacccagtc tccagactcc ctggctgtgt ctccgggcga gagggccacc     60

atccactgca agtccagcca gactcttttg tacagctcca acaatagaca ctccattgct    120

tggtaccaac agagaccagg acagcctcct aaattactcc tttattgggc atctatgcgg    180

ctttccgggg tccctgaccg attcagtggc agcgggtctg ggacagattt cactctcacc    240

atcaacaacc tgcaggctga ggatgtggcc atctattact gtcaccaata ttccagtcat    300

cccccgacgt tcggccacgg gaccagggtg gagatcaaag gtggaggatc cggcggcgga    360

ggcgaggtgc agctggtgga gtctggggga ggcttggtcc agcctggagg gtccctgaga    420

ctctcctgtg cagcctctgg attcaccttc agcacatacg ctatgaattg ggtccgccag    480

gctccaggga aggggctgga gtgggttgga aggatcaggt ccaagtacaa caattatgca    540

acctactatg ccgactctgt gaagggtaga ttcaccatct caagagatga ttcaaagaac    600

tcactgtatc tgcaaatgaa cagcctgaaa accgaggaca cggccgtgta ttactgtgtg    660

agacacggta acttcggcaa ttcttacgtg tcttggtttg cttattgggg acaggggaca    720

ctggtgactg tgtcttccgg aggatgtggc ggtggagaag tggccgcact ggagaaagag    780

gttgctgctt tggagaagga ggtcgctgca cttgaaaagg aggtcgcagc cctggagaaa    840


<210> SEQ ID NO 15
<211> LENGTH: 278
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30
```

```
Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Gln Val Gln Leu Val Gln Ser Gly Gly Gly
        115                 120                 125

Val Phe Lys Pro Gly Gly Ser Leu Arg Leu Ser Cys Glu Ala Ser Gly
    130                 135                 140

Phe Thr Phe Thr Glu Tyr Tyr Met Thr Trp Val Arg Gln Ala Pro Gly
145                 150                 155                 160

Lys Gly Leu Glu Trp Leu Ala Tyr Ile Ser Lys Asn Gly Glu Tyr Ser
                165                 170                 175

Lys Tyr Ser Pro Ser Ser Asn Gly Arg Phe Thr Ile Ser Arg Asp Asn
            180                 185                 190

Ala Lys Asn Ser Val Phe Leu Gln Leu Asp Arg Leu Ser Ala Asp Asp
        195                 200                 205

Thr Ala Val Tyr Tyr Cys Ala Arg Ala Asp Gly Leu Thr Tyr Phe Ser
    210                 215                 220

Glu Leu Leu Gln Tyr Ile Phe Asp Leu Trp Gly Gln Gly Ala Arg Val
225                 230                 235                 240

Thr Val Ser Ser Gly Gly Cys Gly Gly Gly Lys Val Ala Ala Leu Lys
                245                 250                 255

Glu Lys Val Ala Ala Leu Lys Glu Lys Val Ala Ala Leu Lys Glu Lys
            260                 265                 270

Val Ala Ala Leu Lys Glu
        275
```

<210> SEQ ID NO 16
<211> LENGTH: 834
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16

```
caggctgtgg tgactcagga gccttcactg accgtgtccc caggcggaac tgtgaccctg     60

acatgcagat ccagcacagg cgcagtgacc acatctaact acgccaattg ggtgcagcag    120

aagccaggac aggcaccaag gggcctgatc gggggtacaa acaaaagggc tccctggacc    180

cctgcacggt tttctggaag tctgctgggc ggaaaggccg ctctgactat taccggggca    240

caggccgagg acgaagccga ttactattgt gctctgtggt atagcaatct gtgggtgttc    300

gggggtggca caaaactgac tgtgctggga gggggtggat ccggcggagg tggacaggtg    360

cagctggtgc agtctggggg aggcgttttc aagcctggag ggtccctgag actctcctgt    420

gaagcctctg gattcacatt tactgaatat tacatgactt gggtccgcca ggctcctggg    480

aaggggctgg agtggcttgc gtatattagt aagaatggtg aatattcaaa atattcaccg    540

tcctcaaacg gccggttcac catctccaga gacaacgcca agaactcagt gtttctgcaa    600
```

```
ttggacagac tgagcgccga cgacacggcc gtctattact gtgcgagagc ggacggatta    660

acatacttct ctgaattact ccaatacatt tttgacctct ggggccaggg agcccgggtc    720

accgtctcct ccggaggatg tggcggtgga aaagtggccg cactgaagga gaaagttgct    780

gctttgaaag agaaggtcgc cgcacttaag gaaaaggtcg cagccctgaa agag          834


<210> SEQ ID NO 17
<211> LENGTH: 276
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Ile Val Leu Thr Gln Ser Pro Gly Thr Leu Ser Leu Ser Pro Gly
1               5                   10                  15

Glu Arg Ala Thr Leu Ser Cys Arg Ala Asn Arg Arg Ile Asp Met Asn
            20                  25                  30

Ala Leu Ala Trp Tyr Gln His Arg Ser Gly Gln Ala Pro Arg Leu Leu
        35                  40                  45

Thr His Gly Val Tyr Asn Arg Ala Thr Gly Ile Pro Asp Arg Phe Ser
    50                  55                  60

Gly Tyr Trp Ser Gly Pro Glu Phe Thr Leu Val Ile Ser Arg Leu Glu
65                  70                  75                  80

Pro Glu Asp Phe Ala Val Tyr Tyr Cys Val His Phe Leu Tyr Glu Asn
                85                  90                  95

Pro Ala Trp Ala Phe Gly Gln Gly Thr Lys Leu Glu Ile Lys Gly Gly
            100                 105                 110

Gly Ser Gly Gly Gly Gly Glu Val Gln Leu Val Glu Ser Gly Gly Gly
        115                 120                 125

Leu Val Gln Pro Gly Gly Ser Leu Arg Leu Ser Cys Ala Ala Ser Gly
    130                 135                 140

Phe Thr Phe Ser Thr Tyr Ala Met Asn Trp Val Arg Gln Ala Pro Gly
145                 150                 155                 160

Lys Gly Leu Glu Trp Val Gly Arg Ile Arg Ser Lys Tyr Asn Asn Tyr
                165                 170                 175

Ala Thr Tyr Tyr Ala Asp Ser Val Lys Gly Arg Phe Thr Ile Ser Arg
            180                 185                 190

Asp Asp Ser Lys Asn Ser Leu Tyr Leu Gln Met Asn Ser Leu Lys Thr
        195                 200                 205

Glu Asp Thr Ala Val Tyr Tyr Cys Val Arg His Gly Asn Phe Gly Asn
    210                 215                 220

Ser Tyr Val Ser Trp Phe Ala Tyr Trp Gly Gln Gly Thr Leu Val Thr
225                 230                 235                 240

Val Ser Ser Ala Ser Thr Lys Gly Glu Val Ala Ala Cys Glu Lys Glu
                245                 250                 255

Val Ala Ala Leu Glu Lys Glu Val Ala Ala Leu Glu Lys Glu Val Ala
            260                 265                 270

Ala Leu Glu Lys
        275


<210> SEQ ID NO 18
<211> LENGTH: 828
<212> TYPE: DNA
<213> ORGANISM: Artificial Sequence
<220> FEATURE:
```

```
<223> OTHER INFORMATION: Description of Artificial Sequence: Synthetic
      polynucleotide

<400> SEQUENCE: 18

gaaattgtgt tgacgcagtc tccaggcacc ctgtccttgt ctccagggga gagagccacc      60

ctctcctgca gggccaatcg gcggattgac atgaacgcct tggcctggta ccagcaccga     120

tctggccagg ctcccaggct cctcacccat ggtgtctata acagggccac tggcatccca     180

gacaggttca gtggctattg gtctgggcca gagttcaccc tcgtcatcag cagactggag     240

cctgaagatt ttgcagtcta ttactgtgta cactttctct acgaaaatcc agcgtgggcg     300

ttcggccagg ggaccaagct ggagatcaag ggtggaggat ccggcggcgg aggcgaggtg     360

cagctggtgg agtctggggg aggcttggtc cagcctggag ggtccctgag actctcctgt     420

gcagcctctg gattcacctt cagcacatac gctatgaatt gggtccgcca ggctccaggg     480

aaggggctgg agtgggttgg aaggatcagg tccaagtaca acaattatgc aacctactat     540

gccgactctg tgaagggtag attcaccatc tcaagagatg attcaaagaa ctcactgtat     600

ctgcaaatga acagcctgaa aaccgaggac acggccgtgt attactgtgt gagacacggt     660

aacttcggca attcttacgt gtcttggttt gcttattggg gacaggggac actggtgact     720

gtgtcttccg cctccaccaa gggcgaagtg gccgcatgtg agaaagaggt tgctgctttg     780

gagaaggagg tcgctgcact tgaaaaggag gtcgcagccc tggagaaa                  828


<210> SEQ ID NO 19
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Glu Val Gln Leu Val Glu Ser Gly Gly Gly
        115                 120                 125

Val Val His Pro Gly Gly Ser Leu Arg Leu Ser Cys Ala Ala Ser Gly
    130                 135                 140

Phe Ser Val Arg Asn Asp Gln Met Ala Trp Val Arg Gln Ala Pro Gly
145                 150                 155                 160

Lys Arg Leu Glu Trp Val Ser Ile Ile Asn Asp Gly Ala Ser Pro Tyr
                165                 170                 175

Tyr Ala Asp Ser Val Lys Gly Arg Phe Ala Met Ser Arg Asp Thr Ser
            180                 185                 190
```

```
Lys Asn Thr Val Phe Leu Gln Met Asn Ser Leu Arg Arg Asp Asp Thr
        195                 200                 205

Ala Val Tyr Phe Cys Ala Arg Gly Ile Ala Ser Phe Phe Asp Val Trp
    210                 215                 220

Gly Arg Gly Thr Leu Val Thr Val Ser Ser Ala Ser Thr Lys Gly Lys
225                 230                 235                 240

Val Ala Ala Cys Lys Glu Lys Val Ala Ala Leu Lys Glu Lys Val Ala
                245                 250                 255

Ala Leu Lys Glu Lys Val Ala Ala Leu Lys Glu
            260                 265
```

<210> SEQ ID NO 20
<211> LENGTH: 801
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20

```
caggctgtgg tgactcagga gccttcactg accgtgtccc caggcggaac tgtgaccctg     60

acatgcagat ccagcacagg cgcagtgacc acatctaact acgccaattg ggtgcagcag    120

aagccaggac aggcaccaag gggcctgatc gggggtacaa acaaaagggc tccctggacc    180

cctgcacggt tttctggaag tctgctgggc ggaaaggccg ctctgactat taccggggca    240

caggccgagg acgaagccga ttactattgt gctctgtggt atagcaatct gtgggtgttc    300

gggggtggca caaaactgac tgtgctggga gggggtggat ccggcggagg tggagaggtg    360

cagctggtgg agtctggagg tggcgtggtc caccctggag gaagcctgag actctcctgt    420

gcagcctctg gattcagcgt caggaacgac cagatggcct gggtccgcca ggctccaggg    480

aagcgactgg agtgggtctc tattattaac gatggtgcta gtccatacta cgcagactct    540

gtgaagggcc gcttcgccat gtccagagac acctccaaga atacagtgtt tcttcagatg    600

aacagcctga gacgtgacga cacagctgtt tatttctgtg cgagggggat cgcctcattc    660

ttcgatgtct ggggccgtgg cacgctggtc actgtctcgt cagcctccac caagggcaaa    720

gtggccgcat gtaaggagaa agttgctgct ttgaaagaga aggtcgccgc acttaaggaa    780

aaggtcgcag ccctgaaaga g                                               801
```

<210> SEQ ID NO 21
<211> LENGTH: 276
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

```
Glu Ile Val Leu Thr Gln Ser Pro Ala Ile Leu Ser Val Ser Pro Gly
1               5                   10                  15

Glu Thr Ala Thr Leu Ser Cys Arg Ala Ser Arg Arg Val Asp Met Asn
            20                  25                  30

Gly Leu Ala Trp Tyr Gln His Arg Pro Gly Gln Ala Pro Arg Leu Leu
        35                  40                  45

Met His Gly Val Tyr Asn Arg Ala Ala Gly Ile Ser Gly Arg Phe Thr
    50                  55                  60

Gly Ser Trp Ser Gly Pro Val Phe Thr Leu Thr Ile Ser Arg Leu Glu
```

```
65                  70                  75                  80

Pro Glu Asp Phe Gly Val Tyr Tyr Cys Gln His Phe Tyr Tyr Glu Thr
                85                  90                  95

Ser Ala Trp Ala Phe Gly Gln Gly Thr Arg Leu Glu Ile Lys Gly Gly
            100                 105                 110

Gly Ser Gly Gly Gly Gly Glu Val Gln Leu Val Glu Ser Gly Gly Gly
        115                 120                 125

Leu Val Gln Pro Gly Gly Ser Leu Arg Leu Ser Cys Ala Ala Ser Gly
    130                 135                 140

Phe Thr Phe Ser Thr Tyr Ala Met Asn Trp Val Arg Gln Ala Pro Gly
145                 150                 155                 160

Lys Gly Leu Glu Trp Val Gly Arg Ile Arg Ser Lys Tyr Asn Asn Tyr
                165                 170                 175

Ala Thr Tyr Tyr Ala Asp Ser Val Lys Gly Arg Phe Thr Ile Ser Arg
            180                 185                 190

Asp Asp Ser Lys Asn Ser Leu Tyr Leu Gln Met Asn Ser Leu Lys Thr
        195                 200                 205

Glu Asp Thr Ala Val Tyr Tyr Cys Val Arg His Gly Asn Phe Gly Asn
    210                 215                 220

Ser Tyr Val Ser Trp Phe Ala Tyr Trp Gly Gln Gly Thr Leu Val Thr
225                 230                 235                 240

Val Ser Ser Ala Ser Thr Lys Gly Glu Val Ala Ala Cys Glu Lys Glu
                245                 250                 255

Val Ala Ala Leu Glu Lys Glu Val Ala Ala Leu Glu Lys Glu Val Ala
            260                 265                 270

Ala Leu Glu Lys
        275
```

<210> SEQ ID NO 22
<211> LENGTH: 828
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22

```
gaaattgtgt tgacgcagtc tccagccatc ctgtctgtgt ctccagggga aaccgccacc     60

ctctcctgca gggccagtcg ccgtgttgac atgaacggcc tcgcctggta ccaacacagg    120

cctggccagg ctcccaggct cctcatgcat ggtgtttata atagggccgc cggcatctca    180

ggcaggttca ctggcagttg gtctgggcca gtcttcactc tcaccatcag cagactggag    240

cctgaagatt ttggagtcta ttactgtcaa cacttttact atgagacttc agcgtgggcg    300

ttcggccagg ggaccaggct ggagatcaaa ggtggaggat ccggcggcgg aggcgaggtg    360

cagctggtgg agtctggggg aggcttggtc cagcctggag ggtccctgag actctcctgt    420

gcagcctctg gattcacctt cagcacatac gctatgaatt gggtccgcca ggctccaggg    480

aaggggctgg agtgggttgg aaggatcagg tccaagtaca acaattatgc aacctactat    540

gccgactctg tgaagggtag attcaccatc tcaagagatg attcaaagaa ctcactgtat    600

ctgcaaatga acagcctgaa aaccgaggac acggccgtgt attactgtgt gagacacggt    660

aacttcggca attcttacgt gtcttggttt gcttattggg gacaggggac actggtgact    720

gtgtcttccg cctccaccaa gggcgaagtg gccgcatgtg agaaagaggt tgctgctttg    780

gagaaggagg tcgctgcact tgaaaaggag gtcgcagccc tggagaaa                 828
```

<210> SEQ ID NO 23
<211> LENGTH: 268
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Glu Val Gln Leu Val Glu Ser Gly Gly Gly
        115                 120                 125

Val Val His Pro Gly Gly Ser Leu Arg Leu Ser Cys Ala Ala Ser Gly
    130                 135                 140

Phe Ser Val Ser His Asp Phe Met Ala Trp Ile Arg Gln Ala Pro Gly
145                 150                 155                 160

Lys Gly Leu Glu Trp Ile Ser Ile Ile Tyr Asn Thr Gly Ser Arg Tyr
                165                 170                 175

Tyr Tyr Ala Asp Ser Val Lys Gly Arg Phe Ala Leu Ser Arg Asp Thr
            180                 185                 190

Ser Asn Asn Thr Leu Ile Leu His Met Ser Gly Leu Arg Arg Asp Asp
        195                 200                 205

Thr Ala Ile Tyr Phe Cys Ala Arg Gly Val Ala Ser Phe Phe Glu Leu
    210                 215                 220

Trp Gly Arg Gly Thr Leu Val Thr Val Ser Ser Ala Ser Thr Lys Gly
225                 230                 235                 240

Lys Val Ala Ala Cys Lys Glu Lys Val Ala Ala Leu Lys Glu Lys Val
                245                 250                 255

Ala Ala Leu Lys Glu Lys Val Ala Ala Leu Lys Glu
            260                 265
```

<210> SEQ ID NO 24
<211> LENGTH: 804
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24

```
caggctgtgg tgactcagga gccttcactg accgtgtccc caggcggaac tgtgaccctg     60

acatgcagat ccagcacagg cgcagtgacc acatctaact acgccaattg ggtgcagcag    120

aagccaggac aggcaccaag ggcctgatc gggggtacaa acaaaagggc tccctggacc    180
```

```
cctgcacggt tttctggaag tctgctgggc ggaaaggccg ctctgactat taccggggca    240

caggccgagg acgaagccga ttactattgt gctctgtggt atagcaatct gtgggtgttc    300

gggggtggca caaaactgac tgtgctggga gggggtggat ccggcggagg tggagaggtg    360

cagctggtgg agtctggagg tggcgtggtc caccctggag gaagcctgag actctcctgt    420

gcagcctctg gattcagcgt cagtcacgac ttcatggcct ggatcaggca ggctccagga    480

aagggactgg agtggatctc tatcatatat aacactggtt ctcgatacta ctacgcagac    540

tctgtgaagg gccgcttcgc cctctccaga gatacgtcca acaacacact gattcttcac    600

atgagcggcc tgagacgtga cgacacggct atttatttct gtgccagggg agtcgcctcg    660

ttctttgaat tgtggggccg tggcaccctg gtcactgtct cgtcagcctc caccaagggc    720

aaagtggccg catgtaagga gaaagttgct gctttgaaag agaaggtcgc cgcacttaag    780

gaaaaggtcg cagccctgaa agag                                           804
```

```
<210> SEQ ID NO 25
<211> LENGTH: 273
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asp Ile Val Met Thr Gln Ser Pro Asp Ser Leu Ala Val Ser Pro Gly
1               5                   10                  15

Glu Arg Ala Thr Ile His Cys Lys Ser Ser Gln Thr Leu Leu Tyr Ser
            20                  25                  30

Ser Asn Asn Arg His Ser Ile Ala Trp Tyr Gln Gln Arg Pro Gly Gln
        35                  40                  45

Pro Pro Lys Leu Leu Leu Tyr Trp Ala Ser Met Arg Leu Ser Gly Val
    50                  55                  60

Pro Asp Arg Phe Ser Gly Ser Gly Ser Gly Thr Asp Phe Thr Leu Thr
65                  70                  75                  80

Ile Asn Asn Leu Gln Ala Glu Asp Val Ala Ile Tyr Tyr Cys His Gln
                85                  90                  95

Tyr Ser Ser His Pro Pro Thr Phe Gly His Gly Thr Arg Val Glu Ile
            100                 105                 110

Lys Gly Gly Gly Ser Gly Gly Gly Gly Gln Val Thr Leu Arg Glu Ser
        115                 120                 125

Gly Pro Ala Leu Val Lys Pro Thr Gln Thr Leu Thr Leu Thr Cys Thr
    130                 135                 140

Phe Ser Gly Phe Ser Leu Ser Thr Ser Gly Met Gly Val Gly Trp Ile
145                 150                 155                 160

Arg Gln Pro Pro Gly Lys Ala Leu Glu Trp Leu Ala His Ile Trp Trp
                165                 170                 175

Asp Asp Asp Lys Arg Tyr Asn Pro Ala Leu Lys Ser Arg Leu Thr Ile
            180                 185                 190

Ser Lys Asp Thr Ser Lys Asn Gln Val Val Leu Thr Met Thr Asn Met
        195                 200                 205

Asp Pro Val Asp Thr Ala Thr Tyr Tyr Cys Ala Gln Ile Asn Pro Ala
    210                 215                 220

Trp Phe Ala Tyr Trp Gly Gln Gly Thr Leu Val Thr Val Ser Ser Gly
225                 230                 235                 240
```

```
Gly Cys Gly Gly Gly Glu Val Ala Ala Leu Glu Lys Glu Val Ala Ala
            245                 250                 255

Leu Glu Lys Glu Val Ala Ala Leu Glu Lys Glu Val Ala Ala Leu Glu
            260                 265                 270

Lys


<210> SEQ ID NO 26
<211> LENGTH: 819
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

gacatcgtga tgacccagtc tccagactcc ctggctgtgt ctccgggcga gagggccacc      60

atccactgca agtccagcca gactcttttg tacagctcca acaatagaca ctccattgct     120

tggtaccaac agagaccagg acagcctcct aaattactcc tttattgggc atctatgcgg     180

ctttccgggg tccctgaccg attcagtggc agcgggtctg ggacagattt cactctcacc     240

atcaacaacc tgcaggctga ggatgtggcc atctattact gtcaccaata ttccagtcat     300

cccccgacgt tcggccacgg gaccagggtg gagatcaaag gtggaggatc cggcggcgga     360

ggccaggtta ccctgagaga gtctggccct gcgctggtga agcccacaca gaccctcaca     420

ctgacttgta ccttctctgg gttttcactg agcacttctg gtatgggtgt aggctggatt     480

cgtcagcctc ccgggaaggc tctagagtgg ctggcacaca tttggtggga tgatgacaag     540

cgctataatc cagccctgaa gagccgactg acaatctcca aggatacctc caaaaaccag     600

gtagtcctca caatgaccaa catggaccct gtggatactg ccacatacta ctgtgctcaa     660

ataaaccccg cctggtttgc ttactggggc caagggactc tggtcactgt gagctccgga     720

ggatgtggcg gtggagaagt ggccgcactg gagaaagagg ttgctgcttt ggagaaggag     780

gtcgctgcac ttgaaaagga ggtcgcagcc ctggagaaa                            819


<210> SEQ ID NO 27
<211> LENGTH: 279
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Phe Asp
            20                  25                  30

Gly Asp Ser Phe Met Asn Trp Tyr Gln Gln Lys Pro Gly Gln Pro Pro
        35                  40                  45

Lys Leu Leu Ile Tyr Thr Thr Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys Gly
            100                 105                 110
```

```
Gly Gly Ser Gly Gly Gly Gly Gln Val Gln Leu Val Gln Ser Gly Gly
        115                 120                 125

Gly Val Phe Lys Pro Gly Gly Ser Leu Arg Leu Ser Cys Glu Ala Ser
    130                 135                 140

Gly Phe Thr Phe Thr Glu Tyr Tyr Met Thr Trp Val Arg Gln Ala Pro
145                 150                 155                 160

Gly Lys Gly Leu Glu Trp Leu Ala Tyr Ile Ser Lys Asn Gly Glu Tyr
                165                 170                 175

Ser Lys Tyr Ser Pro Ser Ser Asn Gly Arg Phe Thr Ile Ser Arg Asp
            180                 185                 190

Asn Ala Lys Asn Ser Val Phe Leu Gln Leu Asp Arg Leu Ser Ala Asp
        195                 200                 205

Asp Thr Ala Val Tyr Tyr Cys Ala Arg Ala Asp Gly Leu Thr Tyr Phe
    210                 215                 220

Ser Glu Leu Leu Gln Tyr Ile Phe Asp Leu Trp Gly Gln Gly Ala Arg
225                 230                 235                 240

Val Thr Val Ser Ser Gly Gly Cys Gly Gly Gly Lys Val Ala Ala Leu
                245                 250                 255

Lys Glu Lys Val Ala Ala Leu Lys Glu Lys Val Ala Ala Leu Lys Glu
            260                 265                 270

Lys Val Ala Ala Leu Lys Glu
        275
```

<210> SEQ ID NO 28
<211> LENGTH: 837
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28

```
gacatcgtga tgacccaatc tccagactct ttggctgtgt ctctagggga gagggccacc     60

atcaactgca aggccagcca aagtgttgat tttgatggtg atagttttat gaactggtac    120

caacagaaac caggacagcc acccaaactc ctcatctata ctacatccaa tctagaatct    180

ggggtcccag acaggtttag tggcagtggg tctgggacag acttcaccct caccatcagc    240

agcctgcagg ctgaggatgt ggcagtttat tactgtcagc aaagtaatga agatccgtac    300

acgttcggac aggggaccaa gcttgagatc aaaggaggcg gatccggcgg aggtggacag    360

gtgcagctgg tgcagtctgg gggaggcgtt ttcaagcctg gagggtccct gagactctcc    420

tgtgaagcct ctggattcac atttactgaa tattacatga cttgggtccg ccaggctcct    480

gggaaggggc tggagtggct tgcgtatatt agtaagaatg gtgaatattc aaaatattca    540

ccgtcctcaa acggccggtt caccatctcc agagacaacg ccaagaactc agtgtttctg    600

caattggaca gactgagcgc cgacgacacg gccgtctatt actgtgcgag agcggacgga    660

ttaacatact tctctgaatt actccaatac atttttgacc tctggggcca gggagcccgg    720

gtcaccgtct cctccggagg atgtggcggt ggaaaagtgg ccgcactgaa ggagaaagtt    780

gctgctttga aagagaaggt cgccgcactt aaggaaaagg tcgcagccct gaaagag       837
```

<210> SEQ ID NO 29
<211> LENGTH: 270
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Glu Val Lys Leu Asp Glu Thr Gly Gly Gly
        115                 120                 125

Leu Val Gln Pro Gly Arg Pro Met Lys Leu Ser Cys Val Ala Ser Gly
    130                 135                 140

Phe Thr Phe Ser Asp Tyr Trp Met Asn Trp Val Arg Gln Ser Pro Glu
145                 150                 155                 160

Lys Gly Leu Glu Trp Val Ala Gln Ile Arg Asn Lys Pro Tyr Asn Tyr
                165                 170                 175

Glu Thr Tyr Tyr Ser Asp Ser Val Lys Gly Arg Phe Thr Ile Ser Arg
            180                 185                 190

Asp Asp Ser Lys Ser Ser Val Tyr Leu Gln Met Asn Asn Leu Arg Val
        195                 200                 205

Glu Asp Met Gly Ile Tyr Tyr Cys Thr Gly Ser Tyr Tyr Gly Met Asp
    210                 215                 220

Tyr Trp Gly Gln Gly Thr Ser Val Thr Val Ser Ser Gly Gly Cys Gly
225                 230                 235                 240

Gly Gly Glu Val Ala Ala Leu Glu Lys Glu Val Ala Ala Leu Glu Lys
                245                 250                 255

Glu Val Ala Ala Leu Glu Lys Glu Val Ala Ala Leu Glu Lys
            260                 265                 270
```

<210> SEQ ID NO 30
<211> LENGTH: 277
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 30

```
Asp Val Val Met Thr Gln Thr Pro Phe Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
```

```
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Gly Gly Gly Ser Gly Gly Gly Gly Gln Val Gln Leu Gln Glu Ser Gly
        115                 120                 125

Pro Gly Leu Val Lys Pro Ser Gln Thr Leu Ser Leu Ser Cys Thr Val
    130                 135                 140

Ser Gly Gly Ser Ser Ser Ser Gly Ala His Tyr Trp Ser Trp Ile Arg
145                 150                 155                 160

Gln Tyr Pro Gly Lys Gly Leu Glu Trp Ile Gly Tyr Ile His Tyr Ser
                165                 170                 175

Gly Asn Thr Tyr Tyr Asn Pro Ser Leu Lys Ser Arg Ile Thr Ile Ser
            180                 185                 190

Gln His Thr Ser Glu Asn Gln Phe Ser Leu Lys Leu Asn Ser Val Thr
        195                 200                 205

Val Ala Asp Thr Ala Val Tyr Tyr Cys Ala Arg Gly Thr Arg Leu Arg
    210                 215                 220

Thr Leu Arg Asn Ala Phe Asp Ile Trp Gly Gln Gly Thr Leu Val Thr
225                 230                 235                 240

Val Ser Ser Gly Gly Cys Gly Gly Gly Lys Val Ala Ala Leu Lys Glu
                245                 250                 255

Lys Val Ala Ala Leu Lys Glu Lys Val Ala Ala Leu Lys Glu Lys Val
            260                 265                 270

Ala Ala Leu Lys Glu
        275


<210> SEQ ID NO 31
<211> LENGTH: 272
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Asp Val Val Met Thr Gln Thr Pro Phe Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Gly Gly Gly Ser Gly Gly Gly Gly Gln Val Thr Leu Arg Glu Ser Gly
        115                 120                 125

Pro Ala Leu Val Lys Pro Thr Gln Thr Leu Thr Leu Thr Cys Thr Phe
    130                 135                 140
```

```
Ser Gly Phe Ser Leu Ser Thr Ser Gly Met Gly Val Gly Trp Ile Arg
145                 150                 155                 160

Gln Pro Pro Gly Lys Ala Leu Glu Trp Leu Ala His Ile Trp Trp Asp
                165                 170                 175

Asp Asp Lys Arg Tyr Asn Pro Ala Leu Lys Ser Arg Leu Thr Ile Ser
            180                 185                 190

Lys Asp Thr Ser Lys Asn Gln Val Val Leu Thr Met Thr Asn Met Asp
        195                 200                 205

Pro Val Asp Thr Ala Thr Tyr Tyr Cys Ala Gln Ile Asn Pro Ala Trp
    210                 215                 220

Phe Ala Tyr Trp Gly Gln Gly Thr Leu Val Thr Val Ser Ser Gly Gly
225                 230                 235                 240

Cys Gly Gly Gly Glu Val Ala Ala Leu Glu Lys Glu Val Ala Ala Leu
                245                 250                 255

Glu Lys Glu Val Ala Ala Leu Glu Lys Glu Val Ala Ala Leu Glu Lys
            260                 265                 270


<210> SEQ ID NO 32
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Phe Asp
            20                  25                  30

Gly Asp Ser Phe Met Asn Trp Tyr Gln Gln Lys Pro Gly Gln Pro Pro
        35                  40                  45

Lys Leu Leu Ile Tyr Thr Thr Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys Gly
            100                 105                 110

Gly Gly Ser Gly Gly Gly Gly Glu Val Lys Leu Asp Glu Thr Gly Gly
        115                 120                 125

Gly Leu Val Gln Pro Gly Arg Pro Met Lys Leu Ser Cys Val Ala Ser
    130                 135                 140

Gly Phe Thr Phe Ser Asp Tyr Trp Met Asn Trp Val Arg Gln Ser Pro
145                 150                 155                 160

Glu Lys Gly Leu Glu Trp Val Ala Gln Ile Arg Asn Lys Pro Tyr Asn
                165                 170                 175

Tyr Glu Thr Tyr Tyr Ser Asp Ser Val Lys Gly Arg Phe Thr Ile Ser
            180                 185                 190

Arg Asp Asp Ser Lys Ser Ser Val Tyr Leu Gln Met Asn Asn Leu Arg
        195                 200                 205

Val Glu Asp Met Gly Ile Tyr Tyr Cys Thr Gly Ser Tyr Tyr Gly Met
    210                 215                 220

Asp Tyr Trp Gly Gln Gly Thr Ser Val Thr Val Ser Ser Gly Gly Cys
225                 230                 235                 240
```

```
Gly Gly Gly Lys Val Ala Ala Leu Lys Glu Lys Val Ala Ala Leu Lys
                245                 250                 255

Glu Lys Val Ala Ala Leu Lys Glu Lys Val Ala Ala Leu Lys Glu
            260                 265                 270


<210> SEQ ID NO 33
<211> LENGTH: 273
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Asp Ile Val Met Thr Gln Ser Pro Asp Ser Leu Ala Val Ser Pro Gly
1               5                   10                  15

Glu Arg Ala Thr Ile His Cys Lys Ser Ser Gln Thr Leu Leu Tyr Ser
            20                  25                  30

Ser Asn Asn Arg His Ser Ile Ala Trp Tyr Gln Gln Arg Pro Gly Gln
        35                  40                  45

Pro Pro Lys Leu Leu Leu Tyr Trp Ala Ser Met Arg Leu Ser Gly Val
    50                  55                  60

Pro Asp Arg Phe Ser Gly Ser Gly Ser Gly Thr Asp Phe Thr Leu Thr
65                  70                  75                  80

Ile Asn Asn Leu Gln Ala Glu Asp Val Ala Ile Tyr Tyr Cys His Gln
                85                  90                  95

Tyr Ser Ser His Pro Pro Thr Phe Gly His Gly Thr Arg Val Glu Ile
            100                 105                 110

Lys Gly Gly Gly Ser Gly Gly Gly Gly Glu Val Lys Leu Asp Glu Thr
        115                 120                 125

Gly Gly Gly Leu Val Gln Pro Gly Arg Pro Met Lys Leu Ser Cys Val
    130                 135                 140

Ala Ser Gly Phe Thr Phe Ser Asp Tyr Trp Met Asn Trp Val Arg Gln
145                 150                 155                 160

Ser Pro Glu Lys Gly Leu Glu Trp Val Ala Gln Ile Arg Asn Lys Pro
                165                 170                 175

Tyr Asn Tyr Glu Thr Tyr Tyr Ser Asp Ser Val Lys Gly Arg Phe Thr
            180                 185                 190

Ile Ser Arg Asp Asp Ser Lys Ser Ser Val Tyr Leu Gln Met Asn Asn
        195                 200                 205

Leu Arg Val Glu Asp Met Gly Ile Tyr Tyr Cys Thr Gly Ser Tyr Tyr
    210                 215                 220

Gly Met Asp Tyr Trp Gly Gln Gly Thr Ser Val Thr Val Ser Ser Gly
225                 230                 235                 240

Gly Cys Gly Gly Gly Glu Val Ala Ala Leu Glu Lys Glu Val Ala Ala
                245                 250                 255

Leu Glu Lys Glu Val Ala Ala Leu Glu Lys Glu Val Ala Ala Leu Glu
            260                 265                 270

Lys


<210> SEQ ID NO 34
<211> LENGTH: 280
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 34

Asp Val Val Met Thr Gln Thr Pro Phe Ser Leu Pro Val Ser Leu Gly
1 5 10 15

Asp Gln Ala Ser Ile Ser Cys Arg Ser Ser Gln Ser Leu Val His Ser
20 25 30

Asn Gly Asn Thr Tyr Leu Arg Trp Tyr Leu Gln Lys Pro Gly Gln Ser
35 40 45

Pro Lys Val Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Phe Cys Ser Gln Ser
85 90 95

Thr His Val Pro Trp Thr Phe Gly Gly Gly Thr Lys Leu Glu Ile Lys
100 105 110

Gly Gly Gly Ser Gly Gly Gly Gly Gln Val Gln Leu Val Gln Ser Gly
115 120 125

Gly Gly Val Phe Lys Pro Gly Gly Ser Leu Arg Leu Ser Cys Glu Ala
130 135 140

Ser Gly Phe Thr Phe Thr Glu Tyr Tyr Met Thr Trp Val Arg Gln Ala
145 150 155 160

Pro Gly Lys Gly Leu Glu Trp Leu Ala Tyr Ile Ser Lys Asn Gly Glu
165 170 175

Tyr Ser Lys Tyr Ser Pro Ser Ser Asn Gly Arg Phe Thr Ile Ser Arg
180 185 190

Asp Asn Ala Lys Asn Ser Val Phe Leu Gln Leu Asp Arg Leu Ser Ala
195 200 205

Asp Asp Thr Ala Val Tyr Tyr Cys Ala Arg Ala Asp Gly Leu Thr Tyr
210 215 220

Phe Ser Glu Leu Leu Gln Tyr Ile Phe Asp Leu Trp Gly Gln Gly Ala
225 230 235 240

Arg Val Thr Val Ser Ser Gly Gly Cys Gly Gly Gly Lys Val Ala Ala
245 250 255

Leu Lys Glu Lys Val Ala Ala Leu Lys Glu Lys Val Ala Ala Leu Lys
260 265 270

Glu Lys Val Ala Ala Leu Lys Glu
275 280

<210> SEQ ID NO 35
<211> LENGTH: 270
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 35

Gln Ser Ala Leu Thr Gln Pro Pro Ser Ala Ser Gly Ser Pro Gly Gln
1 5 10 15

Ser Val Thr Ile Ser Cys Thr Gly Thr Ser Ser Asp Val Gly Gly Tyr
20 25 30

Asn Tyr Val Ser Trp Tyr Gln His His Pro Gly Lys Ala Pro Lys Leu
35 40 45

Ile Ile Ser Glu Val Asn Asn Arg Pro Ser Gly Val Pro Asp Arg Phe
50 55 60

```
Ser Gly Ser Lys Ser Gly Asn Thr Ala Ser Leu Thr Val Ser Gly Leu
65                  70                  75                  80

Gln Ala Glu Asp Glu Ala Glu Tyr Tyr Cys Ser Ser Tyr Thr Asp Ile
                85                  90                  95

His Asn Phe Val Phe Gly Gly Gly Thr Lys Leu Thr Val Leu Gly Gly
            100                 105                 110

Gly Ser Gly Gly Gly Gly Glu Val Lys Leu Asp Glu Thr Gly Gly Gly
        115                 120                 125

Leu Val Gln Pro Gly Arg Pro Met Lys Leu Ser Cys Val Ala Ser Gly
    130                 135                 140

Phe Thr Phe Ser Asp Tyr Trp Met Asn Trp Val Arg Gln Ser Pro Glu
145                 150                 155                 160

Lys Gly Leu Glu Trp Val Ala Gln Ile Arg Asn Lys Pro Tyr Asn Tyr
                165                 170                 175

Glu Thr Tyr Tyr Ser Asp Ser Val Lys Gly Arg Phe Thr Ile Ser Arg
            180                 185                 190

Asp Asp Ser Lys Ser Ser Val Tyr Leu Gln Met Asn Asn Leu Arg Val
        195                 200                 205

Glu Asp Met Gly Ile Tyr Tyr Cys Thr Gly Ser Tyr Tyr Gly Met Asp
    210                 215                 220

Tyr Trp Gly Gln Gly Thr Ser Val Thr Val Ser Ser Gly Gly Cys Gly
225                 230                 235                 240

Gly Gly Glu Val Ala Ala Leu Glu Lys Glu Val Ala Ala Leu Glu Lys
                245                 250                 255

Glu Val Ala Ala Leu Glu Lys Glu Val Ala Ala Leu Glu Lys
            260                 265                 270


<210> SEQ ID NO 36
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Val Val Met Thr Gln Thr Pro Phe Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Gly Gly Gly Ser Gly Gly Gly Gly Gln Val Gln Leu Gln Glu Ser Gly
        115                 120                 125

Pro Gly Leu Val Lys Pro Ser Gln Thr Leu Ser Leu Ser Cys Thr Val
    130                 135                 140

Ser Gly Gly Ser Ser Ser Ser Gly Ala His Tyr Trp Ser Trp Ile Arg
```

```
145                 150                 155                 160

Gln Tyr Pro Gly Lys Gly Leu Glu Trp Ile Gly Tyr Ile His Tyr Ser
                165                 170                 175

Gly Asn Thr Tyr Tyr Asn Pro Ser Leu Lys Ser Arg Ile Thr Ile Ser
            180                 185                 190

Gln His Thr Ser Glu Asn Gln Phe Ser Leu Lys Leu Asn Ser Val Thr
        195                 200                 205

Val Ala Asp Thr Ala Val Tyr Tyr Cys Ala Arg Gly Thr Arg Leu Arg
    210                 215                 220

Thr Leu Arg Asn Ala Phe Asp Ile Trp Gly Gln Gly Thr Leu Val Thr
225                 230                 235                 240

Val Ser Ser Gly Gly Cys Gly Gly Gly Lys Val Ala Ala Leu Lys Glu
                245                 250                 255

Lys Val Ala Ala Leu Lys Glu Lys Val Ala Ala Leu Lys Glu Lys Val
            260                 265                 270

Ala Ala Leu Lys Glu
        275


<210> SEQ ID NO 37
<211> LENGTH: 272
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Gln Val Thr Leu Arg Glu Ser Gly Pro Ala
        115                 120                 125

Leu Val Lys Pro Thr Gln Thr Leu Thr Leu Thr Cys Thr Phe Ser Gly
    130                 135                 140

Phe Ser Leu Ser Thr Ser Gly Met Ser Val Gly Trp Ile Arg Gln Pro
145                 150                 155                 160

Pro Gly Lys Ala Leu Glu Trp Leu Ala Asp Ile Trp Trp Asp Asp Lys
                165                 170                 175

Lys Asp Tyr Asn Pro Ser Leu Lys Ser Arg Leu Thr Ile Ser Lys Asp
            180                 185                 190

Thr Ser Lys Asn Gln Val Val Leu Lys Val Thr Asn Met Asp Pro Ala
        195                 200                 205

Asp Thr Ala Thr Tyr Tyr Cys Ala Arg Ser Met Ile Thr Asn Trp Tyr
    210                 215                 220
```

```
Phe Asp Val Trp Gly Ala Gly Thr Thr Val Thr Val Ser Ser Gly Gly
225                 230                 235                 240

Cys Gly Gly Gly Glu Val Ala Ala Leu Glu Lys Glu Val Ala Ala Leu
                245                 250                 255

Glu Lys Glu Val Ala Ala Leu Glu Lys Glu Val Ala Ala Leu Glu Lys
            260                 265                 270


<210> SEQ ID NO 38
<211> LENGTH: 273
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys Gly Gly Gly Ser Gly Gly
            100                 105                 110

Gly Gly Glu Val Gln Leu Val Glu Ser Gly Gly Gly Leu Val Gln Pro
        115                 120                 125

Gly Gly Ser Leu Arg Leu Ser Cys Ala Ala Ser Gly Phe Thr Phe Ser
    130                 135                 140

Thr Tyr Ala Met Asn Trp Val Arg Gln Ala Pro Gly Lys Gly Leu Glu
145                 150                 155                 160

Trp Val Gly Arg Ile Arg Ser Lys Tyr Asn Asn Tyr Ala Thr Tyr Tyr
                165                 170                 175

Ala Asp Ser Val Lys Gly Arg Phe Thr Ile Ser Arg Asp Asp Ser Lys
            180                 185                 190

Asn Ser Leu Tyr Leu Gln Met Asn Ser Leu Lys Thr Glu Asp Thr Ala
        195                 200                 205

Val Tyr Tyr Cys Val Arg His Gly Asn Phe Gly Asn Ser Tyr Val Ser
    210                 215                 220

Trp Phe Ala Tyr Trp Gly Gln Gly Thr Leu Val Thr Val Ser Ser Gly
225                 230                 235                 240

Gly Cys Gly Gly Gly Lys Val Ala Ala Leu Lys Glu Lys Val Ala Ala
                245                 250                 255

Leu Lys Glu Lys Val Ala Ala Leu Lys Glu Lys Val Ala Ala Leu Lys
            260                 265                 270

Glu


<210> SEQ ID NO 39
<211> LENGTH: 5
<212> TYPE: PRT
<213> ORGANISM: Artificial Sequence
<220> FEATURE:
```

<223> OTHER INFORMATION: Description of Artificial Sequence: Synthetic peptide

<400> SEQUENCE: 39

Ala Pro Ser Ser Ser
1 5

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 40

Ala Pro Ser Ser Ser Pro Met Glu
1 5

<210> SEQ ID NO 41
<211> LENGTH: 217
<212> TYPE: PRT
<213> ORGANISM: Homo sapiens

<400> SEQUENCE: 41

Ala Pro Glu Leu Leu Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys Gly Gln
100 105 110

Pro Arg Glu Pro Gln Val Tyr Thr Leu Pro Pro Ser Arg Glu Glu Met
115 120 125

Thr Lys Asn Gln Val Ser Leu Thr Cys Leu Val Lys Gly Phe Tyr Pro
130 135 140

Ser Asp Ile Ala Val Glu Trp Glu Ser Asn Gly Gln Pro Glu Asn Asn
145 150 155 160

Tyr Lys Thr Thr Pro Pro Val Leu Asp Ser Asp Gly Ser Phe Phe Leu
165 170 175

Tyr Ser Lys Leu Thr Val Asp Lys Ser Arg Trp Gln Gln Gly Asn Val
180 185 190

Phe Ser Cys Ser Val Met His Glu Ala Leu His Asn His Tyr Thr Gln
195 200 205

Lys Ser Leu Ser Leu Ser Pro Gly Lys
210 215

<210> SEQ ID NO 42
<211> LENGTH: 217
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

```
Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 43
<211> LENGTH: 217
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 43

```
Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
```

```
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn Arg Tyr Thr Gln
        195                 200                 205

Lys Ser Leu Ser Leu Ser Pro Gly Lys
    210                 215


<210> SEQ ID NO 44
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Ser Gln Ser Ala Leu Thr Gln Pro Pro Ser Ala Ser Gly Ser Pro Gly
1               5                   10                  15

Gln Ser Val Thr Ile Ser Cys Thr Gly Thr Ser Ser Asp Val Gly Gly
            20                  25                  30

Tyr Asn Tyr Val Ser Trp Tyr Gln His His Pro Gly Lys Ala Pro Lys
        35                  40                  45

Leu Ile Ile Ser Glu Val Asn Asn Arg Pro Ser Gly Val Pro Asp Arg
    50                  55                  60

Phe Ser Gly Ser Lys Ser Gly Asn Thr Ala Ser Leu Thr Val Ser Gly
65                  70                  75                  80

Leu Gln Ala Glu Asp Glu Ala Glu Tyr Tyr Cys Ser Ser Tyr Thr Asp
                85                  90                  95

Ile His Asn Phe Val Phe Gly Gly Gly Thr Lys Leu Thr Val Leu Gly
            100                 105                 110

Gly Gly Ser Gly Gly Gly Gly Gln Val Thr Leu Arg Glu Ser Gly Pro
        115                 120                 125

Ala Leu Val Lys Pro Thr Gln Thr Leu Thr Leu Thr Cys Thr Phe Ser
    130                 135                 140

Gly Phe Ser Leu Ser Thr Ser Gly Met Gly Val Gly Trp Ile Arg Gln
145                 150                 155                 160

Pro Pro Gly Lys Ala Leu Glu Trp Leu Ala His Ile Trp Trp Asp Asp
                165                 170                 175

Asp Lys Arg Tyr Asn Pro Ala Leu Lys Ser Arg Leu Thr Ile Ser Lys
            180                 185                 190

Asp Thr Ser Lys Asn Gln Val Val Leu Thr Met Thr Asn Met Asp Pro
        195                 200                 205

Val Asp Thr Ala Thr Tyr Tyr Cys Ala Gln Ile Asn Pro Ala Trp Phe
    210                 215                 220

Ala Tyr Trp Gly Gln Gly Thr Leu Val Thr Val Ser Ser Gly Gly Cys
225                 230                 235                 240

Gly Gly Gly Glu Val Ala Ala Leu Glu Lys Glu Val Ala Ala Leu Glu
                245                 250                 255
```

```
Lys Glu Val Ala Ala Leu Glu Lys Glu Val Ala Ala Leu Glu Lys
            260                 265                 270


<210> SEQ ID NO 45
<211> LENGTH: 276
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Phe Asp
            20                  25                  30

Gly Asp Ser Phe Met Asn Trp Tyr Gln Gln Lys Pro Gly Gln Pro Pro
        35                  40                  45

Lys Leu Leu Ile Tyr Thr Thr Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys Gly
            100                 105                 110

Gly Gly Ser Gly Gly Gly Gly Gln Val Gln Leu Gln Glu Ser Gly Pro
        115                 120                 125

Gly Leu Val Lys Pro Ser Gln Thr Leu Ser Leu Ser Cys Thr Val Ser
    130                 135                 140

Gly Gly Ser Ser Ser Ser Gly Ala His Tyr Trp Ser Trp Ile Arg Gln
145                 150                 155                 160

Tyr Pro Gly Lys Gly Leu Glu Trp Ile Gly Tyr Ile His Tyr Ser Gly
                165                 170                 175

Asn Thr Tyr Tyr Asn Pro Ser Leu Lys Ser Arg Ile Thr Ile Ser Gln
            180                 185                 190

His Thr Ser Glu Asn Gln Phe Ser Leu Lys Leu Asn Ser Val Thr Val
        195                 200                 205

Ala Asp Thr Ala Val Tyr Tyr Cys Ala Arg Gly Thr Arg Leu Arg Thr
    210                 215                 220

Leu Arg Asn Ala Phe Asp Ile Trp Gly Gln Gly Thr Leu Val Thr Val
225                 230                 235                 240

Ser Ser Gly Gly Cys Gly Gly Gly Lys Val Ala Ala Leu Lys Glu Lys
                245                 250                 255

Val Ala Ala Leu Lys Glu Lys Val Ala Ala Leu Lys Glu Lys Val Ala
            260                 265                 270

Ala Leu Lys Glu
        275


<210> SEQ ID NO 46
<211> LENGTH: 510
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46
```

```
Asp Ile Val Met Thr Gln Ser Pro Asp Ser Leu Ala Val Ser Pro Gly
1               5                   10                  15

Glu Arg Ala Thr Ile His Cys Lys Ser Ser Gln Thr Leu Leu Tyr Ser
            20                  25                  30

Ser Asn Asn Arg His Ser Ile Ala Trp Tyr Gln Gln Arg Pro Gly Gln
        35                  40                  45

Pro Pro Lys Leu Leu Leu Tyr Trp Ala Ser Met Arg Leu Ser Gly Val
    50                  55                  60

Pro Asp Arg Phe Ser Gly Ser Gly Ser Gly Thr Asp Phe Thr Leu Thr
65                  70                  75                  80

Ile Asn Asn Leu Gln Ala Glu Asp Val Ala Ile Tyr Tyr Cys His Gln
                85                  90                  95

Tyr Ser Ser His Pro Pro Thr Phe Gly His Gly Thr Arg Val Glu Ile
            100                 105                 110

Lys Gly Gly Gly Ser Gly Gly Gly Gly Glu Val Gln Leu Val Glu Ser
        115                 120                 125

Gly Gly Gly Leu Val Gln Pro Gly Gly Ser Leu Arg Leu Ser Cys Ala
    130                 135                 140

Ala Ser Gly Phe Thr Phe Ser Thr Tyr Ala Met Asn Trp Val Arg Gln
145                 150                 155                 160

Ala Pro Gly Lys Gly Leu Glu Trp Val Gly Arg Ile Arg Ser Lys Tyr
                165                 170                 175

Asn Asn Tyr Ala Thr Tyr Tyr Ala Asp Ser Val Lys Gly Arg Phe Thr
            180                 185                 190

Ile Ser Arg Asp Asp Ser Lys Asn Ser Leu Tyr Leu Gln Met Asn Ser
        195                 200                 205

Leu Lys Thr Glu Asp Thr Ala Val Tyr Tyr Cys Val Arg His Gly Asn
    210                 215                 220

Phe Gly Asn Ser Tyr Val Ser Trp Phe Ala Tyr Trp Gly Gln Gly Thr
225                 230                 235                 240

Leu Val Thr Val Ser Ser Gly Gly Cys Gly Gly Gly Glu Val Ala Ala
                245                 250                 255

Leu Glu Lys Glu Val Ala Ala Leu Glu Lys Glu Val Ala Ala Leu Glu
            260                 265                 270

Lys Glu Val Ala Ala Leu Glu Lys Gly Gly Gly Asp Lys Thr His Thr
        275                 280                 285

Cys Pro Pro Cys Pro Ala Pro Glu Ala Ala Gly Gly Pro Ser Val Phe
    290                 295                 300

Leu Phe Pro Pro Lys Pro Lys Asp Thr Leu Met Ile Ser Arg Thr Pro
305                 310                 315                 320

Glu Val Thr Cys Val Val Val Asp Val Ser His Glu Asp Pro Glu Val
                325                 330                 335

Lys Phe Asn Trp Tyr Val Asp Gly Val Glu Val His Asn Ala Lys Thr
            340                 345                 350

Lys Pro Arg Glu Glu Gln Tyr Asn Ser Thr Tyr Arg Val Val Ser Val
        355                 360                 365

Leu Thr Val Leu His Gln Asp Trp Leu Asn Gly Lys Glu Tyr Lys Cys
    370                 375                 380

Lys Val Ser Asn Lys Ala Leu Pro Ala Pro Ile Glu Lys Thr Ile Ser
385                 390                 395                 400

Lys Ala Lys Gly Gln Pro Arg Glu Pro Gln Val Tyr Thr Leu Pro Pro
                405                 410                 415

Ser Arg Glu Glu Met Thr Lys Asn Gln Val Ser Leu Trp Cys Leu Val
```

```
            420                 425                 430

Lys Gly Phe Tyr Pro Ser Asp Ile Ala Val Glu Trp Glu Ser Asn Gly
        435                 440                 445

Gln Pro Glu Asn Asn Tyr Lys Thr Thr Pro Pro Val Leu Asp Ser Asp
    450                 455                 460

Gly Ser Phe Phe Leu Tyr Ser Lys Leu Thr Val Asp Lys Ser Arg Trp
465                 470                 475                 480

Gln Gln Gly Asn Val Phe Ser Cys Ser Val Met His Glu Ala Leu His
                485                 490                 495

Asn His Tyr Thr Gln Lys Ser Leu Ser Leu Ser Pro Gly Lys
            500                 505                 510


<210> SEQ ID NO 47
<211> LENGTH: 278
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Gln Val Gln Leu Val Gln Ser Gly Gly Gly
        115                 120                 125

Val Phe Lys Pro Gly Gly Ser Leu Arg Leu Ser Cys Glu Ala Ser Gly
    130                 135                 140

Phe Thr Phe Thr Glu Tyr Tyr Met Thr Trp Val Arg Gln Ala Pro Gly
145                 150                 155                 160

Lys Gly Leu Glu Trp Leu Ala Tyr Ile Ser Lys Asn Gly Glu Tyr Ser
                165                 170                 175

Lys Tyr Ser Pro Ser Ser Asn Gly Arg Phe Thr Ile Ser Arg Asp Asn
            180                 185                 190

Ala Lys Asn Ser Val Phe Leu Gln Leu Asp Arg Leu Ser Ala Asp Asp
        195                 200                 205

Thr Ala Val Tyr Tyr Cys Ala Arg Ala Asp Gly Leu Thr Tyr Phe Ser
    210                 215                 220

Glu Leu Leu Gln Tyr Ile Phe Asp Leu Trp Gly Gln Gly Ala Arg Val
225                 230                 235                 240

Thr Val Ser Ser Gly Gly Cys Gly Gly Gly Lys Val Ala Ala Leu Lys
                245                 250                 255

Glu Lys Val Ala Ala Leu Lys Glu Lys Val Ala Ala Leu Lys Glu Lys
            260                 265                 270
```

```
Val Ala Ala Leu Lys Glu
        275


<210> SEQ ID NO 48
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn Arg Tyr Thr Gln
        195                 200                 205

Lys Ser Leu Ser Leu Ser Pro Gly Lys
    210                 215


<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Asp Lys Thr His Thr Cys Pro Pro Cys Pro
1               5                   10


<210> SEQ ID NO 50
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 50

```
Gly Gly Gly Asp Lys Thr His Thr Cys Pro Pro Cys Pro
1               5                   10
```

<210> SEQ ID NO 51
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 51

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 52
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 52

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly
            100                 105                 110
```

<210> SEQ ID NO 53
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 53

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Asp Lys Arg Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Gln Ile Asn Pro Ala Trp Phe Ala Tyr Trp Gly Gln Gly Thr
            100                 105                 110

Leu Val Thr Val Ser Ser
        115
```

<210> SEQ ID NO 54
<211> LENGTH: 111
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 54

```
Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Phe Asp
            20                  25                  30

Gly Asp Ser Phe Met Asn Trp Tyr Gln Gln Lys Pro Gly Gln Pro Pro
        35                  40                  45

Lys Leu Leu Ile Tyr Thr Thr Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys
            100                 105                 110
```

<210> SEQ ID NO 55
<211> LENGTH: 110
<212> TYPE: PRT
<213> ORGANISM: Homo sapiens

<400> SEQUENCE: 55

```
Asp Ile Val Met Thr Gln Ser Pro Asp Ser Leu Ala Val Ser Pro Gly
1               5                   10                  15

Glu Arg Ala Thr Ile His Cys Lys Ser Ser Gln Thr Leu Leu Tyr Ser
            20                  25                  30

Ser Asn Asn Arg His Ser Ile Ala Trp Tyr Gln Gln Arg Pro Gly Gln
        35                  40                  45

Pro Pro Lys Leu Leu Leu Tyr Trp Ala Ser Met Arg Leu Ser Gly Val
    50                  55                  60
```

```
Pro Asp Arg Phe Ser Gly Ser Gly Ser Gly Thr Asp Phe Thr Leu Thr
65                  70                  75                  80

Ile Asn Asn Leu Gln Ala Glu Asp Val Ala Ile Tyr Tyr Cys His Gln
                85                  90                  95

Tyr Ser Ser His Pro Pro Thr Phe Gly His Gly Thr Arg Val
            100                 105                 110


<210> SEQ ID NO 56
<211> LENGTH: 126
<212> TYPE: PRT
<213> ORGANISM: Homo sapiens

<400> SEQUENCE: 56

Gln Val Gln Leu Val Gln Ser Gly Gly Gly Val Phe Lys Pro Gly Gly
1               5                   10                  15

Ser Leu Arg Leu Ser Cys Glu Ala Ser Gly Phe Thr Phe Thr Glu Tyr
            20                  25                  30

Tyr Met Thr Trp Val Arg Gln Ala Pro Gly Lys Gly Leu Glu Trp Leu
        35                  40                  45

Ala Tyr Ile Ser Lys Asn Gly Glu Tyr Ser Lys Tyr Ser Pro Ser Ser
    50                  55                  60

Asn Gly Arg Phe Thr Ile Ser Arg Asp Asn Ala Lys Asn Ser Val Phe
65                  70                  75                  80

Leu Gln Leu Asp Arg Leu Ser Ala Asp Asp Thr Ala Val Tyr Tyr Cys
                85                  90                  95

Ala Arg Ala Asp Gly Leu Thr Tyr Phe Ser Glu Leu Leu Gln Tyr Ile
            100                 105                 110

Phe Asp Leu Trp Gly Gln Gly Ala Arg Val Thr Val Ser Ser
        115                 120                 125


<210> SEQ ID NO 57
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

gaggtkcagc tggtggagtc tgggggtggc ttggtccagc cggggggtc cctgagactc     60

tcttgtgcag cctctggatt cagcgtcagc tacgactata tggcctgggt ccgccaggct    120

ccagggaagg gactggagtg ggtctctatt atttatggtg gtggtagtcc atattacgca    180

gactctgtga agggccgatt cgccatctcc agagacacct ccaggaatac actggatctt    240

caaatgagca gcctgagacg tgacgacagc ggtgtttact tctgtgcgag gggactcgcc    300

tcgctcttcg atctctgggg ccgaggcacc ctggtcactg tctcgtcagc atccccgacc    360

agccccaagg tcttcccgct gagcctcgac agcaccagc                           399


<210> SEQ ID NO 58
<211> LENGTH: 846
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58

gaaattgtgt tgacrcagtc tccaggcacc ctgtctttgt ctccaggaga aacagccacc     60
```

ctctcctgca gggccagtcg gcgtgttaac gtcaactacc tagcctggta tcaacacaga 120
cctggccaga gtcccaggct cctcatgtac ggtccttaca acaggcccac tggcatcccg 180
ggcaggttct ggggcgagtg gtctgggcca ctcttcactc tcaacatcga cagactggag 240
cctgttgatc gagcagtcta ttactgtcta cactttgact ctgatacttc ttcgtgggcg 300
ttcggccgag ggaccaaggt ggaggtcaaa cgaactgtgg ctgcaccatc ttcttcactc 360
ttccaaaaac atctgaagca gttttaatct caacttctct catcaaaccc gggggggag 420 atcaagaccg atgggccagc cacggttggt tggaccggca cgggggccgg cccacagcga 480
aaaaaagggg gagacccaga gtgtgagggc actagagggg tggggacaga cccttctggg 540
gacttgaagg gggagagtcg cccccacatg cccaaccggg ggcccaccac cgggcggttt 600
cacggacgtt attaacgggc cggaattttt cccccgtgtt tcatacaagc ccccccctgg 660
aggggggaaa caaaccccgc caaaaagggg cctttattct caaaccaaca acgcgcgccc 720
ccaaaccctc caaaattttt ccccccaaac caaacacaaa cccccccccc cccccccccc 780
cccccccccc cccccccccc cccccccccc cccccccccc cccccccccc cccccccccc 840
cccccc 846

<210> SEQ ID NO 59
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 59
gaggtkcagc tggtggagtc tgggggtggc ttggtccagc cggggggtc cctgagactc 60 tcttgtgcag cctctggatt cagcgtcagc tacgactata tggcctgggt ccgccaggct 120
ccagggaagg gactggagtg ggtctctatt atttatggtg gtggtagtcc atattacgca 180
gactctgtga agggccgatt cgccatctcc agagacacct ccaggaatac actggatctt 240
caaatgagca gcctgagacg tgacgacagc ggtgtttact tctgtgcgag gggactcgcc 300
tcgctcttcg atctctgggg ccgaggcacc ctggtcactg tctcgtcagc a 351

<210> SEQ ID NO 60
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 60
gaaattgtgt tgacrcagtc tccaggcacc ctgtctttgt ctccaggaga aacagccacc 60
ctctcctgca gggccagtcg gcgtgttaac gtcaactacc tagcctggta tcaacacaga 120
cctggccaga gtcccaggct cctcatgtac ggtccttaca acaggcccac tggcatcccg 180
ggcaggttct ggggcgagtg gtctgggcca ctcttcactc tcaacatcga cagactggag 240
cctgttgatc gagcagtcta ttactgtcta cactttgact ctgatacttc ttcgtgggcg 300
ttcggccgag ggaccaaggt ggaggtcaaa cga 333

<210> SEQ ID NO 61
<211> LENGTH: 117
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 61

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Val Ser Tyr Asp
            20                  25                  30

Tyr Met Ala Trp Val Arg Gln Ala Pro Gly Lys Gly Leu Glu Trp Val
        35                  40                  45

Ser Ile Ile Tyr Gly Gly Gly Ser Pro Tyr Tyr Ala Asp Ser Val Lys
    50                  55                  60

Gly Arg Phe Ala Ile Ser Arg Asp Thr Ser Arg Asn Thr Leu Asp Leu
65                  70                  75                  80

Gln Met Ser Ser Leu Arg Arg Asp Asp Ser Gly Val Tyr Phe Cys Ala
                85                  90                  95

Arg Gly Leu Ala Ser Leu Phe Asp Leu Trp Gly Arg Gly Thr Leu Val
            100                 105                 110

Thr Val Ser Ser Ala
        115
```

<210> SEQ ID NO 62
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

```
Glu Ile Val Leu Thr Gln Ser Pro Gly Thr Leu Ser Leu Ser Pro Gly
1               5                   10                  15

Glu Thr Ala Thr Leu Ser Cys Arg Ala Ser Arg Arg Val Asn Val Asn
            20                  25                  30

Tyr Leu Ala Trp Tyr Gln His Arg Pro Gly Gln Ser Pro Arg Leu Leu
        35                  40                  45

Met Tyr Gly Pro Tyr Asn Arg Pro Thr Gly Ile Pro Gly Arg Phe Trp
    50                  55                  60

Gly Glu Trp Ser Gly Pro Leu Phe Thr Leu Asn Ile Asp Arg Leu Glu
65                  70                  75                  80

Pro Val Asp Arg Ala Val Tyr Tyr Cys Leu His Phe Asp Ser Asp Thr
                85                  90                  95

Ser Ser Trp Ala Phe Gly Arg Gly Thr Lys Val Glu Val Lys Arg
            100                 105                 110
```

<210> SEQ ID NO 63
<211> LENGTH: 1000
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

```
caggtgcagc tggtrcagtc tgggacttaa tcctctacac acacccatat ctcctacgct     60

ccataacgga cctactttgc actaatcctt aggacacgcc gactcctcct cggggtaaac    120

tctataaaga tgacaaaaga tagtaaccta ggaatagaac aatgcaatat actaaagaac    180
```

```
tgatccttga cactgctacc gcctaggtat tcgcaatata acaaatatca tcatccgacc    240

caagtatatg ctggatttgt taaaatagtc agagaactat atctatctgc aatggcttac    300

agctaagcca gaatctacaa taaaaacaac aagcgggaac gcttccaaag aaaaaaacca    360

tatactcagg tctgttcacc atctcaatca ccgactttca cacatttttt cccaggctta    420

caaagatatt cagggttttt ttttcctttt ccattccaga ggaaccacag tgcagcgtgt    480

cagtaggggg gtaaggaaaa taagcctggt tcctcagtgt gtctctctgg caagtcttgg    540

ggcgcctcct ttagaaataa tctcacccca gccccccgcc acctccaggg aatggacgag    600

tagtcgagac aaatcttccc ccttatgtta gaagaaacaa ccaacccaga taaaatgccg    660

cggaagcgtc acatttctcc caaactcaac ctatatcgca tctaacaggg gataaagcag    720

ctcaaaaaaa gacacggcgg cctgtatgtg ggagagatcg gtttctctcc ttacagaacg    780

gagacccccg cgaattaaaa atggggccaa gagaaaagag ttaatttttc ttctgggtat    840

gtgatggggg gggagaataa tctgcgcacc agaccacagg gtagctgcgt acgtctcggg    900

gggtccctga gactctcctg tgcagcctct ggattcagcg tcaggaacga ccagatggcc    960

tgggtccgcc aggctccagg gaagcgactg gagtgggtct                         1000
```

<210> SEQ ID NO 64
<211> LENGTH: 822
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 64

```
gaaattgtgt tgacrcagtc tccaggcacc ctgtccttgt ctccagggga gagagccacc     60

ctctcctgca gggccaatcg gcggattgac atgaacgcct tggcctggta ccagcaccga    120

tctggccagg ctcccaggct cctcacccat ggtgtctata acagggccac tggcatccca    180

gacaggttca gtggctattg gtctgggcca gagttcaccc tcgtcatcag cagactggag    240

cctgaagatt ttgcagtcta ttactgtgta cactttctct acgaaaatcc agcgtgggcg    300

ttcggccgag ggaccaagat agaggtcaag cgaactgtgg ctgcaccatc tgctcacatc    360

ttccaaccat atgatgagca cttgaaatct gaaactgcct catcacccct ggcggggaaa    420

aacaagaacg gtgggggcgc cacaggtgcc aaaaacttta tgtcgctccg ggcaaaagcc    480

cccgtggaat ttcatgaaaa aggggtaccc attagtagac cgcaaaatgc cgggccaaat    540

ctcctaaata acagaggtag aattaaccaa acagatgtcc aaagaacttt gctggaacac    600

cgtaagcggt atcaaagagg aggggggaga gaaccggggg gcccctgccg gatatatatc    660

tgtaaacagc cgggccaatg gatttcctcc cccctgtggg ccctaaaaaa agggggtgtt    720

cttaaaccca caaaaaaagg gaaaacggtg tcccgggaaa cacacctttc tcccaatatt    780

atttcgcgcg gggaaaaaaa gaaaaacaaa aaaaaaaacc cc                       822
```

<210> SEQ ID NO 65
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 65

```
gaggtgcagc tggtggagtc tgggggtagc tgcgtacgtc tcggggggtc cctgagactc     60

tcctgtgcag cctctggatt cagcgtcagg aacgaccaga tggcctgggt ccgccaggct    120

ccagggaagc gactggagtg ggtctctatt attaacgatg gtgctagtcc atactacgca    180

gactctgtga agggccgctt cgccatgtcc agagacacct ccaagaatac agtgtttctt    240

cagatgaaca gcctgagacg tgacgacaca gctgtttatt tctgtgcgag ggggatcgcc    300

tcattcttcg atgtctgggg ccgtggcacg ctggtcgctg tctcgtcagc a             351


<210> SEQ ID NO 66
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66

gaaattgtgt tgacrcagtc tccaggcacc ctgtccttgt ctccagggga gagagccacc     60

ctctcctgca gggccaatcg gcggattgac atgaacgcct tggcctggta ccagcaccga    120

tctggccagg ctcccaggct cctcacccat ggtgtctata acagggccac tggcatccca    180

gacaggttca gtggctattg gtctgggcca gagttcaccc tcgtcatcag cagactggag    240

cctgaagatt ttgcagtcta ttactgtgta cactttctct acgaaaatcc agcgtgggcg    300

ttcggccgag ggaccaagat agaggtcaag cga                                 333


<210> SEQ ID NO 67
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Glu Val Gln Leu Val Glu Ser Gly Gly Ser Cys Val Arg Leu Gly Gly
1               5                   10                  15

Ser Leu Arg Leu Ser Cys Ala Ala Ser Gly Phe Ser Val Arg Asn Asp
            20                  25                  30

Gln Met Ala Trp Val Arg Gln Ala Pro Gly Lys Arg Leu Glu Trp Val
        35                  40                  45

Ser Ile Ile Asn Asp Gly Ala Ser Pro Tyr Tyr Ala Asp Ser Val Lys
    50                  55                  60

Gly Arg Phe Ala Met Ser Arg Asp Thr Ser Lys Asn Thr Val Phe Leu
65                  70                  75                  80

Gln Met Asn Ser Leu Arg Arg Asp Asp Thr Ala Val Tyr Phe Cys Ala
                85                  90                  95

Arg Gly Ile Ala Ser Phe Phe Asp Val Trp Gly Arg Gly Thr Leu Val
            100                 105                 110

Ala Val Ser Ser Ala
        115


<210> SEQ ID NO 68
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 68

```
Glu Ile Val Leu Thr Gln Ser Pro Gly Thr Leu Ser Leu Ser Pro Gly
1               5                   10                  15

Glu Arg Ala Thr Leu Ser Cys Arg Ala Asn Arg Arg Ile Asp Met Asn
            20                  25                  30

Ala Leu Ala Trp Tyr Gln His Arg Ser Gly Gln Ala Pro Arg Leu Leu
        35                  40                  45

Thr His Gly Val Tyr Asn Arg Ala Thr Gly Ile Pro Asp Arg Phe Ser
    50                  55                  60

Gly Tyr Trp Ser Gly Pro Glu Phe Thr Leu Val Ile Ser Arg Leu Glu
65                  70                  75                  80

Pro Glu Asp Phe Ala Val Tyr Tyr Cys Val His Phe Leu Tyr Glu Asn
                85                  90                  95

Pro Ala Trp Ala Phe Gly Arg Gly Thr Lys Ile Glu Val Lys Arg
            100                 105                 110
```

<210> SEQ ID NO 69
<211> LENGTH: 402
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 69

```
gaggtkcagc tggtggagtc tgggggtggc gtggtccacc ctggggggtc cctgagactc     60

tcctgtgcag cctctggatt cagcgtcagt cacgacttca tggcctggat ccgccaggct    120

ccaggaaagg gactggagtg gatctctatc atatataaca ctggttctcg atactactac    180

gcagactctg tgaagggccg cttcgccctc tccagagata cgtccaacaa cacactgatt    240

cttcacatga gcggcctgag acgtgacgac acggctattt atttctgtgc caggggagtc    300

gcctcgttct tcgaattgtg gggccgtggc accctggtca ctgtctcgtc agcctccacc    360

aagggcccat cggtcttccc cctggcaccc tcctccaaga gc                       402
```

<210> SEQ ID NO 70
<211> LENGTH: 836
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 70

```
gaaacgacac tcacgcagtc tccagccatc ctgtctgtgt ctccagggga aaccgccacc     60

ctctcctgca gggccagtcg ccgtgttgac atgaacggcc tcgcctggta ccaacacagg    120

cctggccagg ctcccaggct cctcatgcat ggtgtttata atagggccgc cggcatctca    180

ggcaggttca ctggcagttg gtctgggcca gtcttcactc tcaccatcag cagactggag    240

cctgaagatt ttggagtcta ttactgtcaa cacttttact atgagacttc agcgtgggcg    300

ttcggccgag ggaccagggt ggagggcaaa cgaactgtgg ctgcaccatc ttctcctatc    360

ttccaaaaaa acaacctccc aatgacagct gtaaatgtaa cataactgtg gcacaatcca    420

tcagcatccg ccgcggaagg gcgagcaaag ggcccccgc cgcccgcccg gggggggggg    480

gggggggtg ggggggccc ccctgggcgg ggggccccac cccccccggc cccccccccgg    540

gcccggcccc cccccccccc cggcccccc ccccgggcgg ggcccccaca gggccccggg    600
```

```
ggggccccct cccccccccc cccaaacccc cccccccccc cccccccccc ccgccgcccc    660

cccccccccc cccccccccc cccccccccc aaaccccccc cccccccccc cccccccccc    720

cccccccccc cccccccccc cccccccccc cccccccccc cccccccccc cccccccccc    780

cccccccccc cccccccccc cccccccccc cccccccccc cccccccccc cccccc        836
```

<210> SEQ ID NO 71
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 71

```
gaggtkcagc tggtggagtc tgggggtggc gtggtccacc ctgggggggtc cctgagactc     60

tcctgtgcag cctctggatt cagcgtcagt cacgacttca tggcctggat ccgccaggct    120

ccaggaaagg gactggagtg gatctctatc atatataaca ctggttctcg atactactac    180

gcagactctg tgaagggccg cttcgccctc tccagagata cgtccaacaa cacactgatt    240

cttcacatga gcggcctgag acgtgacgac acggctattt atttctgtgc caggggagtc    300

gcctcgttct tcgaattgtg gggccgtggc accctggtca ctgtctcgtc agcc          354
```

<210> SEQ ID NO 72
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 72

```
gaaacgacac tcacgcagtc tccagccatc ctgtctgtgt ctccagggga aaccgccacc     60

ctctcctgca gggccagtcg ccgtgttgac atgaacggcc tcgcctggta ccaacacagg    120

cctggccagg ctcccaggct cctcatgcat ggtgtttata atagggcgc cggcatctca    180

ggcaggttca ctggcagttg gtctgggcca gtcttcactc tcaccatcag cagactggag    240

cctgaagatt ttggagtcta ttactgtcaa cacttttact atgagacttc agcgtgggcg    300

ttcggccgag ggaccagggt ggagggcaaa cga                                 333
```

<210> SEQ ID NO 73
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 73

```
Glu Val Gln Leu Val Glu Ser Gly Gly Gly Val Val His Pro Gly Gly
1               5                   10                  15

Ser Leu Arg Leu Ser Cys Ala Ala Ser Gly Phe Ser Val Ser His Asp
            20                  25                  30

Phe Met Ala Trp Ile Arg Gln Ala Pro Gly Lys Gly Leu Glu Trp Ile
        35                  40                  45

Ser Ile Ile Tyr Asn Thr Gly Ser Arg Tyr Tyr Tyr Ala Asp Ser Val
    50                  55                  60

Lys Gly Arg Phe Ala Leu Ser Arg Asp Thr Ser Asn Asn Thr Leu Ile
65                  70                  75                  80
```

Leu His Met Ser Gly Leu Arg Arg Asp Asp Thr Ala Ile Tyr Phe Cys
85 90 95

Ala Arg Gly Val Ala Ser Phe Phe Glu Leu Trp Gly Arg Gly Thr Leu
100 105 110

Val Thr Val Ser Ser Ala
115

<210> SEQ ID NO 74
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 74

Glu Thr Thr Leu Thr Gln Ser Pro Ala Ile Leu Ser Val Ser Pro Gly
1 5 10 15

Glu Thr Ala Thr Leu Ser Cys Arg Ala Ser Arg Arg Val Asp Met Asn
20 25 30

Gly Leu Ala Trp Tyr Gln His Arg Pro Gly Gln Ala Pro Arg Leu Leu
35 40 45

Met His Gly Val Tyr Asn Arg Ala Ala Gly Ile Ser Gly Arg Phe Thr
50 55 60

Gly Ser Trp Ser Gly Pro Val Phe Thr Leu Thr Ile Ser Arg Leu Glu
65 70 75 80

Pro Glu Asp Phe Gly Val Tyr Tyr Cys Gln His Phe Tyr Tyr Glu Thr
85 90 95

Ser Ala Trp Ala Phe Gly Arg Gly Thr Arg Val Glu Gly Lys Arg
100 105 110

<210> SEQ ID NO 75
<211> LENGTH: 369
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 75
caggtgcagc tgtgcggagt cgggccagga ctggtgaagc cttcacagac cttgtccctc 60
agttgcactg tctctggtgg ctccagcagt agtggtgctc actactggag ttggatccgc 120
cagtacccag ggaagggcct ggagtggatt ggttacatcc attacagtgg gaacacttac 180
tacaacccgt ccctcaagag tcgaattacc atatcacaac acacgtctga gaaccagttc 240
tccctgaagc tcaactctgt gactgttgca gacacggccg tctattactg tgcgagaggg 300
acccgtctcc ggacactacg gaatgctttt gatatttggg gccaggggac aagggtcacc 360
gtctcttca 369

<210> SEQ ID NO 76
<211> LENGTH: 330
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 76
cagtctgccc tgactcagcc tccctccgcg tccgggtctc ctggacagtc agtcaccatc 60

```
tcctgcactg gaaccagcag tgacgttggt ggttataact atgtttcctg gtaccaacac    120

cacccaggca aagcccccaa actcataatt tctgaggtca ataaccggcc ctcaggggtc    180

cctgatcgtt tctctggctc caagtctggc aacacggcct ccctgaccgt ctctgggctc    240

caggctgagg atgaggctga atattactgc agctcataca cagacatcca caatttcgtc    300

ttcggcggag ggaccaagct gaccgtccta                                      330


<210> SEQ ID NO 77
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Gln Val Gln Leu Cys Gly Val Gly Pro Gly Leu Val Lys Pro Ser Gln
1               5                   10                  15

Thr Leu Ser Leu Ser Cys Thr Val Ser Gly Gly Ser Ser Ser Ser Gly
            20                  25                  30

Ala His Tyr Trp Ser Trp Ile Arg Gln Tyr Pro Gly Lys Gly Leu Glu
        35                  40                  45

Trp Ile Gly Tyr Ile His Tyr Ser Gly Asn Thr Tyr Tyr Asn Pro Ser
    50                  55                  60

Leu Lys Ser Arg Ile Thr Ile Ser Gln His Thr Ser Glu Asn Gln Phe
65                  70                  75                  80

Ser Leu Lys Leu Asn Ser Val Thr Val Ala Asp Thr Ala Val Tyr Tyr
                85                  90                  95

Cys Ala Arg Gly Thr Arg Leu Arg Thr Leu Arg Asn Ala Phe Asp Ile
            100                 105                 110

Trp Gly Gln Gly Thr Arg Val Thr Val Ser Ser
        115                 120


<210> SEQ ID NO 78
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln His His Pro Gly Lys Ala Pro Lys Leu
        35                  40                  45

Ile Ile Ser Glu Val Asn Asn Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Glu Tyr Tyr Cys Ser Ser Tyr Thr Asp Ile
                85                  90                  95

His Asn Phe Val Phe Gly Gly Gly Thr Lys Leu Thr Val Leu
            100                 105                 110
```

```
<210> SEQ ID NO 79
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79

caggtgcagc tggtgcagtc tgggggaggc gttttcaagc ctggagggtc cctgagactc     60

tcctgtgaag cctctggatt cacatttact gaatattaca tgacttgggt ccgccaggct    120

cctgggaagg ggctggagtg gcttgcgtat attagtaaga atggtgaata ttcaaaatat    180

tcaccgtcct caaacggccg gttcaccatc tccagagaca acgccaagaa ctcagtgttt    240

ctgcaattgg acagactgag cgccgacgac acggccgtct attactgtgc gagagcggac    300

ggattaacat acttctctga attactccaa tacatttttg acctctgggg ccagggagcc    360

cgggtcaccg tctcctcg                                                  378


<210> SEQ ID NO 80
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Met Glu Thr Asp Thr Leu Leu Leu Trp Val Leu Leu Leu Trp Val Pro
1               5                   10                  15

Gly Ser Thr Gly Asp Gln Val Gln Leu Val Gln Ser Gly Gly Gly Val
            20                  25                  30

Phe Lys Pro Gly Gly Ser Leu Arg Leu Ser Cys Glu Ala Ser Gly Phe
        35                  40                  45

Thr Phe Thr Glu Tyr Tyr Met Thr Trp Val Arg Gln Ala Pro Gly Lys
    50                  55                  60

Gly Leu Glu Trp Leu Ala Tyr Ile Ser Lys Asn Gly Glu Tyr Ser Lys
65                  70                  75                  80

Tyr Ser Pro Ser Ser Asn Gly Arg Phe Thr Ile Ser Arg Asp Asn Ala
                85                  90                  95

Lys Asn Ser Val Phe Leu Gln Leu Asp Arg Leu Ser Ala Asp Asp Thr
            100                 105                 110

Ala Val Tyr Tyr Cys Ala Arg Ala Asp Gly Leu Thr Tyr Phe Ser Glu
        115                 120                 125

Leu Leu Gln Tyr Ile Phe Asp Leu Trp Gly Gln Gly Ala Arg Val Thr
    130                 135                 140

Val Ser Ser
145


<210> SEQ ID NO 81
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Met Glu Thr Asp Thr Leu Leu Leu Trp Val Leu Leu Leu Trp Val Pro
1               5                   10                  15
```

-continued

```
Gly Ser Thr Gly Asp Glu Thr Thr Leu Thr Gln Ser Pro Asp Ser Leu
            20                  25                  30

Ala Val Ser Pro Gly Glu Arg Ala Thr Ile His Cys Lys Ser Ser Gln
        35                  40                  45

Thr Leu Leu Tyr Ser Ser Asn Asn Arg His Ser Ile Ala Trp Tyr Gln
    50                  55                  60

Gln Arg Pro Gly Gln Pro Pro Lys Leu Leu Leu Tyr Trp Ala Ser Met
65                  70                  75                  80

Arg Leu Ser Gly Val Pro Asp Arg Phe Ser Gly Ser Gly Ser Gly Thr
                85                  90                  95

Asp Phe Thr Leu Thr Ile Asn Asn Leu Gln Ala Glu Asp Val Ala Ile
            100                 105                 110

Tyr Tyr Cys His Gln Tyr Ser Ser His Pro Pro Thr Phe Gly His Gly
        115                 120                 125

Thr Arg Val Glu Leu Arg
    130


<210> SEQ ID NO 82
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82

gaaacgacac tcacgcagtc tccagactcc ctggctgtgt ctccgggcga gagggccacc      60

atccactgca agtccagcca gactcttttg tacagctcca acaatagaca ctccattgct     120

tggtaccaac agagaccagg acagcctcct aaattactcc tttattgggc atctatgcgg     180

ctttccgggg tccctgaccg attcagtggc agcgggtctg ggacagattt cactctcacc     240

atcaacaacc tgcaggctga ggatgtggcc atctattact gtcaccaata ttccagtcat     300

cccccgacgt tcggccacgg gaccagggtg gagctcaga                            339
```

BISPECIFIC MOLECULES COMPRISING AN HIV-1 ENVELOPE TARGETING ARM

This application is a continuation of U.S. application Ser. No. 15/514,420 filed Mar. 24, 2017 which is a U.S. National Stage application of PCT/US2015/053027, filed Sep. 29, 2015, which claims the benefit of and priority to U.S. Ser. No. 62/056,834 filed Sep. 29, 2014, and U.S. Ser. No. 62/206,586 filed Aug. 18, 2015, the contents of each of which are hereby incorporated by reference in their entireties.

GOVERNMENT SUPPORT

This invention was made with government support under Grant Nos. U19 AI067854 and UM1 AI100645 awarded by the National Institutes of Health. The government has certain rights in the invention.

REFERENCE TO A JOINT RESEARCH AGREEMENT

The inventions claimed in this application were made under a joint research agreement between Duke University, Macrogenics, Inc., and The University of North Carolina, Chapel Hill.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

All patents, patent applications and publications cited herein are hereby incorporated by reference in their entirety. The disclosure of these publications in their entireties are hereby incorporated by reference into this application in order to more fully describe the state of the art as known to those skilled therein as of the date of the invention described herein.

SEQUENCE LISTING

The instant application contains a Sequence Listing which has been submitted electronically in ASCII format and is hereby incorporated by reference in its entirety. Said ASCII copy, created on Jun. 29, 2020, is named 1234300_00344 US2_SL.txt and is 117,071 bytes in size.

TECHNICAL FIELD

The invention is directed to HIV-1 antibodies and bispecific molecules comprising an HIV-1 binding domain and an effector cell binding domain, and their uses.

BACKGROUND

Highly Active Antiretroviral Therapy (HAART) has been effective in reducing the viral burden and ameliorating the effects of HIV-1 infection in infected individuals. However, despite this therapy the virus persists in the individual due to latent reservoir of HIV infected cells which evade this treatment. Thus, there is a need for therapeutic agents for treatment of HIV-1 infected individuals, as well as agents that target virus infected cells and have to potential to reduce the latent reservoir of HIV-1 infected cells.

SUMMARY OF THE INVENTION

The present invention is directed to bispecific molecules, e.g. covalently linked polypeptide chains to form antibodies, covalent diabodies and/or covalent diabody molecules and their use in the treatment of HIV-1. In certain aspects, the bispecific molecules of the present invention can bind to two different targets or epitopes on two different cells wherein the first epitope is expressed on a different cell type than the second epitope, such that the bispecific molecules can bring the two cells together. In certain aspects, the bispecific molecules of the present invention can bind to two different cells, wherein the bispecific molecules comprises an arm with the binding specificity of A32, 7B2, CH27, CH28 or CH44, which arm binds to the HIV-1 envelope expressed on a first cell, e.g. HIV infected cell, and a second arm with the binding specificity for an epitope expressed on a different cell type than the first cell, such that the bispecific molecules can bring the two cells together. In certain embodiment, the second cell is in effector cell which expresses CD3 or CD16.

In certain embodiments an antibody binds specifically to a particular target, even where the specific epitope may not be know, peptide or polysaccharide (such as an antigen present on the surface of a pathogen, for example gp120, gp41, or CD3) and do not bind in a significant amount to other proteins or polysaccharides present in the sample or subject. Specific binding can be determined by methods known in the art. Various competitive binding assays are known in the art. With reference to an antibody antigen complex, in certain embodiments specific binding of the antigen and antibody has a KD of less than about $10^6$ Molar, such as less than about $10^6$ Molar, $10^7$ Molar, $10^8$ Molar, $10^9$, or even less than about $10^{10}$ Molar.

In certain aspects the invention provides bispecific molecules comprising a first polypeptide chain and a second polypeptide chain, covalently bonded to one another, wherein:

- (I) the first polypeptide chain comprises in the N- to C-terminal direction:
  - (i) a domain (A) comprising a binding region of the light chain variable domain of a first immunoglobulin (VL1) having the binding specificity of the A32, 7B2, CH28, or envelope antibody;
  - (ii) a domain (B) comprising a binding region of a heavy chain variable domain of a second immunoglobulin (VH2) specific for an epitope (2), wherein domains (A) and (B) are separated from one another by a peptide linker 1; and
  - (iii) a domain (C) comprising a heterodimer promoting domain including a K coil or E coil; wherein the heterodimer promoting domain (C) and domain B are separated by a peptide linker 2;
- (II) the second polypeptide chain comprises in the N- to C-terminal direction:
  - (i) a domain (D) comprising a binding region of a light chain variable domain of the second immunoglobulin (VL2) specific for the epitope (2);
  - (ii) a domain (E) comprising a binding region of a heavy chain variable domain of the first immunoglobulin (VH1) having the binding specificity of the A32, 7B2, CH28, or CH44 HIV-1 antibody, wherein domains (D) and (E) are separated from one another by a peptide linker 1; and
  - (iii) a domain (F) comprising a heterodimer promoting domain including a K coil or E coil; wherein the heterodimer promoting domain (F) and domain (E) are separated by a peptide linker 2; and wherein:

the domains (A) and (B) do not associate with one another to form an epitope binding site;

the domains (D) and (E) do not associate with one another to form an epitope binding site; and the domains (A) and (E) associate to form a binding site that binds the HIV-1 envelope like A32, 7B2, CH28, or CH44 antibody (1); and the domains (B) and (D) associate to form a binding site that binds the epitope (2).

In certain aspects the invention provides bispecific molecules comprising a first polypeptide chain, a second polypeptide chain, and a third polypeptide chain, wherein some of the polypeptides are covalently bonded (See FIG. 8), and wherein:

(I) the first polypeptide chain comprises in the N- to C-terminal direction:

(i) a domain (A) comprising a binding region of the light chain variable domain of a first immunoglobulin (VL1) having the binding specificity of the A32, 7B2, CH28, or CH44 HIV-1 antibody;

(ii) a domain (B) comprising a binding region of a heavy chain variable domain of a second immunoglobulin (VH2) specific for an epitope (2), wherein domains (A) and (B) are separated from one another by a peptide linker 1;

(iii) a domain (C) comprising a heterodimer promoting domain including a K coil or E coil; wherein the heterodimer promoting domain (C) and domain B are separated by a peptide linker 2;

(iv) a CH2-CH3 domain, wherein the CH2-CH3 domain and domain (C) are separated by a peptide linker 3 or a spacer-linker 3;

(II) the second polypeptide chain comprises in the N- to C-terminal direction:

(i) a domain (D) comprising a binding region of a light chain variable domain of the second immunoglobulin (VL2) specific for the epitope (2);

(ii) a domain (F) comprising a binding region of a heavy chain variable domain of the first immunoglobulin (VH1) having the binding specificity of the A32, 7B2, CH28, or CH44 HIV-1 antibody, wherein domains (D) and (E) are separated from one another by a peptide linker 1;

(iii) a domain (F) comprising a heterodimer promoting domain including a K coil or E coil; wherein the heterodimer promoting domain (F) and domain (E) are separated by a peptide linker 2;

(III) the third polypeptide chain comprises in the N- to C-terminal direction:

(i) a peptide linker 3, (ii) a CH2-CH3 domain, and wherein:

the domains (A) and (B) do not associate with one another to form an epitope binding site;

the domains (D) and (E) do not associate with one another to form an epitope binding site;

the domains (A) and (E) associate to form a binding site that binds the HIV-1 envelope lik A32, 7B2, CH28, or CH44 antibody (I);

the domains (B) and (D) associate to form a binding site that binds the epitope (2); and the CH2-CH3 domains of the first and third polypeptide form an Fc chain.

A bispecific molecule comprising a first polypeptide chain, a second polypeptide chain, and a third polypeptide chain, wherein some of the polypeptides are covalently bonded (See FIG. 8), and wherein:

(I) the first polypeptide chain comprises in the N- to C-terminal direction:

(i) a peptide linker 3 followed by a CH2-CH3 domain;

(ii) a domain (A) comprising a binding region of the light chain variable domain of a first immunoglobulin (VL1) having the binding specificity of the A32, 7B2, CH28, or CH44 HIV-1 antibody, wherein the CH2-CH3 domain and domain (A) are separated by a peptide linker 4;

(iii) a domain (B) comprising a binding region of a heavy chain variable domain of a second immunoglobulin (VH2) specific for an epitope (2), wherein domains (A) and (B) are separated from one another by a peptide linker 1;

(iv) a domain (C) comprising a heterodimer promoting domain including a K coil or F coil; wherein the heterodimer promoting domain (C) and domain B are separated by a peptide linker 2;

(II) the second polypeptide chain comprises in the N- to C-terminal direction:

(i) a domain (D) comprising a binding region of a light chain variable domain of the second immunoglobulin (VL2) specific for the epitope (2);

(ii) a domain (E) comprising a binding region of a heavy chain variable domain of the first immunoglobulin (VH1) having the binding specificity of the A32, 7B2, CH28, or CH44 HIV-1 antibody, wherein domains (D) and (E) are separated from one another by a peptide linker 1;

(iii) a domain (F) comprising a heterodimer promoting domain including a K coil or E coil; wherein the heterodimer promoting domain (F) and domain (F) are separated by a peptide linker 2;

(III) the third polypeptide chain comprises in the N- to C-terminal direction:

(i) a peptide linker 3, (ii) a CH2-CH3 domain, and wherein:

the domains (A) and (B) do not associate with one another to form an epitope binding site;

the domains (D) and (E) do not associate with one another to form an epitope binding site;

the domains (A) and (F) associate to form a binding site that binds the HIV-1 envelope like A32, 7B2, CH28, or CH44 antibody (1);

the domains (B) and (D) associate to form a binding site that binds the epitope (2); and the CH2-CH3 domains of the first and third polypeptide form an Fc chain.

In certain embodiments, the CH2-CH3 domain of polypeptide chain 1 is the of the "knob" design and the CH2-CH3 domain of the third polypeptide chain is of the "hole" design, or vice versa.

In certain embodiments, the epitope (2) is a CD3 epitope or a CD16 epitope, In certain embodiments, the bispecific molecule binds HIV envelope with the specificity of A32 antibody and also binds CD3. In certain embodiments, the bispecific molecule binds HIV envelope with the specificity of 7B2 antibody and also binds CD3. In certain embodiments, the bispecific molecule binds HIV envelope with the specificity of CH28 antibody and also binds CD3. In certain embodiments, the bispecific molecule binds HIV envelope with the specificity of CH44antibody and also binds CD3. In certain embodiments, the bispecific molecule binds HIV envelope with the specificity of A32 antibody and also binds CD16. In certain embodiments, the bispecific molecule binds HIV envelope with the specificity of 7B2 antibody and also binds CD16. In certain embodiments, the bispecific molecule binds HIV envelope with the specificity of CH28 antibody and also binds CD16. In certain embodiments, the bispecific molecule binds HIV envelope with the specificity of CH44antibody and also binds CD16.

In certain embodiments, the domains (A) and (E) associate to form a binding site that binds the HIV-1 envelope with the binding specificity of the A32, 7B2, CH28, or CH44 antibody. In certain embodiments, the domains (A) and (E) associate to form a binding site that binds the A32, 7B2, CH27, CH28, or CH44 HIV-1 antibody epitope.

In certain embodiments, the domain (A) binding region of the A32 immunoglobulin (VL1) comprises the VL-A32 CDR3, CDR2, and CDR1. In certain embodiments, wherein the domain (E) binding region of the A32 immunoglobulin (VH1) comprises the VH-A32 CDR3, CDR2, and CDR1. In certain embodiments, the domain (A) binding region of the 7B2 immunoglobulin (VL1) comprises the VL-7B2 CDR3, CDR2, and CDR1. In certain embodiments, the domain (E) binding region of the 7B2 immunoglobulin (VH1) comprises the VH-7B2 CDR3, CDR2, and CDR1. In certain embodiments, the domain (A) binding region of the CH28 immunoglobulin (VL1) comprises the VL-CH28 CDR3, CDR2, and CDR1. In certain embodiments, the domain (E) binding region of the CH28 immunoglobulin (VH1) comprises the VH-CH28 CDR3, CDR2, and CDR1. In certain embodiments, the domain (A) binding region of the CH44 immunoglobulin (VL1) comprises the VL-CH44 CDR3, CDR2, and CDR1. In certain embodiments, the domain (E) binding region of the CH44 immunoglobulin (VH1) comprises the VH-CH44 CDR3, CDR2, and CDR1.

In certain embodiments, the domain (A) comprises VL-A32, VL-7B2, VL-CH28, or VL-CH44. In certain embodiments, the domain (E) comprises VH-A32, VH-7B2, VH-CH28, VH-CH44.

In certain embodiments, the first polypeptide comprises SEQ ID NO: 9, SEQ ID NO: 13, SEQ ID NO: 17, SEQ ID NO: 21. SEQ ID NO: 25, or SEQ ID NO: 44. In certain embodiments, the second polypeptide comprises SEQ ID NO: 11, SEQ ID NO: 15, SEQ ID NO: 19, SEQ ID NO: 23, SEQ ID NO: 27, or SEQ NO: 45. In certain embodiments, the bispecific molecule comprises the complementary second polypeptide, and wherein the second polypeptide comprises SEQ ID NO: 11, SEQ ID NO: 15, SEQ ID NO: 19, SEQ) NO: 23, SEQ ID NO: 27 or SEQ ID NO: 45.

In certain embodiments, the bispecific molecule comprises the first polypeptide of SEQ ID NO: 9, SEQ ID NO: 13, SEQ ID NO: 17, SEQ ID NO: 21, SEQ ID NO: 25, or SEQ ID NO: 44 and the second polypeptide of SEQ ID NO: 11, SEQ ID NO: 15, SEQ ID NO: 19, SEQ ID NO: 23, SEQ ID NO: 27, or SEQ ID NO: 45.

In certain embodiments, the bispecific molecule comprises the first polypeptide of SEQ ID NO: 9, and the complementary second polypeptide of SEQ ID NO: 11. In certain embodiments, the bispecific molecule comprises the first polypeptide of SEQ ID NO: 13, and the complementary second polypeptide of SEQ ID NO: 15. In certain embodiments, the bispecific molecule comprises the first polypeptide of SEQ ID NO: 17, and the complementary second polypeptide of SEQ ID NO: 19. In certain embodiments, the bispecific molecule comprises the first polypeptide of SEQ ID NO: 21, and the complementary second polypeptide of SEQ ID NO: 23. In certain embodiments, the bispecific molecule comprises the first polypeptide of SEQ ID NO: 25, and the complementary second polypeptide of SEQ ID NO: 27.

In certain embodiments, the bispecific molecule comprises consisting essentially of the first polypeptide of SEQ NO: 9. SEQ ID NO: 13, SEQ ID NO: 17, SEQ ID NO: 21, SEQ ID NO: 25, or SEQ ID NO: 44 and the second polypeptide of SEQ ID NO: 11, SEQ ID NO: 15, SEQ ID NO: 19, SEQ ID NO: 23, SEQ ID NO: 27, or SEQ ID NO: 45.

In certain embodiments, the bispecific molecule comprises consisting of the first polypeptide of SEQ ID NO: 9, SEQ ID NO: 13, SEQ ID NO: 17, SEQ ID NO: 21, SEQ NO: 25, or SEQ ID NO: 44 and the second polypeptide of SEQ ID NO: 11, SEQ ID NO: 15, SEQ ID NO: 19, SEQ ID NO: 23, SEQ ID NO: 27, or SEQ ID NO: 45.

In certain embodiments, the bispecific molecule comprises SEQ ID NO: 46, 47 and 48. In certain embodiments, the bispecific molecule consists essentially of SEQ ID NO: 46, 47 and 48. In certain embodiments, the bispecific molecule consists of SEQ ID NO: 46, 47 and 48. In certain embodiments, the first polypeptide of the bispecific molecule comprises SEQ ID NO: 46, the second polypeptide of the bispecific molecule comprises SEQ ID NO: 47, and the third polypeptide of the bispecific molecule comprises SEQ ID NO: 48.

In certain aspects, the invention provides a composition comprising any one of the bispecific molecules or any combination thereof. In certain embodiments, the composition comprises a composition comprising a bispecific molecule comprising a first arm with the binding specificity of HIV-1 antibody A32, HIV-1 antibody 7B2, HIV-1 antibody CH28, HIV-1 antibody CH44 and a second arm targeting CD3 or CD16. In certain embodiment, the bispecific molecule comprises an Fc portion or any other modification which extends its serum half-life. In certain embodiments, the composition further comprises a second bispecific molecule comprising a first arm with the binding specificity of the HIV-1 antibody A32, HIV-1 antibody 7B2, HIV-1 antibody CH28, HIV-1 antibody CH44 and a second arm targeting CD3 or CD16, wherein the first and second bispecific molecules are different.

In certain aspects, the invention provides a method to treat or prevent HIV-1 infection in a subject in need thereof comprising administering to the subject a composition comprising any one of the bispecific molecules of the invention or a combination of any one of the bispecific molecules in a therapeutically effective amount. In certain embodiments, the methods of claim further comprise administering a latency activating agent. In some embodiments, the latency activating agent is vorinostat, romidepsin, panobinostat, disulfiram, JQ1, bryostatin, PMA, inonomycin, or any combination thereof.

In certain aspects, the invention provides nucleic acids comprising nucleotides encoding the bispecific molecules of the invention. In certain aspects, the invention provides a vector comprising nucleic acids comprising nucleotides encoding the bispecific molecules of the invention. Provided are also compositions comprising a vector comprising a nucleic acid encoding the bispecific molecules. In certain aspects the invention provide a cell line comprising vectors or nucleic acids encoding the bispecific molecules of the invention, wherein the vectors encode polypeptide chains for expression of the bispecific molecules of the invention, e.g., polypeptide chain 1 and polypeptide chain 2, or polypeptide chain 1, polypeptide chain 2 and polypeptide chain 3. In certain embodiments, the vector is suitable for gene delivery and expression. In certain embodiment, the vector is an adenoviral vector, an adeno associated virus based vector, or a combination thereof.

In certain aspects, the invention provides a bispecific molecule comprising a polypeptide with a dual affinity retargeting reagent (DART), wherein the DART comprises a diabody molecule comprising a first polypeptide chain and a second polypeptide chain, covalently bonded to one another, wherein:

(A) the first polypeptide chain comprises:

(i) a domain (A) comprising a binding region of the light chain variable domain of a first immunoglobulin (VL1) specific for the first epitope (I); wherein the first VIA comprises, consists essentially of, consists of the VL or VLCDR1, VLCDR2, and VLCDR3 from A32, 7B2, CH27, CH28, or CH44 HIV-1 antibody, (ii) a domain (B) comprising a binding region of a heavy chain variable domain of a second immunoglobulin (VH2) specific for a second target, e.g an epitope (2), wherein domains (A) and (B) are separated from one another by a peptide linker; and (iii) a domain (C) comprising a heterodimer promoting domain;

(B) the second polypeptide chain comprises:

(i) a domain (D) comprising a binding region of a light chain variable domain of the second immunoglobulin (VL2) specific for the epitope (2);

(ii) a domain (E) comprising a binding region of a heavy chain variable domain of the first immunoglobulin. (VH1) specific for the first epitope (I); wherein the first VH1 comprises, consists essentially of, consists of the VH or VHCDR1, VHCDR2, and VHCDR3 from A32, 7B2, CH27, CH28, or CH44 HIV-1 antibody, wherein domains (D) and (E) are separated from one another by a peptide linker, and (iii) a domain (F) comprising a heterodimer promoting domain, and wherein:

the domains (A) and (B) do not associate with one another to form an epitope binding site;

the domains (D) and (E) do not associate with one another to form an epitope binding site;

the domains (A) and (E) associate to form a binding site that binds the A32, 7B2, CH27, CH28, or CH44 HIV-1 antibody epitope (1); the domains (B) and (D) associate to form a binding site that binds the second target, e.g., epitope (2).

In certain embodiments, the invention provides bispecific molecules, wherein the HIV antibodies VH and VL domains, and the CD3 and CD16 VH and VL domains are in a different orientation. For example, in a non-limiting embodiment, the VL1 domain in polypeptide chain 1 is from CD3, and VH2 domain is from an HIV envelope binding antibody. In this embodiment, the VH1 domain of polypeptide 2 is from CD3, and VL2 domain is from is from an HIV envelope binding antibody.

In certain aspects, the invention provides a bispecific molecule capable of specific binding to HIV-1 envelope and to an epitope of CD3, wherein the bispecific molecule comprises a first polypeptide chain and a second polypeptide chain, covalently bonded to one another, wherein:

A. the first polypeptide chain comprises, in the N-terminal to C-terminal direction:
  i. a Domain 1, comprising
    (1) a sub-Domain (1A), which comprises a VL Domain of a monoclonal antibody capable of binding to CD3 (VLCD3); and
    (2) a sub-Domain (1B), which comprises a VH Domain of a monoclonal antibody capable of binding to HIV-1 (VHHIV-1), wherein the sub-Domains 1A and 1B are separated from one another by a peptide linker (e.g. SEQ ID NO:1);
  ii. a Domain 2, wherein the Domain 2 is an E-coil Domain (e.g. SEQ ID NO:7) or a K-coil Domain (e.g. SEQ ID NO:8), wherein the Domain 2 is separated from the Domain 1 by a peptide linker (SEQ ID NO:2); and B. the second polypeptide chain comprises, in the N-terminal to C-terminal direction:
  i. a Domain 1, comprising
    (1) a sub-Domain (1A), which comprises a VL Domain of a monoclonal antibody capable of binding to HIV-1 (VLHIV-1); and
    (2) a sub-Domain (1B), which comprises a VH Domain of a monoclonal antibody capable of binding to CD3 (VHCD3), wherein the sub-Domains 1A and 1B are separated from one another by a peptide linker (e.g. SEQ ID NO:1); and
  ii. a Domain 2, wherein the Domain 2 is a K-coil Domain (e.g. SEQ ID NO:8) or an E-coil Domain (SEQ ID NO:7), wherein the Domain 2 is separated from the Domain 1 by a peptide linker (SEQ ID NO:2); and wherein the Domain 2 of the first and the second polypeptide chains are not both E-coil Domains or both K-coil Domains and wherein:

(a) the VL Domain of the first polypeptide chain and the VH Domain of the second polypeptide chain form an Antigen Binding Domain capable of specifically binding to an epitope of CD3; and (b) the VL Domain of the second polypeptide chain and the VH Domain of the first polypeptide chain form an Antigen Binding Domain capable of specifically binding to HIV-1 envelope.

A bispecific molecule capable of specific binding to HIV-lenvelope and to an epitope of CD16, wherein the bispecific molecule comprises a first polypeptide chain and a second polypeptide chain, covalently bonded to one another, wherein:

A. the first polypeptide chain comprises, in the N-terminal to C-terminal direction:
  i. a Domain 1, comprising
    (1) a sub-Domain (1A), which comprises a VL Domain of a monoclonal antibody capable of binding to CD16 (VLCD16); and
    (2) a sub-Domain (1B), which comprises a VH Domain of a monoclonal antibody capable of binding to HIV-1 (VHHIV-1), wherein the sub-Domains 1A and 1B are separated from one another by a peptide linker (e.g. SEQ ID NO:1);
  ii. a Domain 2, wherein the Domain 2 is an E-coil Domain (SEQ ID NO:7) or a K-coil Domain (e.g. SEQ ID NO:8), wherein the Domain 2 is separated from the Domain 1 by a peptide linker (SEQ ID NO:2); and B. the second polypeptide chain comprises, in the N-terminal to C-terminal direction:
  i. a Domain 1, comprising
    (1) a sub-Domain (1A), which comprises a VL Domain of a monoclonal antibody capable of binding to HIV-1 (VLHIV-1); and
    (2) a sub-Domain (1B), which comprises a VH Domain of a monoclonal antibody capable of binding to CD16 (VHCD16), wherein the sub-Domains 1A and 1B are separated from one another by a peptide linker (e.g. SEQ ID NO:1); and
  ii. a Domain 2, wherein the Domain 2 is a K-coil Domain e.g. SEQ ID NO:8) or an E-coil Domain (e.g. SEQ ID NO:7), wherein the Domain 2 is separated from the Domain 1 by a peptide linker (SEQ ID NO:2); and wherein the Domain 2 of the first and the second polypeptide chains are not both E-coil Domains or both K-coil Domains and wherein:

(a) the VL Domain of the first polypeptide chain and the VH Domain of the second polypeptide chain form an Antigen Binding Domain capable of specifically binding to an epitope of CD16; and (b) the VL Domain of the second polypeptide chain and the VH Domain of the first polypeptide chain form an Antigen Binding Domain capable of specifically binding to HIV-1 envelope.

In certain embodiments, the bispecific molecule binds to the HIV-1 envelope like the HIV antibody from which it is derived. In certain embodiments, the bispecific molecule binds to the A32-HIV-1 envelope epitope, i.e. the bispecific molecule binds to the HIV-1 envelope like the A32 antibody, and CD3, or CD16. In certain embodiments, the bispecific molecule binds to the 7B2-HIV1 envelope epitope and CD3, or CD16. In certain embodiments, the bispecific molecule binds to the CH27-HIV-1 envelope epitope and CD3, or CD16. In certain embodiments, the bispecific molecule binds to the CH28-HIV-1 envelope epitope and CD3, or CD16. In certain embodiments, the bispecific molecule binds to the CH44-HIV-1 envelope epitope and CD3, or CD16.

In certain embodiments, the bispecific molecule has the binding specificity of the A32 HIV-1-envelope antibody. In certain embodiments, the bispecific molecule has the binding specificity of the 7B2 HIV-1-envelope antibody. The bispecific molecule has the binding specificity of the CH27 HIV-1-envelope antibody. The bispecific molecule has the binding specificity of the CH28 HIV-1-envelope antibody. In certain embodiments, the bispecific molecule has the binding specificity of the CH44 HIV-1-envelope antibody.

In certain embodiments a bispecific molecule of the invention comprises, consists essentially of or consists of sequences as described herein, e.g. Table 2 and Table 3)

In certain embodiments a bispecific molecule of the invention comprises, consists essentially of or consists of SEQ ID NO: 9 and 11; SEQ ID NO: 13 and 15, SEQ ID NO: 17 and 19; SEQ ID NO; 21 and 23; SEQ ID NO: 25 and 27; SEQ ID NO; 44 and 45 (See Table 2 and Table 3).

In certain aspects the invention provides compositions comprising any of the bispecific molecule described herein, or a combination thereof. In certain embodiments, these compositions are formulated as pharmaceutical composition for therapeutic use.

In certain aspects the invention is directed to nucleic acids which encode the bispecific molecules of the invention. In certain embodiments, these nucleic acids are comprised in a vector, and are operably linked to a promoter. In certain aspects the invention provides cell lines, or isolated cells, which comprise nucleic acids for the expression of the bispecific molecules of the invention.

In certain aspects, the invention provides compositions comprising the bispecific molecules of the invention or nucleic acids encoding the same for use in methods of treating or preventing HIV infection. In some embodiments, these methods further comprise administering a Latency Activating Reagent. Non-limiting examples of these include HDAC inhibitors, e.g, vorinostat, romidepsin, panobinostat, disulfiram, JQ1, bryostatin, PMA, inonomycin, or any combination thereof. In some embodiments, this combination therapy targets the pool of latently infected HIV cells.

In certain aspects, the invention provides methods treating or preventing an HIV infection in a subject, the method comprising administering to the subject a composition comprising any one of the bispecific molecules of the invention, or a combination thereof in a therapeutically sufficient amount. In certain embodiments, the methods further comprise administering a latency activating agent.

BRIEF DESCRIPTION OF THE DRAWINGS

FIG. 5 shows the sequences of CH27, CH28 and CH44 HIV-1 antibodies. CDRs are indicated in the sequences (SEQ ID Nos: 57-74).

FIG. 6 shows the nucleotide sequences encoding VH and VL chains of A32 antibody and amino acid sequences of VH and VL chains of A32 (SEQ ID Nos 75-78 in order of appearance).

FIG. 7 shows nucleotide sequences encoding VH and VK chains of 7B2 antibody and amino acid sequences of VH and VK chains of 7B2 (SEQ ID NO: 79-82 in order of appearance).

FIG. 8A illustrates the structure of a bispecific molecule composed of two polypeptide chains. FIGS. 8B and 8C illustrate the structures of two versions of the first, second and third polypeptide chains of a three chain bispecific molecule with an Fc domain (Version 1, FIG. 8B; Version 2, FIG. 8C).

FIG. 9 shows various sequences: Linker 1 (SEQ ID NO; 1); Linker 2 (SEQ ID NO: 2); Heterodimer promoting domain and K-coil and E coil sequences (SEQ ID Nos: 3-6, land 8); Linker 3 (DKTHTCPPCP (SEQ ID No: 49); Linker 4—SEQ ID NOS: 39, 40; CH2-CH3 fragments—SEQ ID Nos; 41-43; CH3 VH chain—SEQ ID NO: 51; CD3VL chain—SEQ ID NO: 52, CD16VH chain—SEQ ID NO 53, CH16 VL chain—SEQ ID NO: 54; 7B2 VL—SEQ IDNO 55; 7b2 VH-SEQ ID NO 56. SEQ ID Nos: 9-38, 44-48 show various bispecific antibodies (See Table 2).

(FIGS. 10A-10B) These DART molecules contain an anti-HIV-1 binding arm (A32 or 7B2) combined with an anti-CD3 binding arm (hXR32). They are composed of two polypeptide chains: one with the VL of anti-CD3 linked to the VH of anti-HIV; the second with the VL of anti-HIV linked to the VH of anti-CD3. The carboxy termini of the chains have an interchain disulfide bond and paired oppositely charged E-coil/K-coil dimerization domains. Control DARTs have one of the arms replaced by an irrelevant one derived from an anti-FITC antibody (4420) or from an anti-RSV antibody, palivizumab (RSV) sequence. (FIG. 10C) Schematic representation of HIV×CD3 DART binding to two distinct antigens simultaneously and redirecting the cytotoxic T cells (effectors) to lyse the Env-expressing, HIV-1 infected cells (targets).

FIGS. 11A-11C show antigen binding by ELISA. DART binding to human CD3 protein (FIG. 11A), to JR-FL gp140 protein (FIG. 11B) or simultaneously to both JR-FL gp140 and human CD3 proteins (FIG. 11C). FIGS. 11D-11F show cell surface binding by FACS. DART binding to primary human T cells expressing CD3 (FIG. 11D), to HEK293-D371 cells expressing HIV-1 Env, CM244, subtype AE (FIG. 11E) or to Jurkat 522-F/Y cells expressing CD3 and HIV-1 Env, HXBC2, subtype B (FIG. 11F). Data are reported as mean fluorescence intensity (MFI). CD3 and Env expression characteristics of the cells are reported in parenthesis. A32 and 7B2 are targeting arms that recognize HIV-1 gp120 and gp41, respectively; CD3 is the effector arm that recognizes CD3ε; 4420 is an irrelevant, negative control arm.

FIG. 12A shows DART concentration dependent killing of $Env^+$ Jurkat 522-F/Y cells in the presence of human T-cells at an E:T ratio of 10:1 for 48 hours with cytolysis measured by LDH release assay; $EC_{50}$ values were 230 and 160 pg/mL for A32×CD3 and 7B2×CD3, respectively. The control DARTs (A32×4420, 7B2×4420, 4420×CD3) were inactive. FIG. 12B shows lack of DART mediated killing of $Env^+$ Jurkat 522-F/Y cells in the absence of effector T-cells with cytolysis measured by LDH release assay. FIG. 12C shows lack of DART redirected T-cell killing of $Env^-$ Jurkat ΔKS cells at an E:T ratio of 10:1 for 48 hours with cytolysis measured by LDH release assay. FIG. 12D shows DART concentration dependent killing of $Env^+$ Jurkat 522-F/Y GF cells in the presence of human T-cells at an E:T ratio of 10:1 for 48 hours with cytolysis measured by LUM assay; $EC_{50}$ values were 172 and 147 pg/mL for A32×CD3 and 7B2×CD3, respectively. FIGS. 12E-12G show 7B2×CD3 DART concentration dependent redirected T cell killing of $Env^+$ Jurkat 522-F/Y GF cells at different E:T ratios (10:1, 5:1, 1:1) and incubation times (24, 48, 72 hours) with cytolysis measured by LUM assay. FIG. 12H shows time course of maximal cytolytic activity with 7B2×CD3 at different E:T ratios (data from FIGS. 12E-12G).

FIGS. 13A-13C show DART concentration dependence. Activated CD4+ T cells from a HIV-1 seronegative donor were infected with HIV-1 subtype B BaL (FIG. 13A), subtype AE CM235 (FIG. 13B) or subtype C 1086.0 (FIG. 13C) IMC and incubated for 48 hours with A32×CD3 (red circles), 7B2×CD3 (blue squares) or 4420×CD3 (black diamonds) in the presence of autologous resting $CD8^+$ T cells at an E:T ratio of 33:1 (filled symbols) or in the absence of effector cells (E:T ratio of 0:1) (open symbols). The data are reported as percentage of specific lysis (% SL). DART concentrations ranged from 0.001 to 1000 ng/mL. FIGS. 13D-13F show time course. The data represent the maximal % SL observed at 6, 24, and 48 hours for each DART against CD4+ T cells infected with HIV-1 subtype B BaL (FIG. 13D), subtype AE CM235 (FIG. 13E) or subtype C 1086.0 (FIG. 13F) IMC and incubated with autologous resting $CD8^+$ T cells at an E:T ratio of 33:1.

FIGS. 14A-14H show HIV×CD3 DARTs induce specific degranulation of CD8+ T-cell. FIGS. 14A-14D show schematic of gating strategy to identify Live/CD3+CD8+CD107+ T cells after their incubation with HIV-1 BaL infected target cells in presence of DARTs for 6 hours. (FIGS. 14E-14G) Dot plots represent the percentage of Live/$CD3^+$ $CD8^+$ $CD107^+$ cells observed in presence of 1 ng/mL of 4420×CD3 (FIG. 14E), 7B2×CD3 (FIG. 14F) or A32×CD3 (FIG. 14G). FIG. 14H shows frequency of the $CD3^+$ $CD4^-$ $CD8^+$ $CD107^+$ T cells observed in each of the five HIV-1 seronegative healthy donors after 6 hours of incubation with the autologous infected $CD4^+$ T cells using the E:T ratio of 33:1. Each symbol represents the average of duplicate stimulations performed for each donor. The lines represent the mean±standard deviation. * indicates $p<0.05$ after Dunnett's test for multiple comparisons.

FIG. 16G shows schematic of gating strategy to identify Live/CD3+CD4+CD107+ Effector (TFL4-) T cells after their incubation with HIV-1 JR-CSF infected target cells in presence of DARTs for 6 hours. FIG. 16H shows the % of live/effector cells (TFL4 negative)/CD3+/CD4+/107a+ cells following a 6 hour incubation with the indicated DARTs and JR-CSF infected targets in n=4 patients. Error bars represent SEM of n=8 (FIGS. 16A-16C, except for combo n=5 and 7B2×4420 n=6), n=5 (FIGS. 16D-16F), and n=4 (FIGS. 16G-16H). * indicates p<0.05 with Dunnett's test for multiple comparisons.

FIG. 18 shows a list of IMC by HIV-1 Subtypes and Neutralization Tier.

FIG. 19 shows Equilibrium Dissociation Constants ($K_D$) for Binding of A32×CD3 and 7B2×CD3 to Recombinant Env and CD3 Protein.

FIG. 20 shows Clinical Characteristics.

FIG. 21 shows that DARTs redirect patient T cells against JR-CSF infected autologous target cells and absolute p24 concentration.

FIG. 22 shows Absolute # of Positive Wells in Latency Clearance Assay with DARTs.

(FIGS. 28A-28B) T cell viability was assessed by staining cells for Annexin V/7-AAD. Viable cells were identified as those that were Annein V and 7-AAD negative. (FIGS. 28C-28D) T cell activation was assessed by staining cells for HLA-DR and CD25 expression. Data points for both analyses are from n=3 patients performed on 3 independent occasions. Error bars represent standard error mean.

DETAILED DESCRIPTION

Figure 1:
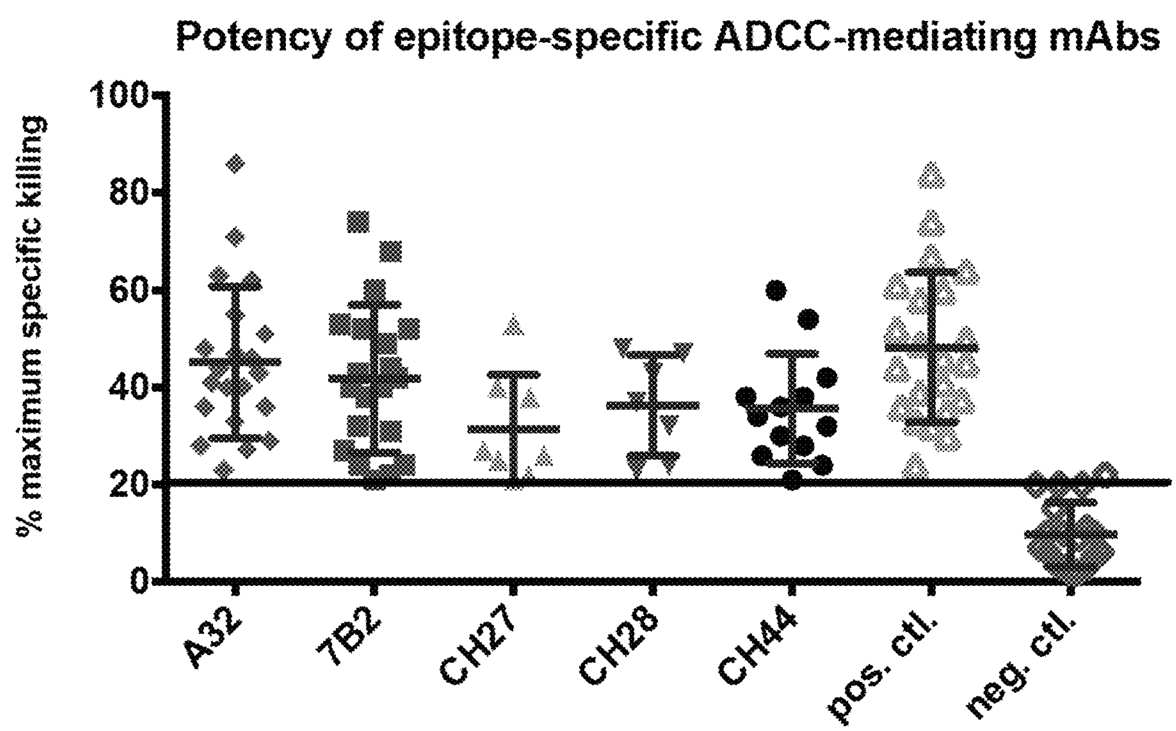
FIG. 1 shows potency of ADCC-mediating mAbs. The ADCC activity of the 5 CHAVI mAbs against the 22 HIV-1 IMC is reported as maximum percentage of specific killing. Each dot represent the average activity of all the positive results for each group of mAbs against the individual IMCs. The lines represent the mean±standard deviation. The black line represent the cut-off for positive response.

Highly active anti-retroviral therapy (HAART) alone or in combination with latency reversing agents fails to reduce the pool of latently infected cells. This is due to limited ability of the CD8+ T cells to eliminate HIV-1 latently infected cells. Dual Affinity Re-Targeting proteins (DARTs) are bispecific, antibody-based molecules that can bind two distinct antigens simultaneously. HIV-1 DARTs contain an HIV-1 binding arm combined with an effector cell binding arm, and are designed to redirect cytotoxic CD3+ T cells to engage and kill HIV-infected cells. A panel of monoclonal antibodies (mAbs) was studied to determine their magnitude and breadth of mediating ADCC against 22 different isolates. The goals were to: 1) identify mAbs that could be used as the HIV-1 binding arms of DARTs; 2) test the resulting DARTs for their ability to mediate killing of HIV-1 infected cells. Provided herein are data related to the potency of the different groups of ADCC-mediating mAbs and the resulting DARTs against HIV-1 Infectious Molecular Clones (IMC)-infected target cells.

Antibodies and Other Binding Molecules

Antibodies

The invention provides polyclonal or monoclonal antibodies, variants, fusion proteins comprising an antibody portion with an antigen recognition site of the required specificity, humanized antibodies, and chimeric antibodies, and any other modified configuration of the immunoglobulin molecule that comprises an antigen recognition site of the required specificity. Throughout this application, the numbering of amino acid residues of the light and heavy chains of antibodies is according to the EU index as in Kabat et al. (1992) SEQUENCES OF PROTEINS OF IMMUNOLOGICAL INTEREST, National Institutes of Health Publication No. 91-3242. In some embodiments, antigen-binding fragment of an antibody is a portion of an antibody that possesses an at least one antigen recognition site. Fragments include for example but not limited to Fab, Fab', $F(ab')_2$ Fv), and single chain (scFv).

Monoclonal antibodies are known in the art. In certain embodiments, monoclonal antibody encompasses not only intact monoclonal antibodies and full-length monoclonal antibodies, but also fragments thereof (such as Fab, Fab', $F(ab')_2$ Fv), single chain (scFv), mutants thereof, fusion proteins comprising an antibody portion, humanized monoclonal antibodies, chimeric monoclonal antibodies, and any other modified configuration of the immunoglobulin molecule that comprises an antigen recognition site of the required specificity and the ability to bind to an antigen. Monoclonal antibodies are not limited as regards to the source of the antibody or the manner in which it is made (e.g., by hybridoma, phage selection, recombinant expression, transgenic animals, etc.).

Methods of making monoclonal antibodies are known in the art. In certain embodiments, the antibodies are produced recombinantly by any means known in the art. In one embodiment, such an antibody is sequenced and the polynucleotide sequence is then cloned into a vector for expression or propagation. The sequence encoding the antibody of interest may be maintained in a vector in a host cell and the host cell can then be expanded and frozen for future use. The polynucleotide sequence of such antibodies may be used for genetic manipulation to generate the bi-specific molecules of the invention as well as a chimeric antibody, a humanized antibody, or a caninized antibody, to improve the affinity, or other characteristics of the antibody. The general principle in humanizing an antibody involves retaining the basic sequence of the antigen-binding portion of the antibody, while swapping the non-human remainder of the antibody with human antibody sequences. There are four general steps to humanize a monoclonal antibody. These are: (1) determining the nucleotide and predicted amino acid sequence of the starting antibody light and heavy variable Domains (2) designing the humanized antibody or caninized antibody, i.e., deciding which antibody framework region to use during the humanizing or canonizing process (3) the actual humanizing or caninizing methodologies/techniques and (4) the transfection and expression of the humanized antibody. See, for example, U.S. Pat. Nos. 4,816,567; 5,807,715; 5,866,692; and 6,331,415.

Bi-Specific Antibodies, Multi-Specific Diabodies and DART™ Diabodies

The provision of non-mono-specific "diabodies" provides a significant advantage over antibodies: the capacity to co-ligate and co-localize cells that express different epitopes. Bivalent diabodies thus have wide-ranging applications including therapy and immunodiagnosis. Bi-valency allows for great flexibility in the design and engineering of the diabody in various applications, providing enhanced avidity to multimeric antigens, the cross-linking of differing antigens, and directed targeting to specific cell types relying on the presence of both target antigens. Due to their increased valency, low dissociation rates and rapid clearance from the circulation (for diabodies of small size, at or below 50 kDa), diabody molecules known in the art have also shown particular use in the field of tumor imaging (Fitzgerald et al. (1997) "*Improved Tumour Targeting By Disulphide Stabilized Diabodies Expressed In Pichia pastoris*," Protein Eng. 10:1221). Of particular importance is the co-ligating of differing cells, for example, the cross-linking of cytotoxic T cells to tumor cells (Staerz et al. (1985) "*Hybrid Antibodies Can Target Sites For Attack By T Cells*," Nature 314:628-631, and Holliger et al. (1996) "*Specific Killing Of Lymphoma Cells By Cytotoxic T-Cells Mediated By A Bispecific Diabody*," Protein Eng. 9:299-305).

Diabody epitope binding domains may also be directed to a surface determinant of a B cell, such as CD19, CD20, CD22, CD30, CD37, CD40, and CD74 (Moore, P. A. et al. (2011) "*Application Of Dual Affinity Retargeting Molecules To Achieve Optimal Redirected T-Cell Killing Of B-Cell Lymphoma*," Blood 117(17):4542-4551; Cheson, B. D. et al. (2008) "Monoclonal *Antibody Therapy For B-Cell Non Hodgkin's Lymphoma*," N. Engl. J. Med. 359(6):613-626; Castillo, J. et al. (2008) "Newer monoclonal antibodies for hematological malignancies," Exp. Hematol. 36(7):755-768. In many studies, diabody binding to effector cell determinants, e.g., Fcγ receptors (FcγR), was also found to activate the effector cell (Holliger et al. (1996) "*Specific Killing Of Lymphoma Cells By Cytotoxic T-Cells Mediated By A Bispecific Diabody*," Protein Eng. 9:299-305; Holliger et al. (1999) "*Carcinoembryonic Antigen (CEA)-Specific T-Cell Activation In Colon Carcinoma Induced By Anti-CD3×Anti-CEA Bispecific Diabodies And B7×Anti-CEA Bispecific Fusion Proteins*," Cancer Res. 59:2909-2916; WO 2006/113665; WO 2008/157379; WO 2010/080538; WO 2012/018687; WO 2012/162068). Normally, effector cell activation is triggered by the binding of an antigen bound antibody to an effector cell via Fc-FcγR interaction; thus, in this regard, diabody molecules may exhibit Ig-like functionality independent of whether they comprise an Fc Domain (e.g., as assayed in any effector function assay known in the art or exemplified herein (e.g., ADCC assay)). By cross-linking tumor and effector cells, the diabody not only brings the effector cell within the proximity of the tumor cells but leads to effective tumor killing (see e.g., Cao et al. (2003) "*Bispecific Antibody Conjugates In Therapeutics*," Adv. Drug. Deliv. Rev. 55:171-197).

The formation of such non-mono-specific diabodies requires the successful assembly of two or more distinct and different polypeptides (i.e., such formation requires that the diabodies be formed through the heterodimerization of different polypeptide chain species). This fact is in contrast to mono-specific diabodies, which are formed through the homodimerization of identical polypeptide chains. Because at least two dissimilar polypeptides (i.e., two polypeptide species) must be provided in order to form a non-mono-specific diabody, and because homodimerization of such polypeptides leads to inactive molecules (Takemura, S. et al. (2000) "*Construction Of A Diabody* (*Small Recombinant Bispecific Antibody*) *Using A Refolding System*," Protein Eng. 13(8):583-588), the production of such polypeptides must be accomplished in such a way as to prevent covalent bonding between polypeptides of the same species (i.e., so as to prevent homodimerization) (Takemura, S. et al. (2000) "*Construction Of A Diabody* (*Small Recombinant Bispecific Antibody*) *Using A Refolding System*," Protein Eng. 13(8): 583-588). The art has therefore taught the non-covalent association of such polypeptides (see, e.g., Olafsen et al. (2004) "*Covalent Disulfide-Linked Anti-CEA Diabody Allows Site-Specific Conjugation And Radiolabeling For Tumor Targeting Applications*," Prot. Engr. Des. Sel. 17:21-27; Asano et al. (2004) "*A Diabody For Cancer Immunotherapy And Its Functional Enhancement By Fusion Of Human Fc Domain*," Abstract 3P-683, J. Biochem. 76(8): 992; Takemura, S. et al. (2000) "*Construction Of A Diabody* (*Small Recombinant Bispecific Antibody*) *Using A Refolding System*," Protein Eng. 13(8):583-588; Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20):19665-19672).

The art has recognized that bi-specific diabodies composed of non-covalently associated polypeptides are unstable and readily dissociate into non-functional monomers (see, e.g., Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20):19665-19672).

In the face of this challenge, the invention provides stable, covalently bonded heterodimeric non-mono-specific diabodies, termed DARTs™ (see, e.g., United States Patent Publications No. 2014-0099318; 2013-0295121; 2010-0174053 and 2009-0060910; European Patent Publication No. EP 2714079; EP 2601216; EP 2376109; EP 2158221 and PCT Publications No. WO 2015/026894; WO2015/026892; WO 2015/021089; WO 2014/159940; WO 2012/162068; WO 2012/018687; WO 2010/080538; Moore, P. A. et al. (2011) "*Application Of Dual Affinity Retargeting Molecules To Achieve Optimal Redirected T-Cell Killing Of B-Cell Lymphoma*," Blood 117(17):4542-4551; Veri, M. C. et al. (2010) "*Therapeutic Control Of B Cell Activation Via Recruitment Of Fcgamma Receptor IIb* (*CD32B*) *Inhibitory Function With A Novel Bispecific Antibody Scaffold*," Arthritis Rheum. 62(7):1933-1943; Johnson, S. et al. (2010) "*Effector Cell Recruitment With Novel Fv-Based Dual-Affinity Re-Targeting Protein Leads To Potent Tumor Cytolysis And in vivo B-Cell Depletion*," J. Mol. Biol. 399(3):436-449), the contents of which publications are herein incorporated by reference in their entirety. Such diabodies comprise two or more covalently complexed polypeptides and involve engineering one or more cysteine residues into each of the employed polypeptide species. For example, the addition of a cysteine residue to the c-terminus of such constructs has been shown to allow disulfide bonding between the polypeptide chains, stabilizing the resulting heterodimer without interfering with the binding characteristics of the bivalent molecule.

Figure 8A:
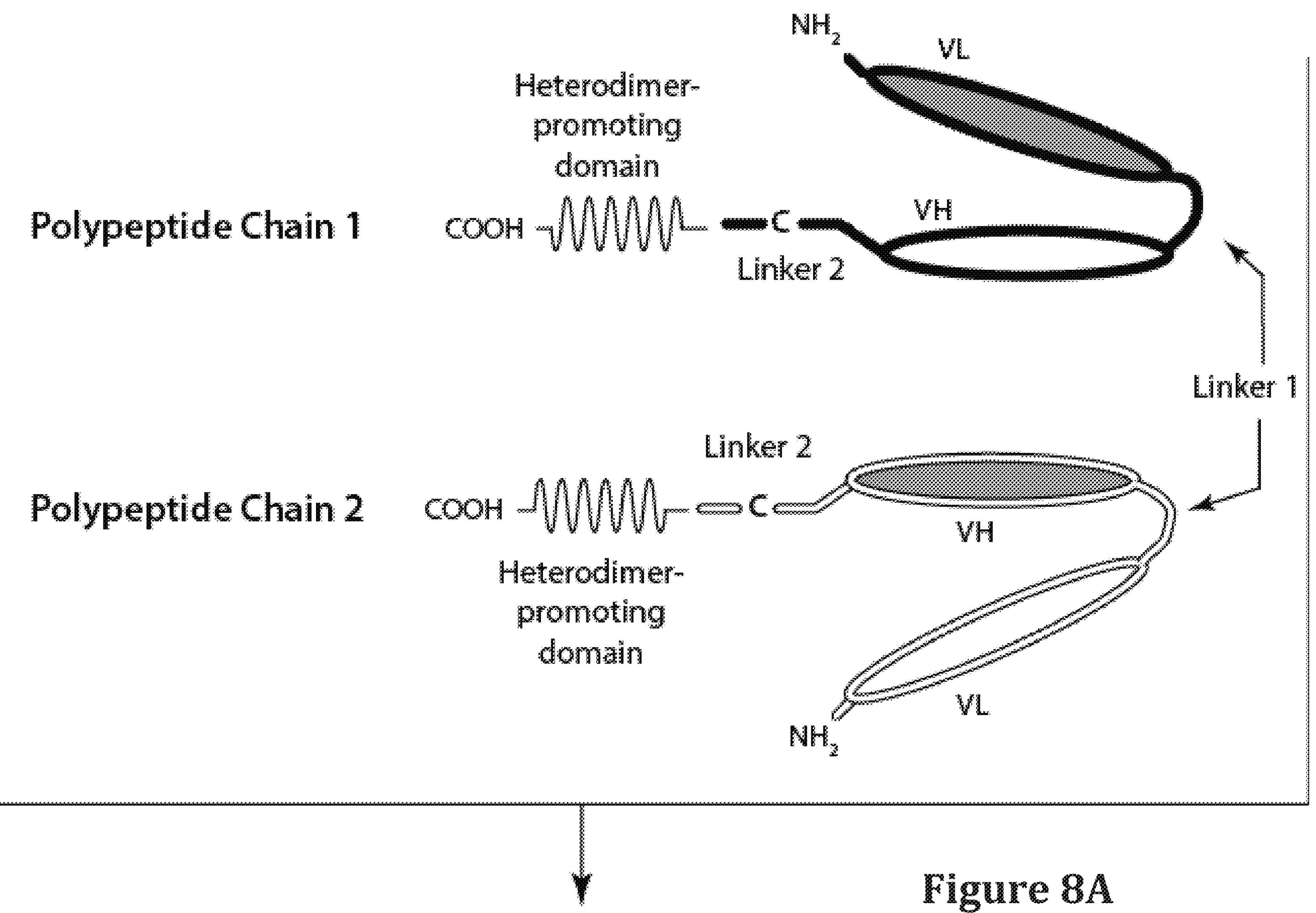
FIG. 8A-C show the structures and domains of the bispecific molecules of the present invention.
Figure 8A:
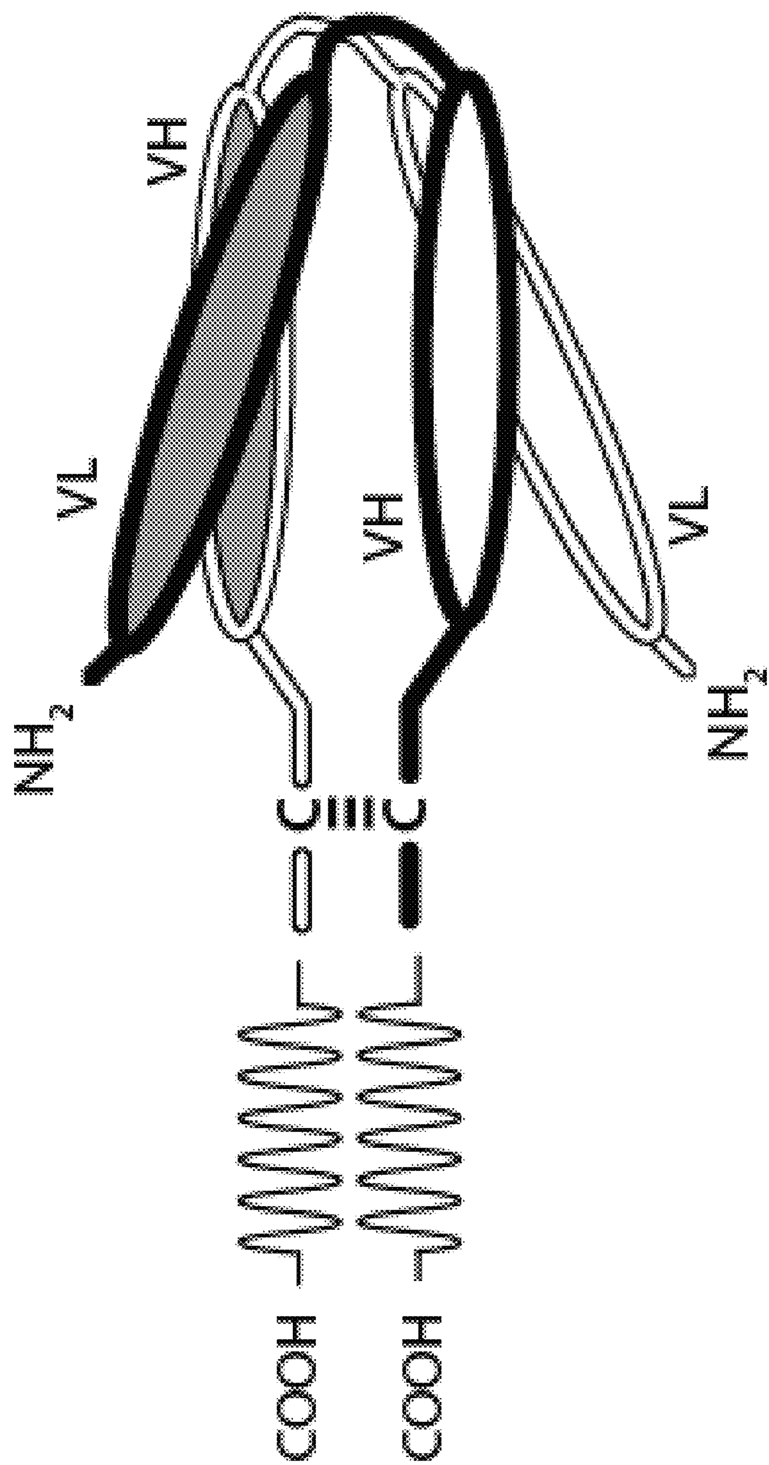

In some embodiments, each of the two polypeptides of the DART™ comprises three Domains (FIG. 8A). The first polypeptide comprises: (i) a Domain that comprises a binding region of a light chain variable Domain of the a first immunoglobulin (VL1), (ii) a second Domain that comprises a binding region of a heavy chain variable Domain of a second immunoglobulin (VH2), and (iii) a third Domain that serves to promote heterodimerization with the second polypeptide and to covalently bond the first polypeptide to the second polypeptide of the diabody. The second polypeptide contains a complementary first Domain (a VL2 Domain), a complementary second Domain (a VH1 Domain) and a third Domain that complexes with the third Domain of the first polypeptide chain in order to promote heterodimerization and covalent bonding with the first polypeptide chain. Such molecules are stable, potent and have the ability to simultaneously bind two or more antigens. They are able to promote redirected T cell (CD3) or NK (CD16) cell mediated killing of cells expressing target antigens.

In certain aspects, the present invention is directed to HIV-1×CD3 and HIV-1×CD16 bi-specific monovalent diabodies that are capable of simultaneous binding to HIV-1 and CD3 or HIV-1 and CD16, and to the uses of such molecules in the treatment of HIV-1 infection.

In certain embodiments, the HIV-1×CD3 and HIV-1×CD16 bi-specific monovalent diabodies of the present invention are composed of two polypeptide chains which associate with one another to form one binding site specific for an epitope of HIV-1 and one binding site specific for an epitope of CD3 or CD16 (see, FIG. 8), so as to be capable of simultaneously binding to HIV-1 and to CD3 or CD16. Thus, such diabodies bind to a "first antigen," which may be either CD3 or HIV-1, and a "second antigen," which is HIV-1 when the first epitope is CD3, and is CD3 when the first epitope is HIV-1. Alternatively, such diabodies bind to a "first antigen," which may be either CD16 or HIV-1, and a "second antigen," which is HIV-1 when the first epitope is CD16, and is CD16 when the first epitope is HIV-1.

In certain embodiments as shown in FIG. 8, the first of such two polypeptide chains will contain, in the N-terminal to C-terminal direction, an N-terminus, the Antigen-Binding Domain of a Light Chain Variable Domain (VL) of a "first" antigen (either CD3 or HIV-1 envelope), the Antigen-Binding Domain of a Heavy Chain Variable Domain (VH) of a second antigen (HIV-1, if the first antigen was CD3; CD3, if the first antigen was HIV-1), a Heterodimerization-Promoting Domain, and a C-terminus. An intervening linker peptide (Linker 1) separates the Antigen-Binding Domain of the Light Chain Variable Domain from the Antigen-Binding Domain of the Heavy Chain Variable Domain. In certain embodiments the Antigen-Binding Domain of the Heavy Chain Variable Domain is linked to the Heterodimerization-Promoting Domain by an intervening linker peptide (Linker 2). In certain embodiments the first of the two polypeptide chains will thus contain, in the N-terminal to C-terminal direction: $VL_{First\ Antigen}$-Linker 1-$VH_{Second\ Antigen}$-Linker 2-Heterodimerization-Promoting Domain.

In certain embodiments, the second of such two polypeptide chains will contain, in the N-terminal to C-terminal direction, an N-terminus, the Antigen-Binding Domain of a Light Chain Variable Domain (VL) of the second antigen, the Antigen-Binding Domain of a Heavy Chain Variable Domain (VH) of the first antigen, a Heterodimerization-Promoting Domain and a C-terminus. An intervening linker peptide (Linker 1) separates the Antigen-Binding Domain of the Light Chain Variable Domain from the Antigen-Binding Domain of the Heavy Chain Variable Domain. In certain embodiments, the Antigen-Binding Domain of the Heavy Chain Variable Domain is linked to the Heterodimerization-Promoting Domain by an intervening linker peptide (Linker 2). In certain embodiments the second of the two polypeptide chains will thus contain, in the N-terminal to C-terminal direction: $VL_{Second\ Antigen}$-Linker 1-$VH_{First\ Antigen}$-Linker 2-Heterodimerization-Promoting Domain.

The Antigen-Binding Domain of the Light Chain Variable Domain of the first polypeptide chain interacts with the Antigen-Binding Domain of the Heavy Chain Variable Domain of the second polypeptide chain in order to form a functional antigen-binding site that is specific for the first antigen (i.e., either HIV-1 envelope or CD3/CD16). Likewise, the Antigen-Binding Domain of the Light Chain Variable Domain of the second polypeptide chain interacts with the Antigen-Binding Domain of the Heavy Chain Variable Domain of the first polypeptide chain in order to form a second functional antigen-binding site that is specific for the second antigen (i.e., either CD3/CD16 or HIV-1 envelope, depending upon the identity of the first antigen). Thus, the selection of the Antigen-Binding Domain of the Light Chain Variable Domain and the Antigen-Binding Domain of the Heavy Chain Variable Domain of the first and second polypeptide chains are coordinated, such that the two polypeptide chains collectively comprise Antigen-Binding Domains of light and Heavy Chain Variable Domains capable of binding to the intended targets, in certain embodiments e.g. HIV-1 envelope and CD3, or CD16.

In certain embodiments the length of Linker 1, which separates such VL and VH domains of a polypeptide chain is selected to substantially or completely prevent such VL and VH domains from binding to one another. Thus the VL and VH domains of the first polypeptide chain are substantially or completely incapable of binding to one another. Likewise, the VL and VH domains of the second polypeptide chain are substantially or completely incapable of binding to one another. In certain embodiments this is due to the linker which separates the VH and VL domains. In certain embodiments, the linker is 5, 6, 7, 8, 9, 10, 11, 12, 13, 14, but no more than 15 amino acids. In certain embodiments an intervening spacer peptide (Linker 1) has the sequence (SEQ ID NO:1): GGGSGGGG.

Linker 2 separates the VH Domain of a polypeptide chain from the Heterodimer-Promoting Domain of that polypeptide chain. Any of a variety of linkers can be used for the purpose of Linker 2. In certain embodiments a sequence for such Linker 2 has the amino acid sequence: GGCGGG (SEQ ID NO:2), which has a cysteine residue that may be used to covalently bond the first and second polypeptide chains to one another via a disulfide bond.

The formation of heterodimers of the first and second polypeptide chains can be driven by the inclusion of Heterodimerization-Promoting Domains. Such domains include GVEPKSC (SEQ ID NO:3) or VEPKSC (SEQ ID NO:4) on one polypeptide chain and GFNRGEC (SEQ ID NO:5) or FNRGEC (SEQ ID NO:6) on the other polypeptide chain (See US2007/0004909 herein incorporated by reference in its entirety).

In certain embodiments, the Heterodimerization-Promoting Domains of the present invention are formed from one, two, three or four tandemly repeated coil domains of opposing charge that comprise a sequence of at least six, at least seven or at least eight charged amino acid residues (Apostolovic, B. et al. (2008) "*pH-Sensitivity of the E3/K3 Heterodimeric Coiled Coil*," Biomacromolecules 9:3173-3180; Arndt, K. M. et al. (2001) "*Helix-stabilized Fv (hsFv) Antibody Fragments: Substituting the Constant Domains of a Fab Fragment for a Heterodimeric Coiled-coil Domain*," J. Molec. Biol. 312:221-228; Arndt, K. M. et al. (2002) "*Comparison of In Vivo Selection and Rational Design of Heterodimeric Coiled Coils*," Structure 10:1235-1248; Boucher, C. et al. (2010) "*Protein Detection By Western Blot Via Coiled—Coil Interactions*," Analytical Biochemistry 399:138-140; Cachia, P. J. et al. (2004) "*Synthetic Peptide Vaccine Development: Measurement Of Polyclonal Antibody Affinity And Cross-Reactivity Using A New Peptide Capture And Release System For Surface Plasmon Resonance Spectroscopy*," J. Mol. Recognit. 17:540-557; De Crescenzo, G. D. et al. (2003) "*Real-Time Monitoring of the Interactions of Two-Stranded de novo Designed Coiled-Coils: Effect of Chain Length on the Kinetic and Thermodynamic Constants of Binding*," Biochemistry 42:1754-1763; Fernandez-Rodriquez, J. et al. (2012) "*Induced Heterodimerization And Purification Of Two Target Proteins By A Synthetic Coiled-Coil Tag*," Protein Science 21:511-519; Ghosh, T. S. et al. (2009) "*End-To-End And End-To-Middle Interhelical Interactions: New Classes Of Interacting Helix Pairs In Protein Structures*," Acta Crystallographica D65:1032-1041; Grigoryan, G. et al. (2008) "*Structural Specificity In Coiled-Coil Interactions*," Curr. Opin. Struc. Biol. 18:477-483; Litowski, J. R. et al. (2002) "*Designing Heterodimeric Two-Stranded a-Helical Coiled-Coils: The Effects Of Hydrophobicity And α-Helical Propensity On Protein Folding, Stability, And Specificity*," J. Biol. Chem. 277:37272-37279; Steinkruger, J. D. et al. (2012) "*The d'-d-d' Vertical Triad is Less Discriminating Than the a'-a-a' Vertical Triad in the Antiparallel Coiled-coil Dimer Motif*," J. Amer. Chem. Soc. 134(5):2626-2633; Straussman, R. et al. (2007) "*Kinking the Coiled Coil—Negatively Charged Residues at the Coiled-coil Interface*," J. Molec. Biol. 366:1232-1242; Tripet, B. et al. (2002) "*Kinetic Analysis of the Interactions between Troponin C and the C-terminal Troponin I Regulatory Region and Validation of a New Peptide Delivery/Capture System used for Surface Plasmon Resonance*," J. Molec. Biol. 323:345-362; Woolfson, D. N. (2005) "*The Design Of Coiled—Coil Structures And Assemblies*," Adv. Prot. Chem. 70:79-112; Zeng, Y. et al. (2008) "*A Ligand-Pseudoreceptor System Based On de novo Designed Peptides For The Generation Of Adenoviral Vectors With Altered Tropism*," J. Gene Med. 10:355-367).

Such repeated coil domains may be exact repeats or may have substitutions. For example, the Heterodimerization-Promoting Domain of the first polypeptide chain may comprise a sequence of eight negatively charged amino acid residues and the Heterodimerization-Promoting Domain of the second polypeptide chain may comprise a sequence of eight negatively charged amino acid residues. It is immaterial which coil is provided to the first or second polypeptide chains, provided that a coil of opposite charge is used for the other polypeptide chain.

In certain embodiments an HIV-1×CD3 bi-specific monovalent diabody of the present invention has a first polypeptide chain having a negatively charged coil. The positively charged amino acid may be lysine, arginine, histidine, etc. and/or the negatively charged amino acid may be glutamic acid, aspartic acid, etc. In certain embodiments the positively charged amino acid is lysine and/or the negatively charged amino acid is glutamic acid. It is possible for only a single Heterodimerization-Promoting Domain to be employed (since such domain will inhibit homodimerization and thereby promote heterodimerization). In certain embodiments both the first and second polypeptide chains of the diabodies of the present invention to contain Heterodimerization-Promoting Domains.

In certain embodiments, one of the Heterodimerization-Promoting Domains will comprise four tandem "E-coil" helical domains (SEQ ID NO:7: EVAALEK-EVAALEK-EVAALEK-EVAALEK), whose glutamate residues will form a negative charge at pH 7, while the other of the Heterodimerization-Promoting Domains will comprise four tandem "K-coil" domains (SEQ ID NO:8: KVAALKE-KVAALKE-KVAALKE-KVAALKE), whose lysine residues will form a positive charge at pH 7. The presence of such charged domains promotes association between the first and second polypeptides, and thus fosters heterodimerization. In some embodiments, the number of K coil and E coil domains can vary and a skilled artisan can readily determine whether a different number of K-coil or E-coil domain lead to heterodimerization.

In certain embodiments, the HIV-1×CD3 or HIV-1×CD16 bi-specific monovalent diabodies of the present invention are engineered so that their first and second polypeptide chains covalently bond to one another via one or more cysteine residues positioned along their length. Such cysteine residues may be introduced into the intervening linker that separates the VL and VH domains of the polypeptides. Alternatively, Linker 2 may contain a cysteine residue.

The invention also includes variants of the antibodies (and fragments) disclosed herein, including variants that retain the ability to bind to recombinant Env protein, the ability to bind to the surface of virus-infected cells and/or ADCC-mediating properties of the antibodies specifically disclosed, and methods of using same to, for example, reduce HIV-1 infection risk. Combinations of the antibodies, or fragments thereof, disclosed herein can also be used in the methods of the invention.

In certain embodiments the invention provides a bispecific antibody. A bispecific or bifunctional antibody is an artificial hybrid antibody having two different heavy/light chain pairs and two different binding sites (see, e.g., Romain Rouet & Daniel Christ "Bispecific antibodies with native chain structure" Nature Biotechnology 32, 136-137 (2014); Byrne et al. "A tale of two specificities: bispecific antibodies for therapeutic and diagnostic applications" Trends in Biotechnology, Volume 31, Issue 11, November 2013, Pages 621-632 Songsivilai and Lachmann, Clin. Exp. Immunol., 79:315-321 (1990); Kostelny et al., J. Immunol. 148:1547-53 (1992) (and references therein)). In certain embodiments the bispecific antibody is a whole antibody of any isotype. In other embodiments a bispecific fragment, for example but not limited to $F(ab)_2$ fragment. In some embodiments, the bispecific antibodies do not include Fc portion, which makes these diabodies relatively small in size and easy to penetrate tissues.

In certain embodiments, the bispecific antibodies could include Fc region. Fc bearing diabodies, for example but not limited to Fc bearing DARTs are heavier, and could bind neonatal Fc receptor, increasing their circulating half-life. See Garber "Bispecific antibodies rise again" Nature Reviews Drug Discovery 13, 799-801 (2014), FIG. 1a; See US Pub 20130295121, US Pub 20140099318 incorporated by reference in their entirety. In certain embodiments, the invention encompasses diabody molecules comprising an Fc domain or portion thereof (e.g. a CH2 domain, or CH3 domain). The Fc domain or portion thereof may be derived from any immunoglobulin isotype or allotype including, but not limited to, IgA, IgD, IgG, IgE and IgM. In some embodiments, the Fc domain (or portion thereof) is derived from IgG. In some embodiments, the IgG isotype is IgG1, IgG2, IgG3 or IgG4 or an allotype thereof. In some embodiments, the diabody molecule comprises an Fc domain, which Fc domain comprises a CH2 domain and CH3 domain independently selected from any immunoglobulin isotype (i.e. an Fc domain comprising the CH2 domain derived from IgG and the CH3 domain derived from IgE, or the CH2 domain derived from IgG1 and the CH3 domain derived from IgG2, etc.). In some embodiments, the Fc domain may be engineered into a polypeptide chain comprising the diabody molecule of the invention in any position relative to other domains or portions of the polypeptide chain (e.g., the Fc domain, or portion thereof, may be c-terminal to both the VL and VH domains of the polypeptide of the chain; may be n-terminal to both the VL and VH domains; or may be N-terminal to one domain and c-terminal to another (i.e., between two domains of the polypeptide chain)).

Other modification s of the bispecific molecules are contemplated to increase the half-life of the bispecific molecules. In some embodiments, these modifications include addition of a polypeptide portion of a serum binding protein. See US20100174053 A1, incorporated by reference.

In some embodiments, the Fc variants of the bispecific molecules of the invention are expected to have increased serum half-life compared to the non-Fc variants. Skilled artisan can readily carry out various assays, including pharmacokinetic studies, to determine the half-life of these molecules.

In some embodiments, the invention encompasses polypeptide chains, each of which polypeptide chains comprise a VH and VL domain, comprising CDRs as described herein. In certain embodiments, the VL and VH domains comprising each polypeptide chain have the same specificity, and the multimer molecule is bivalent and monospecific. In other embodiments, the VL and VH domains comprising each polypeptide chain have differing specificity and the multimer is bivalent and bispecific.

In some embodiments, the polypeptide chains in multimers further comprise an Fc domain. Dimerization of the Fc domains leads to formation of a diabody molecule that exhibits immunoglobulin-like functionality, i.e., Fc mediated function (e.g., Fc-Fc.gamma.R interaction, complement binding, etc.).

Formation of bispecific molecule as described supra requires the interaction of differing polypeptide chains. Such interactions are difficult to achieve with efficiency within a single cell recombinant production system, due to the many variants of potential chain mispairings. One solution to increase the probability of mispairings, is to engineer "knobs-into-holes" type mutations into the desired polypeptide chain pairs. Such mutations favor heterodimerization over homodimerization. For example, with respect to Fc-Fc-interactions, an amino acid substitution (preferably a substitution with an amino acid comprising a bulky side group forming a 'knob', e.g., tryptophan) can be introduced into the CH2 or CH3 domain such that steric interference will prevent interaction with a similarly mutated domain and will obligate the mutated domain to pair with a domain into which a complementary, or accommodating mutation has been engineered, i.e., 'the hole' (e.g., a substitution with glycine). Such sets of mutations can be engineered into any pair of polypeptides comprising the diabody molecule, and further, engineered into any portion of the polypeptides chains of the pair. Methods of protein engineering to favor heterodimerization over homodimerization are well known in the art, in particular with respect to the engineering of immunoglobulin-like molecules, and are encompassed herein (see e.g., Ridgway et al. (1996) "'Knobs-Into-Holes' Engineering Of Antibody CH3 Domains For Heavy Chain Heterodimerization," Protein Engr. 9:617-621, Atwell et al. (1997) "Stable Heterodimers From Remodeling The Domain Interface Of A Homodimer Using A Phage Display Library," J. Mol. Biol. 270: 26-35, and Xie et al. (2005) "A New Format Of Bispecific Antibody: Highly Efficient Heterodimerization, Expression And Tumor Cell Lysis," J. Immunol. Methods 296:95-101; each of which is hereby incorporated herein by reference in its entirety).

The invention also encompasses diabody molecules comprising variant Fc or portion thereof), which variant Fc domain comprises at least one amino acid modification (e.g. substitution, insertion deletion) relative to a comparable wild-type Fc domain or hinge-Fc domain (or portion thereof). Molecules comprising variant Fc domains or hinge-Fc domains (or portion thereof) (e.g., antibodies) normally have altered phenotypes relative to molecules comprising wild-type Fc domains or hinge-Fc domains or portions thereof. The variant phenotype may be expressed as altered serum half-life, altered stability, altered susceptibility to cellular enzymes or altered effector function as assayed in an NK dependent or macrophage dependent assay. Fc domain variants identified as altering effector function are known in the art. For example International Application WO04/063351, U.S. Patent Application Publications 2005/0037000 and 2005/0064514.

The bispecific diabodies of the invention can simultaneously bind two separate and distinct epitopes. In certain embodiments the epitopes are from the same antigen. In other embodiments, the epitopes are from different antigens. In non-limiting embodiments a at least one epitope binding site is specific for a determinant expressed on an immune effector cell (e.g. CD3, CD16, CD32, CD64, etc.) which are expressed on T lymphocytes, natural killer (NK) cells or other mononuclear cells. In one embodiment, the diabody molecule binds to the effector cell determinant and also activates the effector cell. In this regard, diabody molecules of the invention may exhibit Ig-like functionality independent of whether they further comprise an Fc domain (e.g., as assayed in any effector function assay known in the art or exemplified herein).

In certain embodiments, the bispecific antibody comprises an HIV envelope binding fragment, for example but not limited to an HIV envelope binding fragment from any of the antibodies described herein. In other embodiments, the bispecific antibody further comprises a second antigen-interaction-site/fragment. In other embodiments, the bispecific antibody further comprises at least one effector domain.

In certain embodiments the bispecific antibodies engage cells for Antibody-Dependent Cell-mediated Cytotoxicity (ADCC). In certain embodiments the bispecific antibodies engage natural killer cells, neutrophil polymorphonuclear leukocytes, monocytes and macrophages. In certain embodiments the bispecific antibodies are T-cell engagers. In certain embodiments, the bispecific antibody comprises an HIV envelope binding fragment and CD3 binding fragment. Various CD3 antibodies are known in the art. See for example U.S. Pat. No. 8,784,821, and United States Patent Publications No. 2014-0099318 providing various disclosure on various CD3 antibodies, which disclosure in incorporated by reference in its entirety. In certain embodiments, the bispecific antibody comprises an HIV envelope binding fragment and CD16 binding fragment.

In certain embodiments the invention provides antibodies with dual targeting specificity. In certain aspects the invention provides bi-specific molecules that are capable of localizing an immune effector cell to an HIV-1 envelope expressing cell, so as facilitate the killing of the HIV-1 envelope expressing cell. In this regard, bispecific antibodies bind with one "arm" to a surface antigen on target cells, and with the second "arm" to an activating, invariant component of the T cell receptor (TCR) complex. The simultaneous binding of such an antibody to both of its targets will force a temporary interaction between target cell and T cell, causing activation of any cytotoxic T cell and subsequent lysis of the target cell. Hence, the immune response is re-directed to the target cells and is independent of peptide antigen presentation by the target cell or the specificity of the T cell as would be relevant for normal MHC-restricted activation of CTLs. In this context it is crucial that CTLs are only activated when a target cell is presenting the bispecific antibody to them, i.e. the immunological synapse is mimicked. Particularly desirable are bispecific antibodies that do not require lymphocyte preconditioning or co-stimulation in order to elicit efficient lysis of target cells.

In certain embodiments, the invention provides antibodies or fragments comprising a CDR(s) of the VH and/or VL chains, or VH and/or VL chains of the inventive antibodies, as the HIV-1 binding arm(s) of a bispecific molecules, e.g. but not limited to DARTS, or toxin labeled HIV-1 binding molecules.

In certain embodiments, such bispecific molecules comprise one portion which targets HIV-1 envelope and a second portion which binds a second target. In certain embodiments, the first portion comprises VH and VL sequences, or CDRs from the antibodies described herein. In certain embodiments, the second target could be, for example but not limited to an effector cell. In certain embodiments the second portion is a T-cell engager. In certain embodiments, the second portion comprises a sequence/paratope which targets CD3. In certain embodiments, the second portion is an antigen-binding region derived from a CD3 antibody, optionally a known CD3 antibody. In certain embodiments, the anti-CD antibody induce T cell-mediated killing. In certain embodiments, the bispecific antibodies are whole antibodies. In other embodiments, the dual targeting antibodies consist essentially of Fab fragments. In other embodiments, the dual targeting antibodies comprise a heavy chain constant region (CH1). In certain embodiments, the bispecific antibody does not comprise Fc region. In certain embodiments, the bispecific antibodies have improved effector function. In certain embodiments, the bispecific antibodies have improved cell killing activity. Various methods and platforms for design of bispecific antibodies are known in the art. See for example US Pub. 20140206846, US Pub. 20140170149, 20100174053, US Pub. 20090060910, US Pub 20130295121, US Pub. 20140099318, US Pub. 20140088295 which contents are herein incorporated by reference in their entirety.

In certain embodiments the invention provides human, humanized and/or chimeric antibodies. Methods to construct such antibodies are well known in the art.

In certain aspects the invention provides use of the antibodies of the invention, including bispecific antibodies, in methods of treating and preventing HIV-1 infection in an individual, comprising administering to the individual a therapeutically effective amount of a composition comprising the antibodies of the invention in a pharmaceutically acceptable form. In certain embodiment, the methods include a composition which includes more than one HIV-1 targeting antibody. In certain embodiments, the HIV-1 targeting antibodies in such combination bind different epitopes on the HIV-1 envelope. In certain embodiments, such combinations of bispecific antibodies targeting more than one HIV-1 epitope provide increased killing of HIV-1 infected cells. In other embodiments, such combinations of bispecific antibodies targeting more than one HIV-1 epitope provide increased breadth in recognition of different HIV-1 subtypes.

The invention also includes variants of the antibodies (and fragments) disclosed herein, including variants that retain the ability to bind to recombinant Env protein, the ability to bind to the surface of virus-infected cells and/or ADCC-mediating properties of the antibodies specifically disclosed, and methods of using same to, for example, reduce HIV-1 infection risk. Combinations of the antibodies, or fragments thereof, disclosed herein can also be used in the methods of the invention.

Homologs and variants of a VL or a VH of an antibody that specifically binds a polypeptide are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

In certain embodiments, the invention provides antibodies which are 99%, 98%, 97%, 96%, 95%, 94%, 93%, 92%, 91%, 90%, 89%, 88%, 87%, 86%, 85%, 84%, 83%, 82%, 81%, 80% identical to the VH and VL amino acid sequences of the antibodies described herein and still maintain their epitope binding breadth and/or potency. In certain embodiments, the invention provides antibodies which are 99%, 98%, 97%, 96%, 95%, 94%, 93%, 92%, 91%, 90%, 89%, 88%, 87%, 86%, 85%, 84%, 83%, 82%, 81%, 80% identical to the CDR1, 2, and/or 3 of VH and CDR1, 2, and/or 3 VL amino acid sequences of the antibodies described herein and still maintain their epitope binding breadth and/or potency.

Figure 8B:
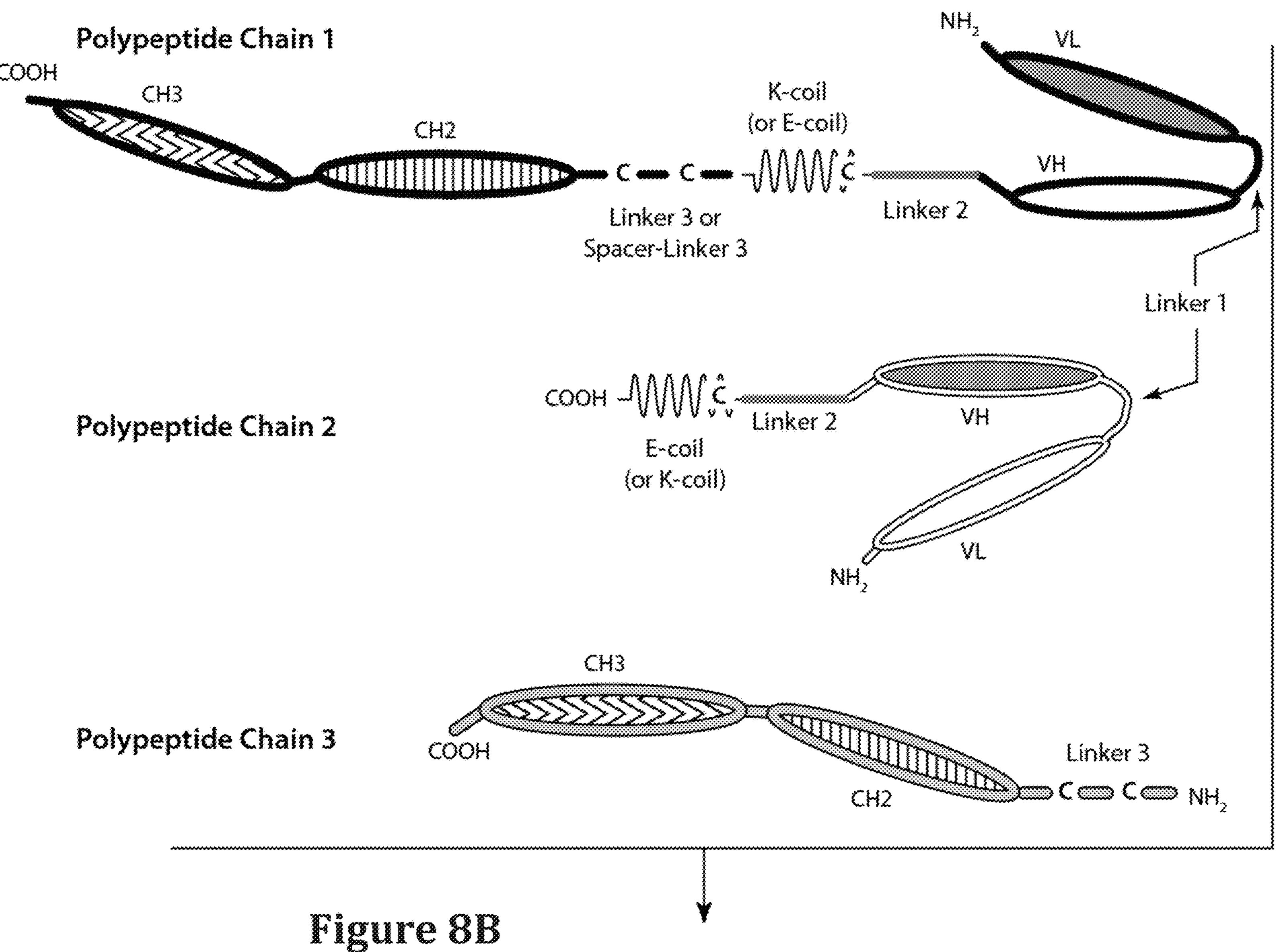
Figure 8B:
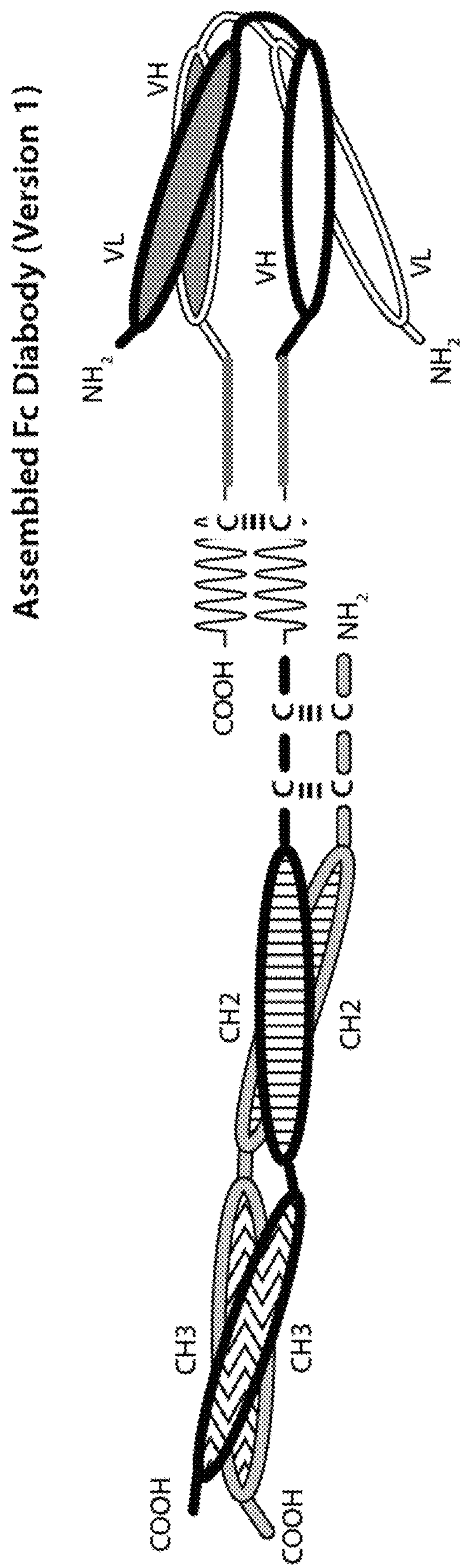
Figure 8C:
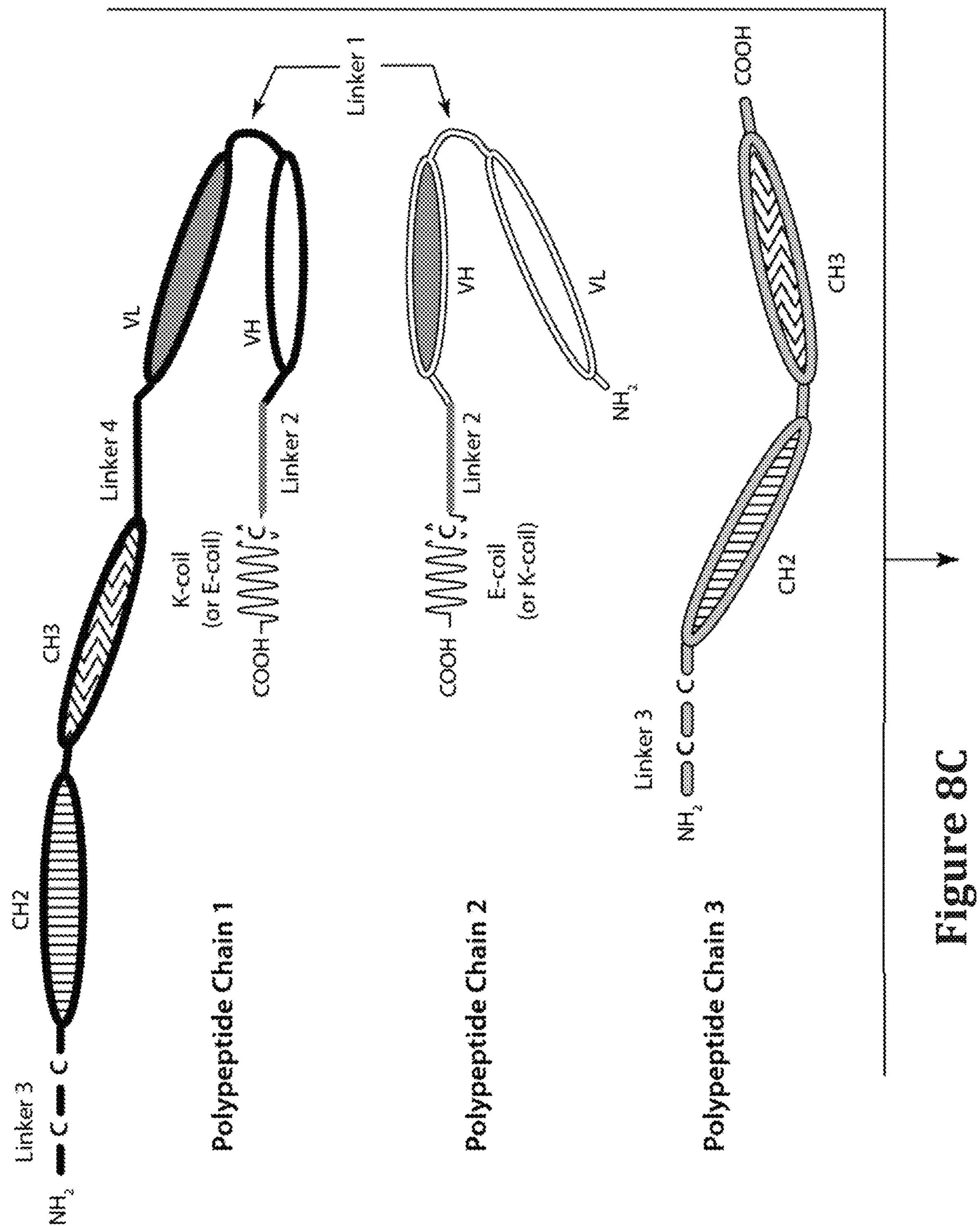
Figure 8C:
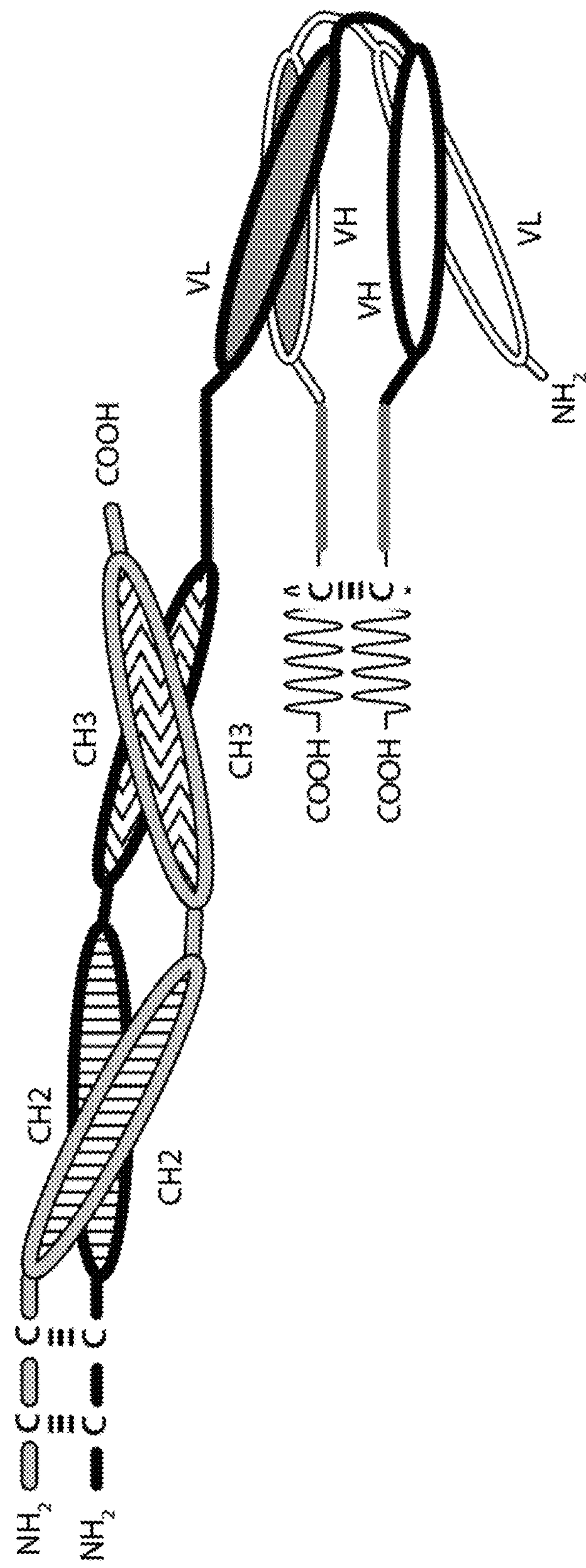

In another aspect, the invention provides Fc bearing bispecific molecules. In some embodiments, the third Domain of one or both of the polypeptides may additionally comprises the sequence of a CH2-CH3 Domain, such that complexing of the diabody polypeptides forms an Fc Domain that is capable of binding to the Fc receptor of cells (such as B lymphocytes, dendritic cells, natural killer cells, macrophages, neutrophils, eosinophils, basophils and mast cells) (FIGS. 8B-8C). Many variations of such molecules have been described (see, e.g., United States Patent Publications No. 2014-0099318; 2013-0295121; 2010-0174053 and 2009-0060910; European Patent Publication No. EP 2714079; EP 2601216; EP 2376109; EP 2158221 and PCT Publications No. WO 2015/026894; WO 2015/026892; WO 2015/021089; WO 2014/159940; WO 2012/162068; WO 2012/018687; WO 2010/080538), the content of each of these publications in herein incorporated by reference in its entirety.

In some embodiments, these Fc-bearing DARTs may comprise three polypeptide chains. The first polypeptide of such a diabody contains three Domains: (i) a VL1-containing Domain, (ii) a VH2-containing Domain, (iii) a Domain that promotes heterodimerization and covalent bonding with the diabody's first polypeptide chain and (iv) a Domain containing a CH2-CH3 sequence. The second polypeptide of such DART™ contains: (i) a VL2-containing Domain, (ii) a VH1-containing Domain and (iii) a Domain that promotes heterodimerization and covalent bonding with the diabody's first polypeptide chain. The third polypeptide of such DART™ comprises a CH2-CH3 sequence. Thus, the first and second polypeptide chains of such DART™ associate together to form a VL1/VH1 binding site that is capable of binding to the epitope, as well as a VL2/VH2 binding site that is capable of binding to the second epitope. The first and second polypeptides are bonded to one another through a disulfide bond involving cysteine residues in their respective third Domains. Notably, the first and third polypeptide chains complex with one another to form an Fc Domain that is stabilized via a disulfide bond. Such diabodies have enhanced potency. Such Fc-bearing DARTs™ may have either of two orientations (Table 1):

TABLE 1

| | | |
|---|---|---|
| First Orientation | 3rd Chain | $NH_2$—CH2—CH3—COOH |
| | 1st Chain | $NH_2$-VL1-VH2-Heterodimer Promoting Domain-CH2—CH3—COOH |
| | 2nd Chain | $NH_2$-VL2-VH1-Heterodimer Promoting Domain-COOH |
| Second Orientation | 3rd Chain | $NH_2$—CH2—CH3—COOH |
| | 1st Chain | $NH_2$—CH2—CH3- VL1-VH2-Heterodimer Promoting Domain-COOH |
| | 2nd Chain | $NH_2$-VL2-VH1-Heterodimer Promoting Domain-COOH |

HIV×CD3 bi-specific monovalent Fc diabodies that are composed of three polypeptide chains which associate with one another to form one binding site specific for an epitope of HIV and one binding site specific for an epitope of CD3 (see, FIG. 8B-8C), so as to be capable of simultaneously binding to HIV and to CD3. Thus, such diabodies bind to a "first antigen," which may be either CD3 or HIV, and a "second antigen," which is HIV when the first epitope is CD3, and is CD3 when the first epitope is HIV.

As shown in FIG. 8B, the first of such three polypeptide chains will contain, in the N-terminal to C-terminal direction, an N-terminus, the Antigen-Binding Domain of a Light Chain Variable Domain (VL) of a "first" antigen (either CD3 or HIV), the Antigen-Binding Domain of a Heavy Chain Variable Domain (VH) of a second antigen (HIV, if the first antigen was CD3; CD3, if the first antigen was HIV), a Heterodimerization-Promoting Domain, and a C-terminus. An intervening linker peptide (Linker 1) separates the Antigen-Binding Domain of the Light Chain Variable Domain from the Antigen-Binding Domain of the Heavy Chain Variable Domain. In non-limiting embodiments, the Antigen-Binding Domain of the Heavy Chain Variable Domain is linked to the Heterodimerization-Promoting Domain by an intervening linker peptide (Linker 2). In the case of an HIV×CD3 bi-specific monovalent Fc diabody, the C-terminus of the Heterodimerization-Promoting Domain is linked to the CH2-CH3 domains of an Fc region ("Fc Domain") by an intervening linker peptide (Linker 3) or by an intervening spacer-linker peptide (Spacer-Linker 3). In non-limiting embodiments, the first of the three polypeptide chains will thus contain, in the N-terminal to C-terminal direction: $VL_{First\ Antigen}$-Linker 1-$VH_{Second\ Antigen}$-Linker 2 Heterodimerization-Promoting Domain-Spacer-Linker 3-Fc Domain.

Alternatively, as shown in FIG. 8C, the first of such three polypeptide chains will contain, in the N-terminal to C-terminal direction, an N-terminus, Linker 3, the CH2-CH3 domains of an Fc region ("Fc Domain"), an intervening spacer peptide (Linker 4), having, for example the amino acid sequence: APSSS (SEQ ID NO:39) or the amino acid sequence APSSSPME (SEQ ID NO:40), the Antigen-Binding Domain of a Light Chain Variable Domain (VL) of the first antigen (either CD3 or HIV), the Antigen-Binding Domain of a Heavy Chain Variable Domain (VII) of the second antigen (HIV, if the first antigen was CD3; CD3, if the first antigen was HIV), a Heterodimerization-Promoting Domain, and a C-terminus. An intervening linker peptide (Linker 1) separates the Antigen-Binding Domain of the Light Chain Variable Domain from the Antigen-Binding Domain of the Heavy Chain Variable Domain. In non-limiting embodiments, the Antigen-Binding Domain of the Heavy Chain Variable Domain is linked to the Heterodimerization-Promoting Domain by an intervening linker peptide (Linker 2). In non-limiting embodiments, the first of the three polypeptide chains will thus contain, in the N-terminal to C-terminal direction: Linker 3-Fc Domain-Linker 4-$VL_{First\ Antigen}$-Linker 1-$VH_{Second\ Antigen}$-Linker 2-Heterodimerization-Promoting Domain.

In non-limiting embodiments, the second of such three polypeptide chains will contain, in the N-terminal to C-terminal direction, an N-terminus, the Antigen-Binding Domain of a Light Chain Variable Domain (VL) of the second antigen, the Antigen-Binding Domain of a Heavy Chain Variable Domain (VH) of the first antigen, a Heterodimerization-Promoting Domain and a C-terminus. An intervening linker peptide (Linker 1) separates the Antigen-Binding Domain of the Light Chain Variable Domain from the Antigen-Binding Domain of the Heavy Chain Variable Domain. In non-limiting embodiments, the Antigen-Binding Domain of the Heavy Chain Variable Domain is linked to the Heterodimerization-Promoting Domain by an intervening linker peptide (Linker 2). In non-limiting embodiments, the second of the three polypeptide chains will thus contain, in the N-terminal to C-terminal direction: $VL_{Second\ Antigen}$-Linker 1-$VH_{First\ Antigen}$-Linker 2-Heterodimerization-Promoting Domain.

In non-limiting embodiments, the third of such three polypeptide chains will contain the linker peptide (Linker 3) and the CH2-CH3 domains of an Fc region ("Fc Domain").

The bispecific molecules of the invention contemplate designs with various linkers to separate the different domain comprised in the polypeptide chains. Specific non-limiting embodiments of the linkers are disclosed herein. Other linkers can be readily determined. Some additional examples of linkers are disclosed in US Pub 20100174053, incorporated by reference in its entirety.

The Antigen-Binding Domain of the Light Chain Variable Domain of the first polypeptide chain interacts with the Antigen-Binding Domain of the Heavy Chain Variable Domain of the second polypeptide chain in order to form a functional antigen-binding site that is specific for the first antigen (i.e., either HIV or CD3). Likewise, the Antigen-Binding Domain of the Light Chain Variable Domain of the second polypeptide chain interacts with the Antigen-Binding Domain of the Heavy Chain Variable Domain of the first polypeptide chain in order to form a second functional antigen-binding site that is specific for the second antigen (i.e., either CD3 or HIV, depending upon the identity of the first antigen). Thus, the selection of the Antigen-Binding Domain of the Light Chain Variable Domain and the Antigen-Binding Domain of the Heavy Chain Variable Domain of the first and second polypeptide chains are coordinated, such that the two polypeptide chains collectively comprise Antigen-Binding Domains of light and Heavy Chain Variable Domains capable of binding to HIV and CD3.

The Fc Domain of the HIV×CD3 bi-specific monovalent Fc diabodies of the present invention may be either a complete Fc region (e.g., a complete IgG Fc region) or only a fragment of a complete Fc region. Although the Fc Domain of the bi-specific monovalent Fc diabodies of the present invention may possess the ability to bind to one or more Fc receptors (e.g., FcγR(s)), In non-limiting embodiments such Fc Domain will cause reduced binding to FcγRIA (CD64), FcγRIIA (CD32A), FcγRIIB (CD32B), FcγRIIIA (CD16a) or FcγRIIIB (CD16b) (relative to the binding exhibited by a wild-type Fc region) or will substantially eliminate the ability of such Fc Domain to bind to such receptor(s). The Fc Domain of the bi-specific monovalent Fc diabodies of the present invention may include some or all of the CH2 Domain and/or some or all of the CH3 Domain of a complete Fc region, or may comprise a variant CH2 and/or a variant CH3 sequence (that may include, for example, one or more insertions and/or one or more deletions with respect to the CH2 or CH3 domains of a complete Fc region). The Fc Domain of the bi-specific monovalent Fc diabodies of the present invention may comprise non-Fc polypeptide portions, or may comprise portions of non-naturally complete Fc regions, or may comprise non-naturally occurring orientations of CH2 and/or CH3 domains (such as, for example, two CH2 domains or two CH3 domains, or in the N-terminal to C-terminal direction, a CH3 Domain linked to a CH2 Domain, etc.).

In non-limiting embodiments the first and third polypeptide chains of the HIV×CD3 bi-specific monovalent Fc diabodies of the present invention each comprise CH2-CH3 domains that complex together to form an immunoglobulin (IgG) Fc Domain. The amino acid sequence of the CH2-CH3 domain of human IgG1 is (SEQ ID NO:41):

```
APELLGGPSV FLFPPKPKDT LMISRTPEVT CVVVDVSHED
PEVKFNWYVD GVEVHNAKTK PREEQYNSTY RVVSVLTVLH
QDWLNGKEYK CKVSNKALPA PIEKTISKAK GQPREPQVYT
LPPSREEMTK NQVSLTCLVK GFYPSDIAVE WESNGQPENN
YKTTPPVLDS DGSFFLYSKL TVDKSRWQQG NVFSCSVMHE
ALHNHYTQKS LSLSPGK
```

Thus the CH2 and/or CH3 Domains of the first and third polypeptide chains may both be composed of SEQ ID NO:41, or a variant thereof.

In non-limiting embodiments the CH2-CH3 domains of the first and third polypeptide chains of the HIV×CD3 bi-specific monovalent Fc diabodies of the present invention to exhibit decreased (or substantially no) binding to FcγRIA (CD64), FcγRIIA (CD32A), FcγRIIB (CD32B), FcγRIIIA (CD16a) or FcγRIIIB (CD16b) (relative to the binding exhibited by the wild-type Fc region (SEQ ID NO:41). Fc variants and mutant forms capable of mediating such altered binding are well known in the art and include amino acid substitutions at positions 234 and 235, a substitution at position 265 or a substitution at position 297 (see, for example, U.S. Pat. No. 5,624,821, herein incorporated by reference). In non-limiting embodiments the CH2-CH3 Domain of the first and/or third polypeptide chains of the HIVx CD3 bi-specific monovalent Fc diabodies of the present invention include a substitution at position 234 with alanine and 235 with alanine.

The CH2 and/or CH3 Domains of the first and third polypeptide chains need not be identical in sequence, and advantageously are modified to foster complexing between the two polypeptide chains. For example, an amino acid substitution (for example a substitution with an amino acid comprising a bulky side group forming a 'knob', e.g., tryptophan) can be introduced into the CH2 or CH3 Domain such that steric interference will prevent interaction with a similarly mutated domain and will obligate the mutated domain to pair with a domain into which a complementary, or accommodating mutation has been engineered, i.e., 'the hole' (e.g., a substitution with glycine). Such sets of mutations can be engineered into any pair of polypeptides comprising the bi-specific monovalent Fc diabody molecule, and further, engineered into any portion of the polypeptides chains of the pair. Methods of protein engineering to favor heterodimerization over homodimerization are well known in the art, in particular with respect to the engineering of immunoglobulin-like molecules, and are encompassed herein (see e.g., Ridgway et al. (1996) "*Knobs-Into-Holes' Engineering Of Antibody CH3 Domains For Heavy Chain Heterodimerization*," Protein Engr. 9:617-621, Atwell et al. (1997) "*Stable Heterodimers From Remodeling The Domain Interface Of A Homodimer Using A Phage Display Library*," J. Mol. Biol. 270: 26-35, and Xie et al. (2005) "*A New Format Of Bispecific Antibody: Highly Efficient Heterodimerization, Expression And Tumor Cell Lysis*," J. Immunol. Methods 296:95-101; each of which is hereby incorporated herein by reference in its entirety). In non-limiting embodiments the 'knob' is engineered into the CH2-CH3 Domains of the first polypeptide chain and the 'hole' is engineered into the CH2-CH3 Domains of the third polypeptide chain. Thus, the 'knob' will help in preventing the first polypeptide chain from homodimerizing via its CH2 and/or CH3 Domains. In non-limiting embodiments, as the third polypeptide chain contains the 'hole' substitution it will heterodimerize with the first polypeptide chain as well as homodimerize with itself. In non-limiting embodiments a knob is created by modifying a native IgG Fc Domain to contain the modification T366W. In non-limiting embodiments a hole is created by modifying a native IgG Fc Domain to contain the modification T366S, L368A and Y407V. To aid in purifying the third polypeptide chain homodimer from the final bi-specific monovalent Fc diabody comprising the first, second and third polypeptide chains, the protein A binding site of the CH2 and CH3 Domains of the third polypeptide chain is mutated by amino acid substitution at position 435 (H435R). Thus, the third polypeptide chain homodimer will not bind to protein A, whereas the bi-specific monovalent Fc diabody will retain its ability to bind protein A via the protein A binding site on the first polypeptide chain.

In non-limiting embodiments a sequence for the CH2 and CH3 Domains of the first polypeptide chain of the HIV× effector (e.g.CD3) bi-specific monovalent Fc diabodies of the present invention will have the "knob-bearing" sequence (SEQ ID NO:42):

```
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLWCLVK GFYPSDIAVE WESNGQPENN

YKTTPPVLDS DGSFFLYSKL TVDKSRWQQG NVFSCSVMHE

ALHNHYTQKS LSLSPGK
```

In non-limiting embodiments a sequence for the CH2 and CH3 Domains of the third polypeptide chain of the HIV× effector (e.g. CD3) bi-specific monovalent Fc diabodies of the present invention will have the "hole-bearing" sequence (SEQ ID NO:43):

```
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLSCAVK GFYPSDIAVE WESNGQPENN

YKTTPPVLDS DGSFFLVSKL TVDKSRWQQG NVFSCSVMHE

ALHNRYTQKS LSLSPGK
```

As will be noted, the CH2-CH3 Domains of SEQ ID NO:42 and SEQ ID NO:43 include a substitution at position 234 with alanine and 235 with alanine, and thus form an Fc Domain exhibit decreased (or substantially no) binding to FcγRIA (CD64), FcγRIIA (CD32A), FcγRIIB (CD32B), FcγRIIIA (CD16a) or FcγRIIIB (CD16b) (relative to the binding exhibited by the wild-type Fc region (SEQ ID NO:41).

In non-limiting embodiments a the first polypeptide chain will have a "knob-bearing" CH2-CH3 sequence, such as that of SEQ ID NO:42. However, as will be recognized, a "hole-bearing" CH2-CH3 Domain (e.g., SEQ ID NO:43) could be employed in the first polypeptide chain, in which case, a "knob-bearing" CH2-CH3 Domain (e.g., SEQ ID NO:42) would be employed in the third polypeptide chain.

In non-limiting embodiments, the Fc domain can be modified by amino acid substitution to increase binding to the neonatal Fc receptor and therefore the half-life of the antibody when administered to a subject. The Fc domain can be an IgA, IgM, IgD, IgE or IgG Fc domain. The Fc domain can be an optimized Fc domain, as described in U.S. Published Patent Application No. 20100093979, incorporated herein by reference. In certain embodiments the antibodies comprise amino acid alterations, or combinations thereof, for example in the Fc region outside of epitope binding, which alterations can improve their properties. Various Fc modifications are known in the art. Amino acid numbering is according to the EU Index in Kabat. In some embodiments, the invention contemplates antibodies comprising mutations that affect neonatal Fc receptor (FcRn) binding, antibody half-life, and localization and persistence of antibodies at mucosal sites. See e.g. Ko S Y et al., Nature 514: 642-45, 2014, at FIG. 1a and citations therein; Kuo, T. and and Averson, V., mAbs 3(5): 422-430, 2011, at Table 1, US Pub 20110081347 (an aspartic acid at Kabat residue 288 and/or a lysine at Kabat residue 435), US Pub 20150152183 for various Fc region mutation, incorporated by reference in their entirety.

In certain embodiments, the antibodies comprise AAAA substitution in and around the Fc region of the antibody that has been reported to enhance ADCC via NK cells (AAA mutations) containing the Fc region aa of S298A as well as E333A and K334A (Shields R I et al JBC, 276: 6591-6604, 2001) and the 4$^{th}$ A (N434A) is to enhance FcR neonatal mediated transport of the IgG to mucosal sites (Shields R I et al. ibid). Other antibody mutations have been reported to improve antibody half-life or function or both and can be incorporated in sequences of the antibodies. These include the DLE set of mutations (Romain G, et al. Blood 124: 3241, 2014), the LS mutations M428L/N434S, alone or in a combination with other Fc region mutations, (Ko S Y et al. Nature 514: 642-45, 2014, at FIG. 1a and citations therein; Zlevsky et al., Nature Biotechnology, 28(2): 157-159, 2010; US Pub 20150152183); the YTE Fc mutations (Robbie G et al Antimicrobial Agents and Chemotherapy 12: 6147-53, 2013) as well as other engineered mutations to the antibody such as QL mutations, IHH mutations (Ko S Y et al. Nature 514: 642-45, 2014, at FIG. 1a and relevant citations; See also Rudicell R et al. J. Virol 88: 12669-82, 201). In some embodiments, modifications, such as but not limited to antibody fucosylation, may affect interaction with Fc receptors (See e.g. Moldt, et al. JVI 86(11): 66189-6196, 2012). In some embodiments, the antibodies can comprise modifications, for example but not limited to glycosylation, which reduce or eliminate polyreactivity of an antibody. See e.g. Chuang, et al. Protein Science 24: 1019-1030, 2015. In some embodiments the antibodies can comprise modifications in the Fc domain such that the Fc domain exhibits, as compared to an unmodified Fc domain enhanced antibody dependent cell mediated cytotoxicity (ADCC); increased binding to Fc.gamma.RIIA or to Fc.gamma.RIIIA; decreased binding to Fc.gamma.RIIB; or increased binding to Fc.gamma.RIIB. See e.g. US Pub 20140328836.

The antibodies, and fragments thereof, described above can be formulated as a composition (e.g., a pharmaceutical composition). Suitable compositions can comprise the ADCC-mediating antibody (or antibody fragment) dissolved or dispersed in a pharmaceutically acceptable carrier (e.g., an aqueous medium). The compositions can be sterile and can be in an injectable form (e.g. but not limited to a form suitable for intravenous injection, or intramascular injection). The antibodies (and fragments thereof) can also be formulated as a composition appropriate for topical administration to the skin or mucosa. Such compositions can take the form of liquids, ointments, creams, gels and pastes. The antibodies (and fragments thereof) can also be formulated as a composition appropriate for intranasal administration. The antibodies (and fragments thereof) can be formulated so as to be administered as a post-coital douche or with a condom. Standard formulation techniques can be used in preparing suitable compositions.

The antibody (and fragments thereof), for example the ADCC-mediating antibodies, described herein have utility, for example, in settings including but not limited to the following:

i) in the setting of anticipated known exposure to HIV-1 infection, the antibodies described herein (or fragments thereof) and be administered prophylactically (e.g., IV, topically or intranasally) as a microbiocide, ii) in the setting of known or suspected exposure, such as occurs in the setting of rape victims, or commercial sex workers, or in any homosexual or heterosexual transmission without condom protection, the antibodies described herein (or fragments thereof) can be administered as post-exposure prophylaxis, e.g., IV or topically, and iii) in the setting of Acute HIV-1 infection (AHI), the antibodies described herein (or fragments thereof) can be administered as a treatment for AHI to control the initial viral load, or for the elimination of virus-infected CD4 T cells.

In accordance with the invention, the ADCC-mediating antibody (or antibody fragments) described herein can be administered prior to contact of the subject or the subject's immune system/cells with HIV-1 or within about 48 hours of such contact. Administration within this time frame can maximize inhibition of infection of vulnerable cells of the subject with HIV-1.

In addition, various forms of the antibodies described herein can be administered to chronically or acutely infected HIV-1 patients and used to kill remaining virus infected cells by virtue of these antibodies binding to the surface of virus infected cells and being able to deliver a toxin to these reservoir cells. In certain embodiments, the antibodies of the invention can be administered in combination with latency activating agents, so as to activate latent reservoir of HIV-infected cells. The expectation is that by activating latent proviral HIV DNA in resting cells, once inactive cells will start producing new virus and they will be recognized and eliminated by the immune system. Non-limiting examples of latency activating agents are HDAC inhibitors, e.g, vorinostat, romidepsin, panobinostat, disulfiram, JQ1, bryostatin, PMA, inonomycin, or any combination thereof. See Bullen et al. Nature Medicine 20, 425-429 (2014).

Suitable dose ranges can depend on the antibody (or fragment) and on the nature of the formulation and route of administration. Optimum doses can be determined by one skilled in the art without undue experimentation. For example, doses of antibodies in the range of 1-50 mg/kg of unlabeled or labeled antibody (with toxins or radioactive moieties) can be used. If antibody fragments, with or without toxins are used or antibodies are used that can be targeted to specific CD4 infected T cells, then less antibody can be used (e.g., from 5 mg/kg to 0.01 mg/kg).

Antibodies of the invention and fragments thereof can be produced recombinantly using nucleic acids comprising nucleotide sequences encoding VH and VL sequences selected from those shown in the figures and examples.

In certain embodiments the invention provides intact/whole antibodies. In certain embodiments the invention provides antigen binding fragments thereof. Typically, fragments compete with the intact antibody from which they were derived for specific binding to the target including separate heavy chains, light chains Fab, Fab', F(ab').sub.2, F(ab)c, diabodies, Dabs, nanobodies, and Fv. Fragments can be produced by recombinant DNA techniques, or by enzymatic or chemical separation of intact immunoglobulins.

Nucleic acid sequences encoding polypeptides for the production of bispecific antibodies with specificities as described herein can be used to produce plasmids for stable expression of recombinant antibodies. Methods for recombinant expression and purification are known in the art. In certain embodiments of Fc, the plasmids also comprise any of the changes to the Fc portion described herein. In some embodiments, these are AAAA substitution in and around the Fc region of the antibody that has been reported to enhance ADCC via NK cells (AAA mutations) containing the Fc region aa of S298A as well as E333A and K334A (Shields R I et al JBC, 276: 6591-6604, 2001) and the 4$^{th}$ A (N434A) is to enhance FcR neonatal mediated transport of the IgG to mucosal sites (Shields R I et al. ibid).

In certain embodiments, the nucleic acids are optimized for recombinant expression in a suitable host cell. In certain embodiments, the vector is suitable for gene delivery and expression. There are numerous expression systems available for expression of proteins including *E. coli*, other bacterial hosts, yeast, and various higher eukaryotic cells such as the COS, CHO, HeLa and myeloma cell lines.

Any suitable cell line can be used for expression of the polypeptides of the invention, including but not limited to CHO cells, 293T cells. In some aspects, the invention provides nucleic acids encoding these antibodies, expression cassettes and vectors including these nucleic acids, and isolated cells that express the nucleic acids which encode the antibodies of the invention are also provided. The polypeptides of the invention can be purified by any suitable method for purification of polypeptides and/or antibodies.

The contents of the various publications cited throughout the specification are incorporated by reference in their entirety.

EXAMPLES

Example 1A: Construction of an HIV-1×CD3 or HIV-1×CD16 Bispecific Molecules and Control Bispecific Molecules Table 2 contains a list of bi-specific diabodies that were designed, expressed and purified. The bi-specific diabodies are heterodimers, or heterotrimer of the recited amino acid sequences. Methods for forming bi-specific diabodies are provided in WO 2006/113665, WO 2008/157379, WO 2010/080538, WO 2012/018687, WO 2012/162068, WO 2012/162067, WO 2014/159940, WO 2015/021089, WO 2015/026892 and WO 2015/026894.

TABLE 2

| Bi-Specific Molecule | Polypeptide Chain Amino Acid Sequences | Nucleic Acid Encoding Sequences |
|---|---|---|
| HIV-1 × CD3 Bi-Specific Diabody (A32 × CD3) (Variable domain from A32, binds to HIV-1 gp120) | SEQ ID NO: 9<br>SEQ ID NO: 11 | SEQ ID NO: 10<br>SEQ ID NO: 12 |
| HIV-1 × CD3 Bi-Specific Diabody (7B2 × CD3) (Variable domain from 7B2, binds to HIV-1 gp41) | SEQ ID NO: 13<br>SEQ ID NO: 15 | SEQ ID NO: 14<br>SEQ ID NO: 16 |
| HIV-1 × CD3 Bi-Specific Diabody (CH28 × CD3) (Variable domain from CH28, binds to HIV-1 gp) | SEQ ID NO: 17<br>SEQ ID NO: 19 | SEQ ID NO: 18<br>SEQ ID NO: 20 |

TABLE 2-continued

| Bi-Specific Molecule | Polypeptide Chain Amino Acid Sequences | Nucleic Acid Encoding Sequences |
|---|---|---|
| HIV-1 × CD3 Bi-Specific Diabody (CH44 × CD3) (Variable domain from CH44, binds to HIV-1 gp) | SEQ ID NO: 21<br>SEQ ID NO: 23 | SEQ ID NO: 22<br>SEQ ID NO: 24 |
| HIV-1 × CD16 Bi-Specific Diabody (7B2 × CD16) (Variable domain from 7B2, binds to HIV-1 gp41) | SEQ ID NO: 25<br>SEQ ID NO: 27 | SEQ ID NO: 26<br>SEQ ID NO: 28 |
| Fluorescein × CD3 Bi-Specific Diabody (4420 × CD3) | SEQ ID NO: 29<br>SEQ ID NO: 30 | |
| Fluorescein × CD16 Bi-Specific Diabody (4420 × CD16) | SEQ ID NO: 31<br>SEQ ID NO: 32 | |
| HIV-1 × Fluorescein Bi-Specific Diabody (7B2 × 4420) (Variable domain from 7B2, binds to HIV-1 gp41) | SEQ ID NO: 33<br>SEQ ID NO: 34 | |
| HIV-1 × Fluorescein Bi-Specific Diabody (A32 × 4420) (Variable domain from A32, binds to HIV-1 gp120) | SEQ ID NO: 35<br>SEQ ID NO: 36 | |
| Palivizumab × CD3 Bi-Specific Diabody (Palivizumab × CD3) | SEQ ID NO: 37<br>SEQ ID NO: 38 | |
| HIV-1 × CD16 Bi-Specific Diabody (A32 × CD16) (Variable domain from A32, binds to HIV-1 gp120) | SEQ ID NO: 44<br>SEQ ID NO: 45 | |
| HIV-1 × CD3 Bi-Specific Diabody with Fc Domain V1 (7B2 × CD3) (Variable domain from 7B2, binds to HIV-1 gp41) | SEQ ID NO: 46<br>SEQ ID NO: 47<br>SEQ ID NO: 48 | |

HIV-1×CD3 bi-specific diabodies are capable of simultaneously binding to HIV-1 and CD3. HIV-1×CD16 bi-specific diabodies are capable of simultaneously binding to HIV-1 and CD16. The control bi-specific diabody (4420×CD3) is capable of simultaneously binding to FITC and CD3. The control bi-specific diabody (4420×CD16) is capable of simultaneously binding to FITC and CD16. The control bi-specific diabody (7B2×4420) is capable of simultaneously binding to HIV-1 and FITC. The control bi-specific diabody (A32×4420) is capable of simultaneously binding to HIV-1 and FITC. The control bi-specific diabody (Palivizumab×CD3) is capable of simultaneously binding to RSV and CD3.

Table 3 shows a summary of some embodiments of bispecific molecules. The information in the specification can be readily used for alternative designs of the listed bispecific molecules, and for design of other bispecific molecules, for example 7B2, CH27, Ch28, CH44 using CDRs, or VH and VL chains from these antibodies.

| HIV × CD3 | | HIV × CD3 Fc V1 | | HIV × CD3 FcV2 | |
|---|---|---|---|---|---|
| | A32 × CD3 One embodiment | | | | |
| One embodiment | SEQ ID Nos: 9 and 11 Together | One embodiment | A32 × CD3 Fc V1 | One embodiment | A32 × CD3 Fc V2 |
| Polypeptide Chain 1 | SEQ ID NO: 9 is one embodiment | Polypeptide Chain 1 | | Polypeptide Chain 1 | |
| NH2-VL(HIV) | SEQ ID NO: 78(FIG. 6) - | NH2-VL(HIV) | SEQ ID NO: 78 | NH2-Linker3 | SEQ ID NO: 49 |
| Linker 1 | SEQ ID NO: 1 | Linker 1 | SEQ ID NO: 1 | CH2—CH3 | SEQ ID NO: 42 (knob bearing) or SEQ ID NO: 43 (hole bearing) |

-continued

| HIV × CD3 | | | | | |
|---|---|---|---|---|---|
| | A32 × CD3 One embodiment | HIV × CD3 Fc V1 | | HIV × CD3 FcV2 | |
| One embodiment | SEQ ID Nos: 9 and 11 Together | One embodiment | A32 × CD3 Fc V1 | One embodiment | A32 × CD3 Fc V2 |
| VH(CD3) | SEQ ID NO: 51 | VH(CD3) | SEQ ID NO: 51 | Linker 4 | SEQ ID NO: 39, 40 |
| Linker 2 | SEQ ID NO: 2 | Linker 2 | SEQ ID NO: 2 | VL(HIV) | SEQ ID NO: 78 |
| Heterodimer promoting domain K coil or E coil | SEQ ID Nos: 3-6 SEQ ID Nos: 7 or 8 | Heterodimer promoting domain K coil or E coil | SEQ ID Nos: 3-6 SEQ ID Nos: 7 or 8 | Linker 1 | SEQ ID NO: 1 |
| | | Linker 3 or Spacer Linker 3 | SEQ ID NO: 49 SEQ ID NO: 50 | VH (CD3) | SEQ ID NO: 51 |
| | | CH2—CH3 | SEQ ID NO: 42 (knob bearing) or SEQ ID NO: 43 (hole bearing) | Linker 2 | SEQ ID NO: 2 |
| | | | | Heterodimer promoting domain K coil or E coil | SEQ ID Nos: 3-6 SEQ ID Nos: 7 or 8 |
| Polypeptide Chain 2 | SEQ ID NO: 11 is one embodiment | Polypeptide Chain 2 | | Polypeptide Chain 2 | |
| NH2-VL(CD3) | SEQ ID NO: 52 | NH2-VL(CD3) | SEQ ID NO: 52 | NH2-VL(CD3) | SEQ ID NO: 52 |
| Linker 1 | SEQ ID NO: 1 | Linker 1 | SEQ ID NO: 1 | Linker 1 | SEQ ID NO: 1 |
| VH(HIV1) | SEQ ID NO: 77 (FIG. 6) | VH(HIV1) | SEQ ID NO: 77 | VH(HIV) | SEQ ID NO: 77 |
| Linker 2 | SEQ ID NO: 2 | Linker 2 | SEQ ID NO: 2 | Linker 2 | SEQ ID NO: 2 |
| Heterodimer promoting domain K coil or E coil | SEQ ID Nos: 3-6 SEQ ID Nos: 7 or 8 | Heterodimer promoting domain K coil or E coil | SEQ ID Nos: 3-6 SEQ ID Nos: 7 or 8 | Heterodimer promoting domain K coil or E coil | SEQ ID Nos: 3-6 SEQ ID Nos: 7 or 8 |
| Polypeptide Chain 3 | NONE | Polypeptide Chain 3 | | Polypeptide Chain 3 | |
| | | NH2- Linker 3 | SEQ ID NO: 49 | NH2- Linker 3 | SEQ ID NO: 49 |
| | | CH2—CH3 | SEQ ID NO: 42 (knob bearing) or SEQ ID NO: 43 (hole bearing) | CH2—CH3 | SEQ ID NO: 42 (knob bearing) or SEQ ID NO: 43 (hole bearing) |

Example 1C: HIV-1 Antibodies with ADCC Activity

Monoclonal Antibodies.

Five mAbs representing those directed against the HIV-1 env gp120 constant region 1 (C1; n=1), CD4 binding site (CD4bs; n=3), and the gp41 Cluster 1 [Pollara J. *Curr. HIV Res.* 2013; 11(8):378-3870]. All the mAbs are listed in Table 1. All but mAbs were generated with a sequence for the Fc region that included amino acid substitutions according to Shields et al to optimize the binding to the Fcγ-Receptor (Fcγ-R) IIIa [Shields R L *J Biol Chem* 2001; 276(9): 6591-6604].

A32 mAb recognizes a conformational epitope in the C1 region of HIV-1 Env gp120 (Wyatt et al, J. Virol. 69:5723-5733 (1995)), could mediate potent ADCC activity and could block a significant proportion of ADCC-mediating Ab activity detectable in HIV-1 infected individuals (Ferrari et al, J. Virol. 85:7029-7036 (2011)).

CH28 or CH44 are HIV-1 CD4 bs neutralizing antibodies.

TABLE 4

| List of mAbs tested for ADCC | | |
|---|---|---|
| gp120 | | gp41 |
| C1 | CD4bs | Cluster I |
| A32 | CH27 CH28 CH44 | 7B2 |

All mAbs were produced in the 3A version to optimize the binding to the Fcγ-Receptor IIIa, but those identified by the symbol (*).

Infectious Molecular Clones (IMC).

The HIV-1 IMCs represented 22 isolates to represent those with various degree of susceptibility to neutralization based on testing with the A3R5 cell line. The list of the IMCs is reported in Table 5.

TABLE 5

| List of IMC by HIV-1 subtype used to generate infected target cells. | | | |
|---|---|---|---|
| A | AE | Bc | C |
| Q23.17 | C1080.C03 | SF162 | MW96.5 |
| | 427299 | BaL | CAP45 |
| | 92TH023 | CH058 | 245-F3-C10 |
| | CM235 | CH040 | TV-1 |
| | CM244 | SUMA | CH0505 |
| | 816763 | WITO | DU151 |
| | | YU2 | DU422 |
| | | | 1086.c |

All IMCs were generated on backbone derived from NHL4-3 isolate as previously described [Edmonds T G. *Virology*. 2010; 408(1):1-13; Adachi A. *J Virol*. 1986; 59(2): 284-291] but for the subtype AE 92TH023 that was generated utilizing the backbone from the 40021 AE HIV-1 Isolate. All IMCs expressed the Renato luciferase reporter gene and preserved all nine viral open reading frames. The Renato luciferase reporter gene was expressed under the control of the HIV-1 Tat gene. Upon HIV-1 infection of the CD4+ T cells, expression of Tat during HIV-1 replication will induce expression of the luciferase and infected cells can be easily quantified by measure of Relative Luminescence Units.

Antibody Dependent Cellular Cytotoxicity (ADCC) Assay.

The assay was performed according to our previously published methods using a luciferase based platform as read-out for the cytotoxicity mediated by the mAbs [Pollara J. *J Virol*. 2014; 88(14):7715-7726]. The effector cells populations were all derived from a single donor with the characterized heterozygous phenotype FN for the amino acid in position 158 of the Fcγ-R IIIa. The effector to target ratio was 30:1 in each assay. The plasma from a HIV-1 infected individuals (A300) and the Palivizumab (anti-RSV) mAb were used as positive and negative control in each assay. All the mAbs were tested together against each IMC. The percentage of specific killing (% SK) was calculated as previously reported. The results were considered positive if the % SK was >20%.

Potency and Breadth of ADCC-Mediating mAbs.

Each mAbs listed in Table 1 was tested individually against each of the 22 IMCs listed in Table 2. The results have been evaluated to identify the maximum ADCC activity as % SK independently from the concentration at which the activity was observed. The mAbs were grouped based on the env gp120 and gp41 regions recognized. The average of the positive responses for each mAb are reported in FIG. 1. The magnitude and breadth of the mAbs is summarized in Table 3. The non-neutralizing Abs directed against gp120 C1 and gp41 cluster 1 provided the broadest spectrum of ADCC by recognizing 21 (95%) and 20 (91%) HIV-1 isolates, respectively. The average % of specific killing (% SK) was 37% for the C1 mAbs and 34% for the gp41 cluster I mAbs. The averages of the maximum % SK of A32 and 7B2 were 45 and 42, respectively. Cumulatively, the CH44 mAb recognized<60% of the isolates tested with a range of activity between 21 and 60% SK.

TABLE 6

| Magnitude and breadth of ADCC-mediating mAbs | | | | | |
|---|---|---|---|---|---|
| | A32 | 7B2 | CH27 | CH28 | CH44 |
| Average Max % SK | 45 | 42 | 31 | 36 | 13 |
| Range | 23-86 | 21-74 | 21-53 | 23-48 | 21-60 |
| # IMCs recognized (%) | 21 (95%) | 20 (91%) | 8 (36%) | 7 (31%) | 14 (59%) |

Example 2: Cell Killing by Dual Affinity Re-Targeting (DART) Molecules A32/CD3 and 7B2/CD3

Dual affinity Re-Targeting molecules A32/CD3 (SEQ ID NOs: 9 and 11) and 7B2/CD3 (SEQ ID NOs: 13 and 15) were designed and expressed. These molecules include an HIV-1 binding arm generated based on the Fab of anti-HIV-1 monoclonal antibodies (mAbs) (mAbs that have the property of binding to the surface of tier 2 transmitted/founder (T/F) virus infected CD4 T cells (i.e. A32 or 7B2) [Ferrari G, J Virol. 2011; 85(14):7029-7036; Pollara J. *Curr. HIV Res*. 2013; 11(8):378-3870], and an effector cell binding arm that can bind the CD3 (αCD3ε arm) or CD16 (αCD16 h3G8 arm) receptors. Appropriate negative controls with an irrelevant binding arm [αfluorescein (4420) or αRSV] instead of the HIV-1 or effector arm have also been developed. The results presented in this example are from experiments with the CD3-DARTs.

Luciferase-based Cytotoxicity Assay.

We optimized a method to quantify the elimination of HIV-1-infected cells by cytotoxic CD8 T cells recruited by the DARTs that is based on the detection of luciferase activity as final readout as previously reported [Pollara J. *J Virol*. 2014; 88(14):7715-7726]. Cryopreserved resting PBMC from normal healthy HIV-1 seronegative donors were activated for 72 hours with anti-human CD3 (clone OKT3; eBioscience)/anti-human CD28 (clone CD28.2; BD Pharmingen). Subsequently, a CD4+ enriched cell population was obtained using magnetic beads, spinoculated in presence of the IMC representing the HIV-1 subtype AE (CM235), B (BaL), and C (1086.c) and cultured, for 72 hours. CD4+ infected target cells were then plated along with resting CD8+ effector cells at 33:1, 11:1, 3:1, and 0:1 effector to target ratios. DARTs (4420×CD3, 7B2×CD3, or A32×CD3) were added to combined cells at concentrations ranging from 0.001 to 1000 ng/ml and incubated for 6, 24, and 48-hour time points. Combined effector and target cells without DARTs, uninfected cells, and target cells alone were included on each plate for control conditions. At the end of each incubation time, Viviren substrate was added to each well and cells were analyzed on a luminometer to measure RLU values through luciferase readout. In presence of the cytotoxic cells of interest the elimination of infected target cells was evaluated using the appropriate already published formula [Pollara J. *J Virol*. 2014; 88(14):7715-7726]. The results are reported as % SK as described for the ADCC assay.

Anti-HIV-1 DARTs-Mediated Cytotoxic Activity.

Figure 2:
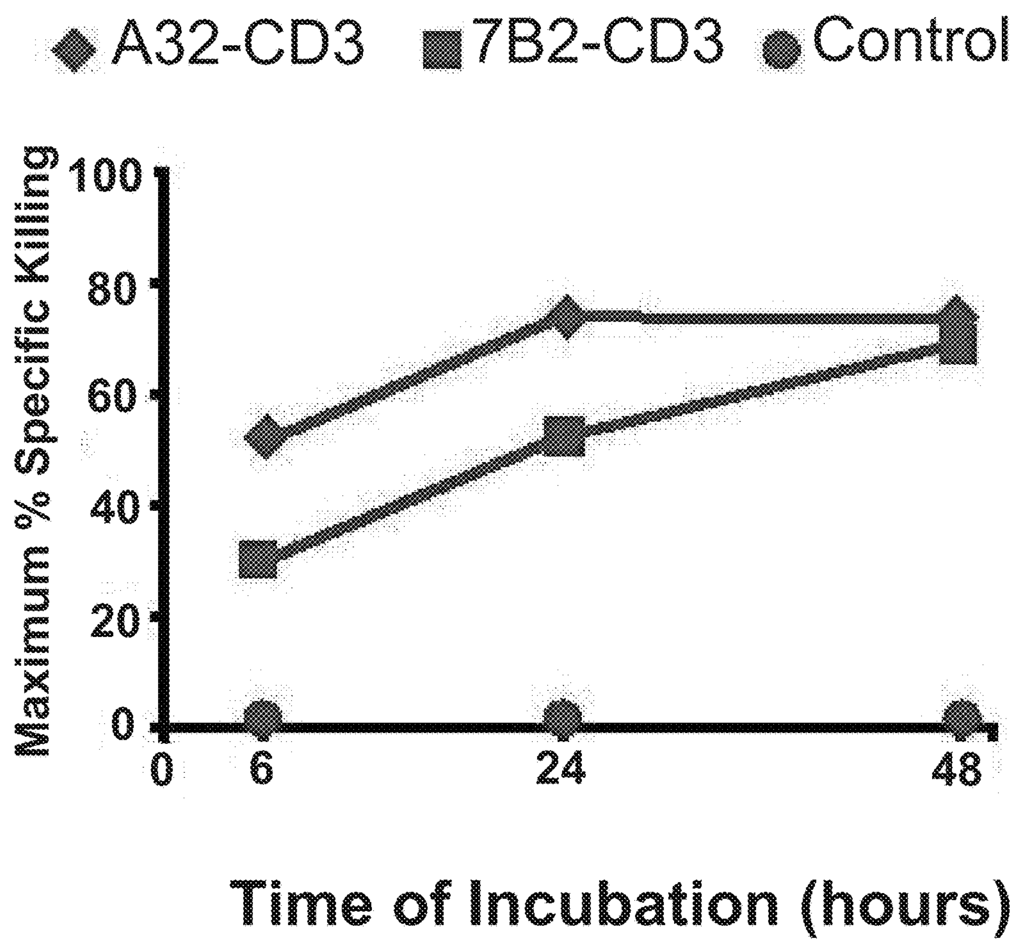
FIG. 2 shows anti-HIV-1-DARTs-mediated cytotoxic activity. Activated CD4+ T cells from a HIV-1 seronegative donor were infected with HIV-1 subtype B BaL, AE CM235, and C 1086.c IMC (top to bottom). The cells were incubated with autologous resting CD8 T cells in the presence of six concentrations of the anti-HIV-1 (A32×CD3 ♦ and 7B2×CD3■) and control (4420×CD3•) DARTs for 6, 24, and 48 hours at an effector to target cell ratio of 33:1. The results are reported as maximum percentage of specific killing observed at each time point.
Figure 2:
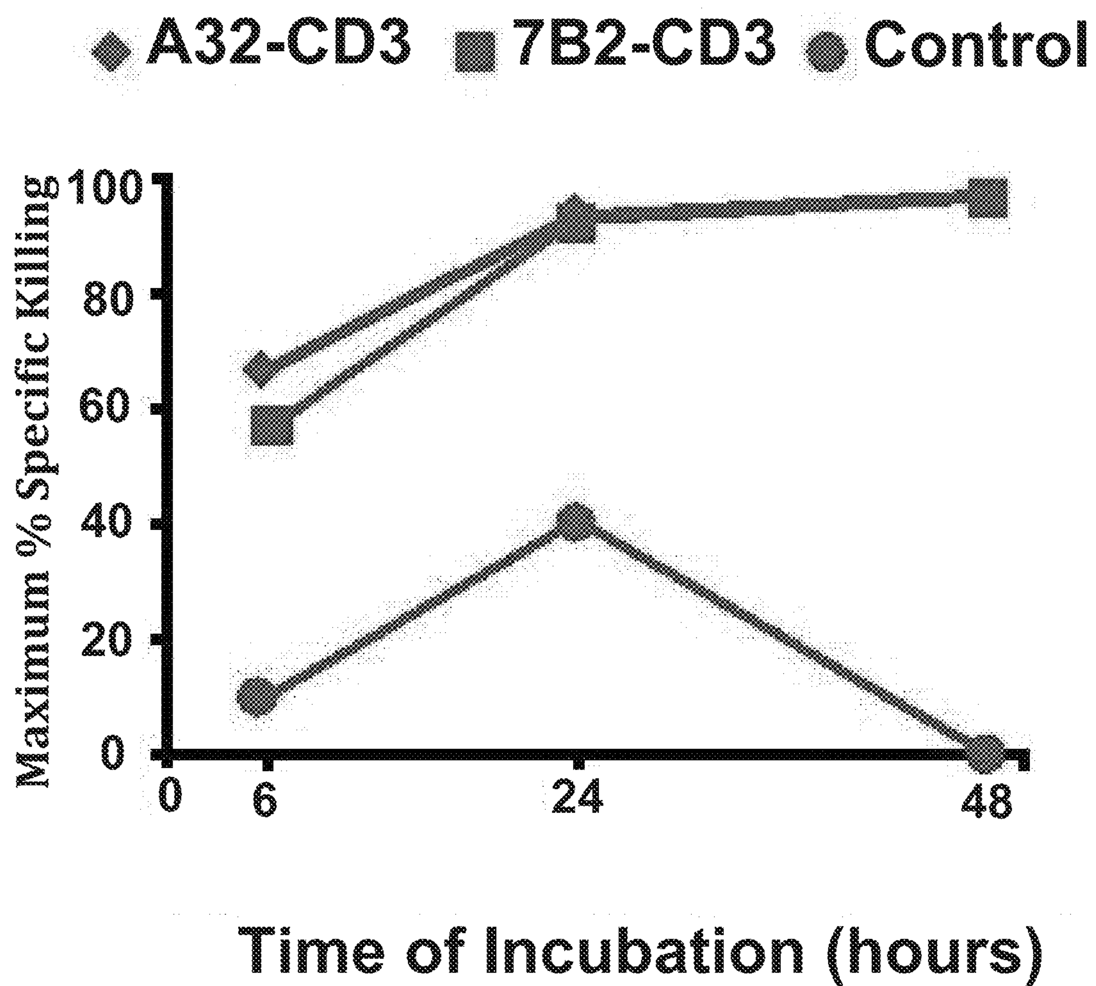
Figure 2:
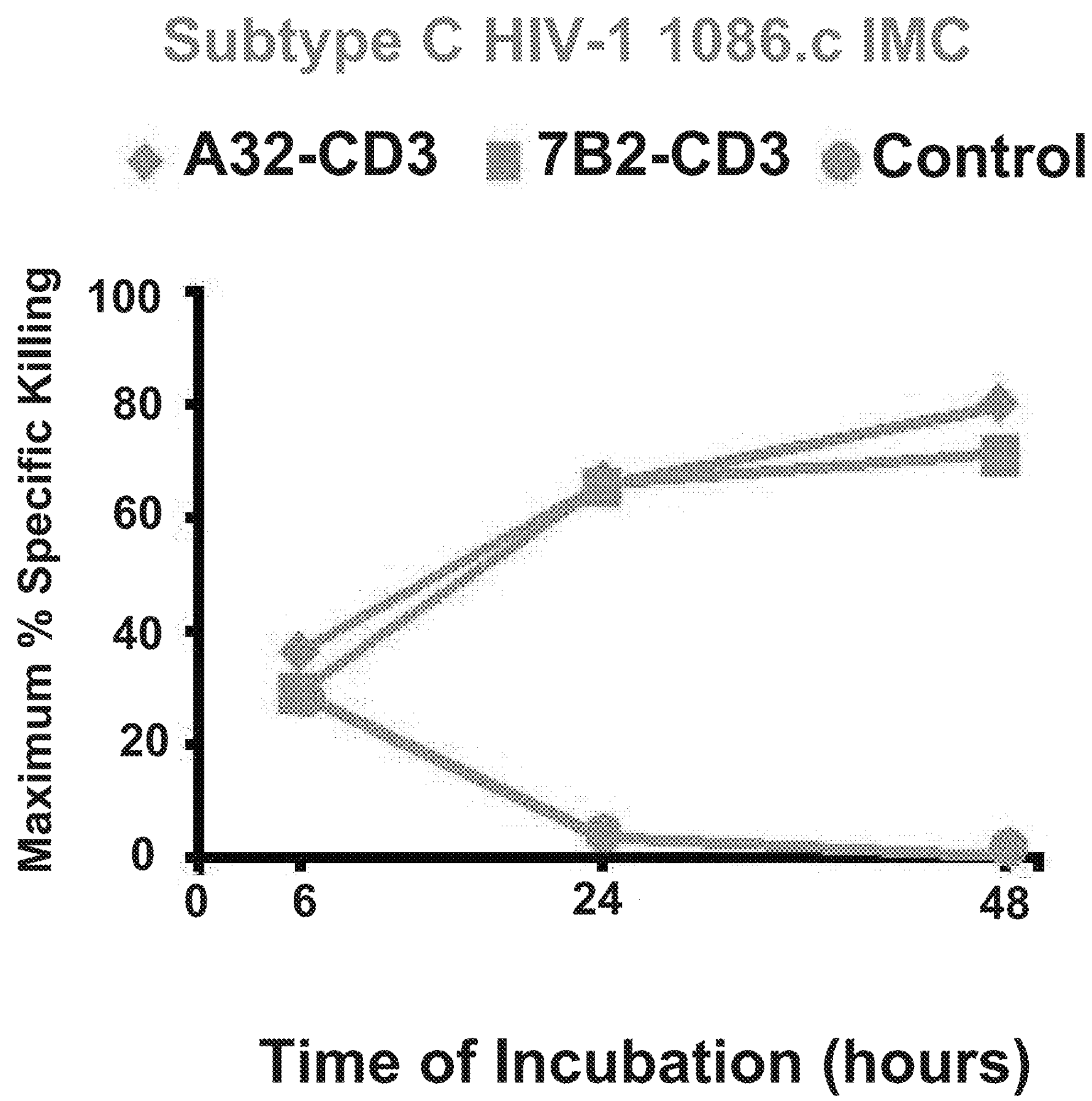
Figure 3:
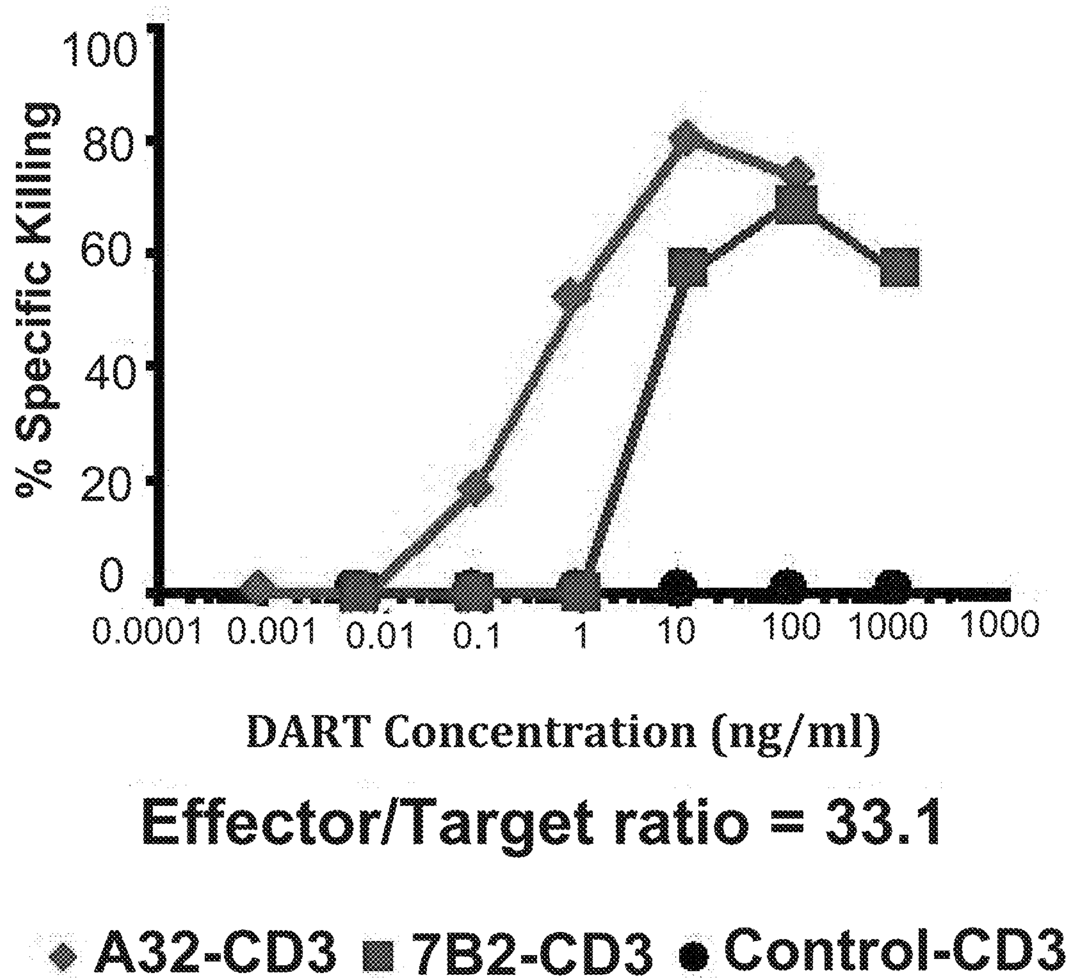
FIG. 3 shows dose dependence of anti-HIV-1 BaL DARTs-mediated cytotoxic activity. Activated CD4+ T cells from a HIV-1 seronegative donor were infected with HIV-1 subtype B BaL. The cells were incubated with autologous resting CD8 T cells in the presence of six concentrations of the anti-HIV-1 (A32×CD3 ♦ and 7B2×CD3■) and control (4420×CD3•) DARTs for 48 hours at an effector to target cell ratio of 33, 11, and 3:1 (top to bottom). The results are reported as percentage of specific killing.
Figure 3:
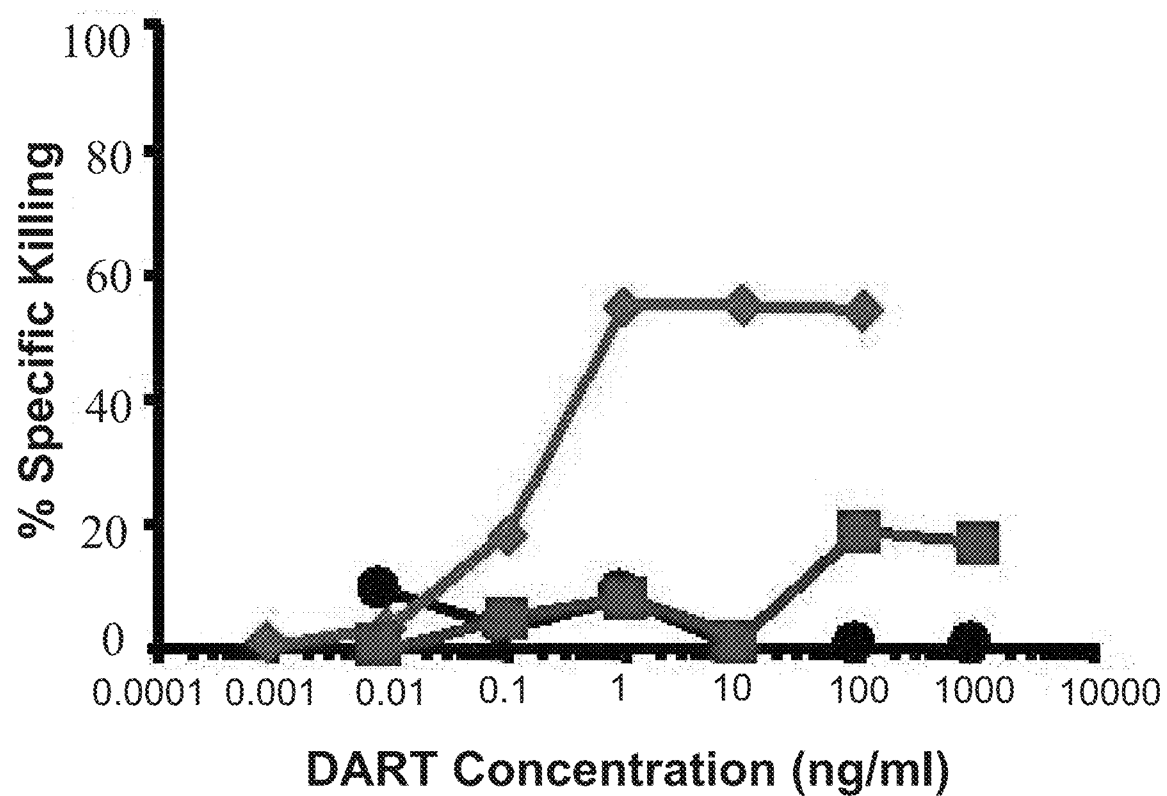
Figure 3:
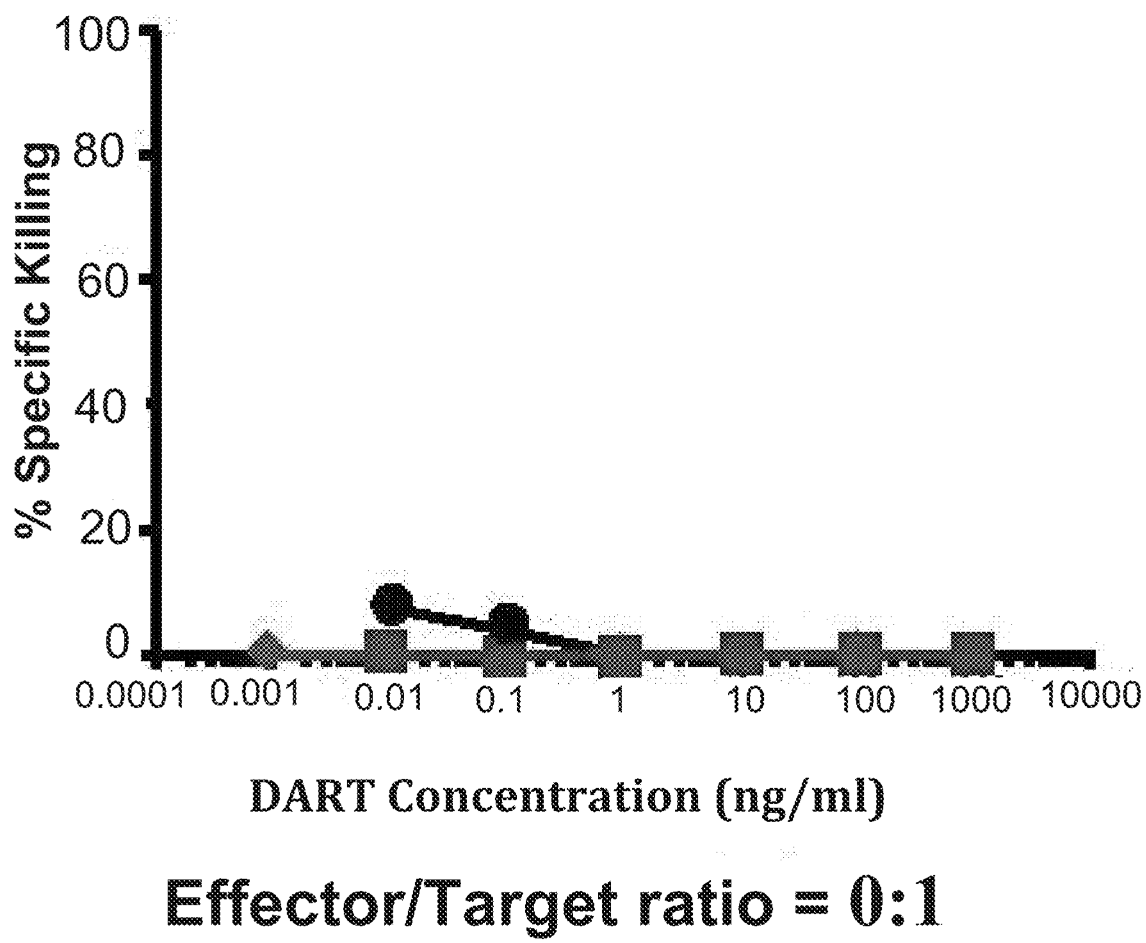

Based on the results described above, two DARTs were generated whose anti-HIV-1 arm was the A32 and 7B2 Fab region and the effector cell binding arm the αCD3ε arm. We studied these two DART molecules for their ability to recognize and mediate the killing of infected CD4+ T cells. Leukapheresis samples obtained from HIV-1 seronegative donor were infected in vitro to generate the target cells as described in the material and method section using our previously described ADCC Luciferase-based assay to detect the cytotoxic effects of the DARTs. We tested the two CD3-DART molecules (7B2×CD3 and A32×CD3) for their ability to redirect the cytotoxicity of resting CD8+ T cells against subtype B BaL, AE CM235, and C 1086.c HIV-1 IMC infected autologous CD4+ T cells. We evaluated DART-mediated cytotoxicity at 6, 24, and 48 hours after incubation of effector and target cells at the effector-to-target ratios of 33, 11, and 3 to 1. Although cytotoxic activity was already observed after 6 hours incubation, the peak cytotoxic activity (>70% SK) was detected at 48 hours using the 33:1 E:T ratio against each HIV-1 IMC (FIG. 2). The activity of the two HIV-1 DARTs was always greater than the background maximum killing observed with the 4420×CD3 control DART. We also observed a dose dependent potency of the two DARTs against each HIV-1 IMC-infected target cell population that is also reflected at the level of each E:T ratio, as illustrated for the BaL IMC (FIG. 3).

Figure 4:
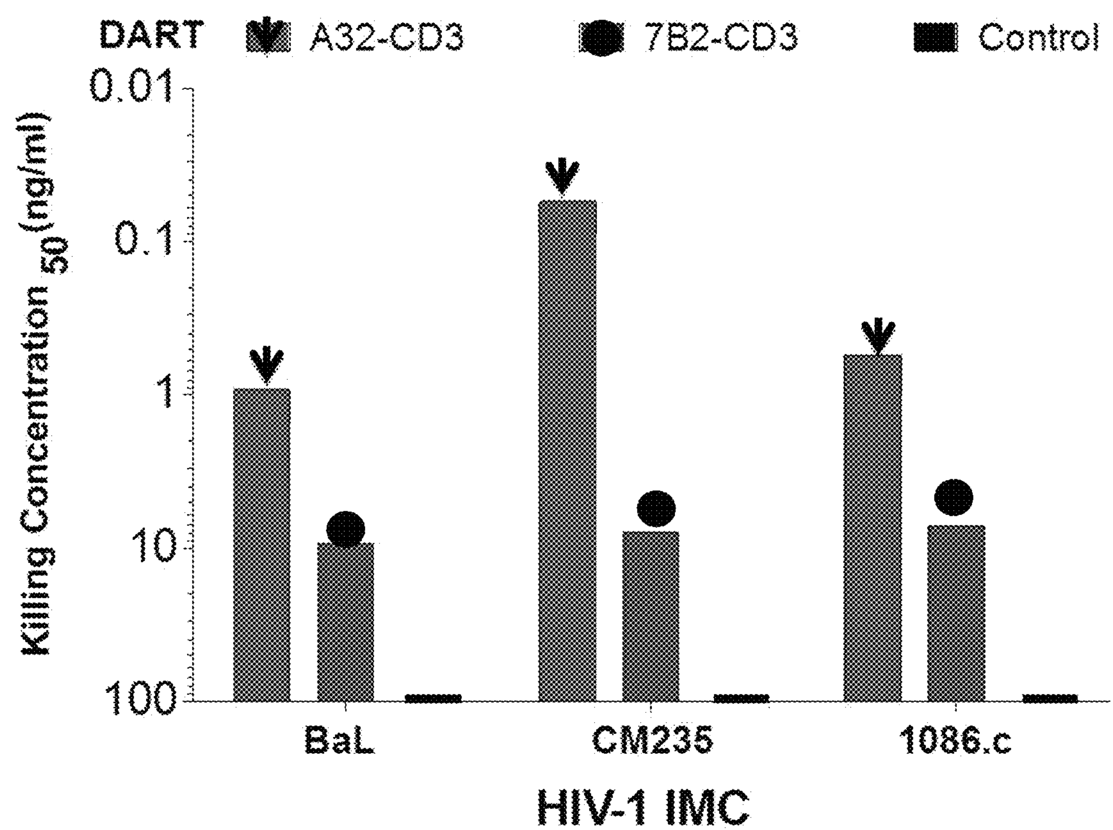
FIG. 4. shows DART concentration to reach 50% Specific Killing. Activated CD4+ T cells from a HIV-1 seronegative donor were infected with HIV-1 subtype B BaL, AE CM235, and C 1086.c IMC. The cells were incubated with autologous resting CD8 T cells in the presence of six concentrations of the anti-HIV (A32×CD3, red; 7B2×CD3, blue) and control (4420×CD3, black) DARTs for 48 hours at an effector to target cell ratio of 33:1. Each bar represent the concentration required to detect 50% specific killing against each infected target population.

The difference in the potency of the two DARTs was also analyzed as the DART concentration at which 50% of specific killing (Killing Concentrations® or $KC_{50}$) was detected at 48 hours with E:T of 33:1. The A32×CD3 DART $KC_{50}$ was always approximately one log lower than the 7B2×CD3 DART $KC_{50}$ (FIG. 4) against each HIV-1 IMC.

These results indicated that DARTs can effectively recruit CD8+ T cells and direct their cytotoxic activity against HIV-1 infected cells.

Example 3: A32/CD16 and 7B2/CD16 DARTs

Dual affinity Re-Targeting molecules A32/CD16 (SEQ ID NOs: 44 and 45) and 7B2/CD16 (SEQ ID NOs: 25 and 27 see Table 2) will be analyzed as described in Example and 6 using Luciferase-based cytotoxicity assay and CD4+ infected target cells along with resting effector cells. For the CD16-DART assay, the effector cells are CD16+ cells, which could be purified by removing CD3+CD20+ cells from whole PBMCs.

The Luciferase-based killing assay, described in Example 2 will be used to examine and compare the potency and kinetics of CD16-DART-enhanced clearance of productive infection as previously proposed for the CD3-DARTs. The procedure will be the same but the negative selection of the effector cells will provide an enriched population of CD16+ cells.

Example 4: CH28 and CH44 DARTs

DART molecules with a HIV-1 arm having the binding specificity of CH28 or CH44, and an effector cell arm targeting CD3 or CD16 will be made and tested in the Luciferase-based killing assay essentially as described in Examples 2 and 3. CH28 or CH44 are HIV-1 CD4 bs neutralizing antibodies. See U.S. Provisional Appl. No. 61/883,220 filed Sep. 27, 2013 and corresponding PCT application. CH28/CD3 comprises SEQ ID NOs: 19 and 19. CH44/CD3 comprises SEQ ID NOs: 21 and 23.

Example 5: Combinations of CD13- and CD16-DARTs

The Luciferase-based killing assay will be used to test whether CD13- and CD16-DARTs in a combination formulation provide enhanced benefits. For each DART combination, we will utilize cells expressing the 3 different Fcγ-R IIIa (CD16) phenotypes and the panel of established IMCs to test the ability of DARTs to recruit simultaneously CD3+ and CD16+ effector cells. These assessments will be conducted using leukapheresis samples collected from HIV-1 seronegative donors.

All documents and other information sources cited herein are hereby incorporated in their entirety by reference.

Example 6: Dual-Affinity-Re-Targeting (DART) Proteins Direct T-Cells-Mediated Cytolysis of Latently HIV-Infected Cells Enhancement of HIV-specific immunity is likely required to eliminate latent HIV infection. To this aim, a novel immunotherapeutic modality has been developed, Dual Affinity Re-Targeting (DART) proteins that are bispecific antibody-based molecules that can bind two distinct cell surface molecules simultaneously. Described herein are HIV×CD3 DARTs designed with a monovalent HIV-1 envelope (Env) binding arm, derived from broadly binding, ADCC-mediating antibodies known to bind to HIV-infected target cells, that is coupled to a monovalent CD3 binding arm designed to engage cytolytic effector T-cells. Thus, DARTs redirect polyclonal T-cells to specifically engage with, and kill Env-expressing cells, including $CD4^+$ T cells infected with different HIV-1 subtypes, thereby obviating the requirement for HIV-specific immunity. Using lymphocytes from patients on suppressive anti-retroviral therapy (ART), DARTs mediated $CD8^+$ T-cell clearance in vitro of $CD4^+$ T-cells superinfected with the HIV-1 strain JR-CSF or infected with autologous reservoir viruses isolated from HIV-infected patient resting $CD4^+$ T-cells. Importantly, DARTs also mediated $CD8^+$ T-cell clearance of HIV from resting $CD4^+$ T cell cultures following induction of latent virus expression. Combined with HIV latency reversing agents, HIV×CD3 DARTs have the potential to be effective immunotherapeutic agents to clear latent HIV-1 reservoirs in HIV-infected individuals.

The inability of antiretroviral therapy (ART) to eradicate HIV was first suggested by the demonstration of latent infection of resting $CD4^+$ T cells (1), and then by the recovery of rare, integrated, replication-competent HIV from the resting $CD4^+$ memory T cells of patients receiving potent ART (2-4). Current ART cannot eradicate HIV infection, because these long-lived $CD4^+$ T cells remain persistently infected and unrecognized by the immune system, with minimal expression of HIV genes or proteins (1, 5, 6). The persistence of quiescent HIV infection, primarily within central memory T cells, is a major obstacle to eradication of HIV infection (2-4, 7-9).

Viral persistence is also manifest in a substantial proportion of treated patients by very low levels of detectable viral RNA (10, 11) that represents expression of viral particles without effective rounds of new replication and does not appear to lead to drug resistance or failure of therapy (12, 13). However, persistent viremia demonstrates an inability of the immune response to recognize and clear HIV-1 infected cells.

Chronically infected individuals generally have rapid viral rebound when ART is withdrawn (14-16). This observation has suggested that the immune system in patients cannot control viremia, unless bolstered by a further intervention. Therapeutic immunization, even in individuals who initiated ART when $CD4^+$ and $CD8^+$ cellular immune responses remain relatively preserved, has thus far been unsuccessful in inducing enhanced anti-HIV immunity that can restrict viremia in the absence of ART (17). Therefore, eliminating the latent pool of HIV-infected cells that persist despite ART, and as well, the unknown cells that are the source of low-level viremia found in most patients despite ART, requires new and innovative strategies. One initial step, the disruption of latency and the induction of viral antigen expression in cells that are latently infected, is under intensive investigation (18, 19). However, as early progress is made in the development of latency reversing agents (LRAs), improvements in the ability to clear persistent infection must be sought as well.

Latently infected cells are very rare, and even if the latent reservoir is as much as 60-times larger than the typical estimates of about 1 infected cell per $10^6$ resting central memory CD4+ cells (20), current LRAs might induce proviral transcription in only a fraction of this population, and the quantity of viral antigen presented might be low (21, 22). Therefore, a novel and robust immune response may be necessary to detect and clear both cells producing low-level viremia, and in quiescently infected cells induced to leave the latent state.

Following the reactivation of latent HIV, viral antigens are presented on the surface of the cell and thus could be targeted by antibodies or antibody-derived molecules. Proof of concept for this approach has been provided by immunotoxins—bifunctional chimeric proteins consisting of a targeting domain, such as an antibody or a ligand, joined to a toxin effector domain (23). Although initial clinical trials using immunotoxins in HIV-infected individuals failed to have sustained impact on immunological or clinical markers (24), immunotoxin 3B3-PE38 (25) has been reported to reduce levels of HIV-infected cells that persist despite ART in the BLT humanized mouse model (26).

Several monoclonal antibodies (mAbs) have been reported as capable of recognizing HIV-1 infected cells and engaging Fc-gamma receptor-bearing cells to mediate antibody dependent cellular cytotoxicity (ADCC) (27), such as A32 and 7B2, non-neutralizing mAbs that bind to conserved residues in gp120 (28) and gp41 (29, 30), respectively. Based on these properties, two Dual Affinity Re-Targeting (DART) proteins (31, 32) were generated in which HIV envelope targeting arms derived from the A32 and 7B2 mAbs were combined with a CD3 effector arm derived from hXR32, a humanized anti-CD3ε mAb, to generate two HIV×CD3 DARTs, A32×CD3 and 7B2×CD3 (FIG. 10).

Bispecific molecules that co-engage T cells with antigen-expressing target cells, such as DARTs and Bi-specific T-cell Engager proteins (BiTEs), have been characterized and developed largely for use in oncology (31-34). They are dependent on the engagement of both of the binding arms to activate and redirect the cytolytic activity of polyclonal T-cells, in a major histocompatibility complex (MHC) independent manner, against the antigen expressing target cells (31-34). This class of bispecific molecules is effective in vivo at doses many-fold lower than those typically employed for mAbs (33, 34), and has been shown to be clinically potent and efficacious with acceptable safety, as evidenced by the approval of blinatumumab, a CD19×CD3 BiTE, for the treatment of relapsed or refractory B-precursor acute lymphoblastic leukemia (ALL) (35, 36). DARTs, which have inter-chain disulfide bonds at their C-termini and are structurally compact, making them well suited for forming stable cell-to-cell contacts between target and effector cells, exhibit greater potency than BiTEs in side-by-side comparisons (32, 37).

Disclosed herein is the ability of HIV×CD3 DARTs to redirect $CD8^+$ T cells against $CD4^+$ cells infected by HIV-1, including ones infected with authentic latent virus isolates emerging from HIV-infected patients' cells in model systems designed to mimic potential clinical HIV eradication strategies. The ability of HIV×CD3 DARTs to recognize conserved HIV-1 antigens on infected cells and simultaneously engage receptors on the membrane of polyclonal effector T-cells, will overcome the need to activate preexisting HIV-specific cytotoxic effector cells (38), thus surmounting a significant hurdle that impedes the effective elimination of the reservoir of infected $CD4^+$ T cells.

HIV Arm Selection for DARTs.

Figures 10A, 10B, 10C:
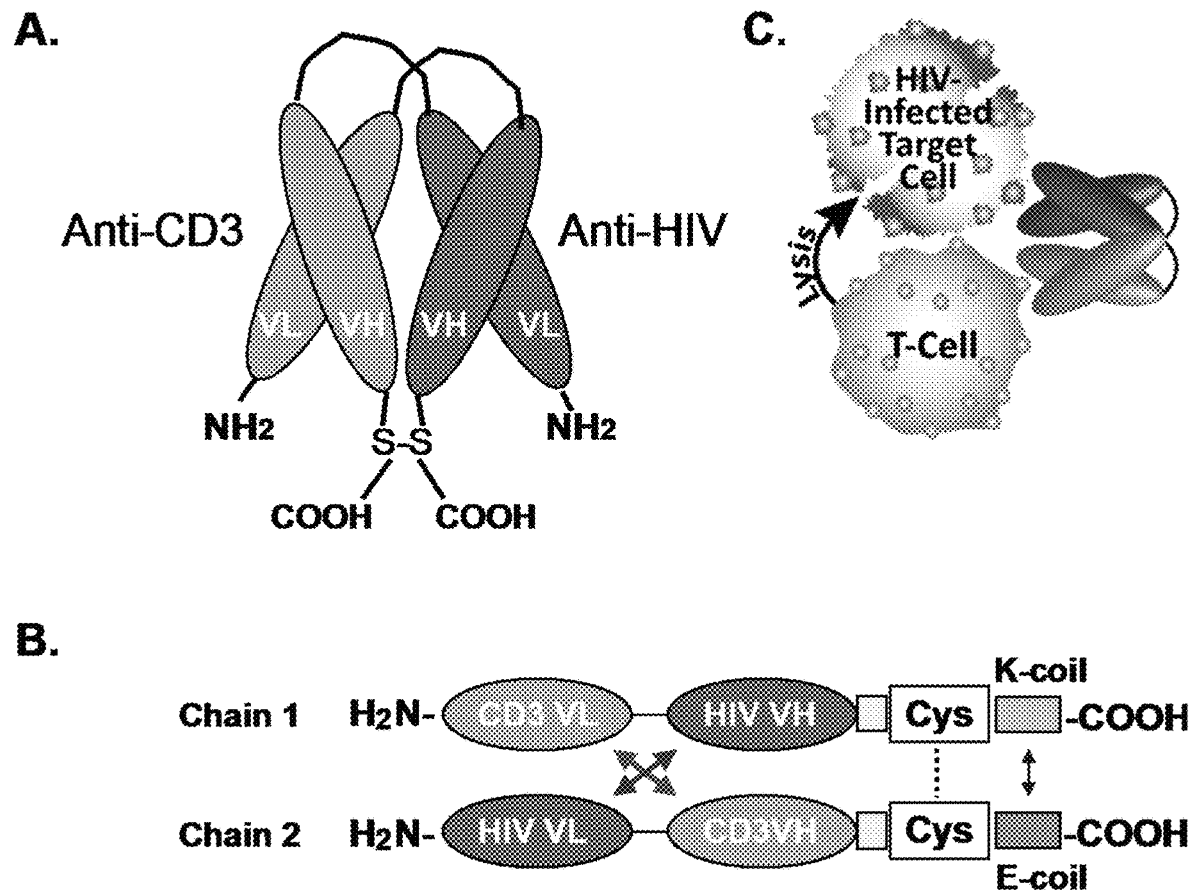
FIGS. 10A-10C show HIV×CD3 DART structure.
Figure 23:
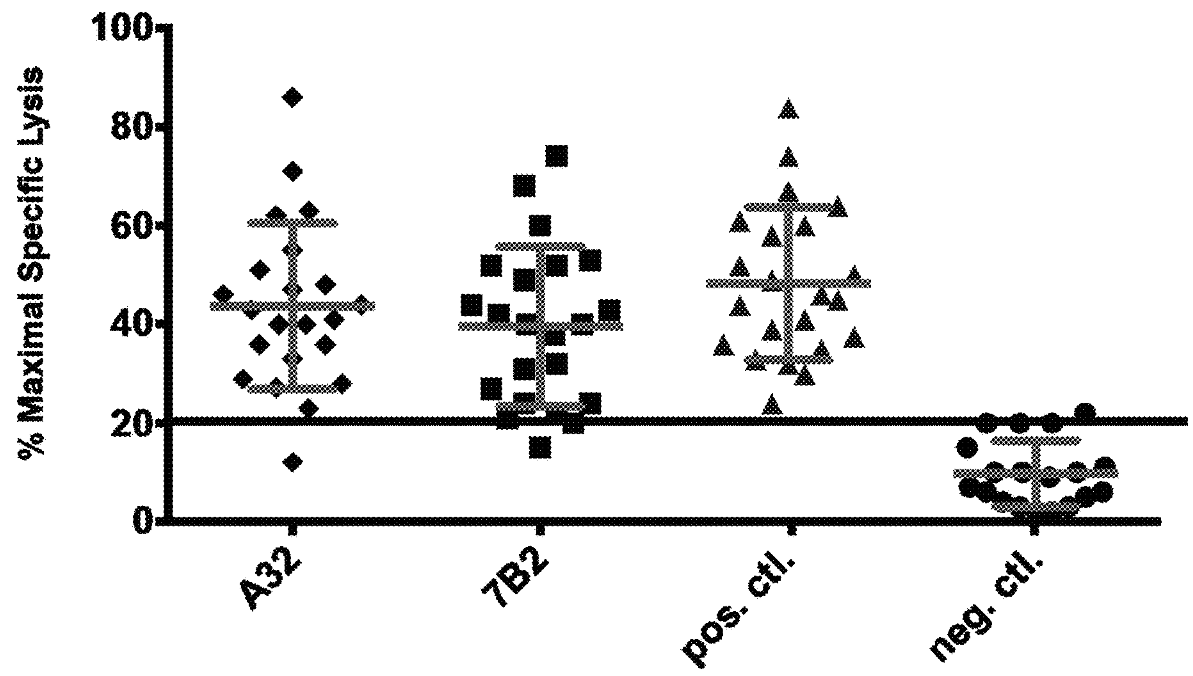
FIG. 23 shows potency and breadth of ADCC-mediating mAbs. The ADCC activities of the A32 (anti-gp120 C1/C2) mAb (♦) and 7B2 (anti-gp41 cluster I) mAb (■) are reported as maximum percentage of specific lysis (% SL) against each of the 22 HIV-1 IMC. Each dot represents one HIV-1 IMC. The results obtained with plasma from one HIV-1 seropositive (positive control; pos ctrl) and one seronegative (negative control; neg ctrl) donor are also reported. The lines represent the mean±standard deviation. The black line represents the cut-off for positive response.
Figure 24:
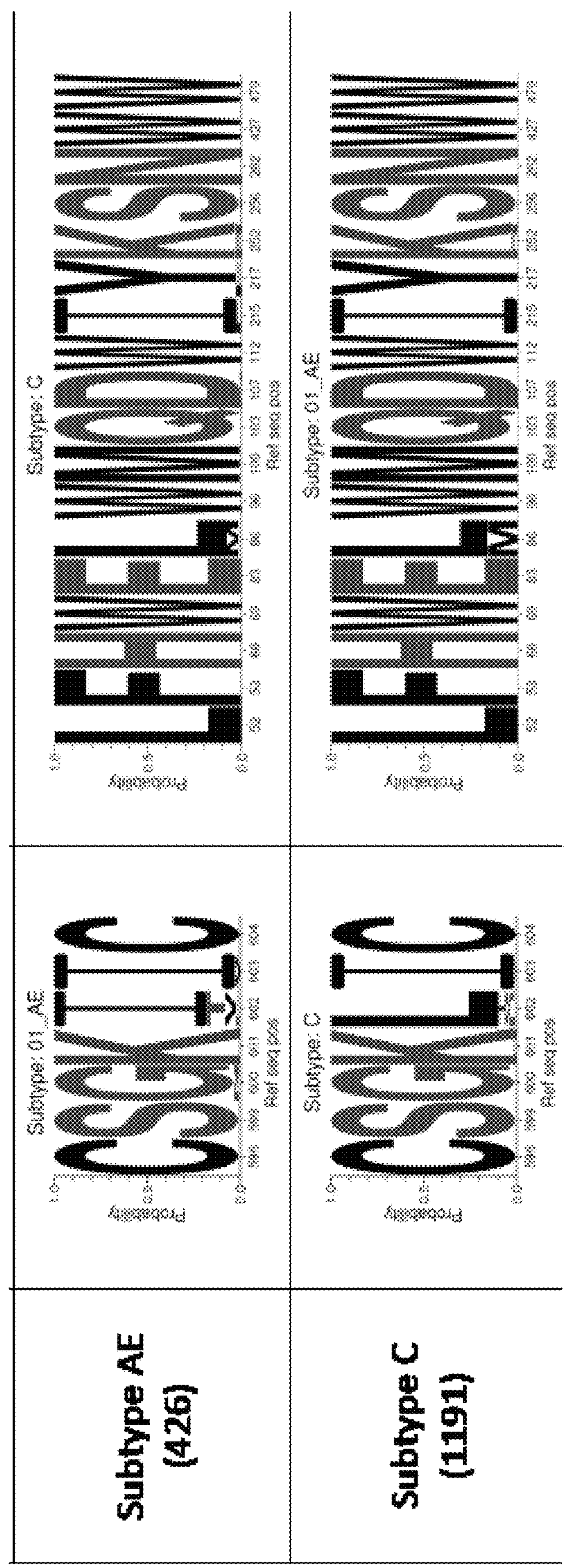
FIG. 24 shows conservation of HIV-1 Env residues known to influence the binding of 7B2 and A32 mAbs. A linear 7-residue sequence in gp41 (gp160 positions 598-604; immunodominant cluster I) is reported to contain the binding site for 7B2 mAb (28, 29). Discontinuous residues in gp120 C1-C4 known to influence A32 mAb binding (based on point mutagenesis studies) occur at positions 52, 53, 66, 69, 83, 86, 96, 100, 103, 107, 112, 215, 217, 252, 256, 262, 427 and 479 (37, 39, 68). The conservation of these residues in the Los Alamos National Laboratory (LANL) HIV1 Env Amino acid Filtered web alignment, a database consisting of 4556 HIV-1 Env sequences with representation of all subtypes, was assessed by QuickAlign analysis (http://www.hiv.lanl.gov/content/sequence/QUICK_ALIGNv2/QuickAlign.html). The height of the residue at each position of Env is proportional to its frequency of distribution among the HIV-1 isolates. Residues are colored according to hydrophobicity: black, hydrophilic; green, neutral; blue, hydrophobic. Based on a crystal structure of a CD4-stabilized gp120 core complexed with a Fab fragment of N5-i5 (an A32-like mAb), residues at 52, 53, 69, 103, 107 and 217 (located in C1-C2) may be direct epitope contacts (27).

A32 mAb binds to a conformational, CD4-inducible epitope in gp120 C1/C2 (within epitope cluster A) (28, 39-41) and 7B2 mAb binds to a linear epitope in gp41 cluster I (29, 30, 42). The two mAbs were tested for their ability to mediate antibody dependent cell-mediated cytotoxicity (ADCC) against a panel of 22 representative HIV-1 infectious molecular clones (IMCs) of subtypes A, AE, B and C (FIG. 18). The A32 mAb recognized 21 (95%) of the HIV-1 isolates with an average percent specific lysis (% SL) of 43.69% (range 12-86%; FIG. 23). The 7B2 mAb recognized 20 (91%) of the HIV-1 isolates with an average % SL of 39.58% (range 15-74%; FIG. 23). In addition to possessing breadth and efficiency in mediating ADCC—indicating epitope accessibility at the surface of HIV-infected cells, a necessary property for HIV×CD3 DARTs—the A32 and 7B2 mAbs are attractive sources for Env binding domains for DARTs as the residues in Env that influence binding by these mAbs are highly conserved among all HIV-1 subtypes (FIG. 24). Based on these properties, two HIV×CD3 DARTs were generated in which HIV targeting arms derived from the A32 and 7B2 mAbs were combined with a CD3 effector arm derived from hXR32, a humanized anti-CD3ε mAb (FIGS. 10A-10C). These HIV×CD3 DARTs are named A32×CD3 and 7B2×CD3. Control DARTs with an irrelevant arm derived from an anti-FITC antibody (4420) or from palivizumab, an antibody to the respiratory syncytial virus (RSV) fusion protein antibody instead of the HIV arm (4420×CD3, RSV×CD3) or CD3 arm (A32×4420, 7B2×4420) were also generated. Control DARTs with an irrelevant arm derived from an anti-FITC antibody (4420) or palivizumab, an antibody to the respiratory syncytial virus (RSV) fusion protein antibody, instead of the HIV (4420×CD3 and RSV×CD3) or CD3 arm (A32×4420 and 7B2×4420) were also generated.

HIV DART Binding Properties.

Figure 11A:
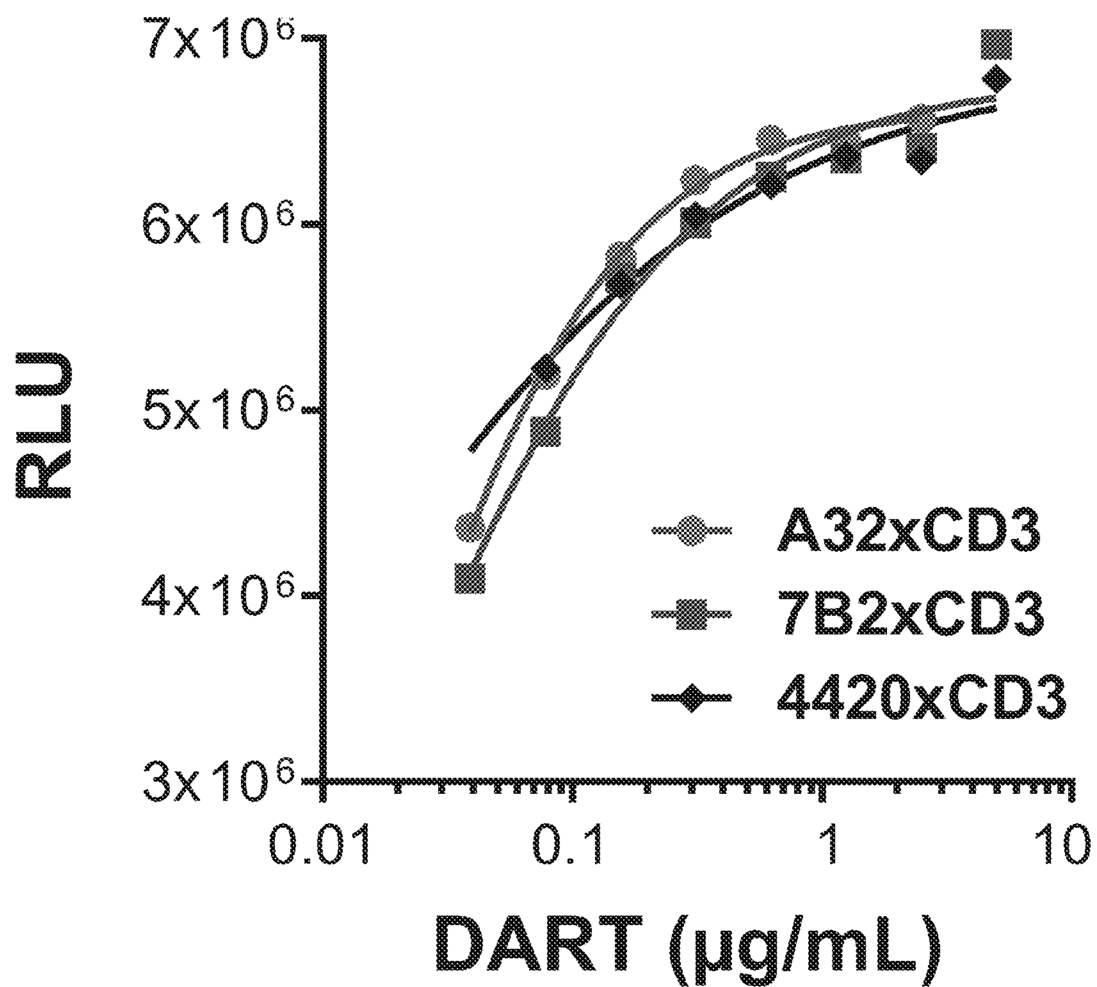
FIGS. 11A-11F show HIV×CD3 DART binding properties.
Figure 11B:
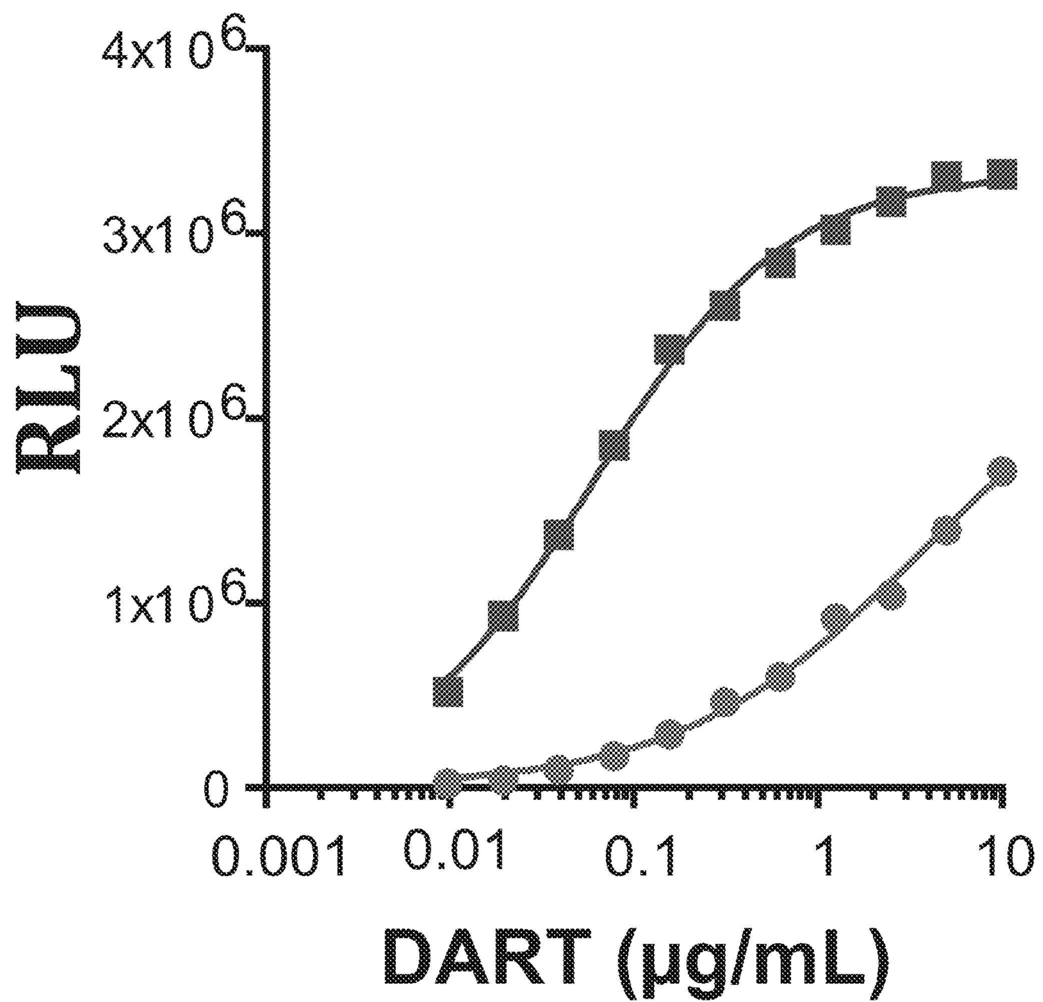
Figure 11C:
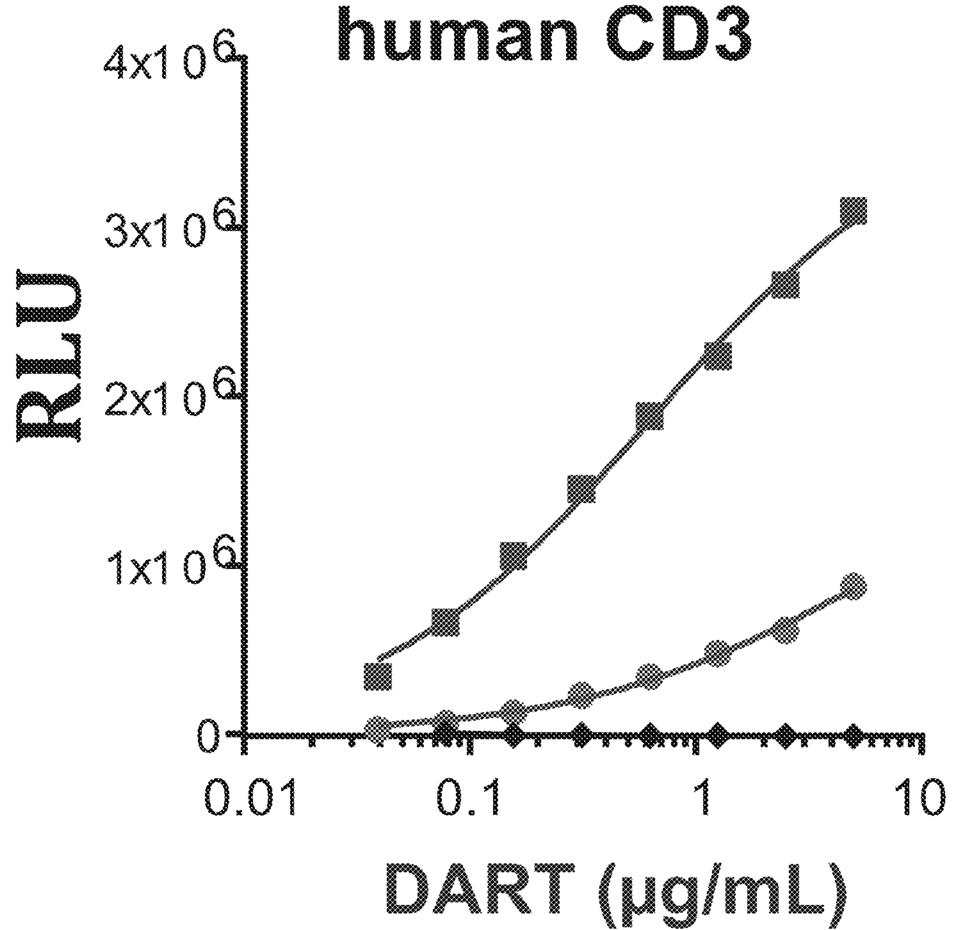

A32×CD3 and 7B2×CD3 each exhibited binding to recombinant human CD3 and HIV-1 Env proteins, individually and simultaneously, as shown by ELISA (FIGS. 11A-11C). While the binding to CD3 protein was similar for both DARTs, the magnitude of binding to JR-FL gp140 CF was greater for 7B2×CD3 than for A32×CD3, likely due to the fact that the conformational A32 epitope is highly CD4-dependent (41-44). Based on surface plasmon resonance (SPR), the equilibrium dissociation constants ($K_D$) for CD3 arm binding were 3.6 and 6.1 nM for A32×CD3 and 7B2×CD3, respectively, and $K_D$ for HIV arm binding was 47.7 nM for A32×CD3 using M.ConS gp140 CFI, and 15.1 nM for 7B2×CD3 using JR-FL gp140 CF, respectively (FIG. 19). Different Env proteins were utilized for these two DARTs in the SPR studies, because A32×CD3 binding to JR-FL gp140 CF was inefficient and 7B2×CD3 binding to M.ConS gp140 CFI, due to its lack of the gp41 cluster I sequence, was precluded.

Figure 11D:
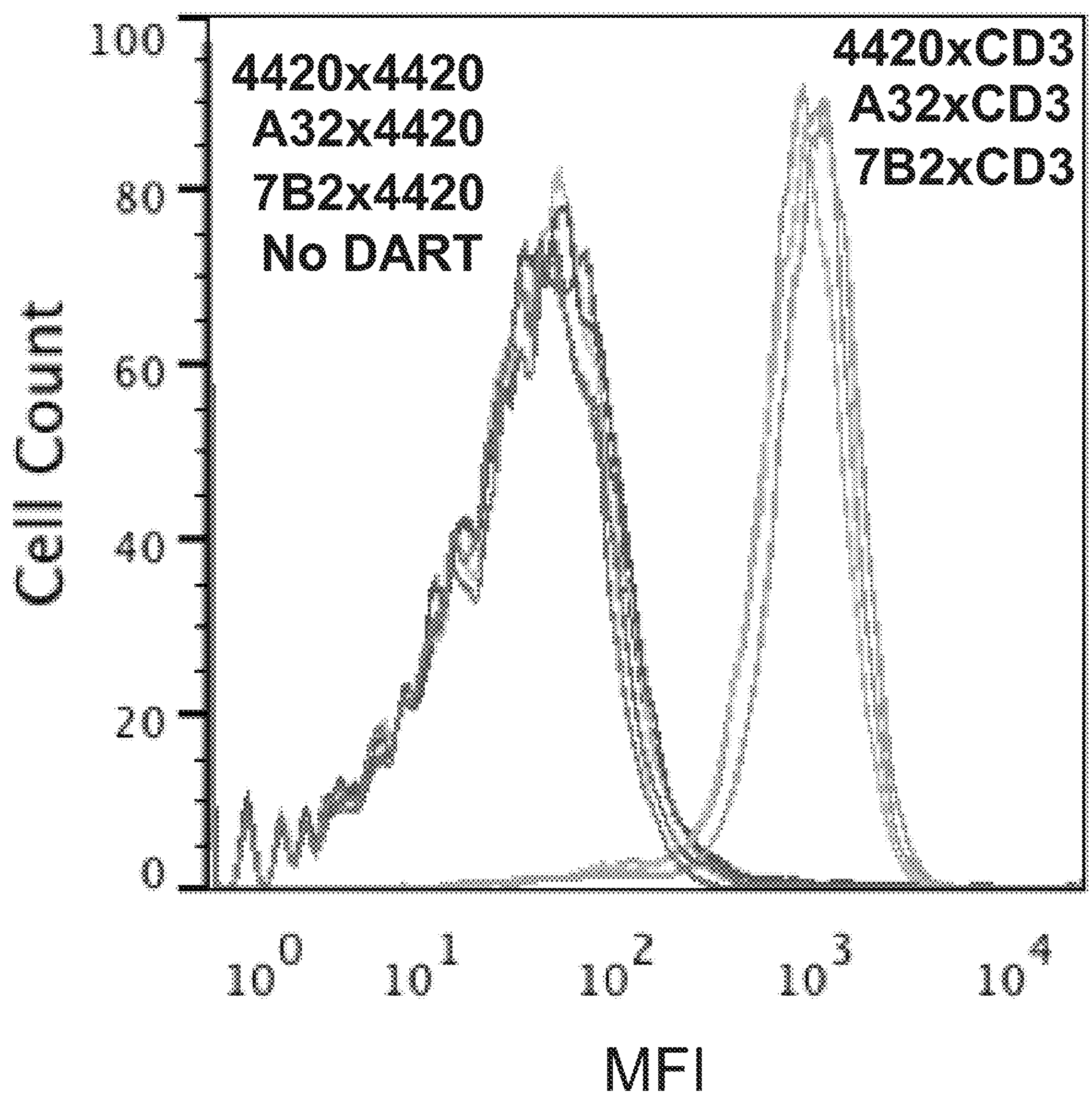
Figure 11E:
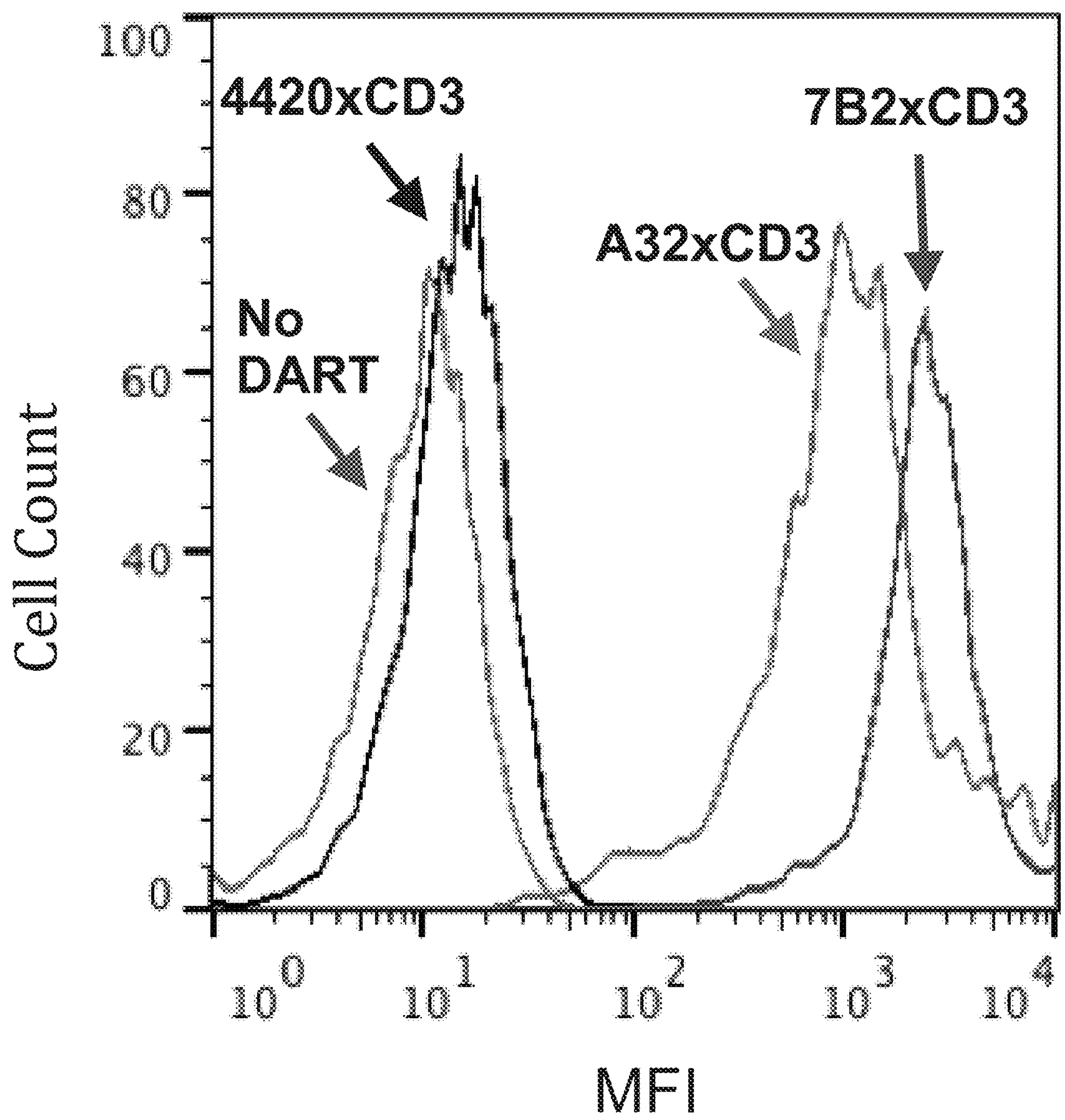
Figure 11F:
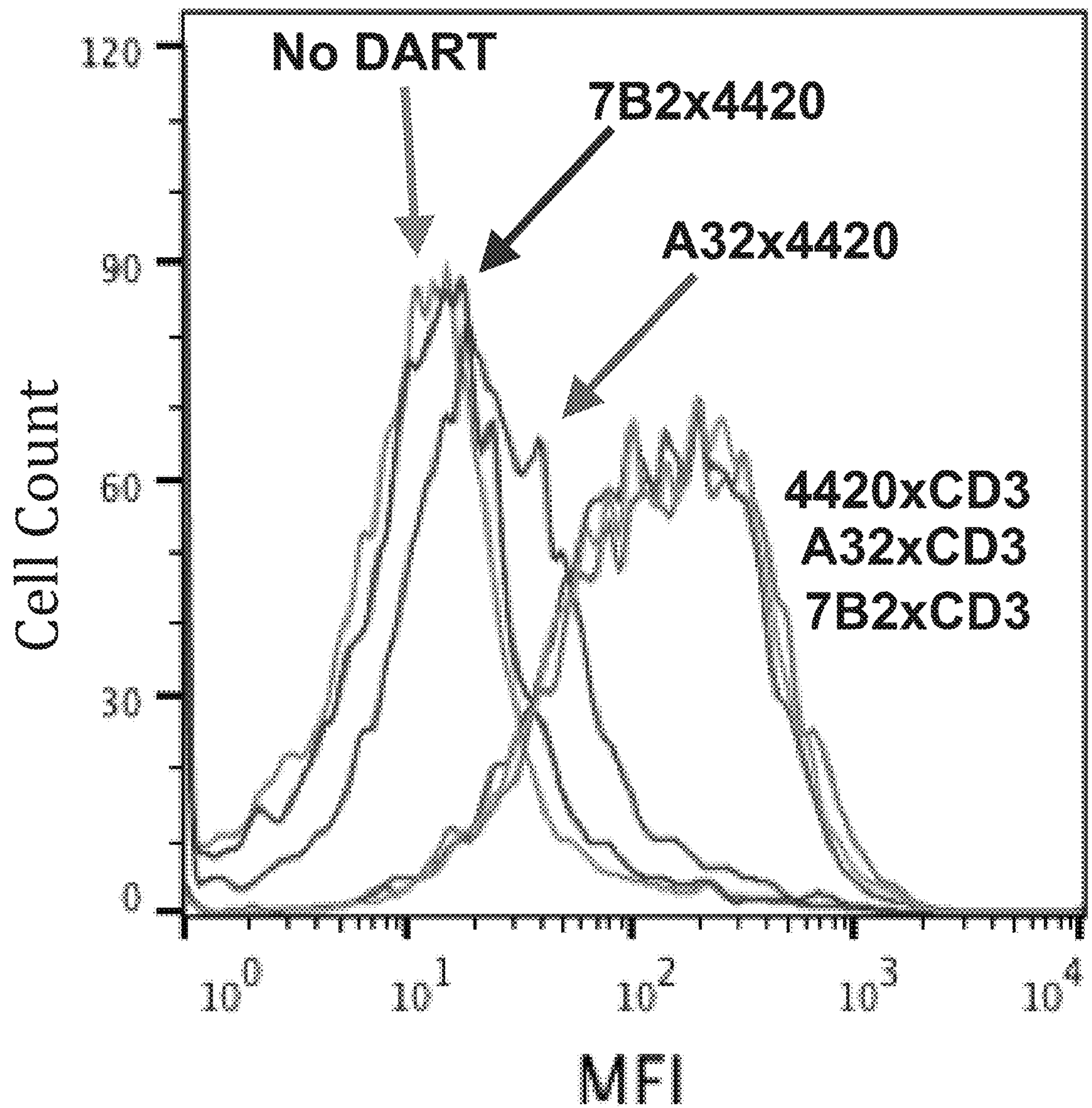
Figure 25:
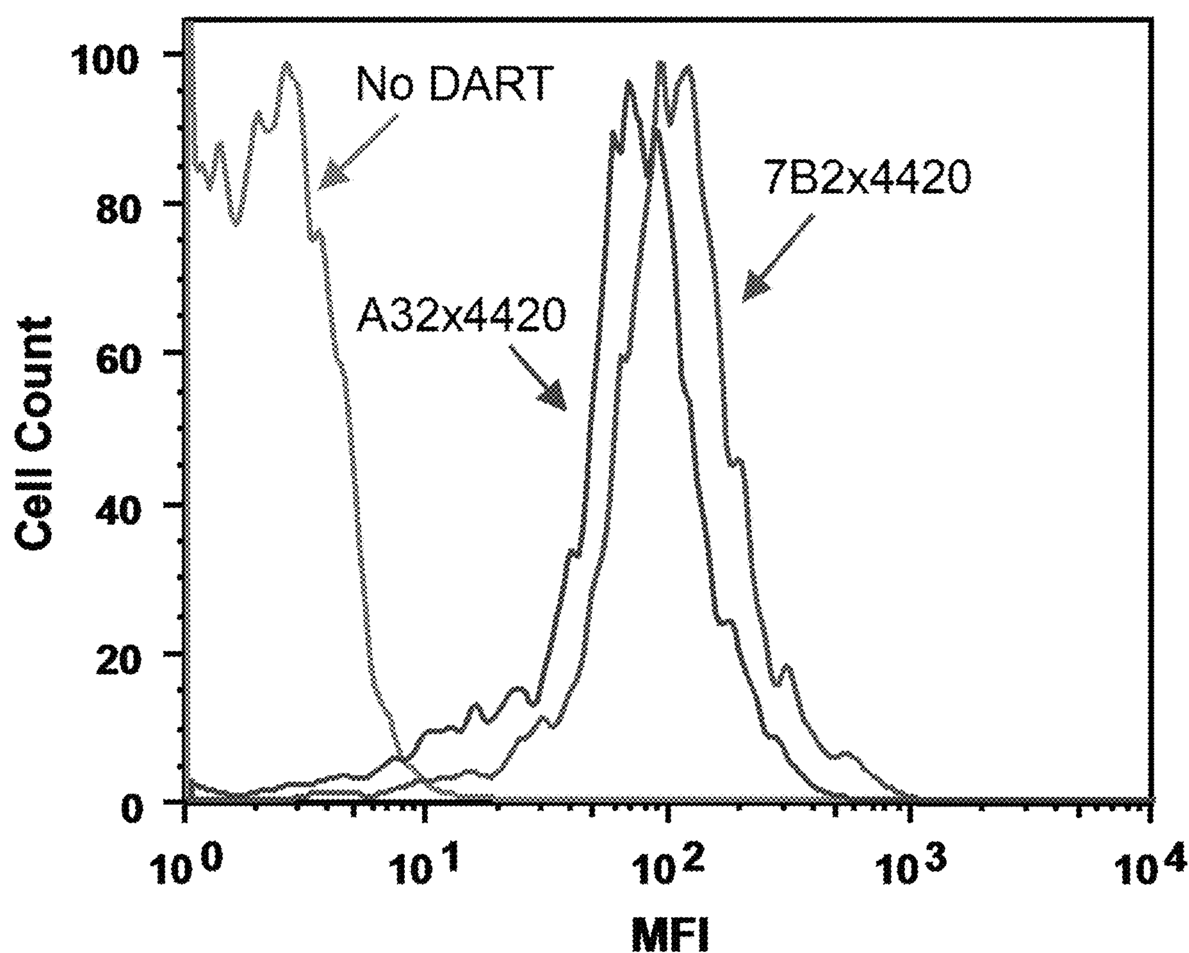
FIG. 25 shows cell surface Env binding of A32×4420 and 7B2×4420 control DARTs. DART binding to HEK293-D371 cells expressing HIV-1 Env, CM244, subtype AE was measured and data are reported as mean fluorescence intensity (MFI). A32 and 7B2 are targeting arms that recognize HIV-1 gp120 and gp41, respectively; 4420 is an irrelevant, negative control arm.
Figures 26A, 26B, 26C, 26D:
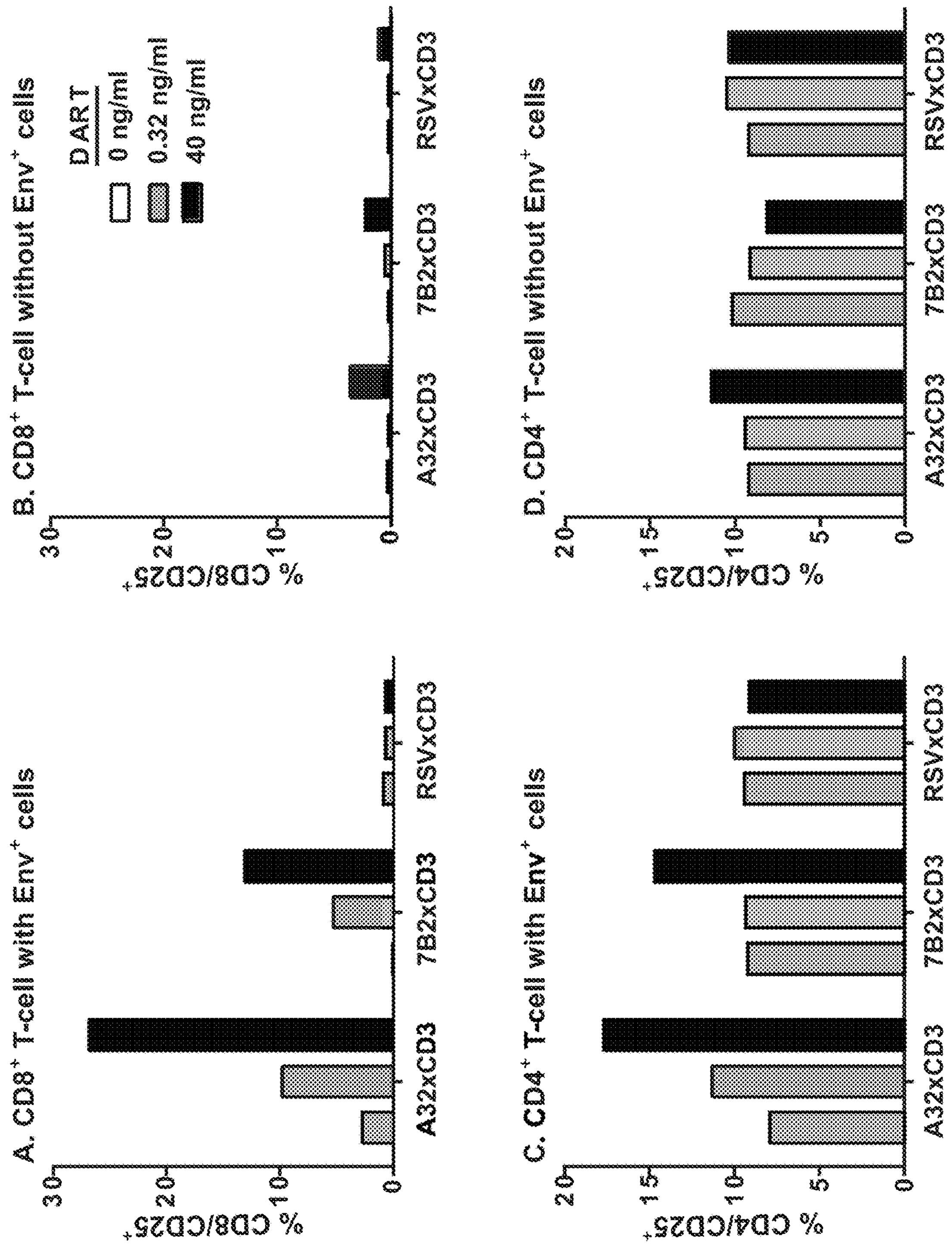
FIGS. 26A-26D show HIV×CD3 DART-mediated T-cell activation depends on co-engagement with target cells. Unstimulated $CD4^+$ or $CD8^+$ T-cells from healthy seronegative donors were incubated with (FIGS. 26A, 26C) and without (FIGS. 26B, 26D) Env expressing Jurkat-522 F/Y cell line in the absence or presence of control (RSV×CD3) or HIV×CD3 (A32×CD3, 7B2×CD3) DARTs at 40, 0.32, and 0 ng/mL for 48 hours. $CD8^+$(FIGS. 26A-26B) and $CD4^+$ (FIGS. 26C-26D) T cell activation was assessed by staining with CD25 Ab cells. The data are reported as frequency (%) of activated ($CD25^+$) T cells. Each bar represent the average of results obtained from 2 different donors.

HIV×CD3 DARTs bind to their cell surface antigens with specificity. DARTs with CD3 effector arms (A32×CD3, 7B2×CD3, 4420×CD3) bind to human $CD3^+$ T cells with similar efficiencies, whereas DARTs with the CD3 arm replaced by an irrelevant arm (A32×4420, 7B2×4420) or with two irrelevant arms (4420×4420) do not bind (FIG. 11D). HIV×CD3 DARTs (A32×CD3, 7B2×CD3) bind efficiently to HEK293-D371 cells that express subtype AE CM244 Env (FIG. 11E), and similar binding activity is observed with the A32×4420 and 7B2×4420 control DARTs (FIG. 25). As expected, the 4420×CD3 control DART does not bind to these cells (FIG. 11E). A32×CD3 and 7B2×CD3 bind to Jurkat-522 F/Y cells, which express both CD3 and subtype B HXBc2 Env (45) and binding via the CD3 arm predominates as shown by the equivalence of 4420×CD3, A32×CD3 and 7B2×CD3 binding. When the CD3 arm is replaced by the irrelevant 4420 arm to ablate CD3 binding, low level binding to the cell surface Env is detected with A32×4420, but not with 7B2×4420 (FIG. 11F).

HIV×CD3 DART Redirected T-Cell Killing of Env-Expressing Cell Lines and Concomitant T-Cell Activation.

Figure 12A:
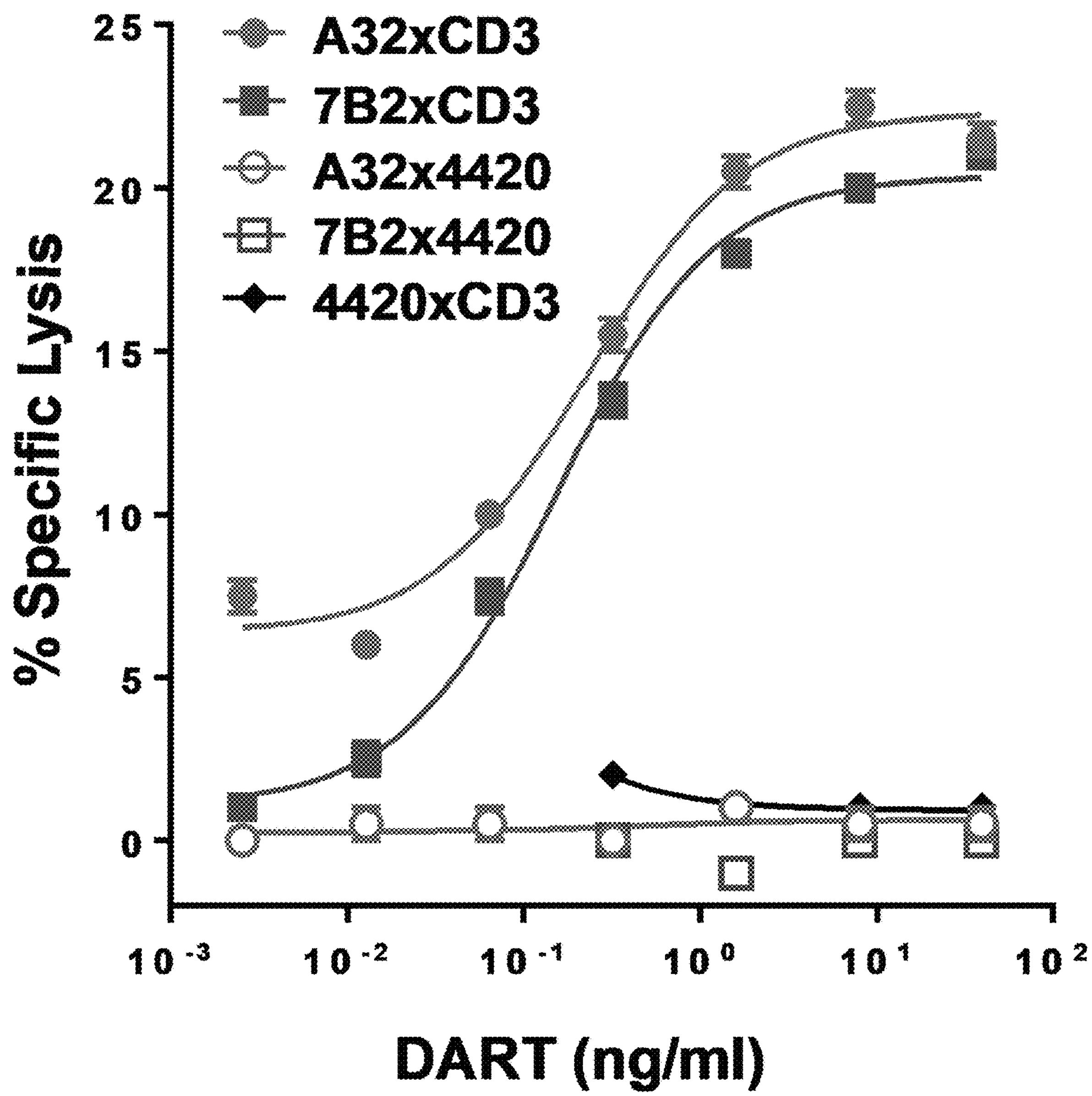
FIGS. 12A-12H show HIV×CD3 DART redirected T-cell killing of $Env^+$ target cells.
Figure 12B:
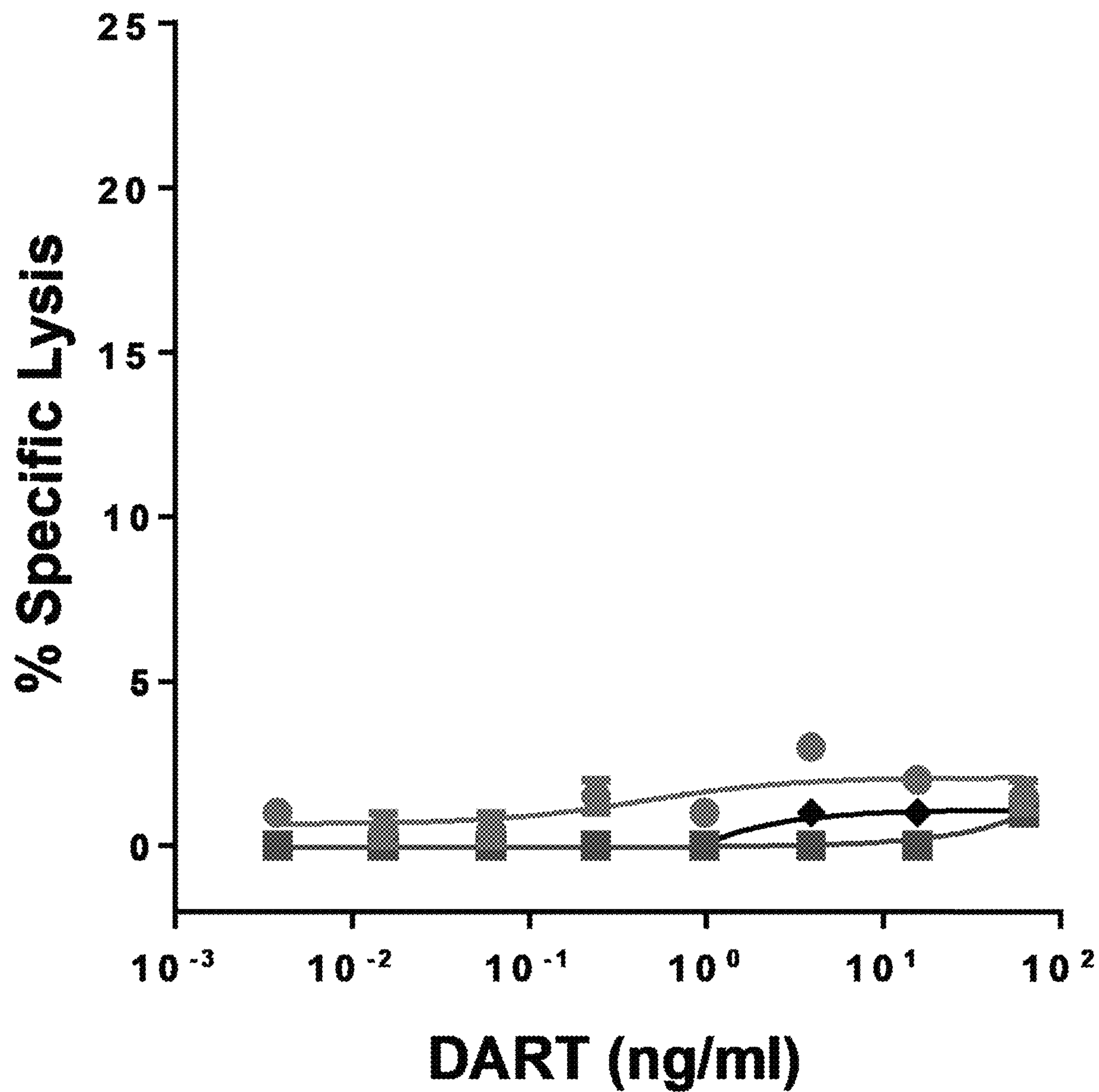
Figure 12C:
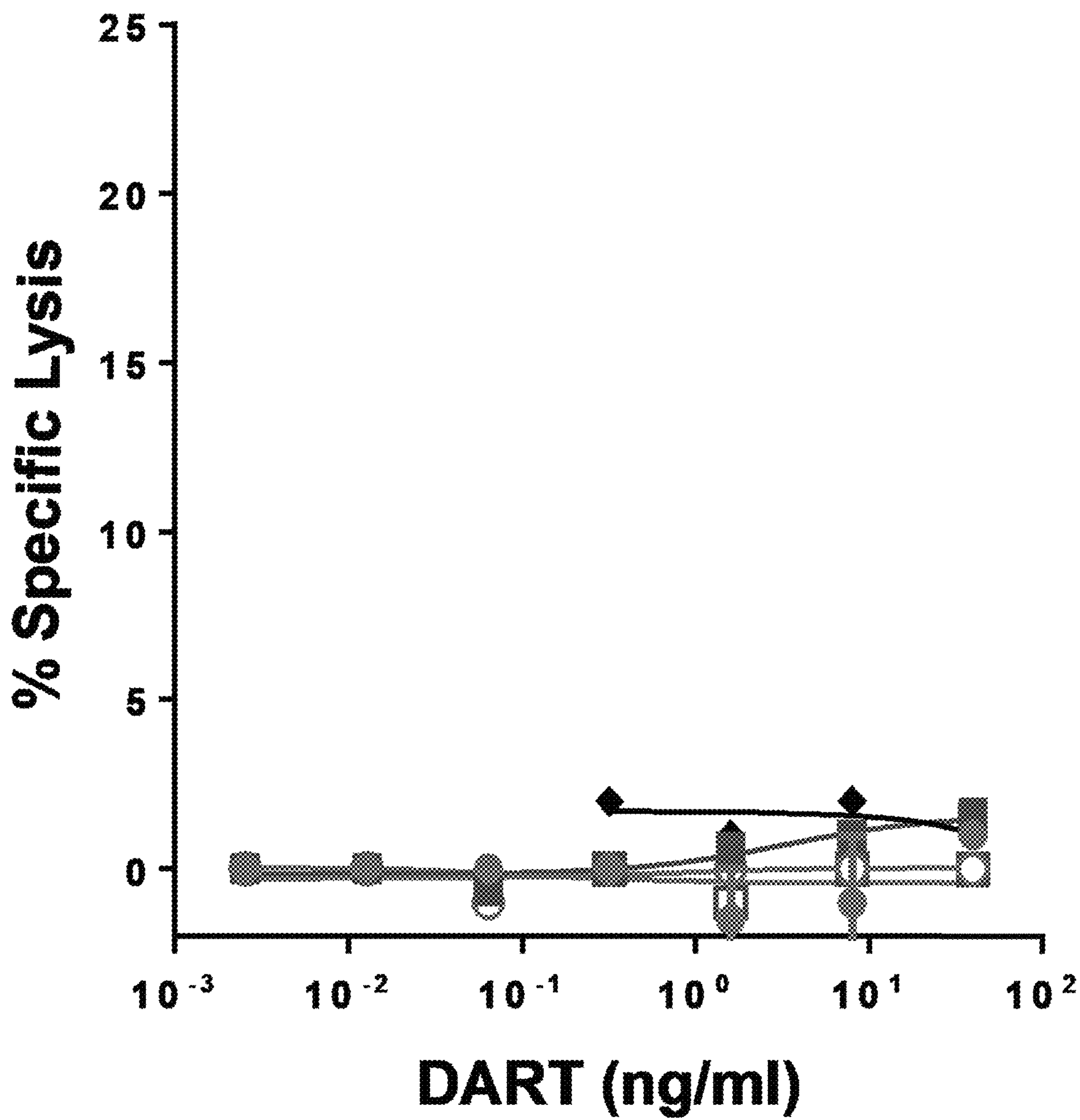

Jurkat 522-F/Y is a human $CD4^+$ cell line that expresses Env and serves as a model for HIV-infected $CD4^+$ T cells and Jurkat-ΔKS is a control cell line that is identical, except for a deletion/frameshift mutation in the Env gene that precludes its expression (45). These cell lines were utilized to evaluate the ability of HIV×CD3 DARTs to mediate redirected T-cell killing of $Env^+$ target cells. Target cell cytolysis was determined by measuring lactate dehydrogenase (LDH) release with the standard assay and the results were confirmed by luminescence (LUM) assay. As measured by LDH release assays, A32×CD3 and 7B2×CD3 redirected human T cells derived from healthy donors to kill the Jurkat-522 F/Y cells in a concentration dependent manner at an E:T ratio of 10:1, and these two HIV×DARTs exhibited similar potencies after 48 h of incubation with fifty percent effective concentrations ($EC_{50}$) of 160-230 pg/mL (FIG. 12A). No DART-mediated redirected T-cell killing of Jurkat-522 F/Y cells occurred with control DARTs (4420×CD3, A32×4420, 7B2×4420) in which the HIV arm or CD3 arm was replaced by an irrelevant one (FIG. 12A). The A32×CD3 and 7B2×CD3 DARTs did not mediate target cell killing when the effector T-cells were omitted (FIG. 12B) or when the target cells lacked Env expression (FIG. 12C). These data demonstrate a strict requirement for Env-expressing target cells and their coengagement with CD3-expressing effector cells for HIV×CD3 DART mediated cytolytic activity.

Figure 12D:
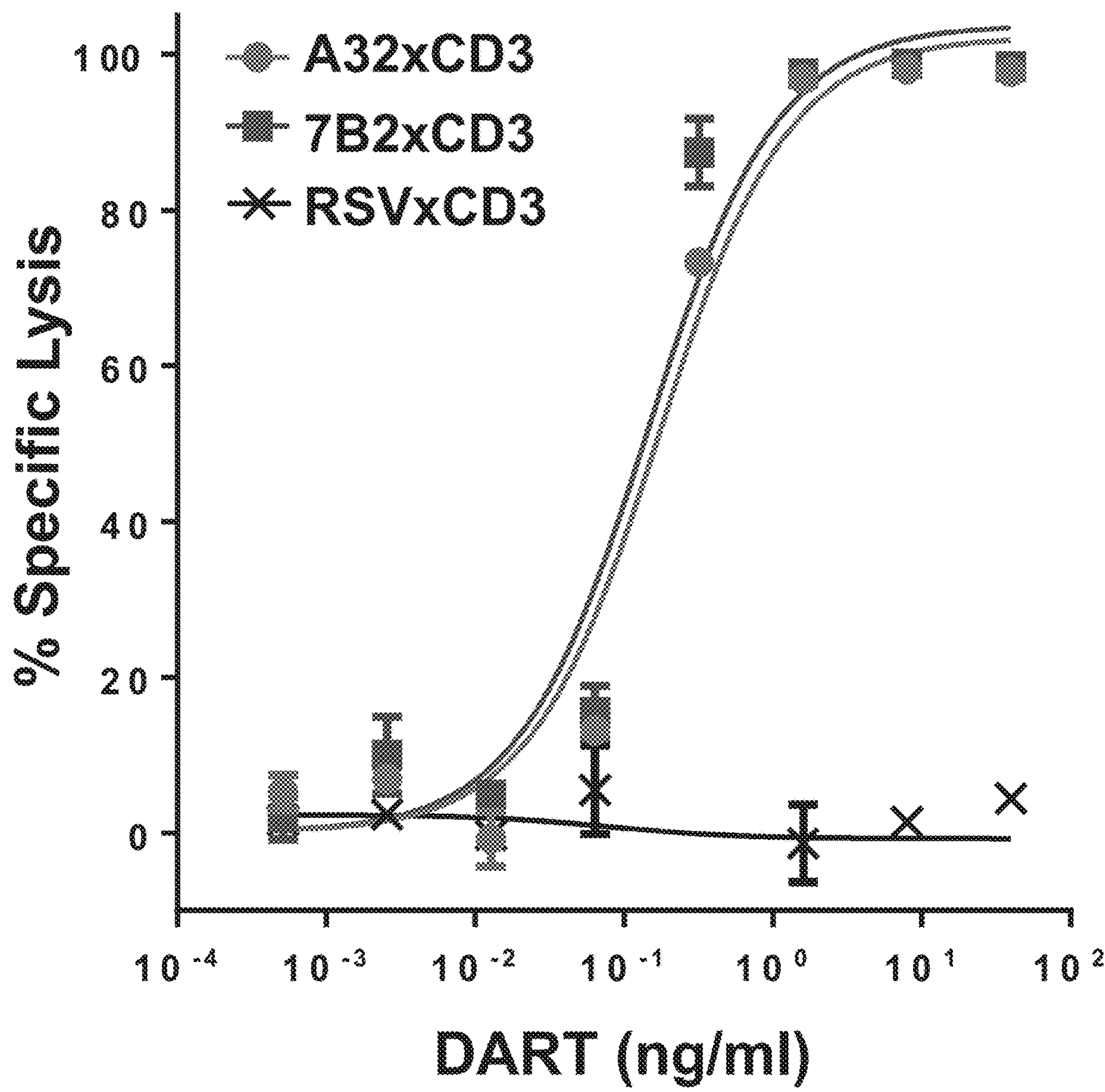
Figure 12E:
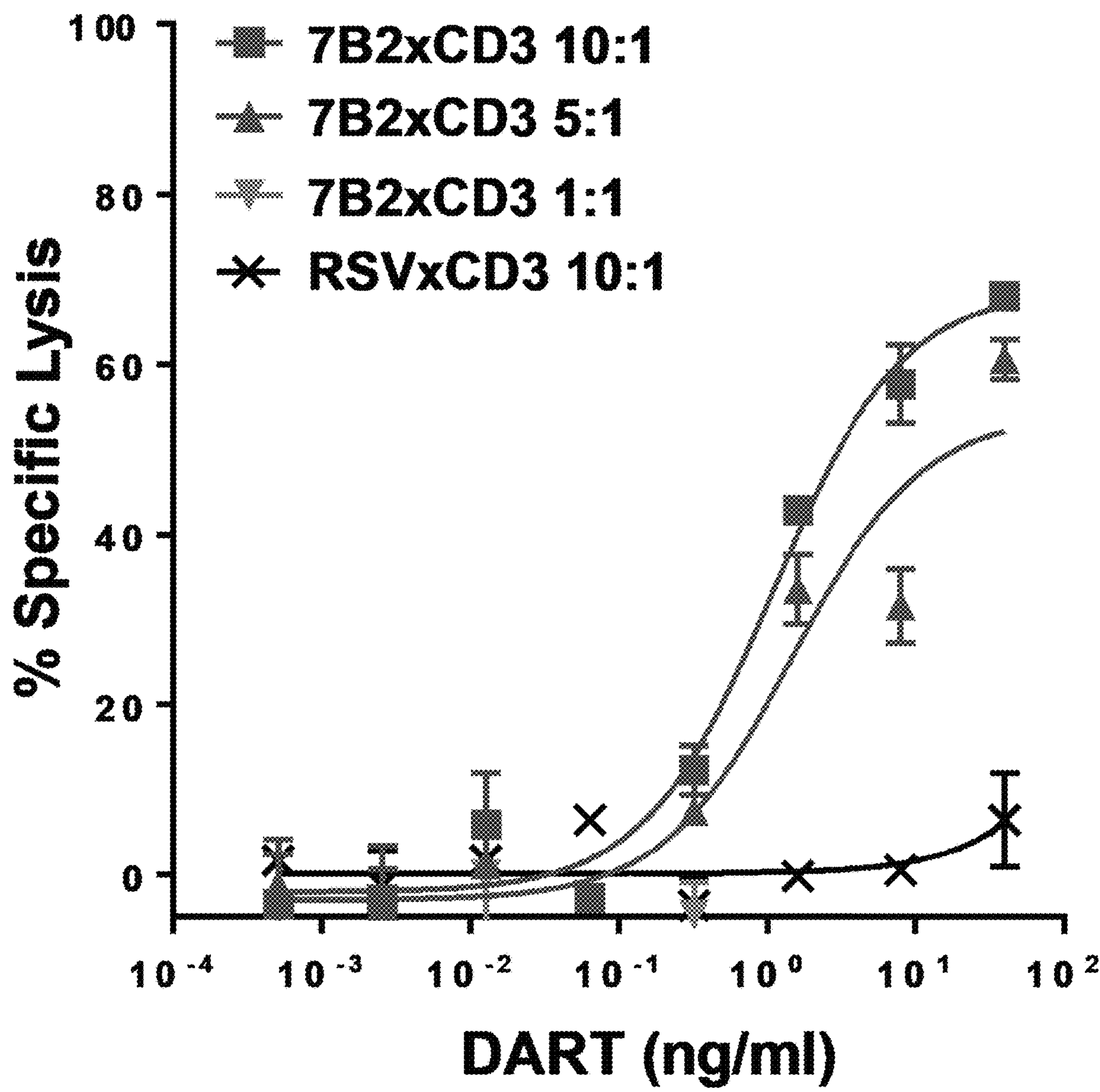
Figure 12F:
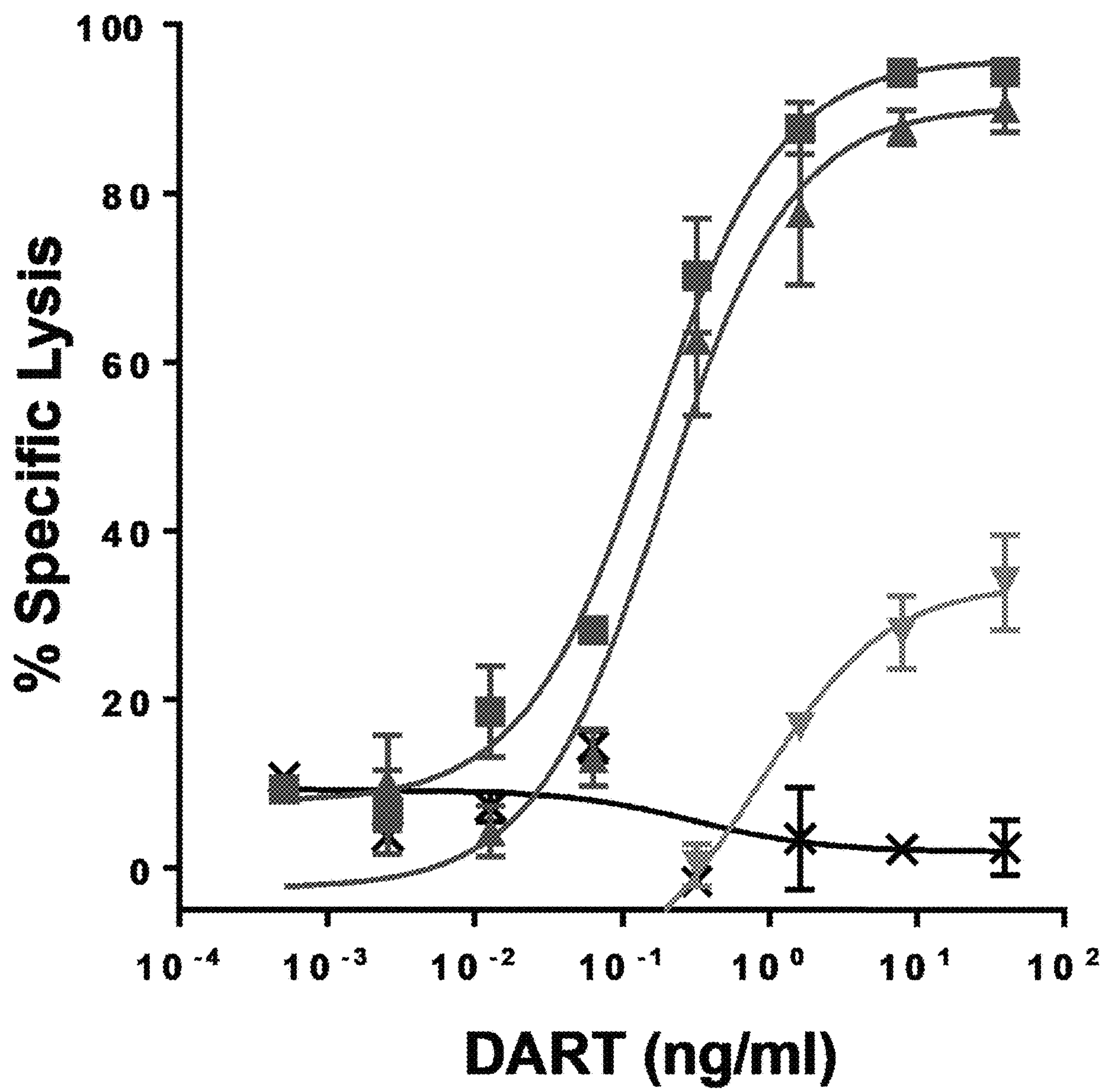
Figure 12G:
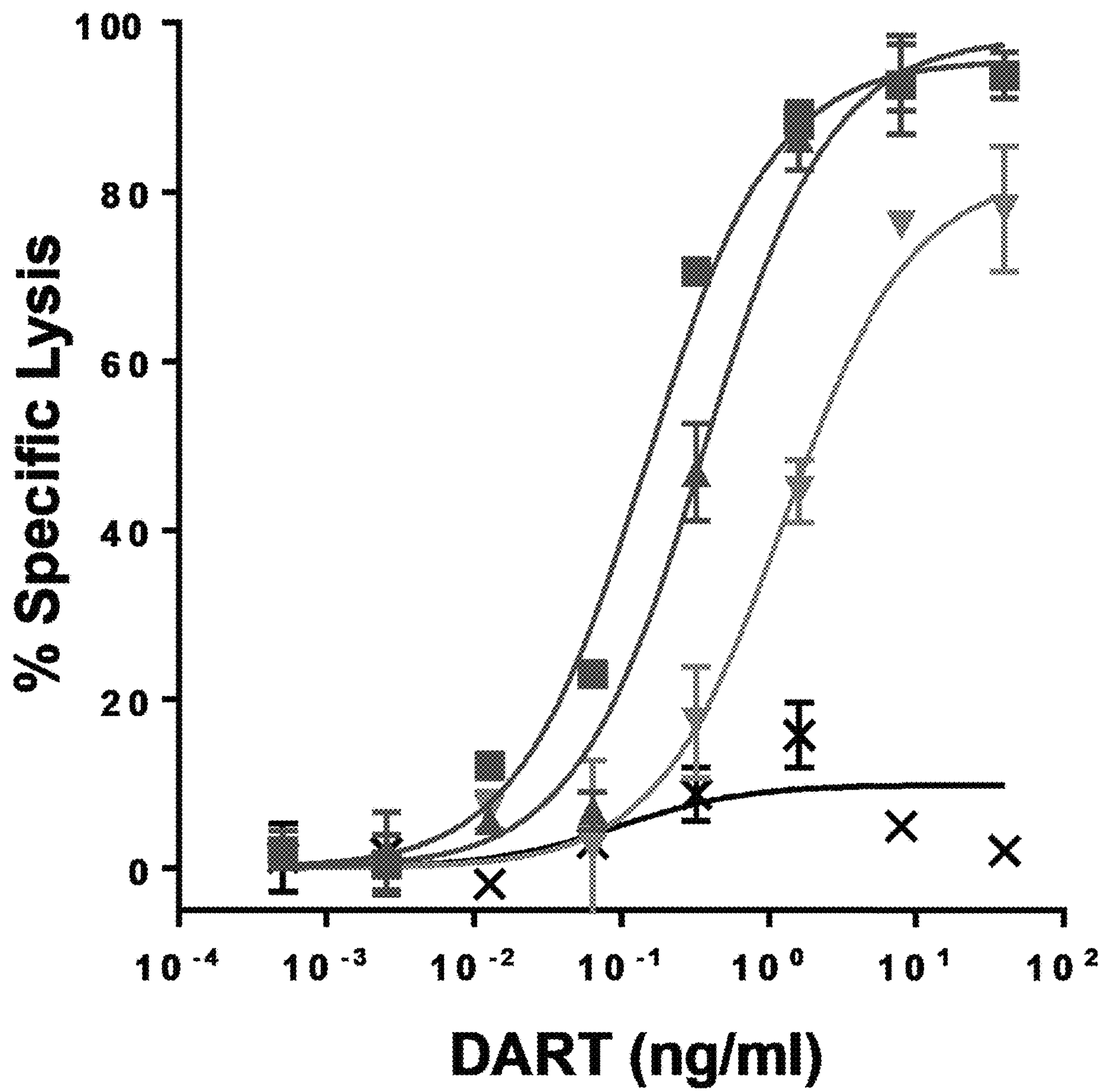
Figure 12H:
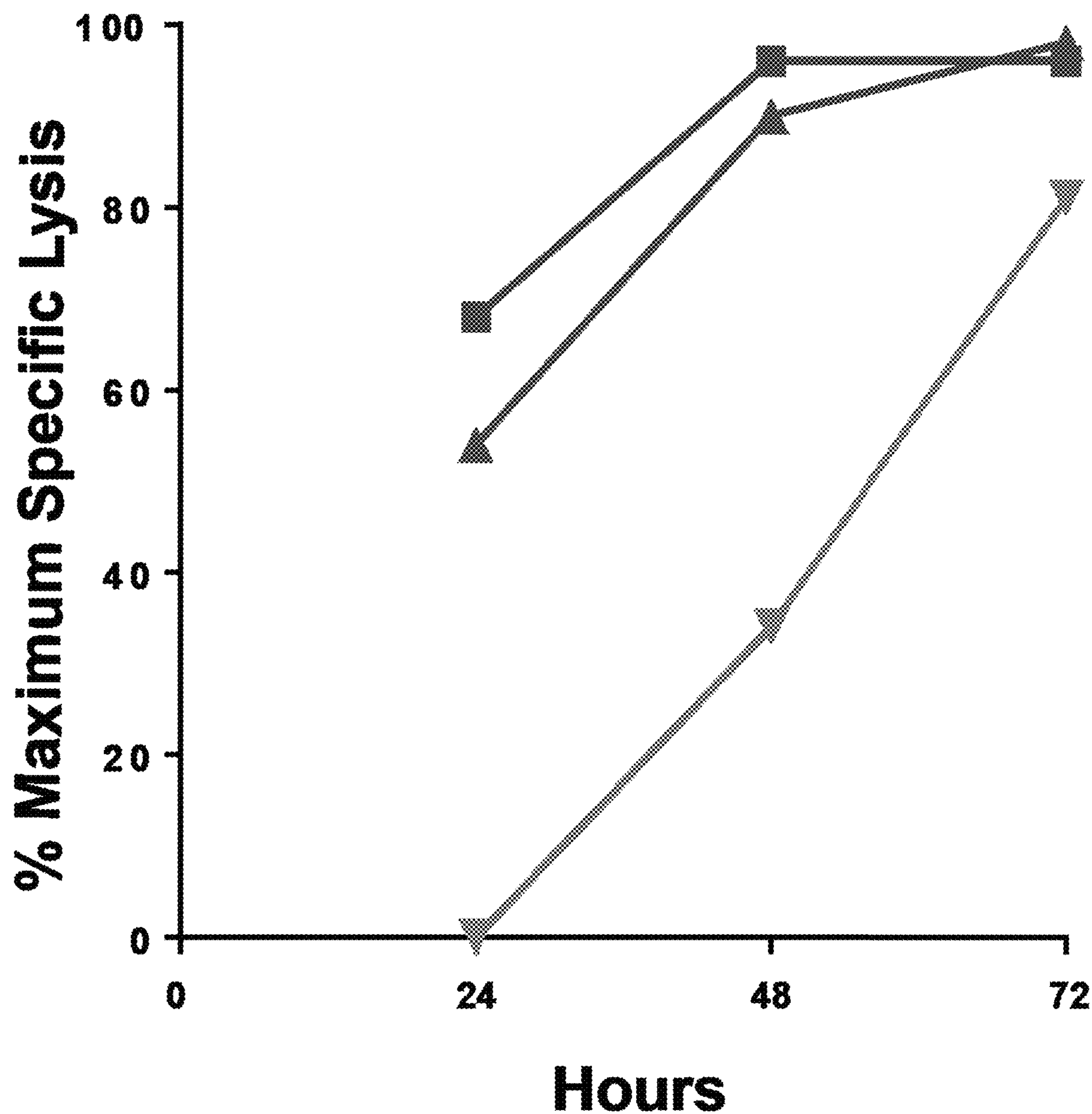

As measured by LUM assays, A32×CD3 and 7B2×CD3 exhibited similar potencies for redirected T-cell killing of Jurkat 522-F/Y GF cells with ECso values of 140-170 pg/mL (FIG. 12D), which were close to those measured with the LDH release assay, indicating consistency across the two different assay modalities. Moreover, with the sensitivity and specificity of the LUM assay, DART-dependent elimination of the $Env^+$ target cells was nearly complete (>98%), while the 4420×CD3 control DART mediated no cytotoxicity (FIG. 12D). HIV×CD3 DART redirected T cell killing activity was time and E:T ratio dependent. Near complete cytolysis with 7B2×CD3 was reached at 48 hours at E:T ratios of 10:1 and 5:1, whereas high level cytolysis (>80%) at an E:T ratio of 1:1 was delayed until 72 hours (FIGS. 12E-12H), suggesting that time is the limiting factor for the efficient elimination of target cells at lower E:T cell ratios.

Figure 13A:
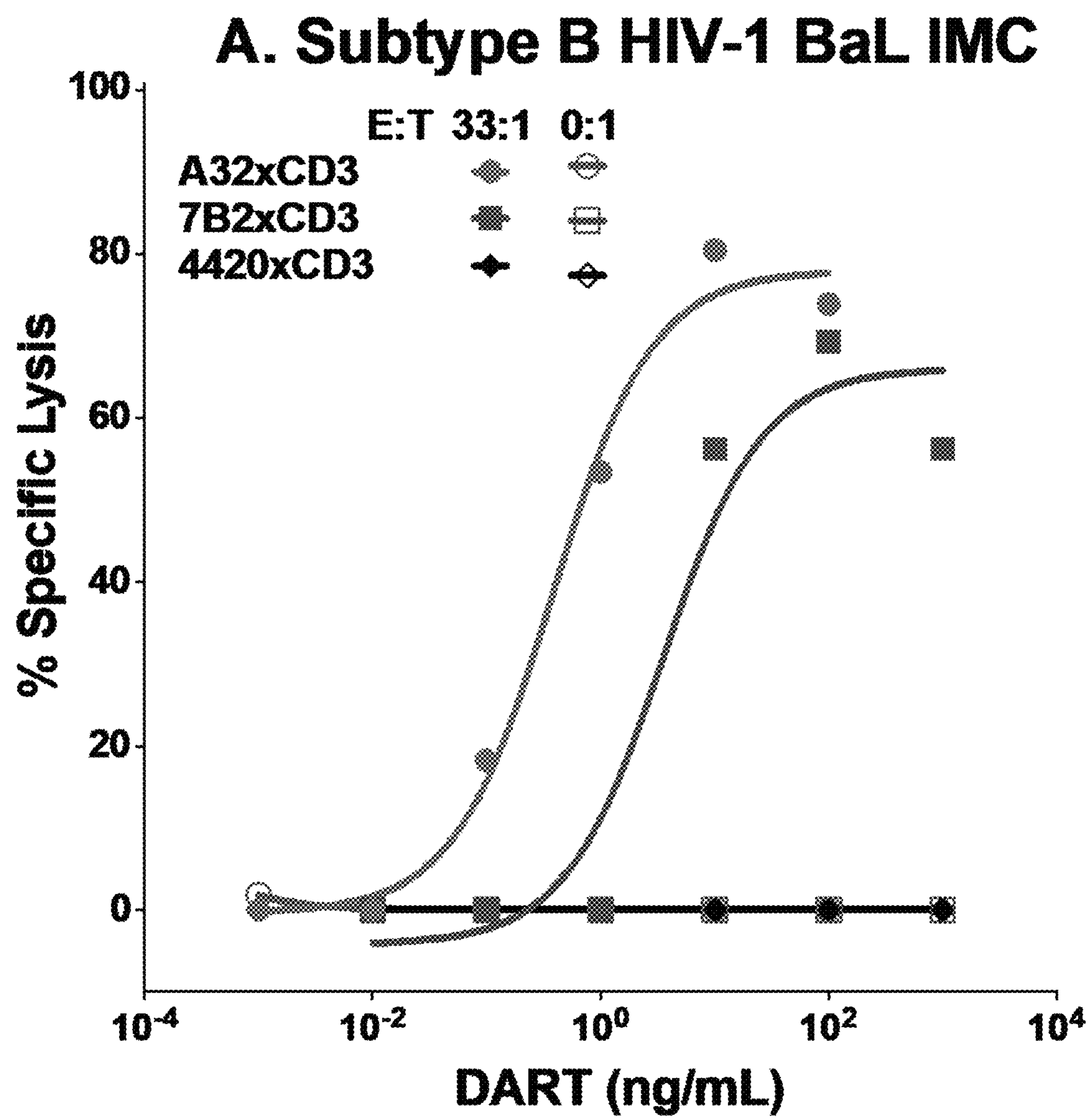
FIGS. 13A-13F show HIV×CD3 DARTs redirect T-cell cytotoxicity against CD4+ cells infected with HIV-1 IMCs of different subtypes.
Figure 13B:
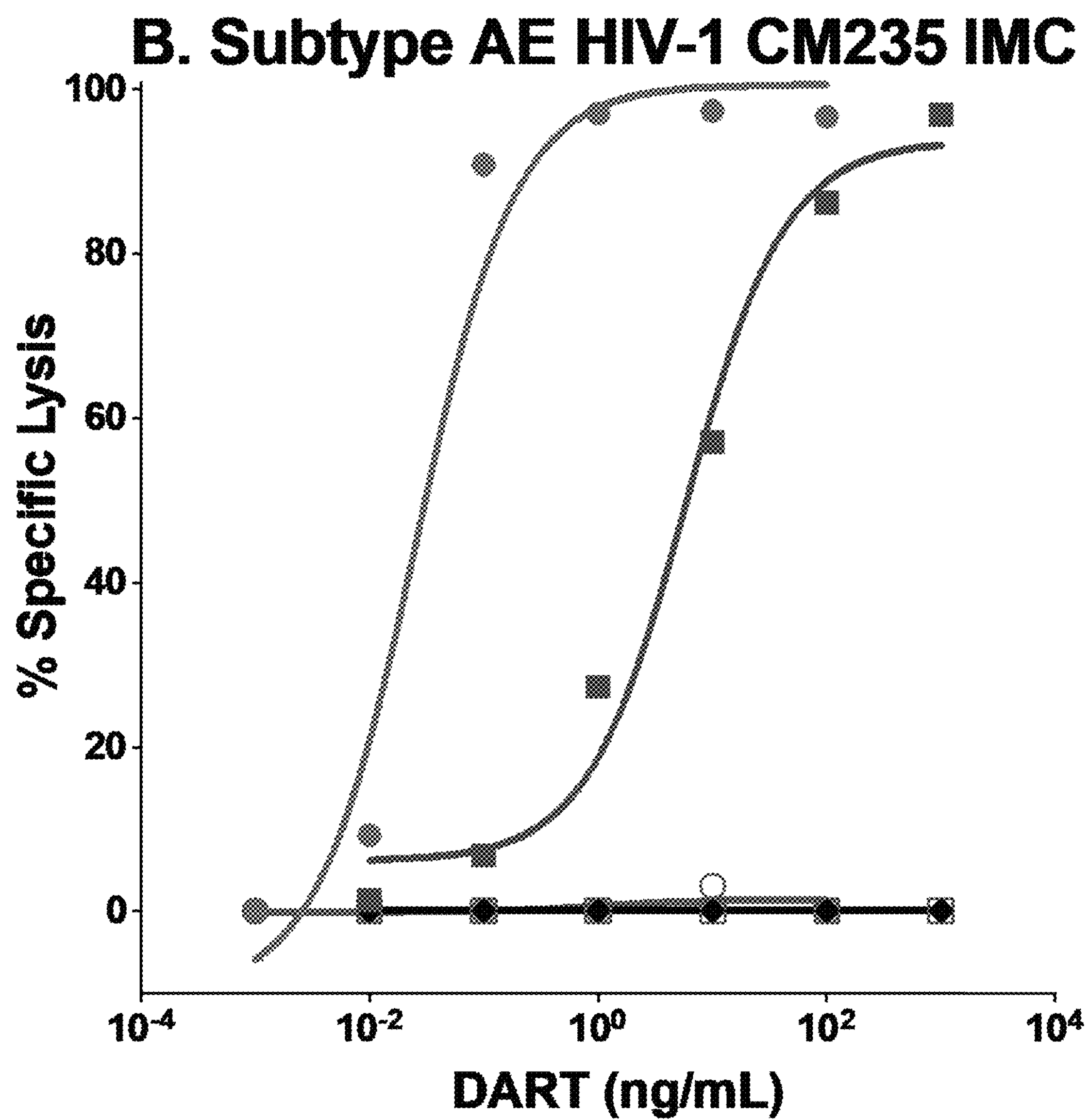
Figure 13C:
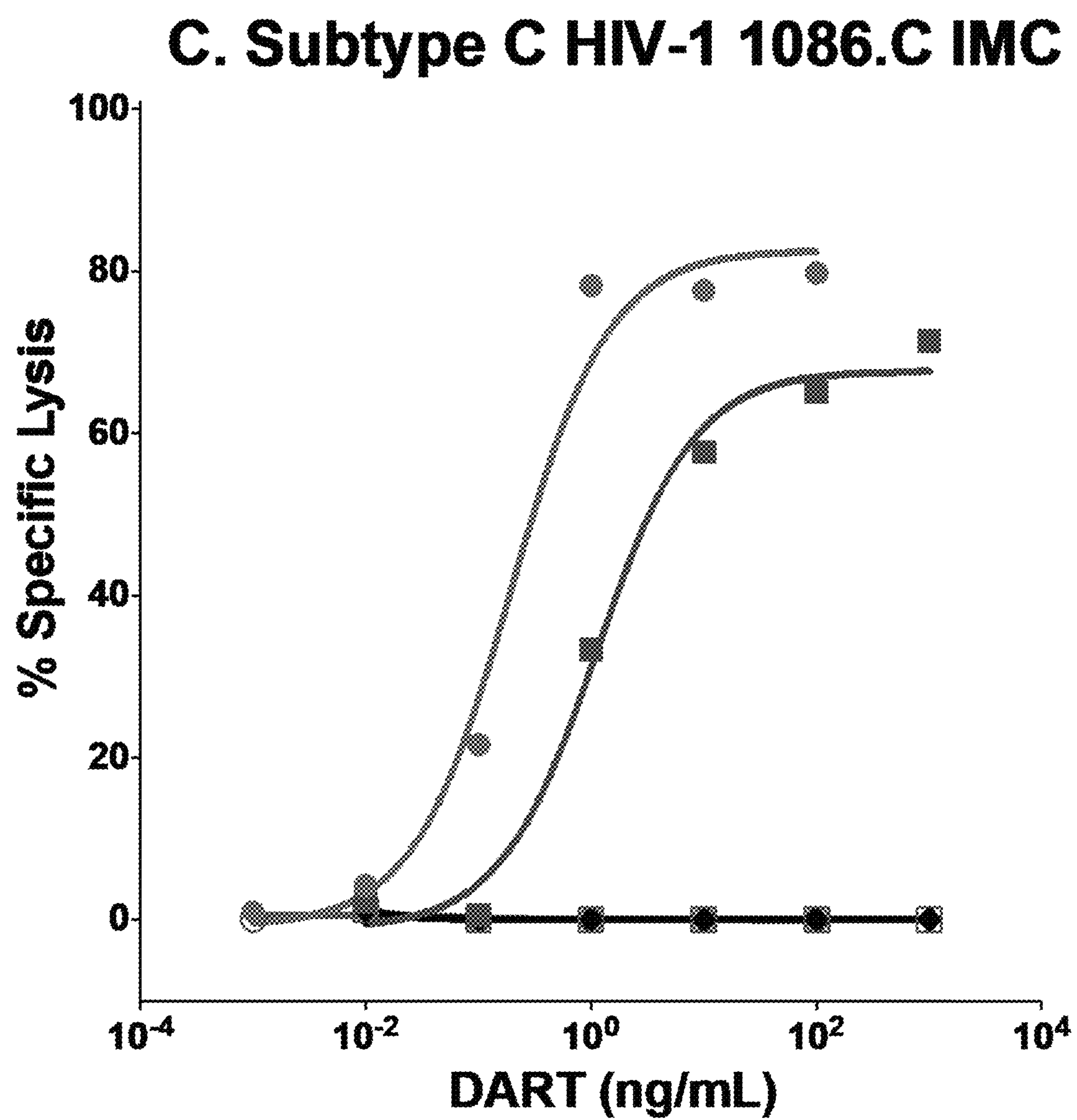
Figure 13D:
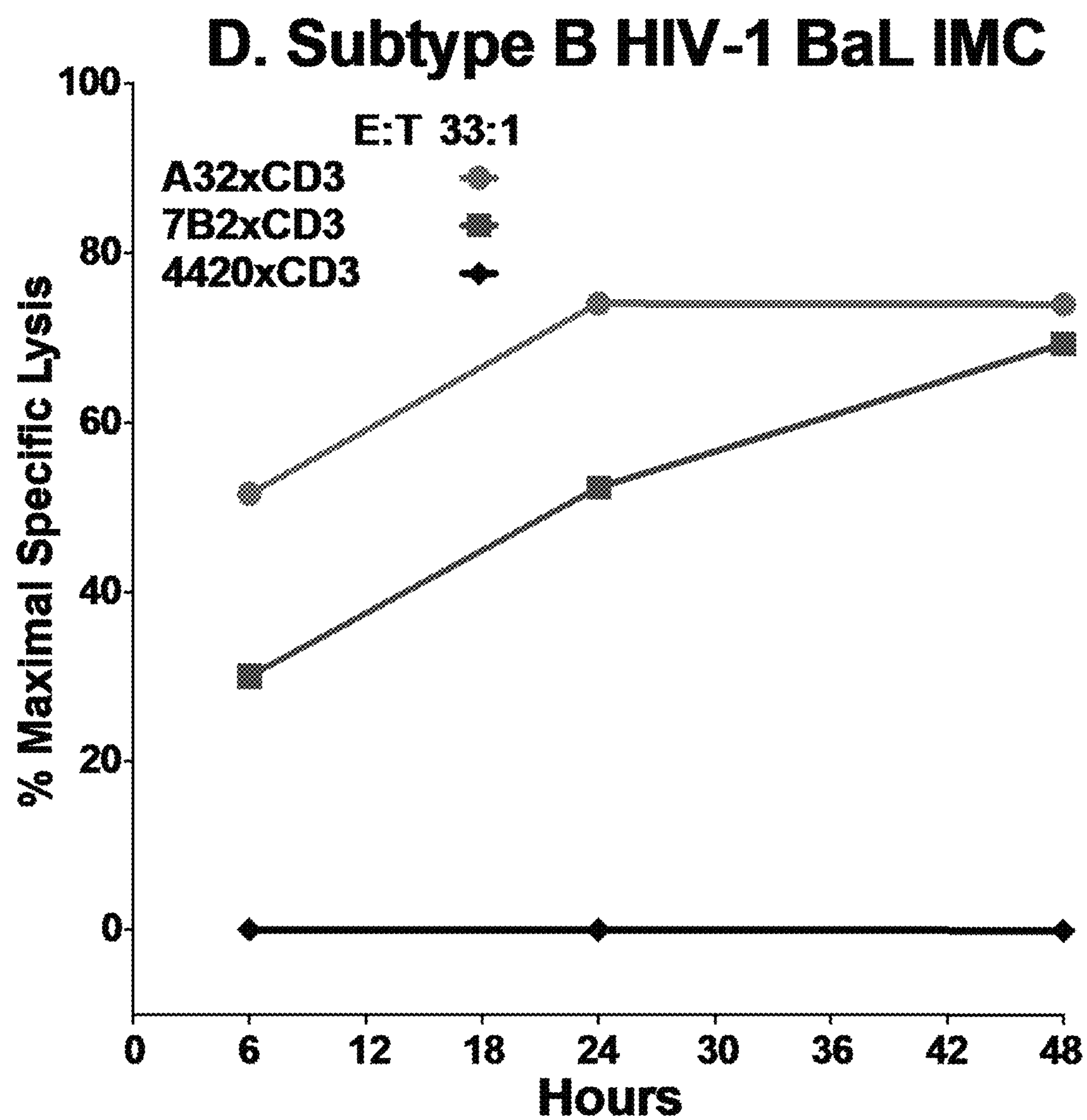
Figure 13E:
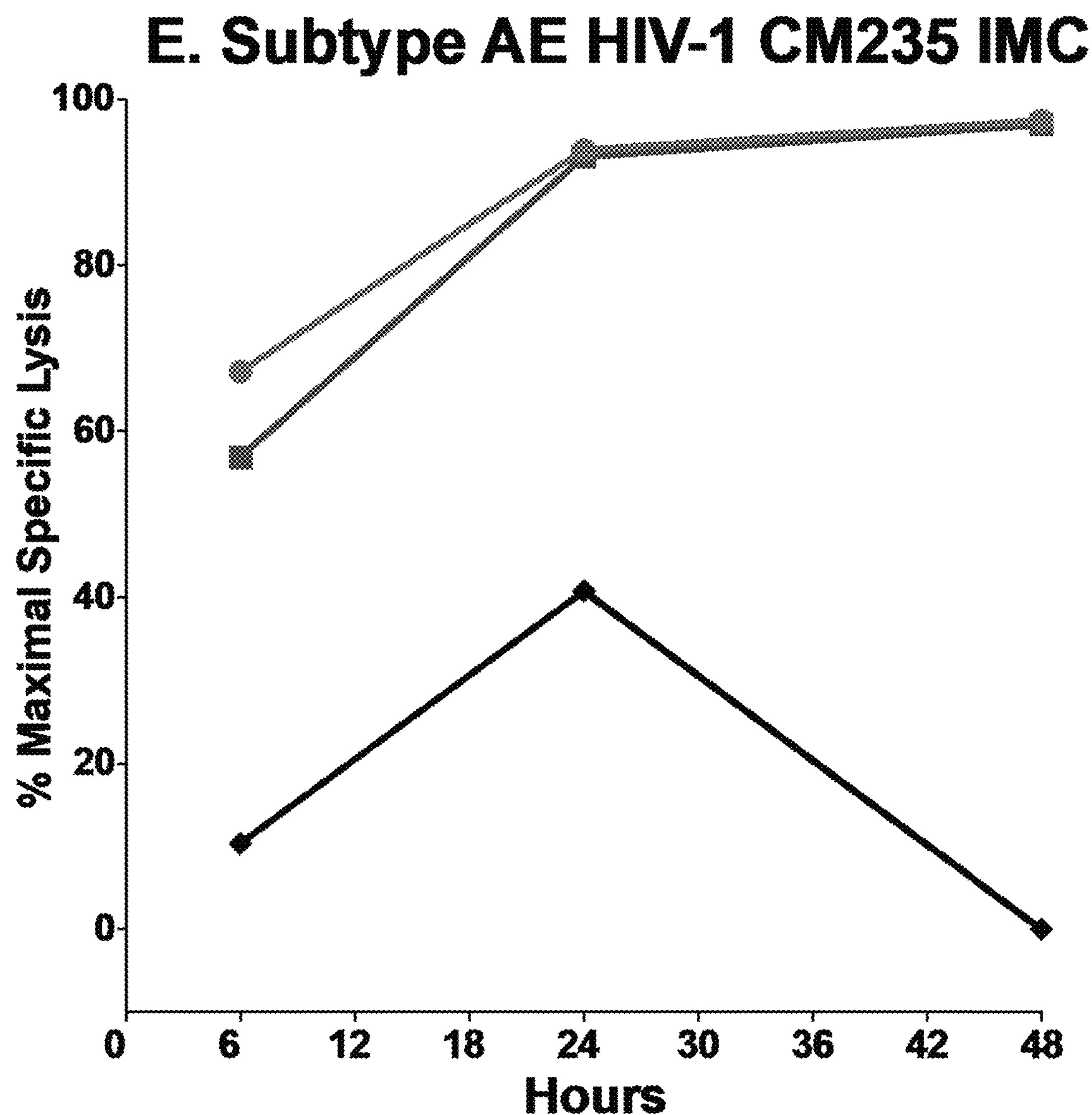
Figure 13F:
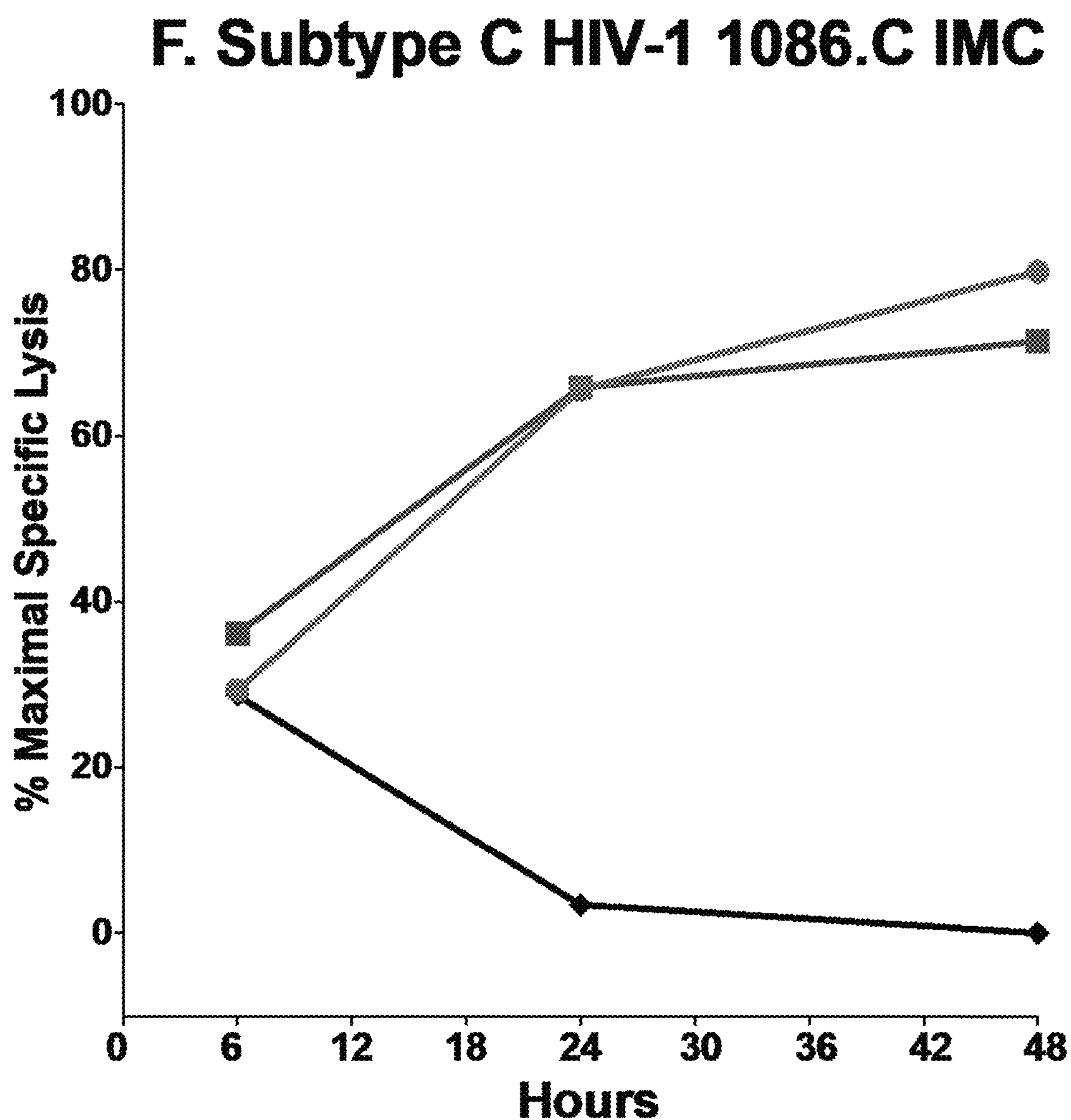

Concomitant with redirecting T-cell killing activity, the HIV×CD3 DARTs induced T-cell activation (measured by upregulation of the activation marker, CD25) in the presence of the $Env^+$ target cells with CD25 upregulated in $CD8^+$ T-cells to a greater extent than in $CD4^+$ T-cells (FIGS. 26A-26D). The overall data demonstrate that A32×CD3 and 7B2×CD3 potently activate and redirect T cells, especially $CD8^+$ T-cells, to specifically kill Env-expressing target cells. Moreover, the killing data confirm that both DARTs were capable of recognizing and binding to Env antigens on the surface of a $CD4^+$ cell line even though the detection of Env binding by FACS analysis was negligible (FIG. 13F).

HIV×CD3 DARTs Bind to the Surface of HIV-Infected $CD4^+$ T Cells and Redirect $CD8^+$ T-Cells to Kill HIV-1 Infected $CD4^+$ Cells Using Lymphocytes from HIV-1 Seronegative Donors.

Figure 27:
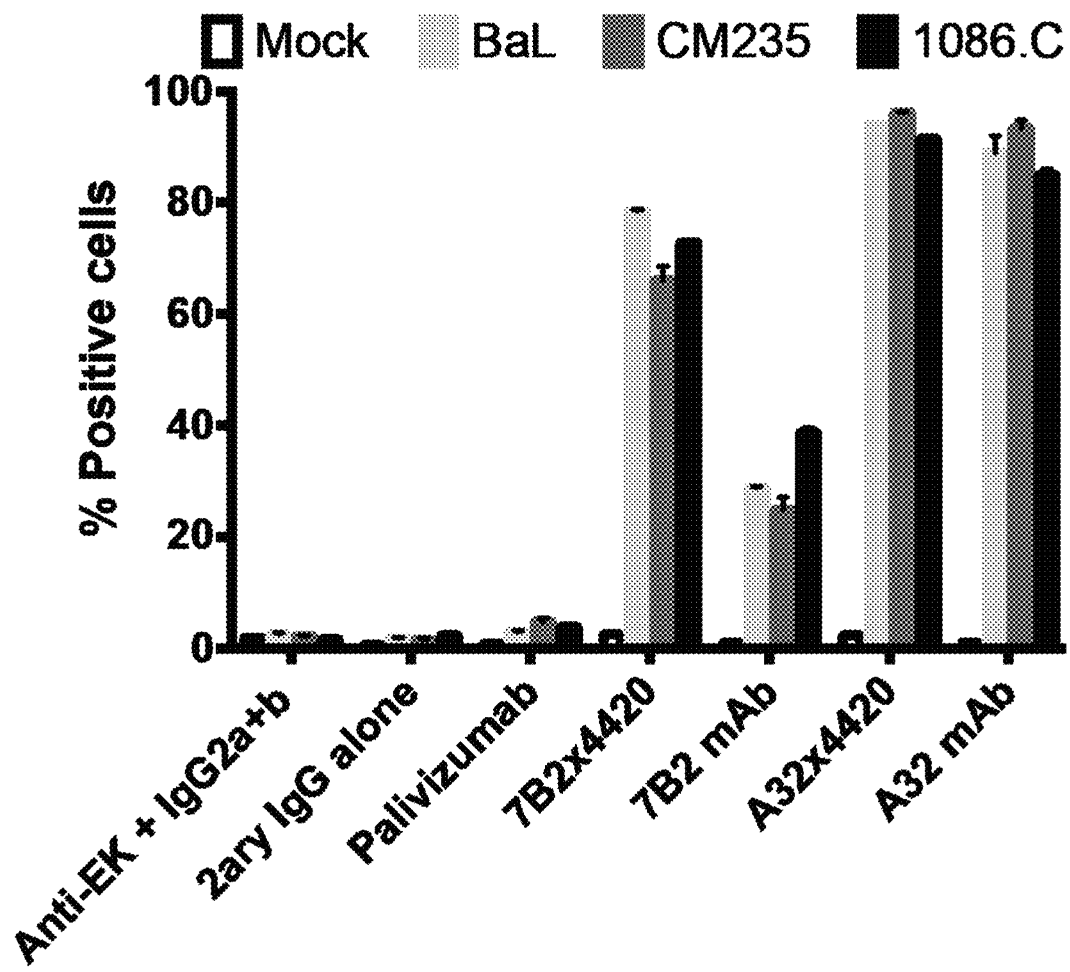
FIG. 27 shows HIV DARTs bind specifically to HIV-1 IMC infected $CD4^+$ T cells. Activated $CD4^+$ T cells obtained from healthy HIV-1 seronegative donors were infected for 48 hours with HIV-1 IMCs representing the HIV-1 subtype B BaL, AE CM235, and C 1086.0 as reported in the methods section. Non-infected $CD4^+$ T cells (mock) were utilized as negative control. The cells were stained using the 7B2×4420 and A32×4420 DART where the CD3 arm was substituted with the irrelevant 4420 protein to avoid binding to the CD3 receptor. After incubation with the DART, the cells were stained with the secondary anti-EK-IgG2a-biotinylated complex to reveal binding of the DARTs. The staining with 7B2 and A32 mAbs, utilizing an indirect staining technique with the secondary mouse anti-human-IgG mAb, was performed as control. The secondary fluoresceinated anti-human IgG Abs and the Palivizumab mAb were utilized as negative controls. The frequency of infected cells was determined by intracellular staining using the anti-p24 mAb as reported in the method section. Each bar represents $CD4^+$ T cells infected with the IMCs and controls as indicated above the graph. The results are reported as frequency (%) of viable infected ($p24^+$) $CD4^+$ T cells that were stained by each of the DARTs, mAbs, and controls as listed on the x-axis.

The A32×4420 and 7B2×4420 DARTs were evaluated for their ability to bind and redirect the killing of $CD4^+$ T cell infected with HIV-1 Infectious molecular clones representing the subtype AE CM235, subtype B BaL, and subtype C 1086.0 HIV-1 isolates. Each IMC was engineered with a luciferase reporter gene to quantitatively measure the cytolysis of infected target cells. To assess binding to infected cell surface Env, A32×4420 and 7B2×4420 DARTs (which lack CD3 effector arms) were compared to the parental A32 and 7B2 mAbs. Similar staining of the $p24^+$ (infected) $CD4^+$ T cells by both HIV×CD3 DARTs independently from the HIV-1 IMC used for the infection (FIG. 27) was observed. Interestingly, staining with the A32×4420 DART recapitulated closely the staining with the A32 mAbs; in contrast, the 7B2×4420 DART recognized>66% of the HIV-1 infected cells (range 66-78%) compared to the >24% recognized by the 7B2 mAb (range 24-38), suggesting that the DART has a better accessibility to the cluster I gp41 epitope compared to the mAb (FIG. 27). The secondary conjugated Abs and the Palivizumab mAb utilized as controls recognized less than <5% HIV-1 infected $CD4^+$ T cells.

The ability of A32×CD3 and 7B2×CD3 to redirect $CD8^+$ T cells from HIV-1 seronegative donors against autologous $CD4^+$ T cells infected with the three HIV-1 IMCs was subsequently investigated. The two HIV×CD3 DARTs redirected autologous $CD8^+$ T effector cells to kill subtype B BaL (FIG. 13A), subtype AE CM235 (FIG. 13B), and subtype C 1086.0 (FIG. 13C) IMC-infected $CD4^+$ target cells in a concentration dependent manner, whereas the control DART (4420×CD3) was inactive. The greater potency exhibited by A32×CD3 ($EC_{50} \leq 1$ ng/mL) compared to 7B2×CD3 ($EC_{50} \sim 10$ ng/mL) in these studies with IMC-infected $CD4^+$ cells contrasts with the similar potencies observed in the studies with Envy cell lines (FIGS. 12A-12C). DART mediated killing of the IMC-infected $CD4^+$ T cells was dependent on the presence of $CD8^+$ effector cells, and no cytolytic activity was observed in their absence (FIGS. 13A-13C). In time course studies, DART-dependent cytolytic activity was evident at 6 hours with maximal activity (>70% cytolysis) at 48 hours (FIGS. 13D-13F).

Figure 14E:
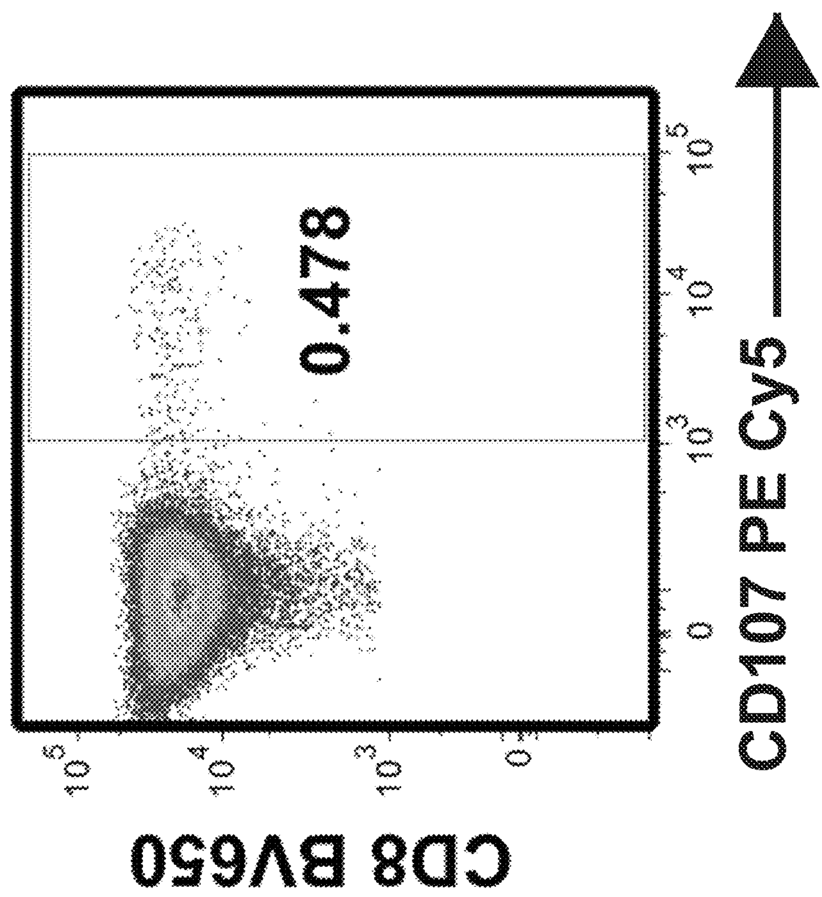
Figure 14F:
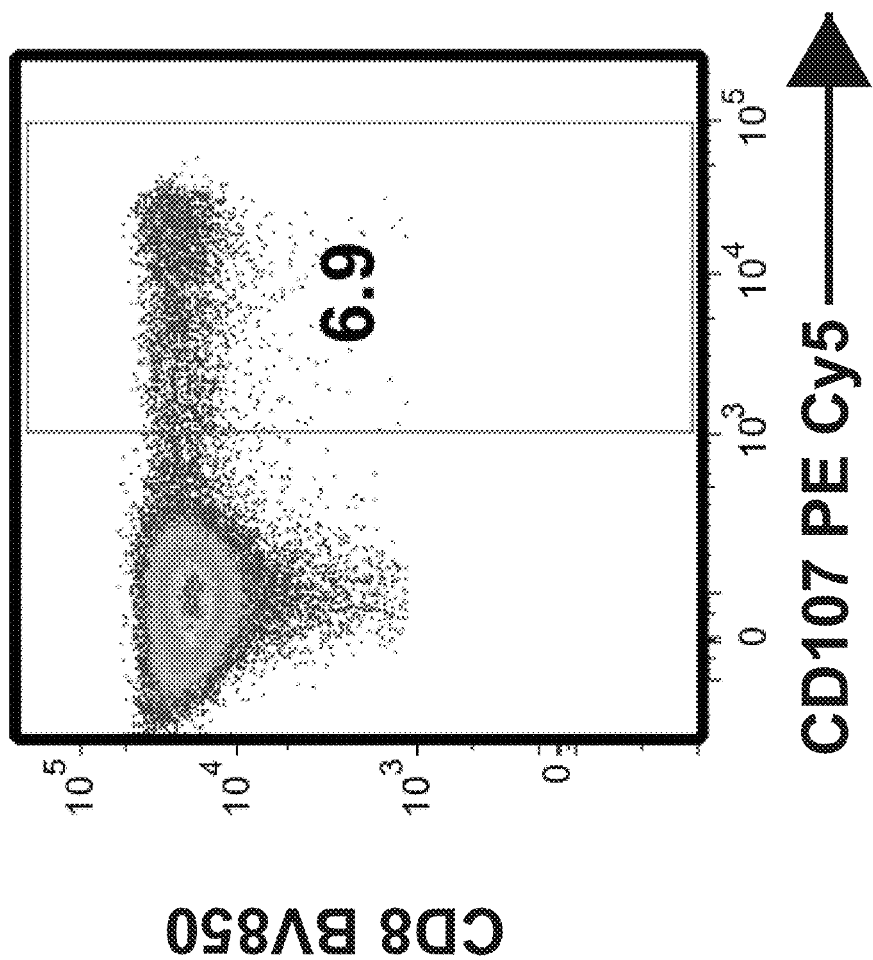
Figure 14G:
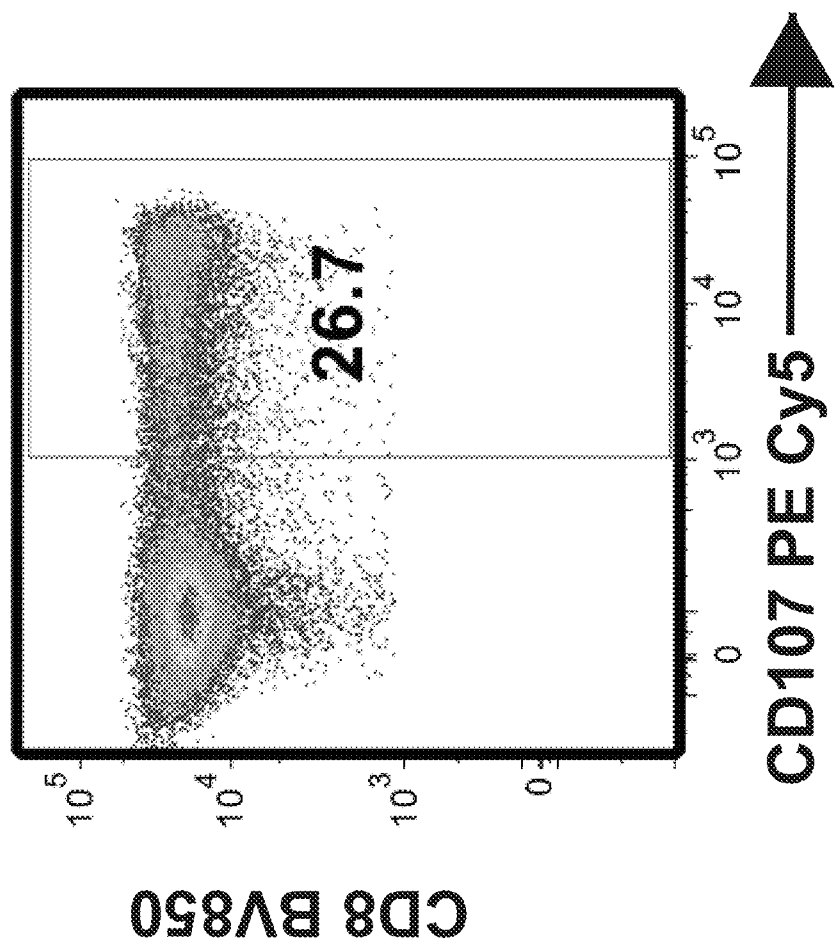
Figure 14H:
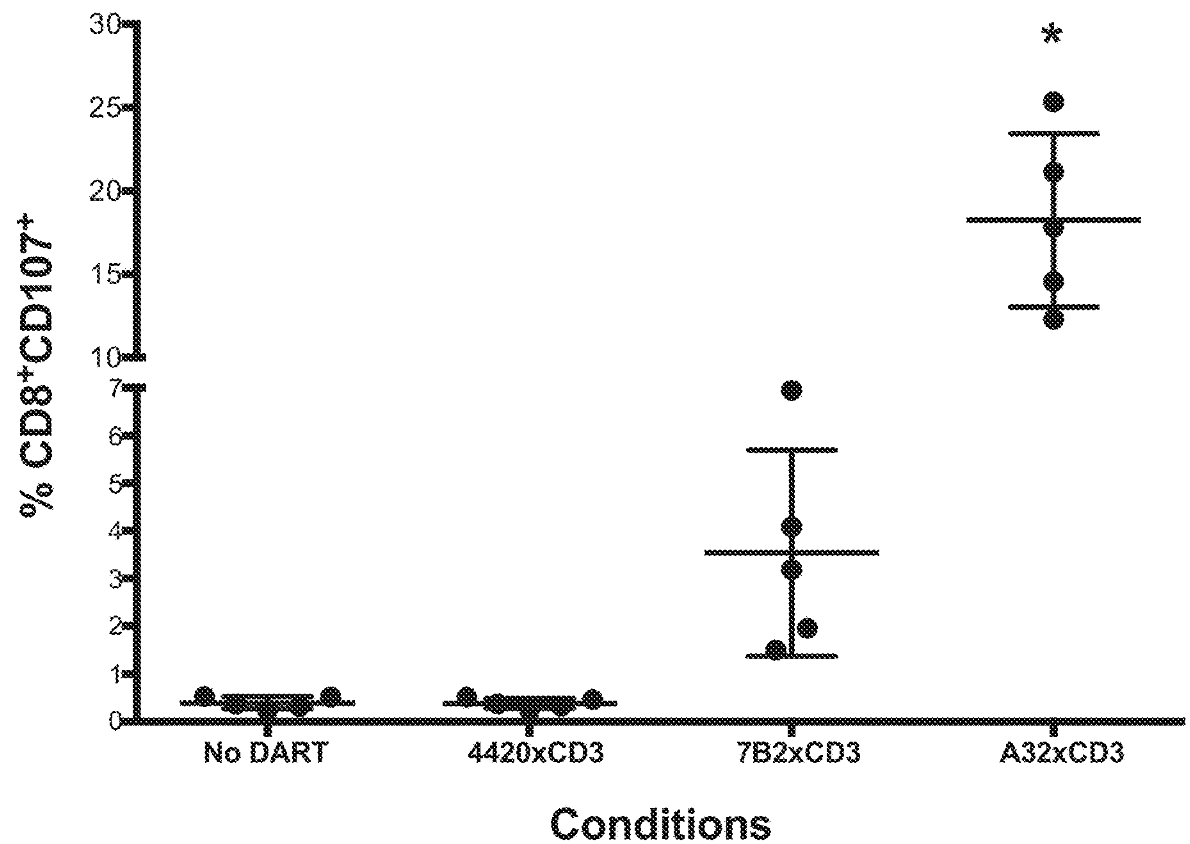

To gain insight into the frequency of effector T cells recruited by the DARTs to kill HIV-1 infected target cells, the ability of DARTs to induce degranulation of the $CD8^+$ T cells obtained from 5 HIV-1 seronegative donors when co-incubated with autologous HIV-1 BaL IMC-infected $CD4^+$ cells under the same conditions used to detect cytolytic activity was assessed. The example of the gating strategy adopted for data analysis is illustrated in FIGS. 14A-14G. The mean frequency of Live/$CD3^+$/$CD8^+$/$CD107^+$ cells (FIG. 14H) under control conditions (absence of HIV×CD3 DART or presence of control DART) was 0.38% (standard deviation 0.10%; range 0.24-0.51), which increased to an average 3.53% (range 1.5-6.9%) or 18.23% (range 12.30-23.35%) in the presence of 1 ng/mL 7B2×CD3 or A32×CD3, respectively. The data demonstrate that HIV×CD3 DARTs can specifically induce degranulation of resting $CD8^+$ T cells in the presence of Env-expressing target cells (autologous HIV-1-infected $CD4^+$ T cells).

HIV×CD3 DART Redirected CD8$^{+}$ T Cell Killing Activity Against JR-CSF Infected Cells from Seronegative Donors.

Figure 15A:
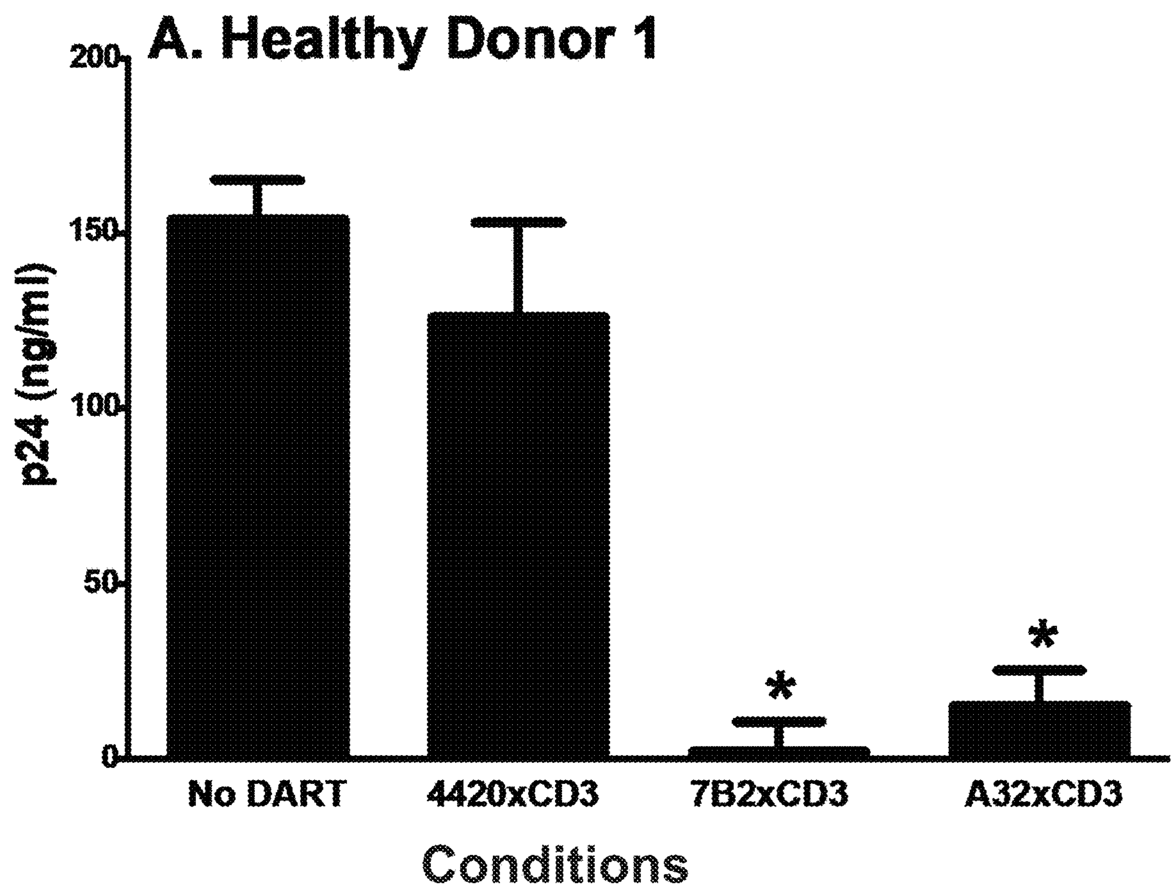
FIGS. 15A-15C show viral clearance assay to assess HIV×CD3 DART redirected CD8+ T cell killing of autologous JR-CSF-infected CD4+ T cells from healthy HIV seronegative donors. Activated $CD4^+$ T cells from HIV seronegative donors were infected with HIV-1 clone JR-CSF and then incubated with autologous resting $CD8^+$ T effector cells at an E:T ratio of 1:1 in the absence (No DART) or presence of HIV×CD3 or control DARTs at a concentration of 100 ng/mL for 7 days. Results are shown for two healthy donors (FIGS. 15A-15B), as well as for healthy donor 2 in the presence of integrase and non-nucleoside reverse transcriptase inhibitors during the co-culture period to inhibit virus replication (FIG. 15C). Each bar represents the absolute p24 concentration detected in culture supernatants. Error bars represent standard error mean (SEM) of n=3. * indicates $p<0.05$ with Dunnett's test for multiple comparisons.
Figure 15B:
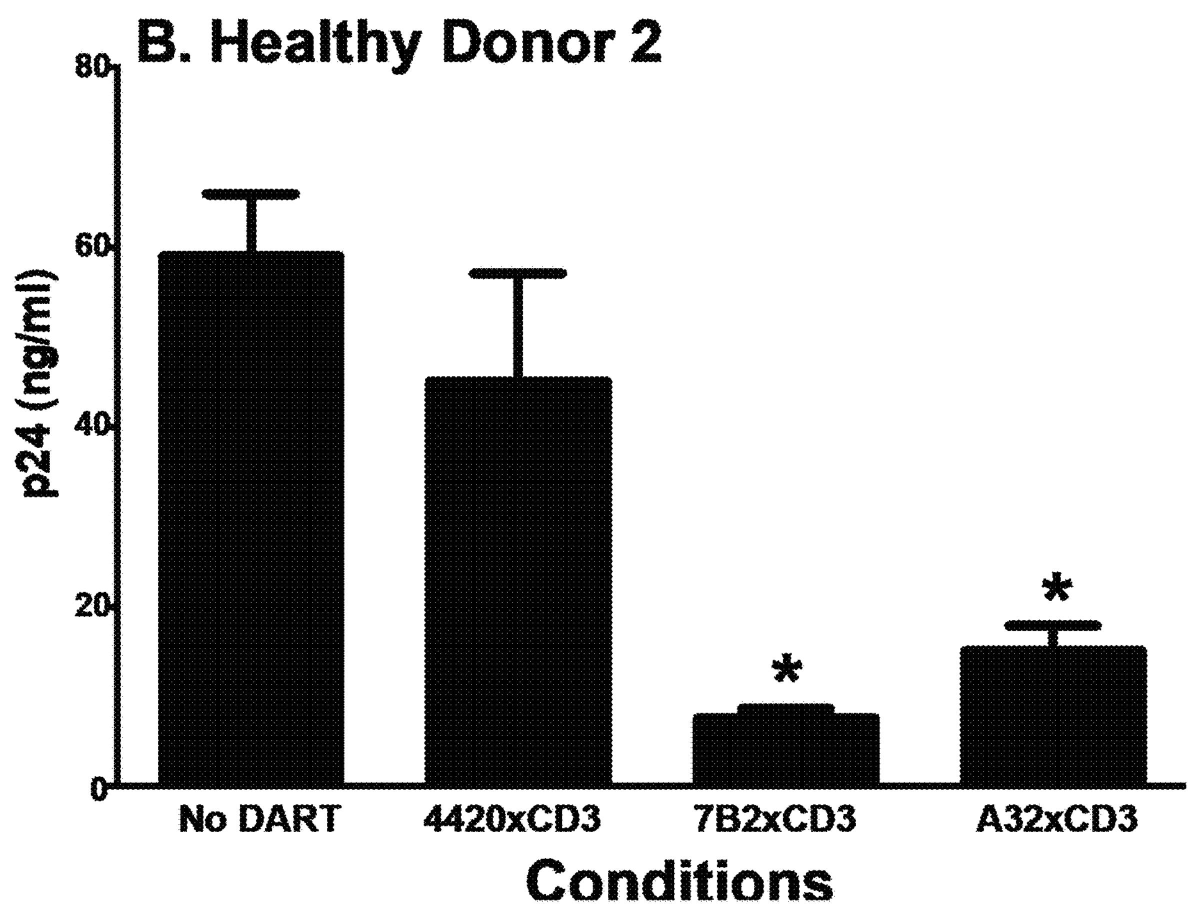
Figure 15C:
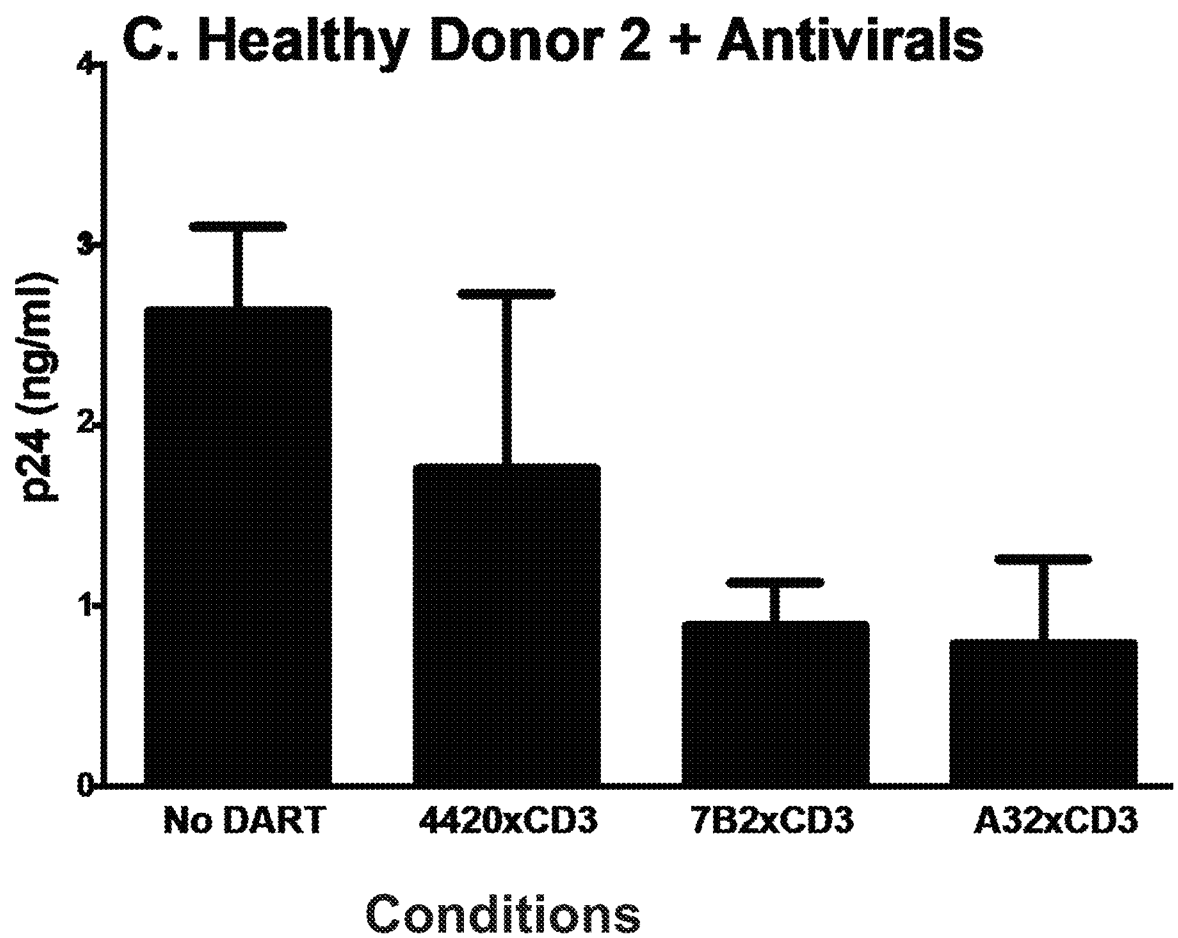

A viral clearance assay measuring HIV gag p24 antigen production was utilized as an alternative method to assess DART redirected T cell killing activity. CD4$^{+}$ cells from healthy donors were superinfected with the HIV-1 Glade B clone JR-CSF and incubated with autologous CD8$^{+}$ T cells at an E:T ratio of 1:1 in the absence or presence of 100 ng/mL DARTs for 7 days. In experiments with two different donors, addition of the control DART (4420×CD3) did not significantly reduce p24 production compared to incubations performed in the absence of DARTs, whereas addition of A32×CD3 or 7B2×CD3 significantly reduced p24 production to a similar extent (by 72-96% or 87-99% respectively; $p<0.01$ Student T test; FIGS. 15A-15B). The viral clearance assay was also conducted in the presence of integrase and non-nucleoside reverse transcriptase inhibitors once infection was established, at the time of addition of effector cells and DARTs, to block further rounds of infection. When antiretrovirals (ARVs) were included in the assay, A32×CD3 and 7B2×CD3 still mediated a trend towards reduction in p24 production, although this did not reach statistical significance likely due to low levels of baseline p24 production with the antiretrovirals (FIG. 15C), suggesting that the DARTs are not acting by inhibition of virus spread but rather through clearance of infected cells.

HIV×CD3 DARTs Redirect CD8$^{+}$ T-Cells to Clear JR-CSF-Superinfected CD4$^{+}$ Cells Using Lymphocytes from Patients on Suppressive ART.

Chronic ART is characterized by dysfunctional and exhausted T cell responses (46, 47) and thus confirmation of robust DART mediated T-cell redirected clearance activity in patient samples ex vivo is critical. The activity of HIV×CD3 DARTs in viral clearance assays with lymphocytes from 8 HIV-infected individuals on suppressive ART was evaluated. All participants were on ART for at least 6 months at the time of study with virus load<50 copies/mL, but otherwise exhibited diverse clinical backgrounds (FIG. 20).

Figure 28A:
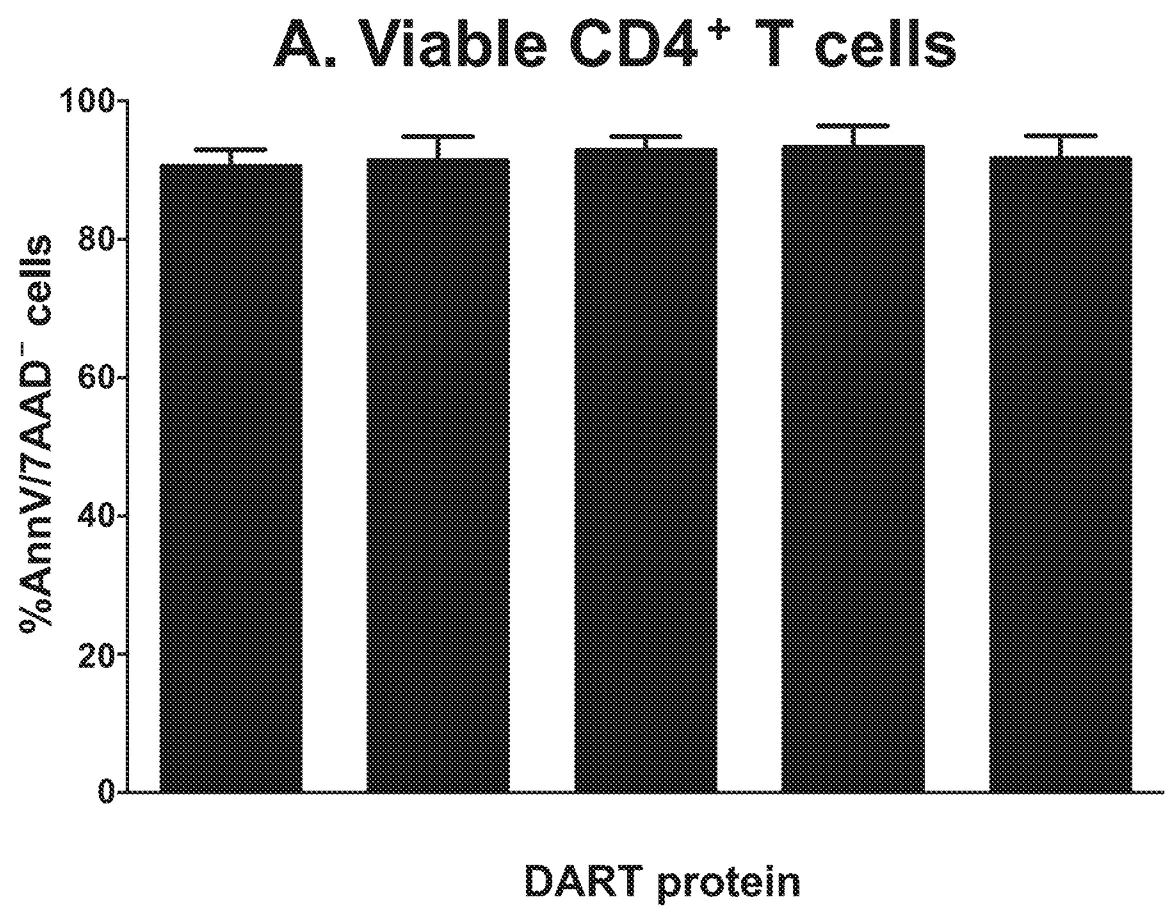
FIGS. 28A-28D show lack of HIV×CD3 DART effects on T cell viability or activation status in the absence of added target cells using PBMC from HIV-1 infected donors. Unstimulated $CD4^+$ or $CD8^+$ T-cells from HIV-infected, ART suppressed were incubated in the absence or presence of control (4420×CD3, 7B2×4420, A32×4420) or active (A32×CD3, 7B2×CD3) DARTs at 100 ng/mL for 7 days.
Figure 28B:
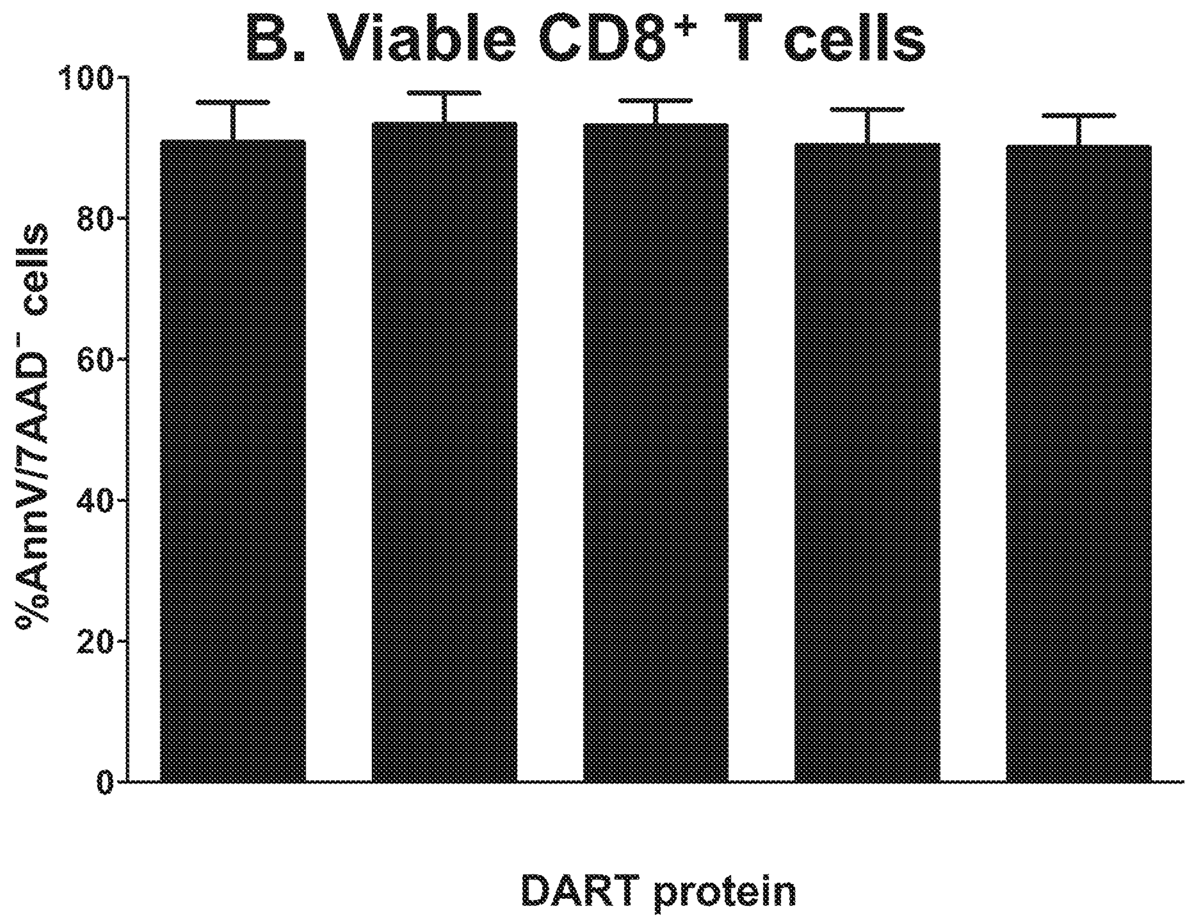
Figure 28C:
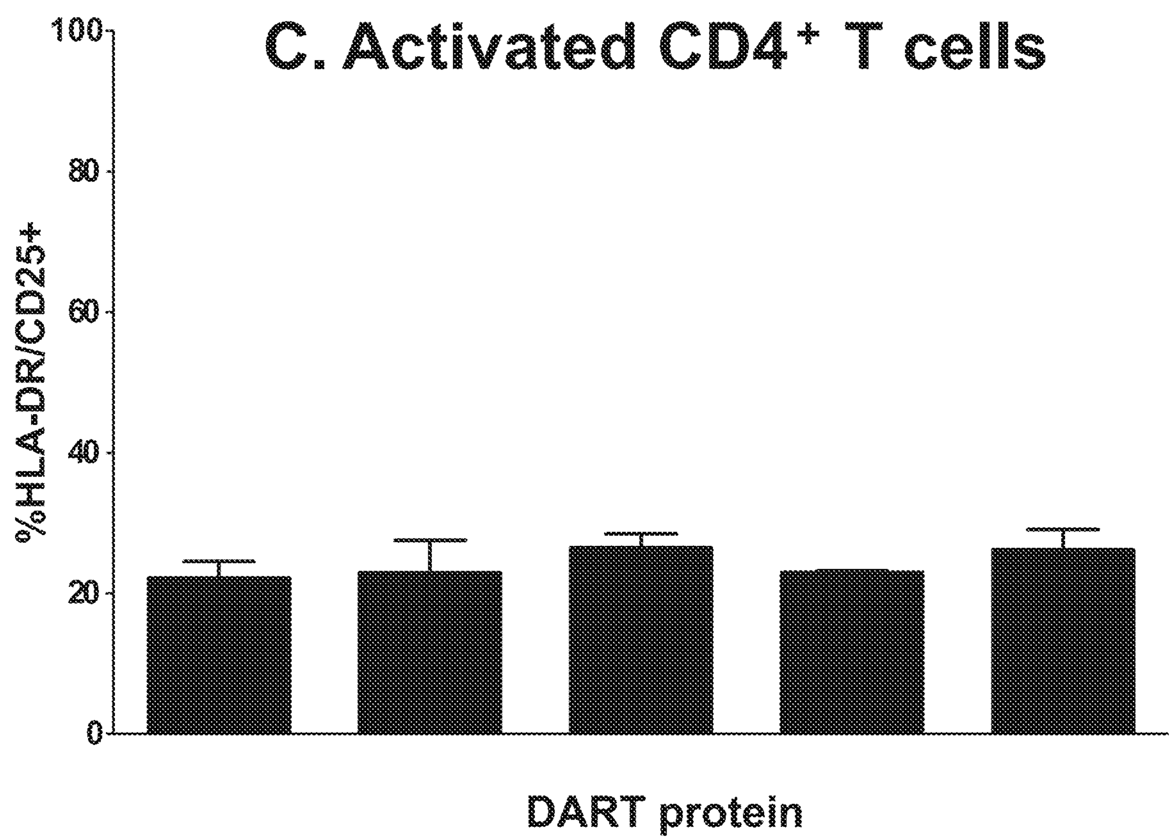
Figure 28D:
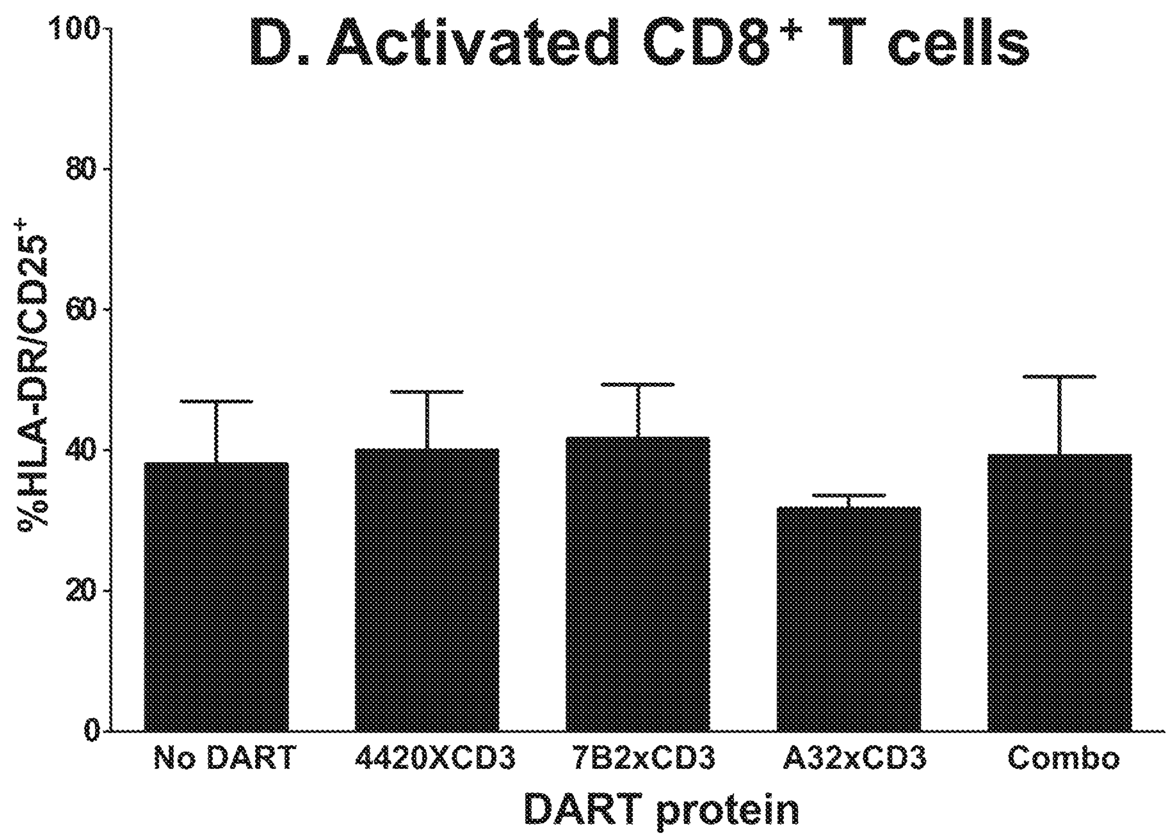

Because T cells from HIV-1 seropositive subjects could be more susceptible to apoptosis than those from seronegative subjects (48), whether HIV×CD3 DARTs, in the absence of target cells, might impact T-cell viability, which could confound the analysis of DART activity with patients' cells, was evaluated. Following 7 days of culture of either CD4$^{+}$ or CD8$^{+}$ T cells from HIV-infected, ART-suppressed patients in the presence of 100 ng/mL DART, which mimics the viral clearance assay conditions, no decreases in T cell viability based on Annexin V/7 AAD staining (FIGS. 28A-28B) was observed. Moreover, no changes in activation markers (HLA-DR, CD25) on unstimulated CD4$^{+}$ or CD8$^{+}$ T cells were observed after culture with HIV×CD3 or control DARTs (FIGS. 28C-28D), suggesting that engagement of the CD3 arm alone does not activate patients' CD8$^{+}$ or CD4$^{+}$ T-cells ex vivo.

Figure 16A:
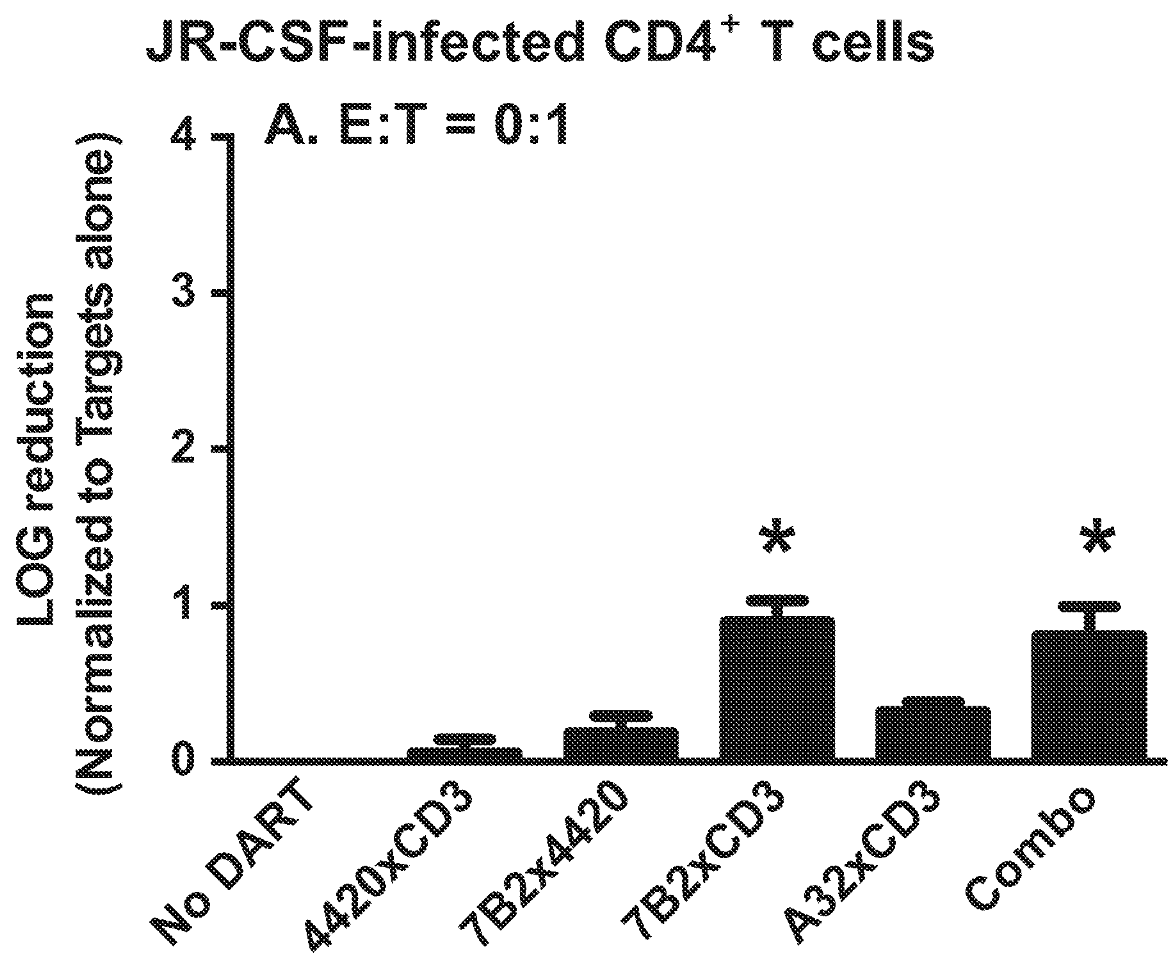
FIGS. 16A-16H show viral clearance assay detects HIV×CD3 DART redirected CD8+ T-cell clearance of JR-CSF or autologous reservoir (AR) virus-infected CD4+ cells using lymphocytes from HIV-infected ART suppressed patients. $CD4^+$ depleted T cells from HIV-infected ART suppressed patients were activated with PHA and infected with HIV-1 subtype B clone JR-CSF (FIGS. 16A-16C) or autologous reservoir (AR) virus isolates (FIGS. 16D-16F) and then incubated without (FIGS. 16A, 16D) or with autologous $CD8^+$ T effector cells at E:T ratios of 1:10 (FIGS. 16B, 16E) or 1:1 (FIGS. 16C, 16F) in the absence (No DART) or presence of HIV×CD3 (A32×CD3, 7B2×CD3) or control (7B2×4420, 4420×CD3) DARTs at a concentration of 100 ng/mL for 7 days. 'Combo' indicates a 1:1 cocktail of 7B2×CD3 and A32×CD3 at a total concentration of 100 ng/mL. Each bar represents the log fold reduction of p24 detected in culture supernatants, calculated as the log (p24 of infected target cells only control divided by p24 of the test condition).
Figure 16B:
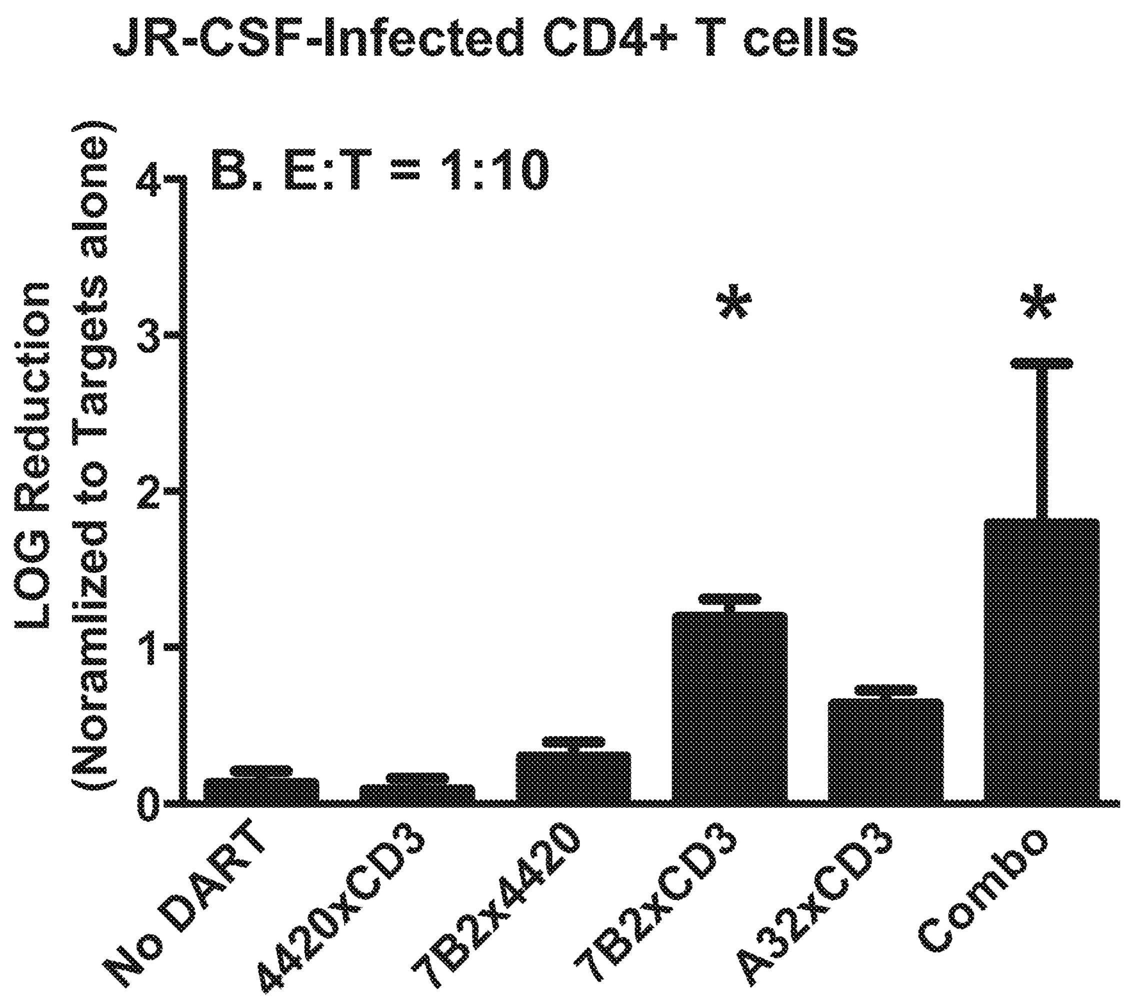
Figure 16C:
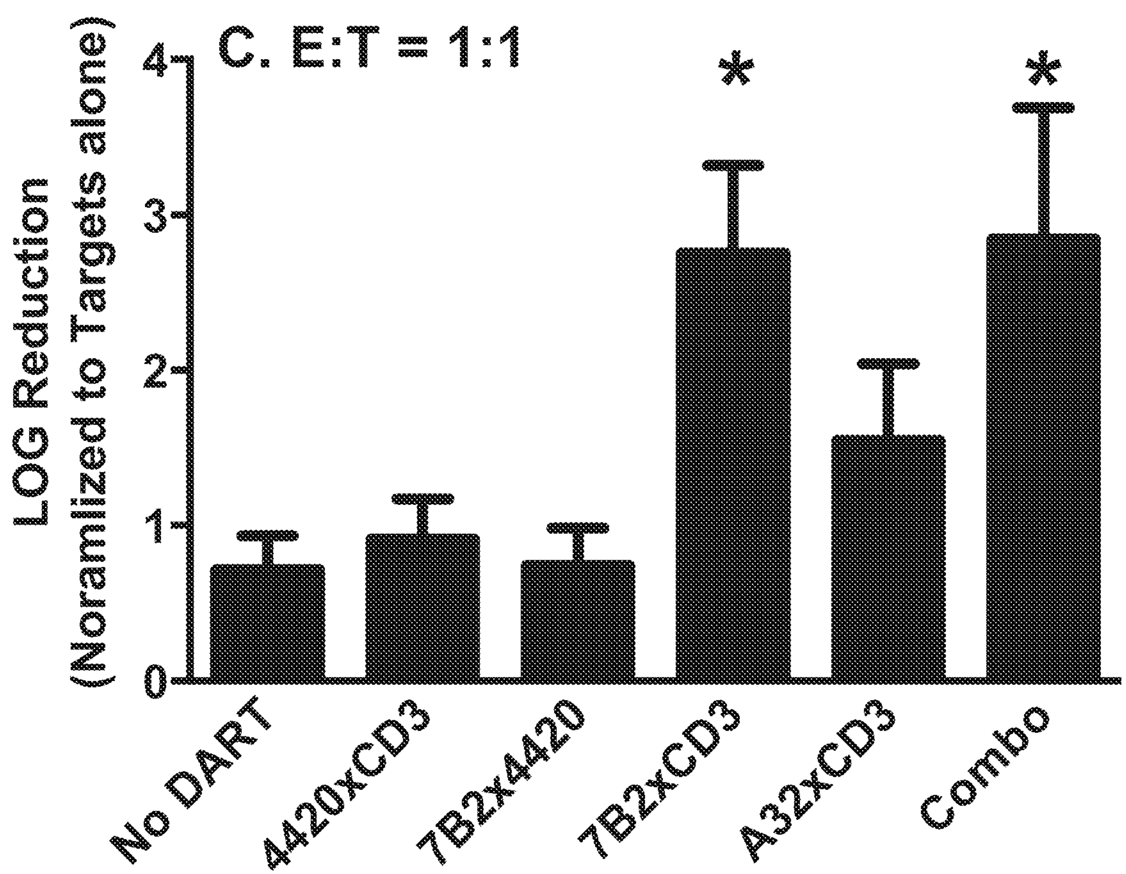
Figure 16D:
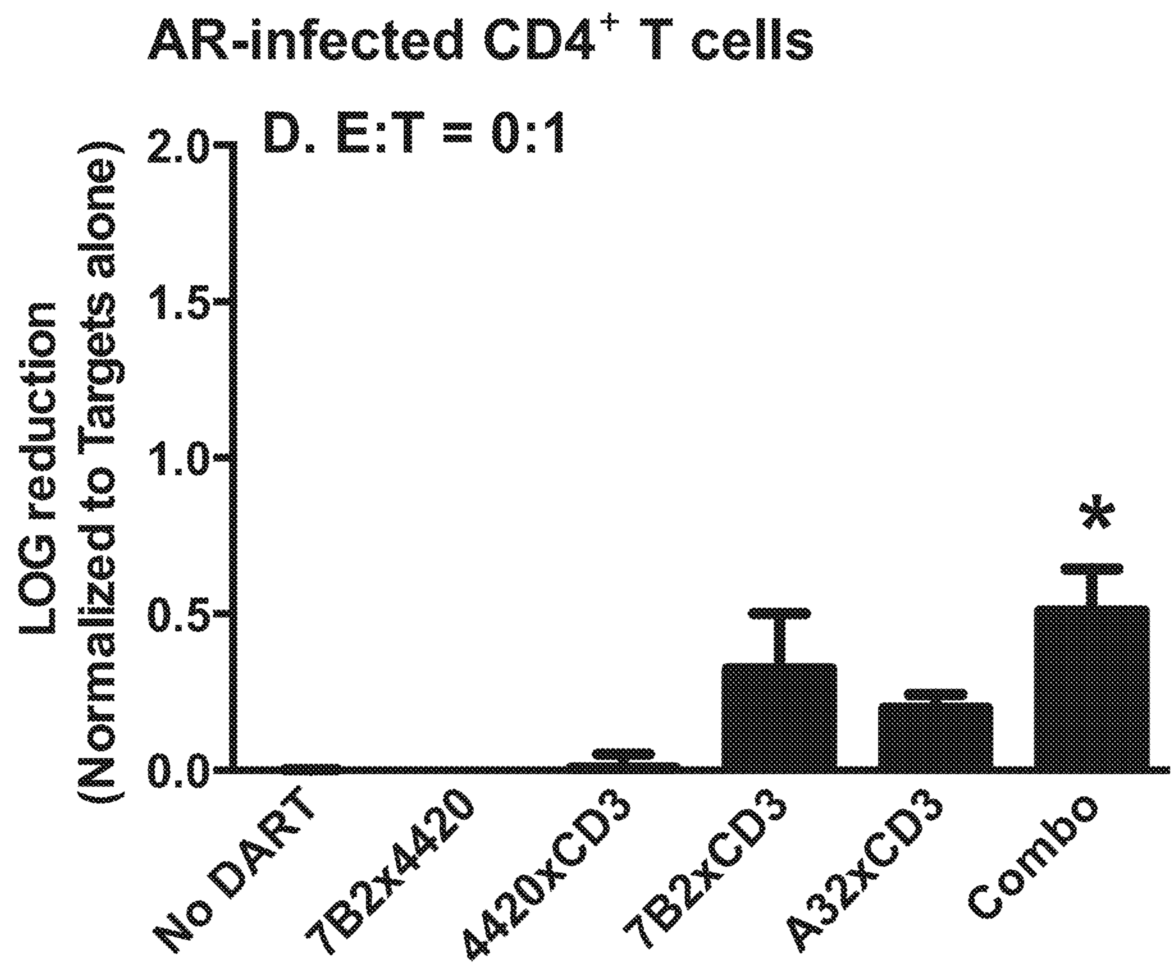
Figure 16E:
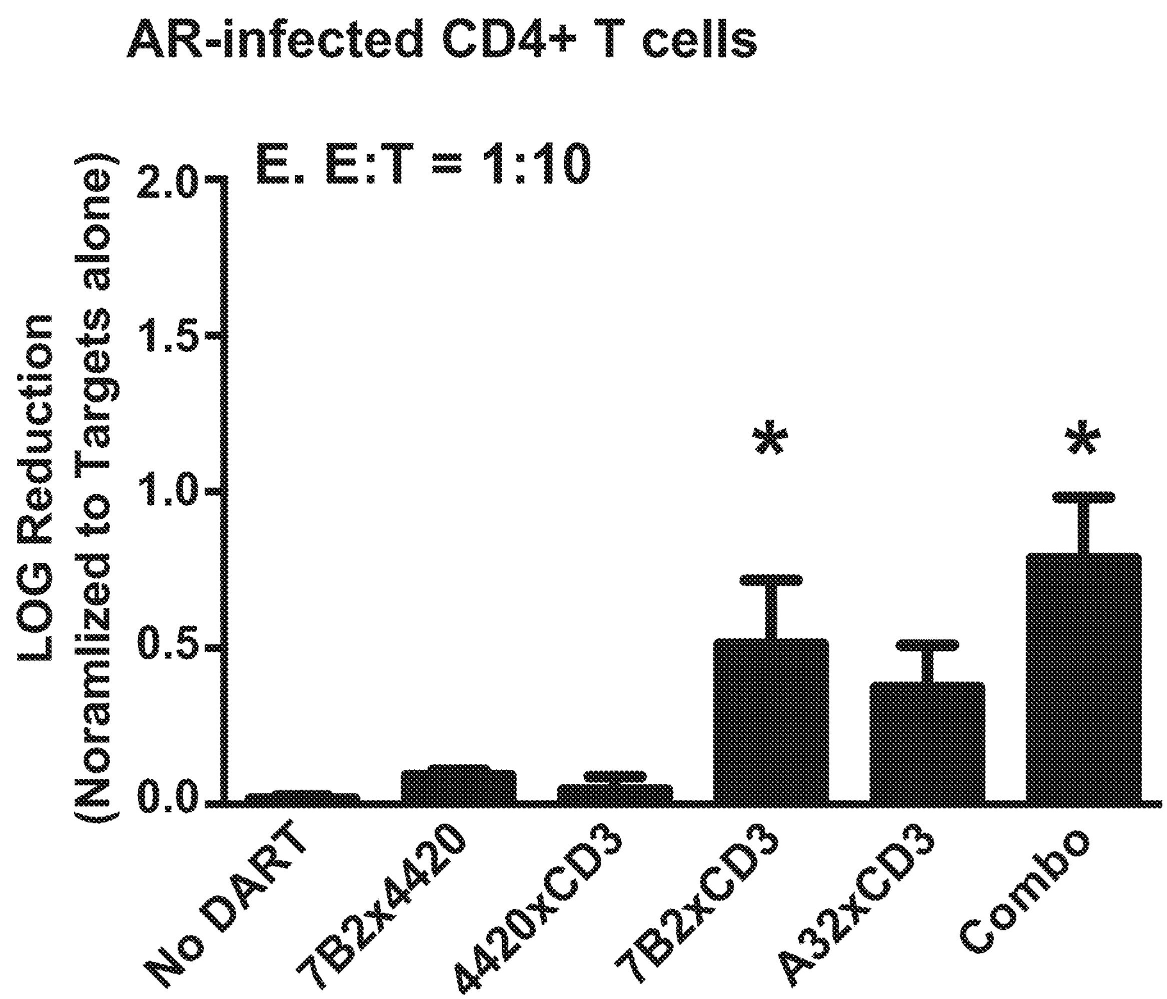
Figure 16F:
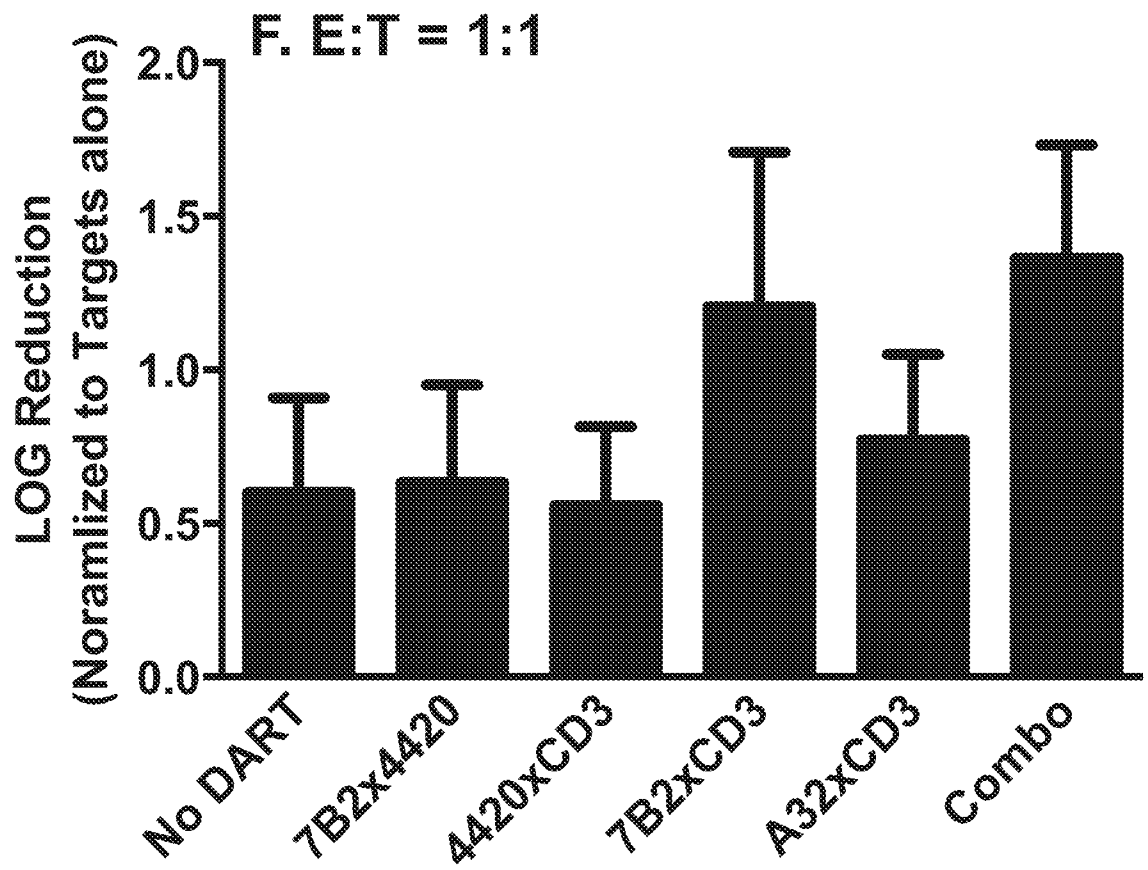
Figure 16G:
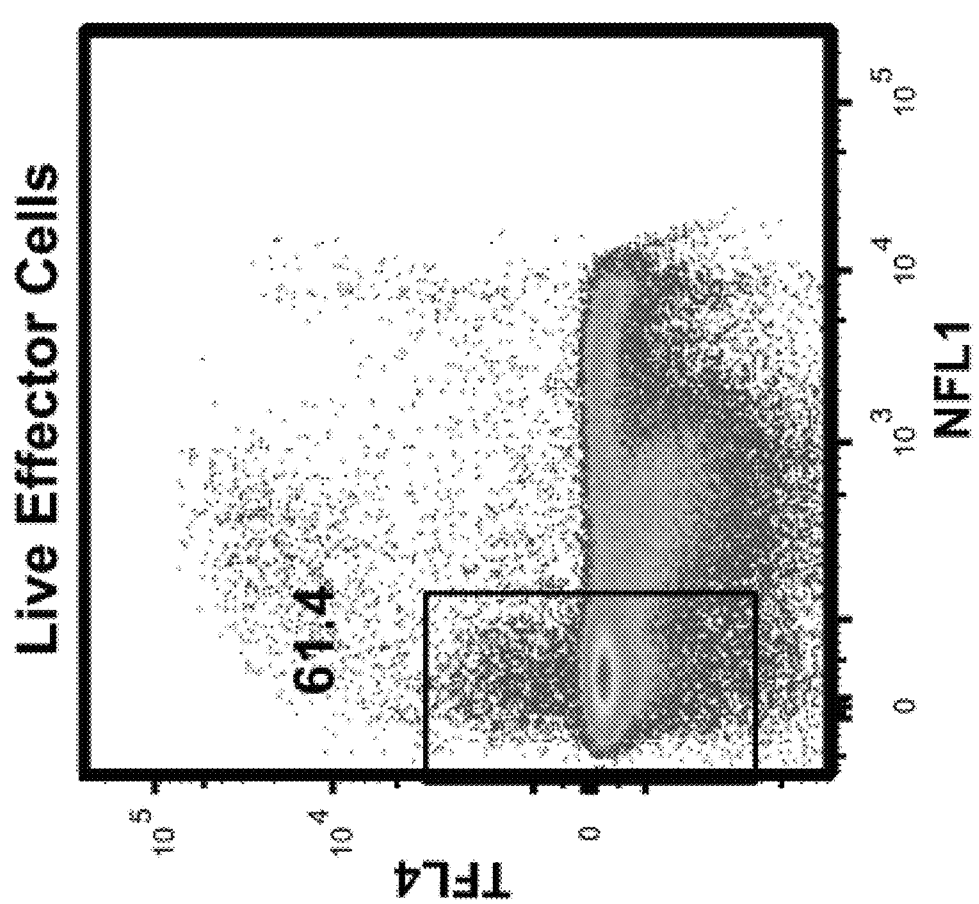
Figure 16G:
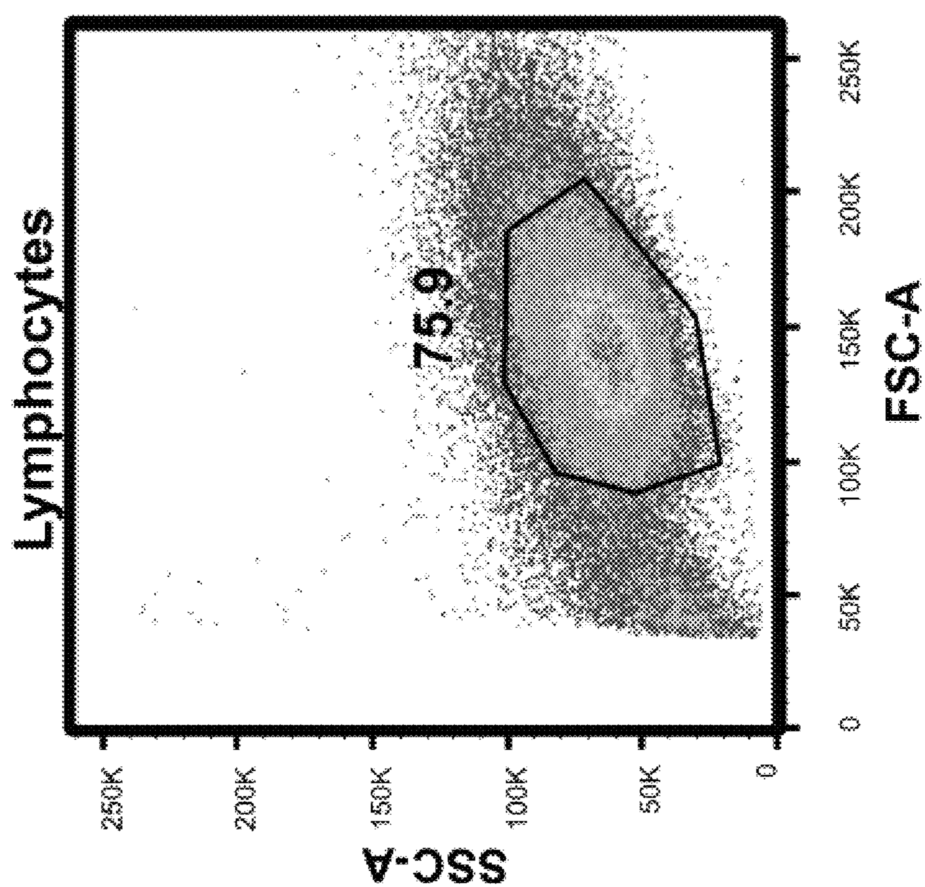
Figure 16G:
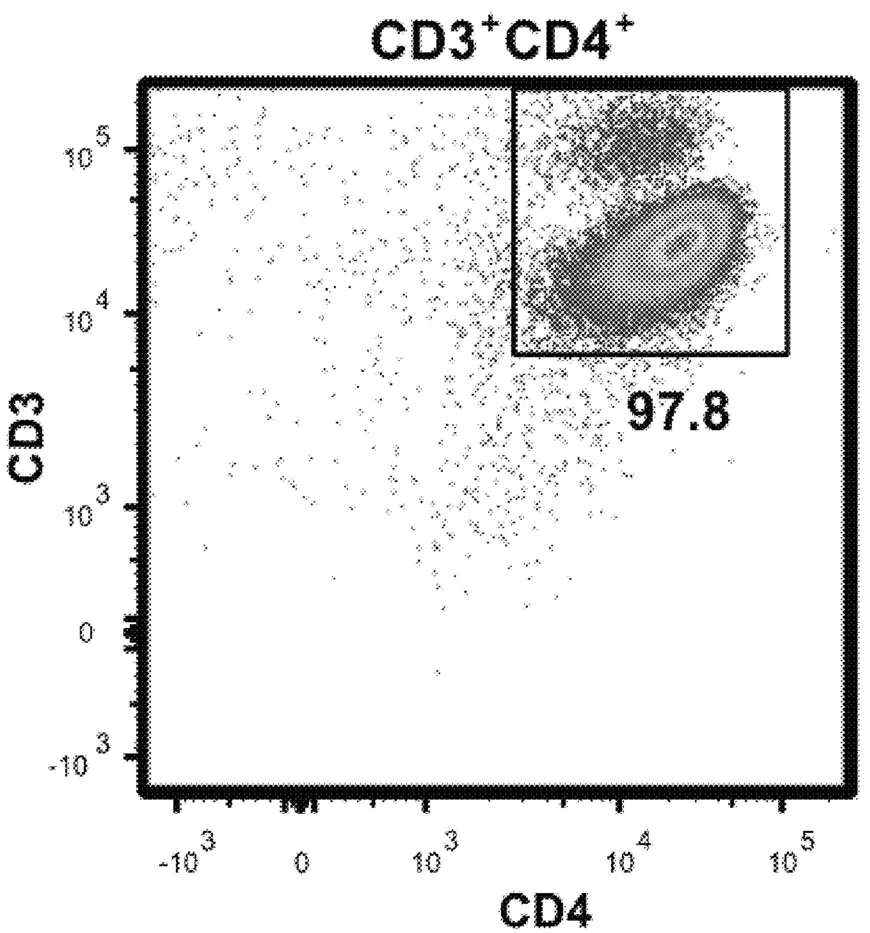
Figure 16G:
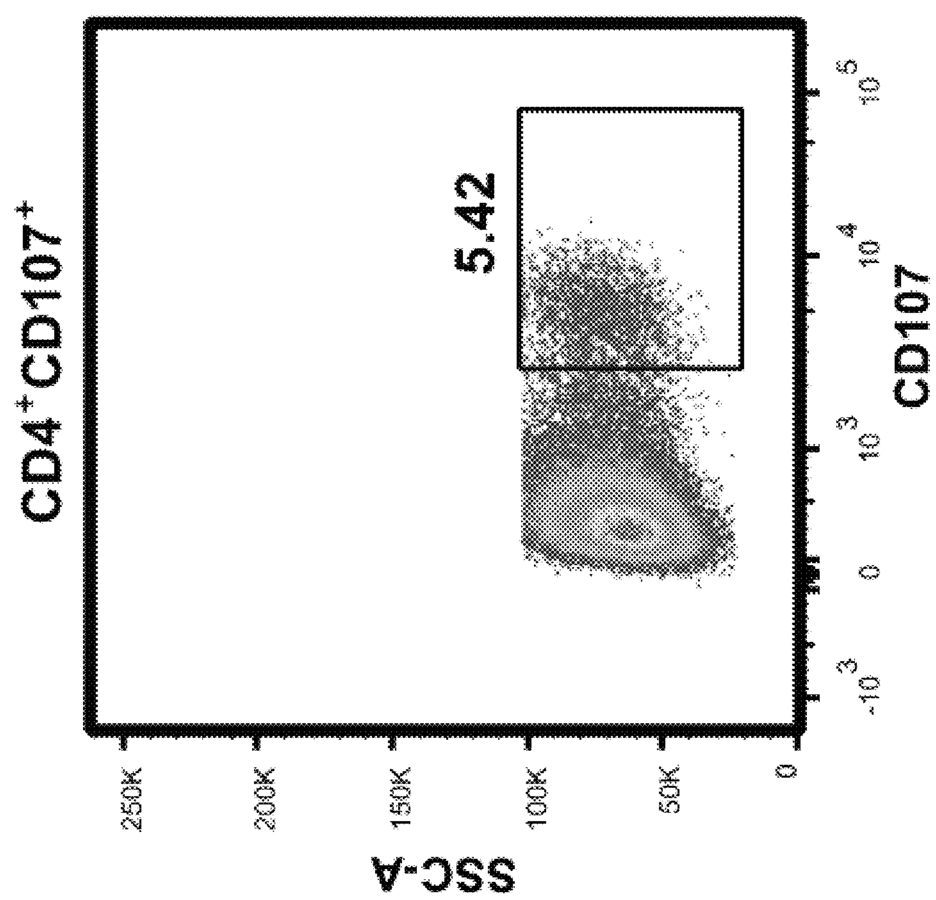
Figure 16H:
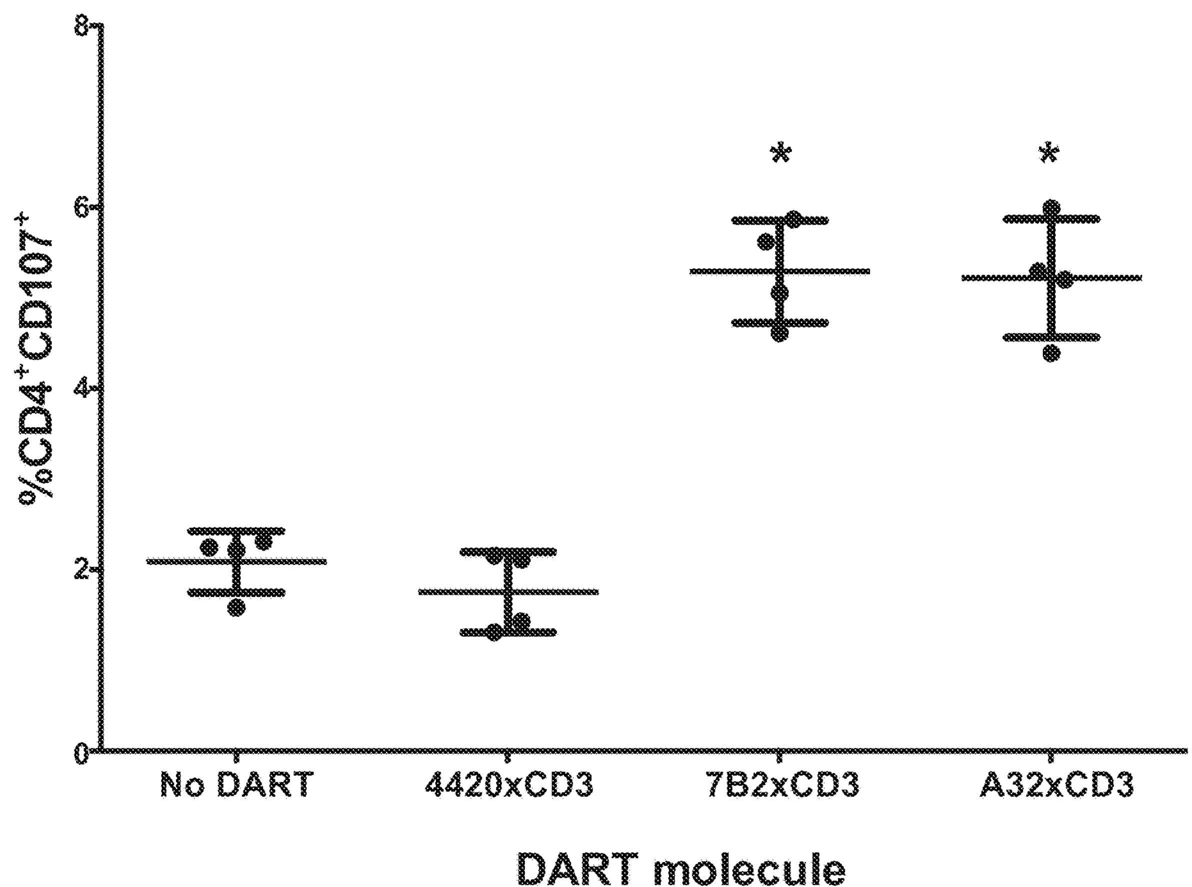

Using the lymphocytes from 8 HIV patients on suppressive ART, viral clearance assays were conducted in which CD4$^{+}$ cells were superinfected with HIV-1 JR-CSF (target cells) and incubated with autologous CD8$^{+}$ cells (effectors) at E:T ratios of 0:1, 1:10 or 1:1 in the absence or presence of 100 ng/mL DARTs for 7 days. HIV×CD3 DART activity occurred even in the absence of added CD8$^{+}$ T cells, indicating, that under these experimental conditions, CD4$^{+}$ T cells may be recruited as effector cells; compared to control, p24 production was reduced by 0.89 log with 7B2×CD3 ($p<0.05$), by 0.32 log with A32×CD3 (p=NS), and by 0.81 with a 1:1 cocktail of both DARTs ($p<0.05$) (FIG. 16A). Indeed, the addition of fully active DARTs led to significantly increased degranulation of CD4+ T cells when in the presence of infected target cells (FIGS. 16G, 16H). The addition of CD8$^{+}$ T cells as effectors resulted in further reductions in p24 levels; compared to the 0.13 log reduction seen with CD8$^{+}$ T cells alone at an E:T of 1:10, p24 production was reduced by 1.2 log with 7B2×CD3 ($p<0.05$), by 0.6 log with A32×CD3 (p=NS), and by 1.8 log with a cocktail of the two DARTs ($p<0.05$) (FIG. 16B). Even more marked reductions were found with the higher E:T ratio of 1:1, where CD8s alone accounted for a 0.7 log reduction, but p24 production was reduced by 2.8 log with 7B2×CD3 ($p<0.05$), by 1.6 log with A32×CD3 (p=NS), and by 2.8 log with a cocktail of the two DARTs ($p<0.05$) (FIG. 16C). Significant reductions were seen even in the absence of any detectable baseline CD8 T cell antiviral activity, and in three cases no virus was able to be recovered following incubation with DARTs (patient 749 with both fully active DARTs, and patients 720 and 725 with 7B2×CD3). The absolute HIV gag p24 antigen values are provided in FIG. 21.

HIV×CD3 DARTs redirect CD8$^{+}$ T-cells to clear autologous reservoir virus (AR)-superinfected CD4$^{+}$ cells using lymphocytes from patients on suppressive ART. The ability of the DARTs to redirect T-cells against target cells expressing Env sequences arising from the latent reservoir through the use of viral clearance assays employing autologous reservoir virus (AR)-infected CD4$^{+}$ target cells from 5 patients (FIGS. 16D-16F) was evaluated. Patient AR virus isolates were generated from pooled supernatants of limiting dilution cultures of mitogen stimulated resting CD4$^{+}$ T cells to reflect the diversity of virus that may be encountered in vivo following reactivation of latent virus. Despite the diversity of the AR virus isolates, DART activity mirrored that seen with JR-CSF-infected target cells. Modest activity was observed with AR-infected target cells in the absence of CD8$^{+}$ effectors (thus attributed to CD4$^{+}$ T cells; FIG. 16D), with p24 production reduced by 0.32 log with 7B2×CD3 and by 0.20 log with A32×CD3 (p=N.S. due to higher variance in response to 7B2×CD3) and by 0.51 log with a 1:1 cocktail of both DARTs ($p<0.05$), whereas no activity was observed with the control DARTs (FIG. 16D). The addition of HIV×CD3 DARTs to a mixture of AR virus-infected CD4+ target cells and autologous CD8+ effector cells led to significantly enhanced reductions in p24 production. At an E:T ratio of 1:10, p24 production was reduced by 0.51 log with 7B2×CD3 ($p<0.05$), by 0.37 log with A32×CD3 and by 0.79 log with a 1:1 cocktail of the two ($p<0.05$), compared to a reduction of only 0.02 log with CD8$^{+}$ cells alone (FIG. 16E). A trend towards decreased p24 production in the presence of HIV×CD3 DARTs was also seen at the higher E:T ratio of 1:1, although the magnitude of the effect was reduced by the variable baseline CD8$^{+}$ activity seen in the absence of DARTs (FIG. 16F). Notably, ex vivo DART activity was observed with lymphocytes from all 5 patients evaluated with at least one of the two HIV×CD3 DARTs, and in all cases with the 1:1 DART cocktail.

HIV×CD3 DARTs Redirect T Cells from HIV-Infected Individuals on Suppressive ART to Clear Virus from Resting CD4' T Cells Following Induction of Latent Virus Expression.

Figure 17A:
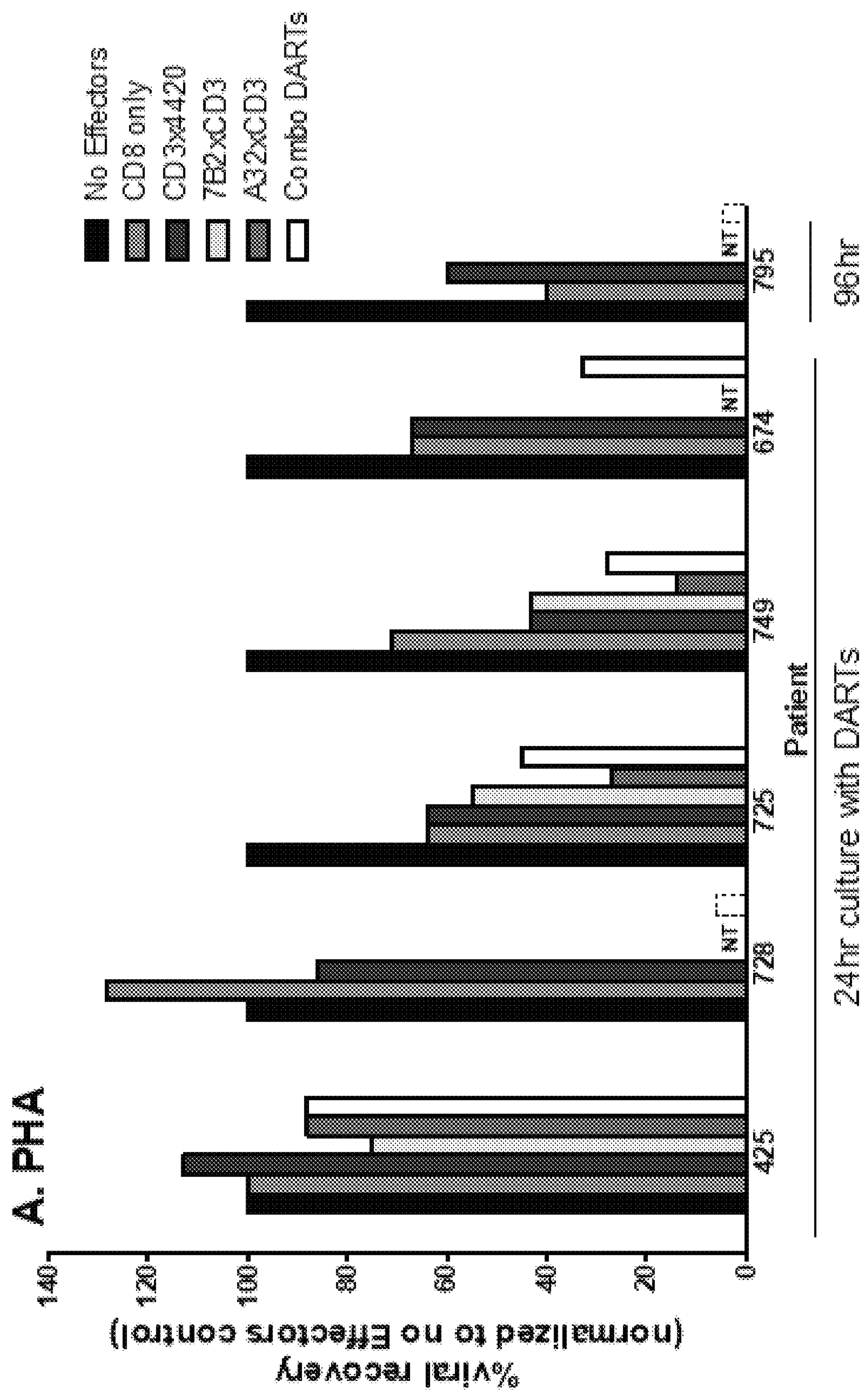
FIGS. 17A-17B show latency clearance assay to assess HIV×CD3 DART redirected $CD8^+$ T-cell activity. Resting $CD4^+$ T cells from HIV-infected, ART suppressed patients were incubated with PHA (FIG. 17A) or vorinostat (FIG. 17B), plated in 12-36 replicate wells depending on the size of the patient's latent reservoir, and co-cultured with autologous $CD8^+$ T cells at an E:T ratio of 1:10 in the absence or presence of HIV×CD3 or control DARTs at 100 ng/mL for 24 hours (or up to 96 hours where indicated), after which DARTs were washed off and CD8-depleted PBMCs from a seronegative donor were added to amplify residual virus. Wells were assessed for the presence or absence of p24 by ELISA at day 15. 'Combo' indicates a 1:1 cocktail of 7B2×CD3 and A32×CD3 at a total concentration of 100 ng/mL. Results are shown as % viral recovery (# of positive wells/total number plated), normalized to a control in which no $CD8^+$ T cells are added. Dashed lines indicate undetectable viral recovery. NT indicated the conditions that were not tested due to low cell availability according to the table shown in FIG. 21.

Ultimately, a reagent used in the "shock and kill" HIV eradication strategy must recognize and clear rare infected cells that are likely to express low levels of antigen as they emerge from latency. A latency clearance assay as previously described (49) was employed. This assay seeks to measure the ability of DARTs to redirect autologous CD8$^{+}$ T cells to reduce viral recovery following induction of resting $CD4^+$ T cells of HIV-infected individuals on suppressive ART. Addition of fully active DARTs or a 1:1 cocktail of A32×CD3 and 7B2×CD3 to a co-culture of $CD8^+$ T cells with PHA-stimulated resting $CD4^+$ T cells at an E:T ratio of 1:10 reduced viral recovery in all 6 out of 6 patients, although the magnitude of reduction varied amongst patients. (FIGS. 17A, 22).

Figure 17B:
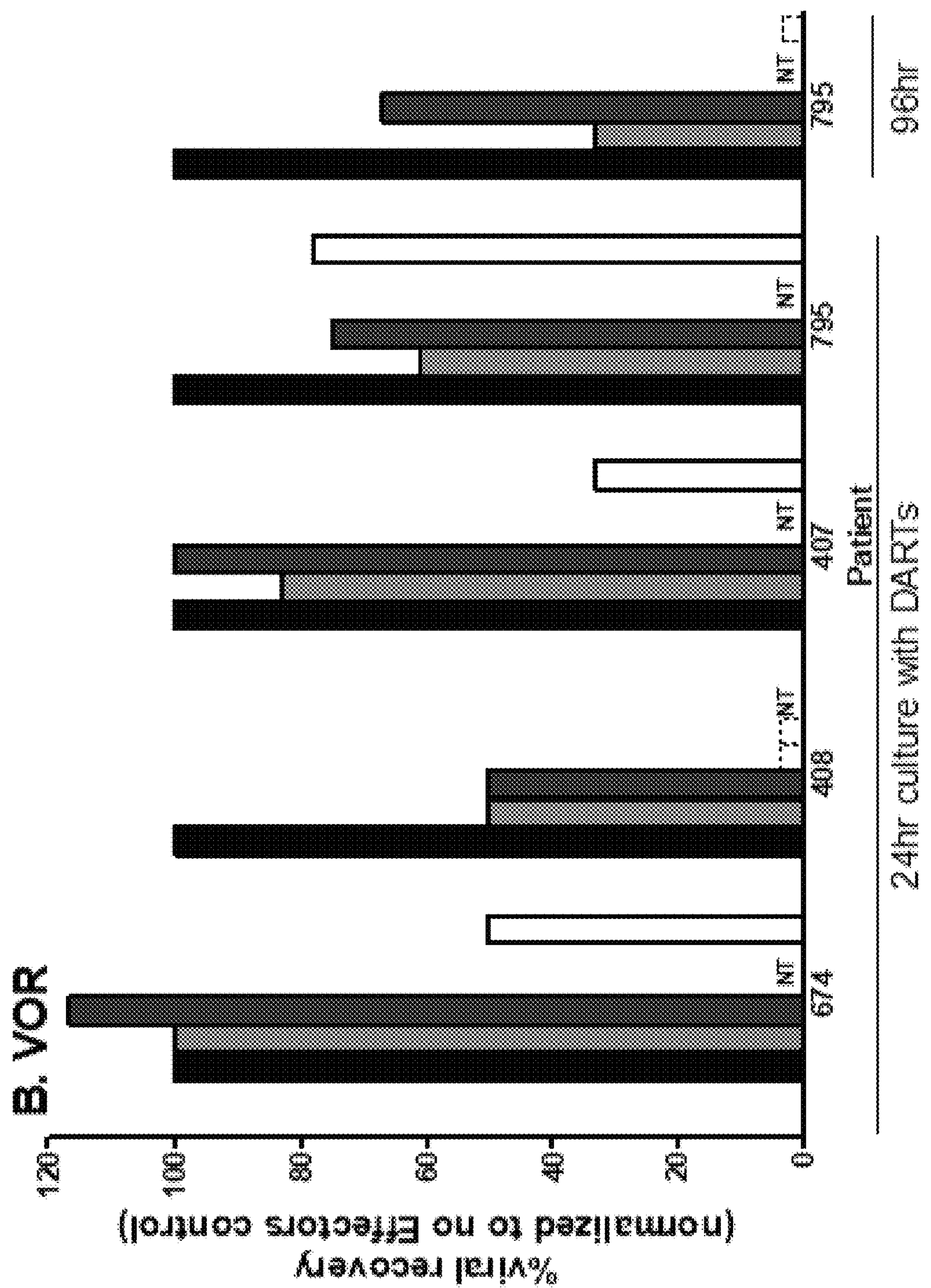

Reversal of HIV latency using maximal mitogen stimulation in vivo is not clinically practical (50). However, the presentation of viral antigen following the reversal of latency with agents that do not result in global T cell activation, such as vorinostat (VOR), may be less robust than that following maximal mitogen stimulation. To evaluate the HIV×CD3 DARTs in a clinically relevant context, a physiologically relevant exposure to VOR that models that obtained following a single 400 mg in vivo dose (18) to induce latent viral envelope expression was used. In this setting, addition of $CD8^+$ cells at an E:T ratio of 1:10 plus fully active DARTs led to a reduction in viral recovery following a 24 hour co-culture period when compared to $CD8^+$ cells without or with control DARTs in 4 of 5 patients tested. In the single patient who did not respond to DARTs after a 24 hour co-culture period (patient 795), extending the co-culture period from 24 hours to 96 hours led to complete ablation of viral recovery (FIGS. 17B, 22).

Discussion

Significant hurdles in the elimination of the latent HIV-1 reservoir include: 1) the limited ability of the immune system to recognize rare HIV-1 infected cells presenting modest levels of HIV antigen prior to or following induction with latency reversing agents (LRA) (38, 51); 2) the presence of $CD8^+$ cytotoxic T lymphocyte escape mutants in the HIV-1 latent reservoir (52); and 3) the low frequency of circulating HIV-specific $CD8^+$ T cells in patients on ART and the necessity to activate them due to inadequate stimuli provided by infected cells (38). Described herein are data that HIV×CD3 DARTs could overcome each of these major obstacles.

HIV×CD3 DARTs with HIV arms derived from the non-neutralizing mAbs A32 and 7B2 were able to recognize HIV-1 Env-expressing cell lines and to elicit redirected T-cell killing activity, even when cell surface Env expression appeared low. In addition, HIV×CD3 DARTs were effective ex vivo in redirecting $CD8^+$ T cells to clear resting $CD4^+$ T cells obtained from aviremic, ART-treated patients following exposure to VOR.

HIV-1 isolates represented in the latent reservoir are reported to include escape mutants generated by the $CD8^+$ T cell responses (52), which may limit the ability of the MHC class I-restricted $CD8^+$ CTL responses induced by natural infection to clear HIV-1 infected cells. The A32 and 7B2 arms of the HIV×CD3 DARTs are based on broadly reactive non-neutralizing anti-HIV mAbs that interact with highly conserved residues in gp120 and gp41, respectively, and efficiently mediate ADCC activity against cells infected with HIV-1 isolates of various subtypes. Of note, the A32 mAb epitope is the earliest one known to be expressed on the surface of infected cells during the syncytia-formation process (53) or following tier 2 virus infection (54) and the 7B2 mAb epitope is accessible on gp41 stumps, which are expressed on the surface of infected cells during budding and retained at the membrane surface when gp120 subunits dissociate (29, 55). These properties are indicative of the accessibility of the A32 and 7B2 epitopes on the surface of infected cells. Importantly, the existence of CTL escape mutants is not a limitation, because CTL epitopes are irrelevant to DART-mediated redirected killing activity. Further, effector T-cells recruited by bispecific molecules like DARTs are polyclonal and not MHC-restricted (33). Consistent with these assertions, A32×CD3 and 7B2×CD3 were effective at redirecting $CD8^+$ T cells from patients to clear $CD4^+$ cells infected by their own autologous reservoir (AR) virus, regardless of the presence of any escape mutations that may have accumulated before initiation of therapy (52). Interestingly, upon in vitro activation of the $CD4^+$ T cells used as target cells, a specific reduction in virus recovery in absence of $CD8^+$ T cells was observed, suggesting that DARTs could also recruit cytotoxic $CD4^+$ T cells under these particular experimental conditions. In line with these, it was found that DARTs induced activation of $CD4^+$ T cells in the presence of Env expressing Jurkat-522 F/Y cells, and were capable of increasing degranulation of $CD4^+$ T cells when co-cultured with infected autologous target cells from HIV positive individuals. Cytotoxic $CD4^+$ T cells have been previously reported in the context of responses to HIV-1 (56) and Cytomegalovirus (57). Further studies will be necessary to determine whether effective DART recruitment and redirection of cytotoxic $CD4^+$ T cells occurs under in vivo settings.

The relative potencies of the A32×CD3 and 7B2×CD3 DARTs varied among the different test systems employed in our studies, most likely due to variations in the characteristics of the Env-expressing target cells and/or effector T-cells. However, whenever one of the DARTs exhibited greater activity than the other, activity similar to that of the more potent DART when combinations of the two DARTs were utilized in the studies with infected patients' cells (FIGS. 16A-16H and 17A-17B) was consistently observed. Thus, combinations of DARTs targeting different HIV epitopes may be an advantageous strategy to maximize both level and breadth of activity, similar to what has been described for combinations of ADCC-mediating (58) or broadly neutralizing anti-HIV-1 mAbs (59, 60).

Eliminating the pool of latently infected cells by HIV-1-specific $CD8^+$ T cell responses is limited by the low frequency of these cells in infected individuals and the need to activate them from the resting state (38). With resting $CD8^+$ T cells from HIV-1 seronegative individuals lacking any previous exposure to HIV-1 antigens, HIV×CD3 DARTs induced degranulation of up to 23% of these resting $CD8^+$ T cells when incubated with the autologous HIV-1 infected target cells destined to be killed. DARTs were also capable of redirecting $CD8^+$ T cells from HIV-1 seropositive individuals who received antiretroviral therapy in viral clearance assays. Therefore, HIV×CD3 DART proteins can effectively recruit and redirect $CD8^+$ T cytotoxic cells independent of previous exposure to HIV antigens, and regardless of any functional impairment that may remain in chronic HIV-1 infection (46, 47, 61).

DART redirected T cell activity against HIV-1 Env-expressing targets was dependent on HIV×CD3 DART concentration, effector:target (E:T) cell ratio and incubation time. The monovalent nature of each of the binding arms of the HIV×CD3 DART molecule ensures that target cell killing depends exclusively upon effector/target cell co-engagement, as has been observed with CD19×CD3 and other DARTs (31, 32, 34). No HIV×CD3 DART-mediated T-cell activation or redirected killing activity was observed in the absence of Env expression on target cells. Similarly, with T-cells from HIV-infected patients on suppressive ART, no T-cell activation was observed in the absence of virus-infected target cells. Because they should elicit cytotoxic activity from circulating T cells only in the proximity of HIV-1 infected Env-expressing target cells, HIV×CD3 DARTs are not expected to elicit widespread systemic effects, such as inflammatory cytokine release, in HIV-infected patients on ART due to the scarcity of the Env-expressing target cells. The specificity of T-cell redirected responses elicited by HIV×CD3 DARTs will be of critical importance clinically, considering that HIV infection induces nonspecific activation of the immune system in both the acute and chronic phases of the disease, in HIV-1 specific T-cell subsets as well as in general CD8+ T cell populations (62-64).

HIV-infected $CD4^+$ T cells expressing cell surface Env are the primary in vivo targets for HIV×CD3 DART-redirected T cell killing activity. Because these target cells also express CD3, the DART molecules could mediate synapses between infected and uninfected $CD4^+$ T cells that, rather than or in addition to redirecting the killing of infected cells, conceivably could facilitate the spread of virus to uninfected cells. However, no evidence to suggest that DARTs enhanced the spread of virus was observed, as DARTs reduced p24 production even in the absence of CD8+ T cells (FIGS. 16A and 16D).

In summary, the experiments described herein demonstrate that HIV×CD3 DARTs, with HIV arms derived from the non-neutralizing A32 and 7B2 mAbs, are specific and potent agents to redirect cytolytic T-cells against target cells consisting of 1) HIV-1 Env-expressing $CD4^+$ cell lines, 2) activated $CD4^+$ cells from seronegative individuals infected with HIV-1 IMCs of different subtypes, 3) activated $CD4^+$ cells from seropositive patients on suppressive ART infected with JR-CSF or autologous reservoir virus, or 4) resting $CD4^+$ cells from HIV-infected patients exposed ex vivo to a T-cell mitogen (phytohemagglutinin, PHA) or latency reversing agent (vorinostat, VOR). Importantly, the studies demonstrated that autologous $CD8^+$ T cells from HIV-infected patients on suppressive ART were efficacious as effector cells in the presence of DARTs. The demonstration of HIV×CD3 DART-mediated T cell killing activity in the presence of vorinostat is particularly notable because it provides evidence of activity against authentic latent virus isolates expressed from HIV-infected patients' cells in a model system designed to mimic potential clinical HIV eradication strategies, similar to earlier findings using ex-vivo expanded CTLs (49). Thus, the disclosed data indicate that HIV×CD3 DARTs are suitable agents for testing in vivo in combination with LRAs in "shock and kill" HIV eradication strategies.

Methods

We have reanalyzed the data using the Dunnett's test for multiple comparisons deemed appropriate due of the relative limited number of samples in our studies. The calculated p values are now indicated in the main text (page 14) and in the legends for FIGS. 5-7. The Methods section for the statistical analyses has also been revised.

Patient Population.

Leukapheresis samples were obtained from HIV seronegative donors or HIV-infected donors with undetectable plasma viremia (<50 copies/mL) on stable ART for at least 6 months, as indicated. Written informed consent was obtained from each patient and the study was approved by the Duke and UNC Biomedical Institutional Review Boards.

Infectious Molecular Clones (IMCs).

HIV-1 IMCs for subtype B BaL, subtype AE CM235 and subtype C 1086.0 were generated with the backbone derived from NHL4-3 isolate as previously described (65, 66). All IMCs expressed the *Renilla* luciferase reporter gene and preserved all nine viral open reading frames. The *Renilla* luciferase reporter gene was expressed under the control of the HIV-1 Tat gene. Upon HIV-1 infection of CD4+ T cells, expression of Tat during HIV-1 replication will induce luciferase expression, which allows quantitation of infected cells by measuring relative luminescence units (RLU).

Construction, Expression, and Purification of HIV×CD3 DARTs.

The DARTs were produced from plasmids that coexpressed two polypeptide chains: one with VL of anti-CD3 linked to VH of anti-HIV; the second with VL of anti-HIV linked to VH of anti-CD3. The carboxy termini of the two polypeptide chains consist of paired oppositely charged E-coil/K-coil dimerization domains, which include an interchain disulfide bond (FIGS. 10A-10C). The HIV arm sequences were derived from the non-neutralizing mAbs, A32 [Genbank accession numbers 3TNM_H and 3TNM_L] and 7B2 [Genbank accession numbers AFQ31502 and AFQ31503], and the CD3 arm sequence was derived from hXR32, a humanized mouse anti-human CD36 mAb (L. Huang, L. S. Johnson, CD3-binding molecules capable of binding to human and nonhuman CD3, U.S. Patent. 20140099318 (2014)). Control DARTs were similarly constructed by replacing either the HIV or CD3 specificity with an irrelevant specificity from an anti-fluorescein mAb (4420) (67) or anti-RSV mAb (palivizumab) (68). DART-encoding sequences were cloned into CET1019AD UCOE vectors (EMD Millipore), transfected into CHO cells and proteins purified as described previously (31). Purified proteins were analyzed by SDS-PAGE (NuPAGE Bis-Tris gel system, Invitrogen) and analytical SEC (TSK GS3000SW×L SE-HPLC, Tosoh Bioscience).

ELISA.

For monospecific binding assays, a MaxiSorp microtiter plate (Nunc) coated with recombinant proteins (human CD3ε/δ heterodimer, JR-FL gp140ΔCF; (69)) in bicarbonate buffer was blocked with 3% BSA and 0.1% Tween-20. DART proteins were applied, followed by sequential addition of biotinylated anti-EK coil antibody and streptavidin-HRP (BD Biosciences). For bispecific binding assays, the plate was coated with JRFL gp140ΔCF and DART application was followed by sequential addition of biotinylated CD3ε/δ and streptavidin-HRP. HRP activity was detected with SuperSignal ELISA Pico chemiluminescent substrate (Thermo Scientific).

SPR Analysis.

HIV×CD3 DART binding to antigens was analyzed by BIAcore 3000 biosensor (GE, Healthcare) as previously described (31, 32). Human CD3ε/δ was immobilized on the CMS sensor chip according to the manufacturer's procedure. DART binding to immobilized CD3 was analyzed to assess the properties of the CD3 arm and HIV-1 Env protein binding to HIV DART captured on immobilized CD3 was analyzed to assess the properties of the HIV arm. JRFL gp140ΔCF was used to assess 7B2×CD3 binding and M.ConS gp140ΔCFI (69) was used to assess A32×CD3 binding. The different Env proteins were utilized because A32×CD3 did not bind efficiently to JR-FL gp140ΔCF and M.ConS gp140ΔCFI lacks the gp41 binding site for 7B2×CD3. Binding experiments were performed in 10 mM HEPES, pH 7.4, 150 mM NaCl, 3 mM EDTA and 0.005% P20 surfactant. Regeneration of immobilized receptor surfaces was performed by pulse injection of 10 mM glycine, pH 1.5. $K_D$ values were determined by a global fit of binding curves to the Langmuir 1:1 binding model (BIA evaluation software v4.1).

Cell Lines.

Jurkat-522 F/Y GF cells, which constitutively express a fusion protein of Copepod Green Fluorescent Protein (copGFP) and Firefly Luciferase (System Biosciences), were generated at Macrogenics from Jurkat-522 F/Y cells by transduction and clone selection. HEK293-D371 cells, which have doxycycline-inducible expression of HIV-1 CM244 (subtype AE) gp140, were obtained from Dr. John Kappes (University of Alabama at Birmingham).

Flow Cytometric Analysis of DART or mAb Binding to Cells.

DARTs at 4 μg/mL were incubated with $10^5$ cells in 200 μL FACS buffer containing 10% human AB serum for 30 minutes at room temperature. After washing, cells were resuspended in 100 μL of 1 μg/mL biotin-conjugated mouse anti-EK antibody (recognizes the E/K heterodimerization region of DART proteins), mixed with 1:500 diluted streptavidin-PE and incubated in the dark for 45 minutes at 2-8° C. Cells were washed, resuspended with FACS buffer, and analyzed with a BD Calibur flow cytometer and FlowJo software (TreeStar, Ashland OR). Binding to IMC-infected $CD4^+$ T cells from normal human donors was conducted as previously described (54) for the A32 and 7B2 mAbs, and with biotin-conjugated mouse anti-EK antibody and 1:500 diluted streptavidin-PE for the HIV×4420 DARTs.

Redirected T-Cell Cytotoxicity Assay Against HIV-1 Env-Expressing Cell Lines and Assessment of T-Cell Activation.

Pan T cells were isolated from healthy human PBMCs with the Dynabeads® Untouched™ Human T Cells Kit (Invitrogen). HIV-1 Env expressing cell lines (1-4×$10^5$ cells/mL) were treated with serial dilutions of DARTs, together with human T cells at an effector:target (E:T) ratio=10:1, or otherwise at varying E:T ratios as indicated, and incubated at 37° C., 5% $CO_2$ overnight. Cytotoxicity was measured by lactate dehydrogenase (LDH) release (CytoTox 96® Non-Radioactive Cytotoxicity Assay, Promega) as described previously (32). With the Jurkat-522 F/Y GF cell line, cytotoxicity was also measured by luminescence using Luciferase-Glo substrate (Promega). Specific lysis was calculated from luminiscence counts (RLU): cytotoxicity (%)=100×(1−(RLU of Sample÷RLU of Control)), where Control=average RLU of target cells incubated with effector cells in the absence of DART. Data were fit to a sigmoidal dose-response function to obtain 50% effective concentration ($EC_{50}$) and percent maximum specific lysis values. T-cell activation was measured by FACS analysis after cells in the assay plate were labeled with CD8-FITC, CD4-APC, and CD25-PE antibodies (BD Biosciences), followed by cell collection by FACS Calibur flow cytometer equipped with acquisition software CellQuest Pro Version 5.2.1 (BD Biosciences). Data analysis was performed using FlowJo software (Treestar, Inc).

Redirected T-Cell Cytotoxicity Assay Against HIV-1 IMC-Infected $CD4^+$ Cells.

Cryopreserved resting PBMC from normal healthy HIV-1 seronegative donors were activated for 72 hours with anti-human CD3 (clone OKT3; eBioscience) and anti-human CD28 (clone CD28.2; BD Pharmingen). Subsequently, a $CD4^+$ enriched cell population (purity>92.3%; average±standard deviation 95.73±2.6%) was obtained by depletion of $CD8^+$ T cells using magnetic beads (Miltenyi Biosciences), spinoculated in presence of the luciferase-expressing IMC representing HIV-1 subtype AE (CM235), B (BaL) or C (1086.C) and cultured for 72 hours. $CD4^+$ infected target cells were incubated with resting $CD8^+$ effector cells (isolated by negative selection from autologous PBMC, $CD8^+$ T cell Isolation Kit, Miltenyi Biosciences) at 33:1, 11:1, 3:1, and 0:1 E:T ratios in the absence or presence of DARTs for 6-48 hours at concentration ranging from 1,000 to 0.0001 ng/mL. Uninfected and infected target cells alone were included as additional controls. Each condition was tested in duplicate. After incubation, ViviRen™ Live Cell Substrate (Promega) was added and RLU measured on a luminometer; percentage specific lysis (% SL) of target cells was determined as described previously (58).

T-Cell Degranulation (CD107) Assay.

As described for the cytotoxicity assay with HIV-1 IMC-infected cells as targets, activated $CD4^+$ cells infected with HIV-1 BaL IMC were plated with resting $CD8^+$ effector cells at a 33:1 E:T ratio in the absence or presence of 1 ng/mL DARTs and incubated for 6 hour. For the CD4 T cell degranulation, activated $CD4^+$ T cells were either infected with JR-CSF and labeled with the viability (NFL1) and target specific (TFL4) markers routinely utilized in our ADCC assay (70) or added to targets as effectors at a 10:1 ratio prior to addition of DARTs. Each condition was tested in duplicate. CD107 PE-Cy5 (clone H4A3; eBioscience) was titered and added during the last six hours of the incubation along with Monensin solution (BD GolgiStop) (71). A panel of antibodies consisting of LIVE/DEAD Aqua stain, anti-CD3 APC-H7 (clone SK7; BD Pharmingen), anti-CD4 BV605 (clone OKT4; Biolegend), anti-CD8 BV650 (clone RPA-T8; Biolegend) was used to detect $CD107^+$ $CD8^+$ T cells. After washing and fixation, samples were acquired on a custom made LSRII (BD Bioscience, San Jose, CA) within the next 24 hours. A minimum of 300,000 total viable events was acquired for each test. The analysis of the data was performed using the Flow-Jo software (Treestar, Ashland, OR).

T-Cell Viability and Activation Assays.

$CD8^+$ T cells and CD8 depleted PBMCs obtained from HIV infected ART suppressed patients were plated at 5×$10^4$ cells per well in 96 well plates with 100 ng/mL of the indicated DART. Cells were cultured in 0.2 mL of cIMDM media supplemented with 10% FBS, 1% Penicillin/Streptomycin and 5U/mL IL-2 for 7 days, and then stained with the following antibodies: HLA-DR-PerCP (clone L243), CD25-PE (clone M-A251), CD8-FITC (clone HIT8a), CD8-PE (clone HIT8a), CD4-FITC (clone RPA-T4), and Annexin V-PE and 7-AAD (all BD biosciences, San Jose, CA).

Redirected T-Cell Viral Clearance Assay.

$CD8^+$ T-cells were isolated from PBMCs by positive selection (EasySep human $CD8^+$ Selection Kit, Stem Cell). CD8-depleted PBMCs were first activated with 2 μg/mL of PHA (Remel, Lenexa, KS) and 60U/mL of IL-2, and then infected by spinoculation at 1200×g for 90 minutes with either JR-CSF or autologous reservoir virus (AR) at an MOI of 0.01 as previously described (47). AR virus was obtained from pooled supernatants of replicate wells from outgrowth assays of resting CD4+ T-cells for each patient performed as previously described (72). Fifty-thousand (5×$10^4$) targets/well were co-cultured with $CD8^+$ T cells in triplicate at the indicated E:T ratio in the absence or presence of 100 ng/mL of DART in 0.2m of cIMDM media supplemented with 10% FBS, 1% Penicillin/Streptomycin and 5 U/mL IL-2. For experiments performed in the presence of antiretrovirals (ARVs), 24 hours after spinoculation cells were washed and 104 of raltegravir and 404 of abacavir were added, and then DARTs and $CD8^+$ T-cells were added to cultures. Supernatant was assayed on day 7 by p24 ELISA (ABL, Rockville, MD). Results are calculated as the log (p24 of infected target cells only control divided by p24 of the test condition).

Latency Clearance Assay (LCA).

The reduction of virus recovery from CD4+ infected cells was assessed by a standard quantitative viral outgrowth assay using the resting CD4+ T cells of aviremic, ART-treated patients, following the addition of antiviral effector cells and/or molecules, as previously described (49). In this case the LCA was used to model the ability of DARTs to clear virus emerging from the latent reservoir under clinically and pharmacologically relevant conditions. Resting CD4+ T-cells were isolated from a leukapheresis product as previously described (72) and exposed to PHA (4 μg/mL) and IL-2 (60U/mL) for 24 hours or vorinostat (VOR) (335 nM, 6 hours) (Merck Research Laboratories), and plated at 0.5 to $1\times10^6$ cells/well in 12 to 36 replicate wells depending on the size of the reservoir. The VOR was then washed off and CD8s added at an E:T of 1:10 as well as 100 ng/mL of the indicated DART. Cells were co-cultured for 24 hours (unless specified otherwise) following which the DART proteins were washed off and allogeneic CD8-depleted PBMCs from an HIV negative donor were added to amplify residual virus. Supernatant was assayed for the presence of p24 antigen on day 15 for each well. Results are calculated as % viral recovery [(# of positive wells/total number plated)×100], normalized to a control in which no CD8+ T cells are added.

Statistical Analysis.

Statistical comparisons between groups were analyzed using the Dunnett's test for multiple comparisons using GraphPad Prism Softward (La Jolla, CA); p values<0.05, calculated with Dunnett correction for multiple comparisons, were considered significant. Dunnett's test for multiple comparisons was deemed appropriate due to the relative limited number of samples in the studies.

References for Example 6

1. Chun T-W et al. In vivo fate of HIV-1-infected T cells: Quantitative analysis of the transition to stable latency. *Nat Med.* 1995; 1(12):1284-1290.
2. Chun T-W et al. Quantification of latent tissue reservoirs and total body viral load in HIV-1 infection. *Nature.* 1997; 387(6629):183-188.
3. Finzi D et al. Identification of a reservoir for HIV-1 in patients on highly active antiretroviral therapy. *Science.* 1997; 278(5341):1295-1300.
4. Wong J K. Recovery of Replication-Competent HIV Despite Prolonged Suppression of Plasma Viremia. *Science.* 1997; 278(5341):1291-1295.
5. Pierson T C et al. Molecular Characterization of Preintegration Latency in Human Immunodeficiency Virus Type 1 Infection. *J Virol.* 2002; 76(17):8518-8531.
6. Pomerantz R J. Reservoirs of Human Immunodeficiency Virus Type 1: The Main Obstacles to Viral Eradication. *Clin Infect Dis.* 2002; 34(1):91-97.
7. Chomont N et al. HIV reservoir size and persistence are driven by T cell survival and homeostatic proliferation. *Nat Med.* 2009; 15(8):893-900.
8. Bosque A, Famiglietti M, Weyrich A S, Goulston C, Planelles V. Homeostatic Proliferation Fails to Efficiently Reactivate HIV-1 Latently Infected Central Memory CD4+ T Cells. *PLoS Pathog.* 2011; 7(10): e 1002288.
9. Soriano-Sarabia N et al. Quantitation of Replication-Competent HIV-1 in Populations of Resting CD4+ T Cells. *J Virol.* 2014; 88(24):14070-14077.
10. Palmer S et al. New Real-Time Reverse Transcriptase-Initiated PCR Assay with Single-Copy Sensitivity for Human Immunodeficiency Virus Type 1 RNA in Plasma. *J Clin Microbiol.* 2003; 41(10):4531-4536.
11. Palmer S et al. Low-level viremia persists for at least 7 years in patients on suppressive antiretroviral therapy. *Proc Natl Acad Sci USA.* 2008; 105(10):3879-3884.
12. Dinoso J B et al. Treatment intensification does not reduce residual HIV-1 viremia in patients on highly active antiretroviral therapy. *Proc Natl Acad Sci USA.* 2009; 106(23):9403-9408.
13. Gandhi R T et al. No Evidence for Decay of the Latent Reservoir in HIV-1-Infected Patients Receiving Intensive Enfuvirtide-Containing Antiretroviral Therapy. *J Infect Dis.*
2010; 201:293-296.
14. Davey R T et al. HIV-1 and T cell dynamics after interruption of highly active antiretroviral therapy (HAART) in patients with a history of sustained viral suppression. *Proc Natl Acad Sci USA.* 1999; 96(26): 15109-15114.
15. Carcelain G et al. Transient Mobilization of Human Immunodeficiency Virus (HIV)-Specific CD4 T-Helper Cells Fails To Control Virus Rebounds during Intermittent Antiretroviral Therapy in Chronic HIV Type 1 Infection. *J Virol.* 2001; 75(1):234-241.
16. Rothenberger M K et al. Large number of rebounding/founder HIV variants emerge from multifocal infection in lymphatic tissues after treatment interruption. *Proc Natl Acad Sci USA.*
2015; pii:201414926 [Epub ahead of print].
17. Robb M L, Kim J H. Shot in the HAART: vaccine therapy for HIV. *The Lancet* infectious diseases. 2014; 14(4):259-260.
18. Archin N M et al. Administration of vorinostat disrupts HIV-1 latency in patients on antiretroviral therapy. *Nature.* 2012; 487(7408):482-485.
19. Denton P W et al. Targeted cytotoxic therapy kills persisting HIV infected cells during ART. *PLoS Pathog.* 2014; 10(1):e1003872.
20. Ho Y-C et al. Replication-Competent Noninduced Proviruses in the Latent Reservoir Increase Barrier to HIV-1 Cure. *Cell.* 2013; 155(3):540-551.
21. Bullen C K, Laird G M, Durand C M, Siliciano J D, Siliciano R F. New ex vivo approaches distinguish effective and ineffective single agents for reversing HIV-1 latency in vivo. *Nat Med.* 2014; 20(4):425-429.
22. Cillo A R et al. Quantification of HIV-1 latency reversal in resting CD4+ T cells from patients on suppressive antiretroviral therapy. *Proc Natl Acad Sci USA.* 2014; 111(19):7078-7083.
23. Pincus S H. Therapeutic potential of anti-HIV immunotoxins. Antiviral research. 1996; 33(1):1-9.
24. Davey R T et al. Use Of Recombinant Soluble Cd4 *Pseudomonas* Exotoxin, A Novel Immunotoxin, For Treatment Of Persons Infected With Human Immunodeficiency Virus. *J Infect Dis.* 1994; ! 170 (November): 1180-1188.
25. Bera T K, Kennedy P E, Berger E A, Barbas CFI, Pastan I. Specific killing of HIV-infected lymphocytes by a recombinant immunotoxin directed against the HIV-1 envelope glycoprotein. Molecular Medicine. 1998; 4(6): 384.
26. Denton P W et al. Generation of HIV latency in humanized BLT mice. *J Virol.* 2012; 86(1):630-634.
27. Pollara J et al. Epitope Specificity of Human Immunodeficiency Virus-1 Antibody Dependent Cellular Cytotoxicity [ADCC] Responses. *Curr HIV Res.* 2013; 11(8):378-387.

28. Acharya P et al. Structural Definition of an Antibody-Dependent Cellular Cytotoxicity Response Implicated in Reduced Risk for HIV-1 Infection. *J Virol.* 2014; 88(21): 12895-12906.

29. Pincus S H et al. In Vivo Efficacy of Anti-Glycoprotein 41, But Not Anti-Glycoprotein 120, Immunotoxins in a Mouse Model of HIV Infection. *J Immunol.* 2003; 170: 2236-2241.

30. Craig R B, Summa C M, *Corti* M, Pincus S H. Anti-HIV Double Variable Domain Immunoglobulins Binding Both gp41 and gp120 for Targeted Delivery of Immunoconjugates. *PLoS ONE.* 2012; 7(10):e46778.

31. Johnson S et al. Effector Cell Recruitment with Novel Fv-based Dual-affinity Re-targeting Protein Leads to Potent Tumor Cytolysis and in Vivo B-cell Depletion. *J Mol Biol.* 2010; 399(3):436-449.

32. Moore P A et al. Application of dual affinity retargeting molecules to achieve optimal redirected T-cell killing of B-cell lymphoma. *Blood.* 2011; 117(17):4542-4551.

33. Nagorsen D, Baeuerle P A. Immunomodulatory therapy of cancer with T cell-engaging BiTE antibody blinatumomab. *Experimental Cell Research.* 2011; 317(9):1255-1260.

34. Chichili G R et al. A CD3×CD123 bispecific DART for redirecting host T cells to myelogenous leukemia: Preclinical activity and safety in nonhuman primates. *Sci Transl Med.* 2015; 7(289):289ra82.

35. Topp M S et al. Phase I I Trial of the Anti-CD19 Bispecific T Cell-Engager Blinatumomab Shows Hematologic and Molecular Remissions in Patients With Relapsed or Refractory B-Precursor Acute Lymphoblastic Leukemia. *J Clin Oncol.* 2014; 32(36):4134-4140.

36. Topp M S et al. Safety and activity of blinatumomab for adult patients with relapsed or refractory B-precursor acute lymphoblastic leukaemia: a multicentre, single-arm, phase 2 study. *Lancet Oncol.* 2014; 16:57-66.

37. Rader C. DARTs take aim at BiTEs. Blood. 2011; 117(17):4403-4404.

38. Shan L et al. Stimulation of HIV-1-Specific Cytolytic T Lymphocytes Facilitates Elimination of Latent Viral Reservoir after Virus Reactivation. *Immunity.* 2012; 36(3): 491-501.

39. Moore J P et al. Exploration of antigenic variation in gp120 from clades A through F of human immunodeficiency virus type 1 by using monoclonal antibodies. *J Virol.* 1994; 68(12):8350-8364.

40. Guan Y et al. Diverse specificity and effector function among human antibodies to HIV-1 envelope glycoprotein epitopes exposed by CD4 binding. *Proc Natl Acad Sci USA.* 2013; 110(1):E69-78.

41. Veillette M et al. Interaction with Cellular CD4 Exposes HIV-1 Envelope Epitopes Targeted by Antibody-Dependent Cell-Mediated Cytotoxicity. *J Virol.* 2014; 88(5): 2633-2644.

42. Zhang M-Y et al. Identification and characterization of a broadly cross-reactive HIV-1 human monoclonal antibody that binds to both gp120 and gp41. *PLoS ONE.* 2012; 7(9):e44241.

43. Wyatt R et al. Involvement of the V1N2 variable loop structure in the exposure of human immunodeficiency virus type 1 gp120 epitopes induced by receptor binding. *J Virol.* 1995; 69(9):5723-5733.

44. Sanders R W et al. A next-generation cleaved, soluble HIV-1 Env Trimer, BG505 SOSIP.664 gp140, expresses multiple epitopes for broadly neutralizing but not non-neutralizing antibodies. *PLoS Pathog.* 2013; 9(9): e 1003618.

45. Cao J, Park I W, Cooper A, Sodroski J. Molecular determinants of acute single-cell lysis by human immunodeficiency virus type 1. *J Virol.* 1996; 70(3):1340-1354.

46. Trautmann L, Janbazian L, Chomont N, The E. Upregulation of PD-1 expression on HIV-specific CD8 T cells leads to reversible immune dysfunction. *Nat Med.* 2006; 12(10):1198-1202.

47. Blackburn S D et al. Coregulation of CD8+ T cell exhaustion by multiple inhibitory receptors during chronic viral infection. *Nat Immunol.* 2008; 10(1):29-37.

48. Groux H. Activation-induced death by apoptosis in CD4+ T cells from human immunodeficiency virus-infected asymptomatic individuals. *J Exp Med.* 1992; 175 (2):331-340.

49. Sung J A et al. *Expanded Cytotoxic T-Cell Lymphocytes Target the Latent Hiv Reservoir. J Infect Dis.* 2015; 1-15.

50. Van Praag R M E et al. OKT3 and IL-2 Treatment for Purging of the Latent HIV-1 Reservoir in Vivo Results in Selective Long-Lasting CD4+ T Cell Depletion—Springer. *J Clin Immunol.* 2001; 21(3):218-226.

51. Durand C M, Blankson J N, Siliciano R F. Developing strategies for HIV-1 eradication. *Trends Immunol.* 2012; 33(11):554-562.

52. Deng K et al. Broad CTL response is required to clear latent HIV-1 due to dominance of escape mutations. *Nature.* 2015; 517(7534):381-385.

53. Finnegan C M, Berg W, Lewis G K, DeVico A L. Antigenic properties of the human immunodeficiency virus envelope during cell-cell fusion. *J Virol.* 2001; 75(22):11096-11105.

54. Ferrari G et al. An HIV-1 gp120 envelope human monoclonal antibody that recognizes a C1 conformational epitope mediates potent antibody-dependent cellular cytotoxicity (ADCC) activity and defines a common ADCC epitope in human HIV-1 serum. *J Virol.* 2011; 85(14): 7029-7036.

55. Moore P L et al. Nature of nonfunctional envelope proteins on the surface of human immunodeficiency virus type 1. *J Virol.* 2006; 80(5):2515-2528.

56. Johnson S et al. Cooperativity of HIV-Specific Cytolytic CD4 T Cells and CD8 T Cells in Control of HIV Viremia. *J Virol.* 2015; 89(15):7494-7505.

57. Casazza J P et al. Acquisition of direct antiviral effector functions by CMV-specific CD4+T lymphocytes with cellular maturation. *J Exp Med.* 2006; 203(13):2865-2877.

58. Pollara J et al. HIV-1 Vaccine-Induced C1 and V2 Env-Specific Antibodies Synergize for Increased Antiviral Activities. *J Virol.* 2014; 88(14):7715-7726.

59. Shingai M et al. Antibody-mediated immunotherapy of macaques chronically infected with SHIV suppresses viraemia. *Nature.* 2013; 503(7475):277-280.

60. Barouch D H et al. Therapeutic efficacy of potent neutralizingHIV-1-specific monoclonal antibodies inSHIV-infected rhesus monkeys. *Nature.* 2013; 503 (7475):224-228.

61. Yamamoto T et al. Surface expression patterns of negative regulatory molecules identify determinants of virus-specific CD8+ T-cell exhaustion in HIV infection. *Blood.* 2011; 117(18):4805-4815.

62. Giorgi J V et al. Elevated levels of CD38+CD8+ T cells in HIV infection add to the prognostic value of low CD4+ T cell levels: results of 6 years of follow-up. The Los Angeles Center, Multicenter AIDS Cohort Study. JAcquir Immune Defic Syndr. 1993; 6(8):904-912.

63. Perfetto S P et al. CD38 expression on cryopreserved CD8+ T cells predicts HIV disease progression. *Cytometry*. 1998; 33(2):133-137.
64. Vinikoor M J et al. Antiretroviral Therapy Initiated During Acute HIV Infection Fails to Prevent Persistent T-Cell Activation. *JAcquir Immune Defic Syndr.* 2013; 62(5):505-508.
65. Edmonds T G et al. Replication competent molecular clones of HIV-1 expressing *Renilla* luciferase facilitate the analysis of antibody inhibition in PBMC. Virology. 2010; 408(1):1-13.
66. Adachi A et al. Production of acquired immunodeficiency syndrome-associated retrovirus in human and non-human cells transfected with an infectious molecular clone. *J Virol.* 1986; 59(2):284-291.
67. Kranz D M, Voss E W. Partial elucidation of an anti-hapten repertoire in BALB/c mice: comparative characterization of several monoclonal anti-fluorescyl antibodies. *Mol Immunol.* 1981; 18(10):889-898.
68. Johnson S et al. Development of a Humanized Monoclonal Antibody (MEDI-493) with Potent In Vitro and In Vivo Activity against Respiratory Syncytial Virus. *J Infect Dis.* 1997; 176 (November): 1215-1224.
69. Liao H-X et al. A group M consensus envelope glycoprotein induces antibodies that neutralize subsets of subtype B and C HIV-1 primary viruses. *Virology.* 2006; 353:268-282.
70. Pollara J et al. High-throughput quantitative analysis of HIV-1 and SIV-specific ADCC-mediating antibody responses. *Cytometry A.* 2011; 79A(8):603-612.
71. Betts M R et al. Sensitive and viable identification of antigen-specific CD8+ T cells by a flow cytometric assay for degranulation. *J Immunol Methods.* 2003; 281(1-2): 65-78.
72. Archin N M et al. Valproic acid without intensified antiviral therapy has limited impact on persistent HIV infection of resting CD4+ T cells. *AIDS.* 2008; 22(10): 1131-1135.

What is claimed is:

1. A bispecific molecule comprising a first polypeptide chain and a second polypeptide chain covalently bonded to one another, wherein:

(I) the first polypeptide chain comprises in the N- to C-terminal direction:

(i) a domain (A) comprising a binding region of the light chain variable domain of a first immunoglobulin (VL1) comprising the VL CDR3, CDR2 and CDR1 of HIV-1 antibody A32 (SEQ ID NO:78) or 7B2 (SEQ ID NO: 55);

(ii) a domain (B) comprising a binding region of a heavy chain variable domain of a second immunoglobulin (VH2) comprising the VH CDR3, CDR2 and CDR1 of an antibody specific for an epitope of CD3 or CD16, wherein domains (A) and (B) are separated from one another by a peptide linker 1; and (iii) a domain (C) comprising a heterodimer promoting domain including a K coil or E coil; wherein the heterodimer promoting domain (C) and domain (B) are separated by a peptide linker 2;

(II) the second polypeptide chain comprises in the N- to C-terminal direction:

(i) a domain (D) comprising a binding region of a light chain variable domain of the second immunoglobulin (VL2) comprising the VL CDR3, CDR2 and CDR1 of an antibody specific for the epitope of CD3 or CD16;

(ii) a domain (E) comprising a binding region of a heavy chain variable domain of the first immunoglobulin (VH1) comprising the VH CDR3, CDR2, and CDR1 of HIV-1 antibody A32 (SEQ ID NO:77), or 7B2 (SEQ ID NO: 56), wherein domains (D) and (E) are separated from one another by a peptide linker 1; and (iii) a domain (F) comprising a heterodimer promoting domain including a K coil or E coil; wherein the heterodimer promoting domain (F) and domain (E) are separated by a peptide linker 2, and wherein:

the domains (A) and (B) do not associate with one another to form an epitope binding site; the domains (D) and (E) do not associate with one another to form an epitope binding site;

the domains (A) and (E) associate to form a binding site that binds the HIV-I envelope like the A32 or 7B2 antibody (1);

the domains (B) and (D) associate to form a binding site that binds the epitope of CD3 or CD16;

the K coil comprises residues 240-267 of SEQ ID NO: 19, and the E coil comprises residues 249-276 of SEQ ID NO: 17; and peptide linker 2 comprises residues 244-248 of SEQ ID NO: 17.

2. The bispecific molecule of claim 1, wherein (i) the VL1 comprises the VL CDR3, CDR2, and CDR1 of HIV-I antibody A32 (SEQ ID NO: 78);

(ii) the VH1 comprises the VH CDR3, CDR2, and CDR1 of HIV-I antibody A32 (SEQ ID NO: 77); and iii) the domains (B) and (D) associate to form a binding site that binds the epitope of CD3.

3. The bispecific molecule of claim 1, wherein (i) the VL1 comprises the VL CDR3, CDR2, and CDR1 of HIV-1 antibody A32 (SEQ ID NO: 78);

(ii) the VH1 comprises the VH CDR3, CDR2, and CDR1 of HIV-1 antibody A32 (SEQ ID NO: 77);

(iii) the VL2 comprises the VL CDR3, CDR2, and CDR1 of anti-CD3 antibody (SEQ ID NO: 52); and (iv) the VH2 comprises the VH CDR3, CDR2, and CDR1 of anti-CD3 antibody (SEQ ID NO:51).

4. The bispecific molecule of claim 1, wherein the domain (A) comprises VL of HIV-1 antibody A32 (SEQ ID NO: 78);

the domain (E) comprises VH of HIV-1 antibody A32 (SEQ ID NO: 77); and the domains (B) and (D) associate to form a binding site that binds the epitope of CD3.

5. The bispecific molecule of claim 1, wherein the domain (A) comprises VL of HIV-1 antibody A32 (SEQ ID NO: 78);

the domain (E) comprises VH of HIV-1 antibody A32 (SEQ ID NO: 77);

the domain (B) comprises VH of anti-CD3 antibody (SEQ ID NO: 51); and the domain (D) comprises VL of anti-CD3 antibody (SEQ ID NO: 52).

6. The bispecific molecule of claim 1, wherein the domain (A) comprises VL of HIV-1 antibody A32 (SEQ ID NO: 78);

the domain (E) comprises VH of HIV-1 antibody A32 (residues 119-241 of SEQ ID NO: 11); and the domains (B) and (D) associate to form a binding site that binds the epitope of CD3.

7. The bispecific molecule of claim 1, wherein the domain (A) comprises VL of HIV-1 antibody A32 (SEQ ID NO: 78);

the domain (E) comprises VH of HIV-1 antibody A32 (residues 119-241 of SEQ ID NO: 11);

the domain (B) comprises VH of anti-CD3 antibody (SEQ ID NO: 51); and the domain (D) comprises VL of anti-CD3 antibody (SEQ ID NO: 52).

8. The bispecific molecule of claim 3, wherein the bispecific molecule further comprises an Fc-domain.

9. The bispecific molecule of claim 3, wherein:

(i) the first polypeptide chain further comprises a CH2-CH3 domain, wherein the CH2-CH3 domain and domain (C) are separated by a peptide linker 3 or a spacer-linker 3;

(ii) the bispecific molecule further comprises a third polypeptide chain comprising in the N- to C-terminal direction a peptide linker 3 and a CH2-CH3 domain; and (iii) the CH2-CH3 domains of the first and third polypeptide form the Fc domain.

10. The bispecific molecule of claim 9, wherein:

(i) the CH2-CH3 domain of the first polypeptide chain comprises SEQ ID NO: 42 and the CH2-CH3 domain of the third polypeptide chain comprises SEQ ID NO: 43; or (ii) the CH2-CH3 domain of the first polypeptide chain comprises SEQ ID NO: 43 and the CH2-CH3 domain of the third polypeptide chain comprises SEQ ID NO: 42.

11. A composition comprising the bispecific molecule of claim 3.

12. The composition of claim 11, further comprising a second bispecific molecule comprising a first arm with the binding specificity of HIV-1 antibody A32, HIV-1 antibody 7B2, HIV-1 antibody CH28, or HIV-1 antibody CH44 and a second arm targeting CD3 or CD16, wherein the first and second bispecific molecules are different.

13. A composition comprising the bispecific molecule of claim 8.

14. The composition of claim 13, further comprising a second bispecific molecule comprising a first arm with the binding specificity of HIV-I antibody A32, HIV-1 antibody 7B2, HIV-1 antibody CH28, or HIV-1 antibody CH44 and a second arm targeting CD3 or CD16, wherein the first and second bi specific molecules are different.

15. A composition comprising the bispecific molecule of claim 9.

16. The composition of claim 15, further comprising a second bispecific molecule comprising a first arm with the binding specificity of HIV-1 antibody A32, HIV-1 antibody 7B2, HIV-1 antibody CH28, or HIV-1 antibody CH44 and a second arm targeting CD3 or CD16, wherein the first and second bispecific molecules are different.

* * * * *